United States Patent
Altman et al.

(10) Patent No.: US 10,738,074 B2
(45) Date of Patent: Aug. 11, 2020

(54) CYCLIC DI-NUCLEOTIDE COMPOUNDS AS STING AGONISTS

(71) Applicants: Merck Sharp & Dohme Corp., Rahway, NJ (US); Michael D. Altman, Needham, MA (US); Brian Andresen, Sharon, MA (US); Wonsuk Chang, Princeton, NJ (US); Matthew Lloyd Childers, Medfield, MA (US); Jared N. Cumming, Winchester, MA (US); Andrew Marc Haidle, Somerville, MA (US); Timothy J. Henderson, Natick, MA (US); James P. Jewell, Newton, MA (US); Min Lu, Brookline, MA (US); Alan B. Northrup, Belmont, CA (US); Ryan D. Otte, Natick, MA (US); Tony Siu, Brookline, MA (US); Benjamin Wesley Trotter, Medfield, MA (US); Quang T. Truong, Morganville, NJ (US)

(72) Inventors: Michael D. Altman, Needham, MA (US); Brian Andresen, Sharon, MA (US); Wonsuk Chang, Princeton, NJ (US); Matthew Lloyd Childers, Medfield, MA (US); Jared N. Cumming, Winchester, MA (US); Andrew Marc Haidle, Somerville, MA (US); Timothy J. Henderson, Natick, MA (US); James P. Jewell, Newton, MA (US); Min Lu, Brookline, MA (US); Alan B. Northrup, Belmont, CA (US); Ryan D. Otte, Natick, MA (US); Tony Siu, Brookline, MA (US); Benjamin Wesley Trotter, Medfield, MA (US); Quang T. Truong, Morganville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/752,144

(22) PCT Filed: Aug. 11, 2016

(86) PCT No.: PCT/US2016/046442
§ 371 (c)(1),
(2) Date: Feb. 12, 2018

(87) PCT Pub. No.: WO2017/027645
PCT Pub. Date: Feb. 16, 2017

(65) Prior Publication Data
US 2018/0230178 A1 Aug. 16, 2018

Related U.S. Application Data
(60) Provisional application No. 62/356,125, filed on Jun. 29, 2016, provisional application No. 62/268,723, (Continued)

(51) Int. Cl.
*A01N 43/04* (2006.01)
*A61K 31/70* (2006.01)
(Continued)

(52) U.S. Cl.
CPC ............ *C07H 21/04* (2013.01); *A61K 39/39* (2013.01); *A61P 35/00* (2018.01); *C07H 19/20* (2013.01);
(Continued)

(58) Field of Classification Search
None
See application file for complete search history.

(56) References Cited

U.S. PATENT DOCUMENTS

| 7,488,802 B2 | 2/2009 | Collins et al. |
| 7,521,051 B2 | 4/2009 | Collins et al. |

(Continued)

FOREIGN PATENT DOCUMENTS

| EP | 3135290 A1 | 1/2018 |
| WO | 2001002369 A2 | 1/2001 |

(Continued)

OTHER PUBLICATIONS

Ablasser et al., Cell intrinsic immunity spreads to bystander cells via the intercellular transfer of cGAMP, Nature, Nov. 28, 2013, 530-546, 503.
Ablasser et al., cGAS produces a 2'-5'-linked cyclic dinucleotide second messenger that activates STING, Nature, Jun. 20, 2013, 380-385, 498.
Ausmees et al., Genetic Data Indicate that Proteins Containing the GGDEF Domain Possess Diguanylate Cyclase Activity, FEMS Microbiology, 2001, 163-167, Letters 204.
Bhattacharya et al., Total Synthesis of 2'-deoxy-2'-arafluoro-tubericidin, -toyocamycin, -sangivamycin and certain related molecules, J. Chem. Soc., Perkin Trans. 1; Organic and Bio-Organic Chemistry, 1995, 1543-1550, 12).

(Continued)

*Primary Examiner* — Patrick T Lewis
(74) *Attorney, Agent, or Firm* — Julie M. Lake; Catherine D. Fitch

(57) ABSTRACT

A class of polycyclic compounds of general formula (II), of general formula (II'), or of general formula (II''), wherein Base¹, Base², Y, $Y^a$, $X^a$, $X^{a1}$, $X^b$, $X^{b1}$, $X^c$, $X^{c1}$, $X^d$, $X^{d1}$, $R^1$, $R^{1a}$, $R^2$, $R^{2a}$, $R^{3a}$, $R^4$, $R^{4a}$, $R^5$, $R^6$, $R^{6a}$, $R^7$, $R^{7a}$, $R^8$, and $R^{8a}$ are defined herein, that may be useful as inductors of type I interferon production, specifically as STING active agents, (Continued)

are provided. Also provided are processes for the synthesis and use of compounds.

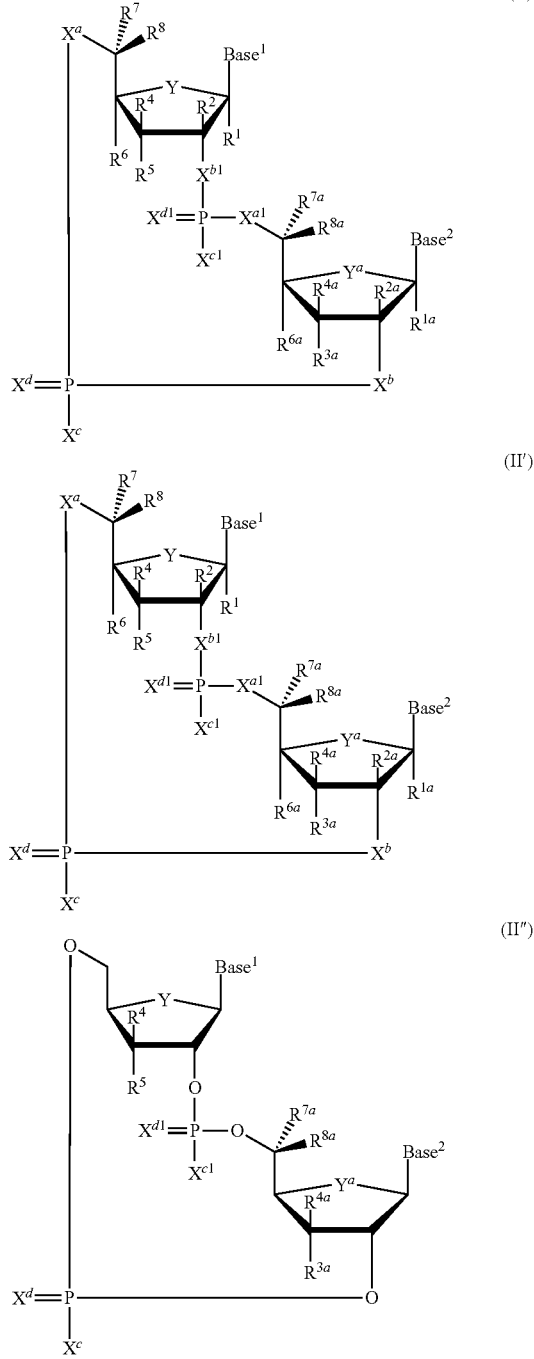

10 Claims, No Drawings

Specification includes a Sequence Listing.

Related U.S. Application Data filed on Dec. 17, 2015, provisional application No. 62/204,677, filed on Aug. 13, 2015.

(51) Int. Cl.

| | | |
|---|---|---|
| *C07H 21/04* | (2006.01) | |
| *C07H 21/02* | (2006.01) | |
| *A61K 39/39* | (2006.01) | |
| *C07H 19/20* | (2006.01) | |
| *C07H 19/23* | (2006.01) | |
| *C07H 21/00* | (2006.01) | |
| *A61P 35/00* | (2006.01) | |
| *A61K 31/7064* | (2006.01) | |
| *A61K 31/7084* | (2006.01) | |
| *A61K 31/708* | (2006.01) | |
| *A61K 31/706* | (2006.01) | |
| *A61K 31/7076* | (2006.01) | |

(52) U.S. Cl.
CPC ............ *C07H 19/23* (2013.01); *C07H 21/00* (2013.01); *C07H 21/02* (2013.01); *A61K 31/706* (2013.01); *A61K 31/708* (2013.01); *A61K 31/7064* (2013.01); *A61K 31/7076* (2013.01); *A61K 31/7084* (2013.01)

(56) References Cited

U.S. PATENT DOCUMENTS

| | | | |
|---|---|---|---|
| 8,008,449 B2 | 8/2011 | Korman et al. | |
| 8,168,757 B2 | 5/2012 | Finnefroch et al. | |
| 8,354,509 B2 | 1/2013 | Carven et al. | |
| 8,383,796 B2 | 2/2013 | Korman et al. | |
| 9,724,408 B2 | 8/2017 | Dubensky, Jr. et al. | |
| 2006/0040887 A1 | 2/2006 | Karaolis | |
| 2006/0167241 A1* | 7/2006 | Hayakawa | C07H 19/10 536/26.2 |
| 2008/0025979 A1 | 1/2008 | Honjo et al. | |
| 2008/0286296 A1 | 11/2008 | Ebensen et al. | |
| 2011/0271358 A1 | 11/2011 | Gordon et al. | |
| 2014/0206640 A1 | 7/2014 | Girijavallabhan et al. | |
| 2014/0329889 A1 | 11/2014 | Vance et al. | |
| 2014/0341976 A1* | 11/2014 | Dubensky, Jr. | C07H 21/02 424/450 |
| 2015/0056224 A1 | 2/2015 | Dubensky, Jr. et al. | |
| 2015/0158886 A1 | 6/2015 | Jones et al. | |
| 2016/0074507 A1 | 3/2016 | Manel et al. | |
| 2016/0287698 A1 | 10/2016 | Yan et al. | |
| 2016/0362441 A1 | 12/2016 | Vernejoul et al. | |
| 2017/0050967 A1 | 2/2017 | Burai et al. | |
| 2017/0158724 A1 | 6/2017 | Adams et al. | |

FOREIGN PATENT DOCUMENTS

| | | |
|---|---|---|
| WO | 2001002369 A3 | 1/2001 |
| WO | WO0210192 | 2/2002 |
| WO | N002057245 | 7/2002 |
| WO | WO02068470 | 9/2002 |
| WO | 2004004771 | 2/2004 |
| WO | 2004056875 | 7/2004 |
| WO | 2004072286 | 8/2004 |
| WO | 2010027827 | 3/2010 |
| WO | 2010047774 | 4/2010 |
| WO | 2010077634 | 7/2010 |
| WO | 2011066342 | 6/2011 |
| WO | 2013019906 | 2/2013 |
| WO | 2013185052 A1 | 12/2013 |
| WO | 2014093936 | 6/2014 |
| WO | WO2014099824 | 6/2014 |
| WO | WO2014099941 | 6/2014 |
| WO | 2014189805 A1 | 11/2014 |
| WO | WO201479335 | 11/2014 |
| WO | WO2014179760 | 11/2014 |
| WO | WO2014189805 | 11/2014 |
| WO | WO2014189806 | 11/2014 |
| WO | WO2015017652 | 2/2015 |
| WO | WO2015074145 | 5/2015 |

(56) References Cited

FOREIGN PATENT DOCUMENTS

| | | |
|---|---|---|
| WO | WO2015077354 | 5/2015 |
| WO | 2015148746 A1 | 10/2015 |
| WO | WO2015161137 | 10/2015 |
| WO | 2015189117 | 12/2015 |
| WO | WO2015185565 | 12/2015 |
| WO | 2016100261 | 6/2016 |
| WO | WO2016096174 | 6/2016 |
| WO | WO2016096577 | 6/2016 |
| WO | 2016120605 | 8/2016 |
| WO | WO2016120305 | 8/2016 |
| WO | WO2016145102 | 9/2016 |
| WO | 2017011522 | 1/2017 |
| WO | 2017011622 | 1/2017 |
| WO | 2017011920 | 1/2017 |
| WO | 2017027645 | 2/2017 |
| WO | 2017027646 | 2/2017 |
| WO | 2017075477 | 5/2017 |
| WO | 2017093933 | 6/2017 |
| WO | 2017100305 | 6/2017 |
| WO | 2017123657 | 7/2017 |
| WO | 2017123669 | 7/2017 |
| WO | 2017161349 | 9/2017 |
| WO | 2017175147 | 10/2017 |
| WO | 2017175156 | 10/2017 |
| WO | 2017216726 | 12/2017 |
| WO | 2018009466 | 1/2018 |

OTHER PUBLICATIONS

Boehr et al., Establishing the Principles of Recognition in the Adenine-Binding Region of an Aminoglycoside Antibiotic Kinase [APH(3')-IIIa], Biochemistry, 2005, 12445-12453, 44(37).
Bookser et al., High-Throughput Five Minute Microwave Accelerated Glycosylation Approach to the Synthesis of Nucleoside Libraries, JOC Article, 2007, 173-179, 72.
Dande et al., Improving RNA Interference in Mammalian Cells by 4'-Thio-Modified Small Interfering RNA (siRNA): Effect on siRNA Activity and Nuclease Stability When Used in Combination with 2'-O-Alkyl Modifications, Journal of Medicinal Chemistry, 2006, 1624-1634, 49(5).
Diner et al., The Innate Immune DNA Sensor cGAS Produces a Noncanonical Cyclic Dinucleotide that Activates Human STING, 3 Cell Reports, Cell Reports, 2013, 1355-1361, 3.
Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, PLOS One, 2014, 1-14, 9-6-e99988.
Ertem et al., Synthesis of RNA oligomers on heterogeneous templates, Nature, 1996, 238-240, 379-18.
Fagundes et al., Building unique bonds to tight misplaced DNA, Cell Research, 2013, 1065-1066, 2-9.
Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.
Gaffney et al., One-Flask Syntheses of c-di-GMP and the [Rp,Rp] and [Rp,Sp] Thiophosphate Analogues, Organic Letters, 2010, 3269-3271, 12-14.
Gao et al., Cyclic [G(2',5')pA(3',5")p] is the Metazoan Second Messenger Produced by DNA-Activated Cyclic GMP-AMP Synthase, Cell, 2013, 1094-1107, 153.
Gao et al., Structure-Function Ananlysis of STING Activation by c[G(2',5')pA(3',5')p] and Targeting by Antiviral DMXAA, Cell, 2013, 748-762, 154.
Gosselin et al., Systematic Synthesis and Biological Evaluation of α- and β-D-Iyxofuranosyl Nucleosides of the Five Naturally Occurring Nucleic Acid Bases, J. Med. Chem, 1987, 982-991, 30.
Ikeuchi et al., Practical synthesis of natural plant-growth regulator 2-azahypoxanthine, its derivatives, and biotin-labeled probes, Organic & Biomolecular Chemistry, 2014, 3813, 12(23).

Joshi et al., Selectivity of montmorillonite catalyzed prebiotic reactions of D, L-nucleotides, Orig Life Evol Biosph, 2007, 3-26, 37-3.
Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/Progenitors and their Niches through STING, Cell Reports, 2015, 71-84, 11.
Kranzusch et al., Structure-Guided Reporgramming of Human cGAS Dinucleotide Linkage Specificity, Cell Inc., Elsevier Inc., 2014, 1011-1021, 158.
Li et al., Cyclic GMP-AMP Synthase is Activated by Double-Stranded DNA-Induced Oligomerization, Immunity, 2013, 1019-1031, 39.
Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs: ERRATUM, Nature Chemical Biology, 2014, 1043, 10.
Li et al., Synthesis of 2'-Deoxy-2'-C—a-methylpurine Nucleosides, Synthesis, 2005, 2865-2870, 2005(17).
Liu et al., Activated STING in a Vascular and Pulmonary Syndrome, The New England Journal of Medicine, 2015, 507, 371-6.
Liu et al., Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or -carbonitrile, Tetrahedron, 1993, 557-570, 49(3).
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
O'Neill et al., Sensing the Dark Side of DNA, Sceince, 2013, 763, 339.
Ora et al., Hydrolytic reactions of cyclic bis(3'-5') diadenylic acid (c-di-AMP), J. Phys. Org. Chem, 2013, 218-225, 26.
Janne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Ren et al., Structural Basis for Molecular Discrimination by a 3',3'-cGAMP Sensing Riboswitch, Cell Reports, 2015, 1-12, 11.
Robins et al., Nucleic acid related compounds. 74. Synthesis and biological activity of 2'(and 3')-deoxy-2'(and 3')-methylenenucleoside analogs that function as mechanism-based inhibitors of S-adenosyl-L-homocysteine hydrolase and/or ribonucleotide reductase, Journal of Medicinal Chemistry, 1992, 2283-2293, 35(12).
Robins et al., Nucleic Acid-Related Compounds. 91. Biomimetic Reactions are in Harmony with Loss of 2'-Substituents as Free Radicals (Not Anions) during Mechanism-Based Inactivation of

(56) References Cited

OTHER PUBLICATIONS

Ribonucleotide Reductases. Differential Interactions of Azide, Halogen, and Alkylthio, J. Am. Chem. Soc., 1996, pp. 11341-11348, 118(46).
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sawai et al., Preparation and Properties of Oligocytidylates with 2'-5' Internucleotide Linkage, Chem. Pharm. Bull. Jpn, 1985, 361-366, 58.
Sawai et al., Synthesis of 2'-5' Linked Oligouridylates in Awueous Medium using the Pd2+ Ion, Chem. Pharm. Bull, 1981, 2237-2245, 29(8).
Seela et al., Fluorinated Pyrrolo[2,3-d]pyrimidine Nucleosides: 7-Fluoro-7-deazapurine 2'-Deoxyribofuranosides and 2'-Deoxy-2'-fluoroarabinofuranosyl Derivatives, Synthesis, 2006, 2005-2012, (12).
Simm et al., Phenotypic Convergence Mediated by Ggdef-Domain-Containing Proteins, 187(19) J Bacteriology 6816 (Oct. 2005); Simm et al., Phenotypic Convergence Mediated by GGDEF-Domain-Containing Proteins, Journal of Bacteriology, 2005, 6816-6823, 187-19.
Sun et al., Cyclic GMP-AMP Synthase is a Cytosolic DNA Sensor That Activates the Type I Interferon Pathway, Science, 2013, 786, 339.
Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.
Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP is an Endogenous Second Messenger in Innate Immune Signaling by Cytosolic DNA, Science 826, 2013, 826-830, 339.
Yi et al., Single Nucleotide Polymorphisms of Human STING Can Affect Innate Immune Response to Cyclic Dinucleotides, PLOS One, 2013, 1-16, 8-10-e77846.
Zeng et al., MAVS, cGAS, and Endogenous Retroviruses in T-Independent B Cell Responses, Science, 2014, 1486-1492, 346-6216.
Zhang et al., Cyclic GMP-AMP Containing Mixed Phosphodiester Linkages is an Endogenous High-Affinity Ligand for STING, Molecular Cell, 2013, 226-235, 51.
Zhou et al., The ER-Associated Protein ZDHHC1 is a Positive Regulator of DNA Virus-Triggered, MITA/STING-Dependent Innate Immune Signaling, Cell Host & Microbe, 2014, 450-461, 16.
Berge, S.M., et al.,, "Pharmaceutical Salts", J. Pharm. Sci, 1977, pp. 1-19, vol. 66, No. 1.
Bruno et al., N-Substituted 2-aminobiphenylpalladium Methanesulfonate Precatalysts and Their Use in C—C and C—N Cross Couplings, the Journal of Organic Chamistry, 2014, 4161-4166, 79.
Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.
Gould, Salt Selections for Basic Drugs, Intl. J. Pharmaceutics, 1986, pp. 201-217, vol. 33.
Heping Shi, et al., Molecular basis for the specific recognition of the metazoan cyclic GMP-AMP by the innate immune adaptor protein STING, PNAS, 2015, 8947-8952, vol. 112/No. 29.
Stahl et al., Aminoquinazoline Compounds as A2A Antagonist, Handbook of Pharmaceutical Salts Properties, Selection, and Use, 2002, 330-331.
Tezuka, T. et al., Synthesis of 2'-Modified Cyclic Bis(3'-5')diadenylic Acids (c-di-AMPs) and Their Promotion of Cell Division in a Freshwater Green Alga, Chem. Lett., 2012, 1723-1725, 41.
Burdette, Dana L., STING is a direct innate immune sensor of cyclic di-GMP, Nature, Oct. 27, 2011, 515-519, 478.
Burdette, Dara L., STING and the innate immune response to nucleic acids in the cytosol, Nature Immunology, Jan. 2013, 19-26, 14(1).
Dubensky, et al., Rationale, progress and development of vaccines utilizing STING-activating cyclic dinucleotide adjuvants, Therapeutic Advances in Vaccines, 2013, 131-143, 1(4).
Fu, Juan, et al., STING agonist formulated cancer vaccines can cure established tumors resistant to PD-1 blockade, Science Translational Medicine, 2015, 1-13, 7.
Sheridan, Cormac, Drug Developers Switch Gears to Inhibit STING, Nature Biotechnology, Mar. 4, 2019, 199-208, 37.

\* cited by examiner

SEQUENCE LISTING

<160> NUMBER OF SEQ ID NOS: 4

<210> SEQ ID NO 1
<211> LENGTH: 414
<212> TYPE: PRT
<213> ORGANISM: Homo Sapien

<400> SEQUENCE: 1

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
```

```
                  260                 265                 270
    Gln Tyr Ser Gln Ala Gly Phe Ser Arg Glu Asp Arg Leu Glu Gln Ala
                275                 280                 285

Lys Leu Phe Cys Gln Thr Leu Glu Asp Ile Leu Ala Asp Ala Pro Glu
                290                 295                 300

Ser Gln Asn Asn Cys Arg Leu Ile Ala Tyr Gln Glu Pro Ala Asp Asp
    305                 310                 315                 320

Ser Ser Phe Ser Leu Ser Gln Glu Val Leu Arg His Leu Arg Gln Glu
                    325                 330                 335

Glu Lys Glu Glu Val Thr Val Gly Ser Leu Lys Thr Ser Ala Val Pro
                340                 345                 350

Ser Thr Ser Thr Met Ser Gln Glu Pro Glu Leu Leu Ile Ser Gly Met
                355                 360                 365

Glu Lys Pro Leu Pro Leu Arg Thr Asp Phe Ser Gly Gly Gly Leu Asn
                370                 375                 380

Asp Ile Phe Glu Ala Gln Lys Ile Glu Trp His Glu Gly Ser Leu Glu
    385                 390                 395                 400

Val Leu Phe Gln Gly Pro His His His His His His
                    405                 410

<210> SEQ ID NO 2
<211> LENGTH: 6482
<212> TYPE: DNA
<213> ORGANISM: Homo Sapien

<400> SEQUENCE: 2
ggaacggctc cgcccactat taatgaaatt aaaaattcca attttaaaaa acgcagcaag      60
agaaacattt gtatgaaaga atgcgtagaa ggaaagaaaa atgtcgtcga catgctgaac     120
aacaagatta atatgcctcc gtgtataaaa aaaatattga acgatttgaa agaaaacaat     180
gtaccgcgcg gcggtatgta caggaagagg tttatactaa actgttacat tgcaaacgtg     240
gtttcgtgtg ccaagtgtga aaaccgatgt ttaatcaagg ctctgacgca tttctacaac     300
cacgactcca agtgtgtggg tgaagtcatg catcttttaa tcaaatccca agatgtgtat     360
aaaccaccaa actgccaaaa aatgaaaact gtcgacaagc tctgtccgtt tgctggcaac     420
tgcaagggtc tcaatcctat ttgtaattat tgaataataa aacaattata aatgctaaat     480 ttgttttttta ttaacgatac aaaccaaacg caacaagaac atttgtagta ttatctataa     540
ttgaaaacgc gtagttataa tcgctgaggt aatatttaaa atcattttca aatgattcac     600
agttaatttg cgacaatata attttatttt cacataaact agacgccttg tcgtcttctt     660
cttcgtattc cttctctttt tcattttct cttcataaaa attaacatag ttattatcgt      720
atccatatat gtatctatcg tatagagtaa attttttgtt gtcataaata tatatgtctt     780
ttttaatggg gtgtatagta ccgctgcgca tagttttttct gtaatttaca acagtgctat     840
tttctggtag ttcttcggag tgtgttgctt taattattaa atttatataa tcaatgaatt     900
tgggatcgtc ggttttgtac aatatgttgc cggcatagta cgcagcttct tctagttcaa     960
ttacaccatt ttttagcagc accggattaa cataactttc caaatgttg tacgaaccgt     1020 taaacaaaaa cagttcacct cccttttcta tactattgtc tgcgagcagt tgtttgttgt     1080
taaaaataac agccattgta atgagacgca caaactaata tcacaaactg gaaatgtcta     1140
tcaatatata gttgctgatc agatctgatc atggagataa ttaaaatgat aaccatctcg     1200
caaataaata agtattttac tgttttcgta acagtttgt aataaaaaaa cctataaata     1260
```

-continued

```
taggatccat gccccactcc agcctgcatc catccatccc gtgtcccagg ggtcacgggg    1320
cccagaaggc agccttggtt ctgctgagtg cctgcctggt gacccttggg gggctaggag    1380
agccaccaga gcacactctc cggtacctgg tgctccacct agcctccctg cagctgggac    1440
tgctgttaaa cggggtctgc agcctggctg aggagctgca ccacatccac tccaggtacc    1500
ggggcagcta ctggaggact gtgcgggcct gcctggggctg cccctccgc cgtggggccc    1560 tgttgctgct gtccatctat ttctactact ccctcccaaa tgcggtcggc ccgcccttca    1620
cttggatgct tgccctcctg ggcctctcgc aggcactgaa catcctcctg ggcctcaagg    1680
gcctggcccc agctgagatc tctgcagtgt gtgaaaaagg gaatttcaac gtggcccatg    1740
ggctggcatg gtcatattac atcggatatc tgcggctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg gctgacccca    1920
acattcgctt cctggataaa ctgccccagc agaccgctga ccgtgctggc atcaaggatc    1980
gggtttacag caacagcatc tatgagcttc tggagaacgg gcagcgggcg ggcacctgtg    2040
tcctggagta cgccaccccc ttgcagactt tgtttgccat gtcacaatac agtcaagctg    2100
gctttagccg ggaggatagg cttgagcagg ccaaactctt ctgccagaca cttgaggaca    2160
tcctggcaga tgccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640 tgttgtacg tattttaata attcattaaa tttataatct ttagggtggt atgttagagc    2700
gaaaatcaaa tgattttcag cgtctttata tctgaattta aatattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaaccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt tgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
```

```
cacgggagaa ggtggtggcg gcggtgccgc cggtataatt tgttctggtt tagtttgttc   3720
gcgcacgatt gtgggcaccg gcgcaggcgc cgctggctgc acaacggaag gtcgtctgct   3780
tcgaggcagc gcttggggtg gtggcaattc aatattataa ttggaataca atcgtaaaa    3840
atctgctata agcattgtaa tttcgctatc gtttaccgtg ccgatattta acaaccgctc   3900
aatgtaagca attgtattgt aaagagattg tctcaagctc ggatcgatcc cgcacgccga   3960
taacaagcct tttcattttt actacagcat tgtagtggcg agacacttcg ctgtcgtcga   4020
ggtttaaacg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200
gcgttttttcc ataggctccg cccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
ggaagcgtgg cgctttctca tagctcacgc tgtaggtatc tcagttcggt gtaggtcgtt   4440
cgctccaagc tgggctgtgt gcacgaaccc cccgttcagc ccgaccgctg cgccttatcc   4500
ggtaactatc gtcttgagtc caacccggta agacacgact tatcgccact ggcagcagcc   4560
actggtaaca ggattagcag agcgaggtat gtaggcggtg ctacagagtt cttgaagtgg   4620
tggcctaact acggctacac tagaaggaca gtatttggta tctgcgctct gctgaagcca   4680
gttaccttcg gaaaaagagt tggtagctct tgatccggca acaaaccac cgctggtagc    4740
ggtggttttt ttgtttgcaa gcagcagatt acgcgcagaa aaaaaggatc tcaagaagat   4800
cctttgatct tttctacggg gtctgacgct cagtggaacg aaaactcacg ttaagggatt   4860
ttggtcatga gattatcaaa aaggatcttc acctagatcc ttttaaatta aaatgaagt    4920
tttaaatcaa tctaaagtat atatgagtaa acttggtctg acagttacca atgcttaatc   4980
agtgaggcac ctatctcagc gatctgtcta tttcgttcat ccatagttgc ctgactcccc   5040
gtcgtgtaga taactacgat acgggagggc ttaccatctg gccccagtgc tgcaatgata   5100
ccgcgagacc cacgctcacc ggctccagat ttatcagcaa taaaccagcc agccggaagg   5160
gccgagcgca gaagtggtcc tgcaacttta tccgcctcca tccagtctat taattgttgc   5220
cgggaagcta gagtaagtag ttcgccagtt aatagtttgc gcaacgttgt tgccattgct   5280
acaggcatcg tggtgtcacg ctcgtcgttt ggtatggctt cattcagctc cggttcccaa   5340
cgatcaaggc gagttacatg atcccccatg ttgtgcaaaa aagcggttag ctccttcggt   5400
cctccgatcg ttgtcagaag taagttggcc gcagtgttat cactcatggt tatggcagca   5460
ctgcataatt ctcttactgt catgccatcc gtaagatgct tttctgtgac tggtgagtac   5520
tcaaccaagt cattctgaga atagtgtatg cggcgaccga gttgctcttg cccggcgtca   5580
atacgggata taccgcgcc acatagcaga actttaaaag tgctcatcat tggaaaacgt     5640
tcttcggggc gaaaactctc aaggatctta ccgctgttga gatccagttc gatgtaaccc   5700
actcgtgcac ccaactgatc ttcagcatct tttactttca ccagcgtttc tgggtgagca   5760
aaaacaggaa ggcaaaatgc cgcaaaaaag gaataaggg cgacacgaa atgttgaata     5820
ctcatactct tcctttttca atattattga agcatttatc agggttattg tctcatgagc   5880
ggatacatat ttgaatgtat ttagaaaaat aaacaaatag gggttccgcg cacatttccc   5940
cgaaaagtgc cacctgacgc gccctgtagc ggcgcattaa gcgcggcggg tgtggtggtt   6000
```

```
                                                            -continued acgcgcagcg tgaccgctac acttgccagc gccctagcgc ccgctccttt cgctttcttc      6060
ccttcctttc tcgccacgtt cgccggcttt ccccgtcaag ctctaaatcg ggggctccct      6120
ttagggttcc gatttagtgc tttacggcac ctcgacccca aaaaacttga ttagggtgat      6180
ggttcacgta gtgggccatc gccctgatag acggtttttc gcccttttgac gttggagtcc     6240 acgttcttta atagtggact cttgttccaa actggaacaa cactcaaccc tatctcggtc      6300
tattcttttg atttataagg gattttgccg atttcggcct attggttaaa aaatgagctg      6360
atttaacaaa aatttaacgc gaattttaac aaaatattaa cgtttacaat ttcccattcg      6420
ccattcaggc tgcgcaactg ttgggaaggg cgatcggtgc gggcctcttc gctattacgc      6480
ca                                                                     6482
```

<210> SEQ ID NO 3
<211> LENGTH: 414
<212> TYPE: PRT
<213> ORGANISM: Homo Sapien

<400> SEQUENCE: 3

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285
```

```
Lys Leu Phe Cys Arg Thr Leu Glu Asp Ile Leu Ala Asp Ala Pro Glu
        290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
            325                 330                 335

Glu Lys Glu Glu Val Thr Val Gly Ser Leu Lys Thr Ser Ala Val Pro
        340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser Gly Gly Gly Leu Asn
        370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
                405                 410

<210> SEQ ID NO 4
<211> LENGTH: 6482
<212> TYPE: DNA
<213> ORGANISM: Homo Sapien

<400> SEQUENCE: 4
ggaacggctc cgcccactat taatgaaatt aaaaattcca attttaaaaa acgcagcaag      60
agaaacattt gtatgaaaga atgcgtagaa ggaaagaaaa atgtcgtcga catgctgaac     120
aacaagatta atatgcctcc gtgtataaaa aaaatattga acgatttgaa agaaaacaat     180
gtaccgcgcg gcggtatgta caggaagagg tttatactaa actgttacat tgcaaacgtg     240
gtttcgtgtg ccaagtgtga aaaccgatgt ttaatcaagg ctctgacgca tttctacaac     300
cacgactcca agtgtgtggg tgaagtcatg catcttttaa tcaaatccca agatgtgtat     360
aaaccaccaa actgccaaaa aatgaaaact gtcgacaagc tctgtccgtt tgctggcaac     420
tgcaagggtc tcaatcctat ttgtaattat tgaataataa acaattata aatgtcaaat      480 ttgttttta ttaacgatac aaaccaaacg caacaagaac atttgtagta ttatctataa      540
ttgaaaacgc gtagttataa tcgctgaggt aatatttaaa atcattttca aatgattcac     600
agttaatttg cgacaatata attttatttt cacataaact agacgccttg tcgtcttctt     660
cttcgtattc cttctctttt tcatttttct cttcataaaa attaacatag ttattatcgt     720
atccatatat gtatctatcg tatagagtaa atttttgtt gtcataaata tatatgtctt     780
ttttaatggg gtgtatagta ccgctgcgca tagttttcc gtaatttaca acagtgctat      840
tttctggtag ttcttcggag tgtgttgctt taattattaa atttatataa tcaatgaatt     900
tgggatcgtc ggttttgtac aatatgttgc cggcatagta cgcagcttct tctagttcaa     960
ttacaccatt tttagcagc accggattaa cataactttc caaatgttg tacgaaccgt     1020 taaacaaaaa cagttcacct cccttttcta tactattgtc tgcgagcagt tgtttgttgt    1080
taaaaataac agccattgta atgagacgca caaactaata tcacaaactg gaaatgtcta    1140
tcaatatata gttgctgatc agatctgatc atggagataa ttaaaatgat aaccatctcg    1200
caaataaata agtattttac tgttttcgta acagttttgt aataaaaaaa cctataaata    1260
taggatccat gccccactcc agcctgcatc catccatccc gtgtcccagg ggtcacgggg    1320
cccagaaggc agccttggtt ctgctgagtg cctgcctggt gacccttgg gggctaggag     1380
```

```
agccaccaga gcacactctc cggtacctgg tgctccacct agcctccctg cagctgggac    1440
tgctgttaaa cggggtctgc agcctggctg aggagctgcg ccacatccac tccaggtacc    1500
ggggcagcta ctggaggact gtgcgggcct gcctgggctg ccccctccgc cgtggggccc    1560
tgttgctgct gtccatctat ttctactact ccctcccaaa tgcggtcggc ccgcccttca    1620
cttggatgct tgccctcctg ggcctctcgc aggcactgaa catcctcctg ggcctcaagg    1680
gcctggcccc agctgagatc tctgcagtgt gtgaaaaagg gaatttcaac gtggcccatg    1740
ggctggcatg gtcatattac atcggatatc tgcggctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg gctgacccca    1920
acattcgctt cctggataaa ctgccccagc agaccggtga ccgtgctggc atcaaggatc    1980
gggtttacag caacagcatc tatgagcttc tggagaacgg gcagcgggcg ggcacctgtg    2040
tcctggagta cgccaccccc ttgcagactt tgtttgccat gtcacaatac agtcaagctg    2100
gctttagccg ggaggatagg cttgagcagg ccaaactctt ctgccggaca cttgaggaca    2160
tcctggcaga tgccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640
ttgttgtacg tattttaata attcattaaa tttataatct taggggtggt atgttagagc    2700
gaaaatcaaa tgattttcag cgtctttata tctgaattta atattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaaccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt tgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
```

```
tcgaggcagc gcttggggtg gtggcaattc aatattataa ttggaataca atcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgttttttcc ataggctccg ccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac cgctggtagc    4740
ggtggttttt ttgtttgcaa gcagcagatt acgcgcagaa aaaaggatc tcaagaagat    4800
cctttgatct tttctacggg gtctgacgct cagtggaacg aaaactcacg ttaagggatt    4860
ttggtcatga gattatcaaa aaggatcttc acctagatcc ttttaaatta aaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga acttaaaag tgctcatcat ggaaaacgt    5640
tcttcggggc gaaaactctc aaggatctta ccgctgttga gatccagttc gatgtaaccc    5700
actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct tcctttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
```

```
ttagggttcc gatttagtgc tttacggcac ctcgacccca aaaaacttga ttagggtgat  6180
ggttcacgta gtgggccatc gccctgatag acggtttttc gccctttgac gttggagtcc  6240
acgttcttta atagtggact cttgttccaa actggaacaa cactcaaccc tatctcggtc  6300
tattcttttg atttataagg gattttgccg atttcggcct attggttaaa aaatgagctg  6360
atttaacaaa aatttaacgc gaattttaac aaaatattaa cgtttacaat ttcccattcg  6420
ccattcaggc tgcgcaactg ttgggaaggg cgatcggtgc gggcctcttc gctattacgc  6480
ca                                                                 6482
```

CYCLIC DI-NUCLEOTIDE COMPOUNDS AS STING AGONISTS

CROSS-REFERENCE TO RELATED APPLICATIONS

This application is a National Stage application of International Patent Application No. PCT/US2016/046442, filed Aug. 11, 2016, which claims priority to U.S. Provisional Patent Application No. 62/356,125, filed Jun. 29, 2016, U.S. Provisional Patent Application No. 62/268,723, filed Dec. 17, 2015, and U.S. Provisional Patent Application No. 62/204,677, filed Aug. 13, 2015.

FIELD OF THE INVENTION

The present disclosure relates to cyclic di-nucleotide compounds and derivatives thereof that may be useful as STING (Stimulator of Interferon Genes) agonists that activate the STING pathway. The present disclosure also relates to processes for the synthesis and to uses of such cyclic di-nucleotide compounds.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize antigens not naturally expressed in the host as foreign and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'-3' cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T cell activation by enhancing the ability of dendritic cells and macrophages to uptake, process, present and cross-present antigens to T cells. The T cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure relates to novel cyclic di-nucleotide compounds of general formula (II), general formula (II'), and/or general formula (II"). In particular, the present disclosure relates to compounds having the general structural formula (II):

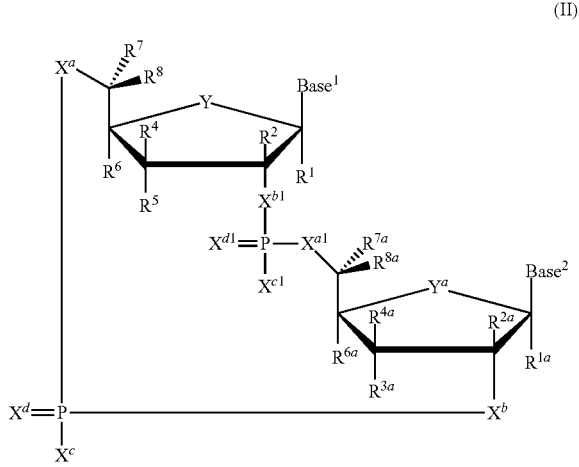

(II)

or pharmaceutically acceptable salts, hydrates, solvates, or prodrugs thereof, as described herein. The present disclosure also relates to compounds having general structural formula (II'):

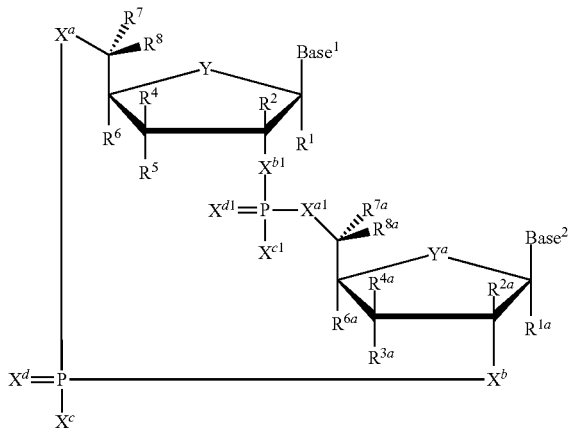

(II')

or pharmaceutically acceptable salts, hydrates, solvates, or prodrugs thereof, as described herein. The present disclosure also relates to compounds having general structural formula (II''):

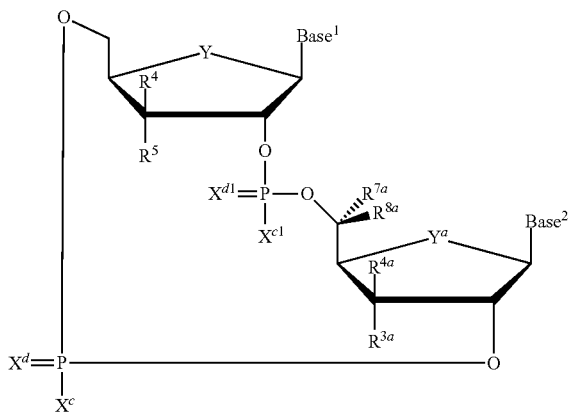

(II'')

or pharmaceutically acceptable salts, hydrates, solvates, or prodrugs thereof, as described herein.

Embodiments of the disclosure include compounds of general formula (II), compounds of general formula (II'), and/or compounds of general formula (II''), and pharmaceutically acceptable salts, hydrates, solvates, or prodrugs thereof, as well as synthesis and isolation of compounds of general formula (II), compounds of general formula (II'), and/or compounds of general formula (II''), and pharmaceutically acceptable salts, hydrates, solvates, or prodrugs thereof. Uses of compounds of general formula (II), compounds of general formula (II'), and/or compounds of general formula (II'') are also disclosed.

Other embodiments, aspects and features of the present disclosure are either further described in or will be apparent from the ensuing description, examples and appended claims.

BRIEF DESCRIPTION OF THE DRAWINGS

Not Applicable

DETAILED DESCRIPTION OF THE INVENTION

The present disclosure includes compounds of general formula (II), compounds of general formula (II'), and/or compounds of general formula (II'') above, and pharmaceutically acceptable salts, hydrates, solvates, or prodrugs thereof. These compounds and their pharmaceutically acceptable salts, hydrates, solvates, and/or prodrugs are useful as agents to induce interferon production.

A first embodiment of the disclosure relates to cyclic di-nucleotide compounds of general formula (II):

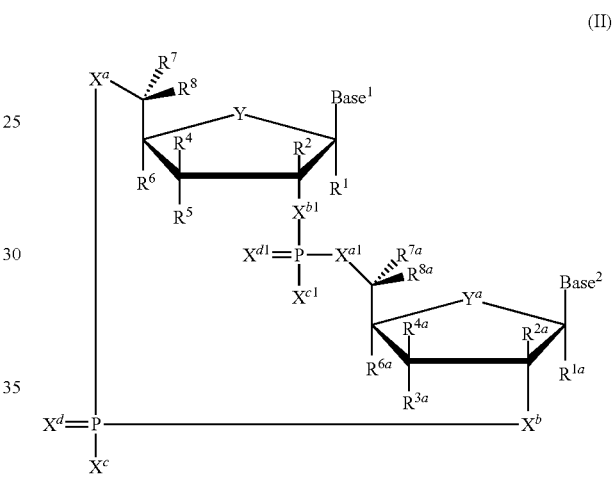

(II)

or a pharmaceutically acceptable salt, hydrate, solvate, or prodrug thereof, wherein $Base^1$ and $Base^2$ are each independently selected from the group consisting of

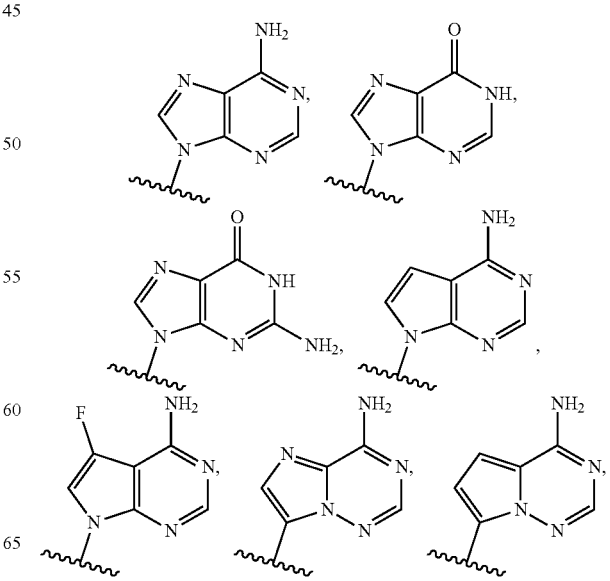

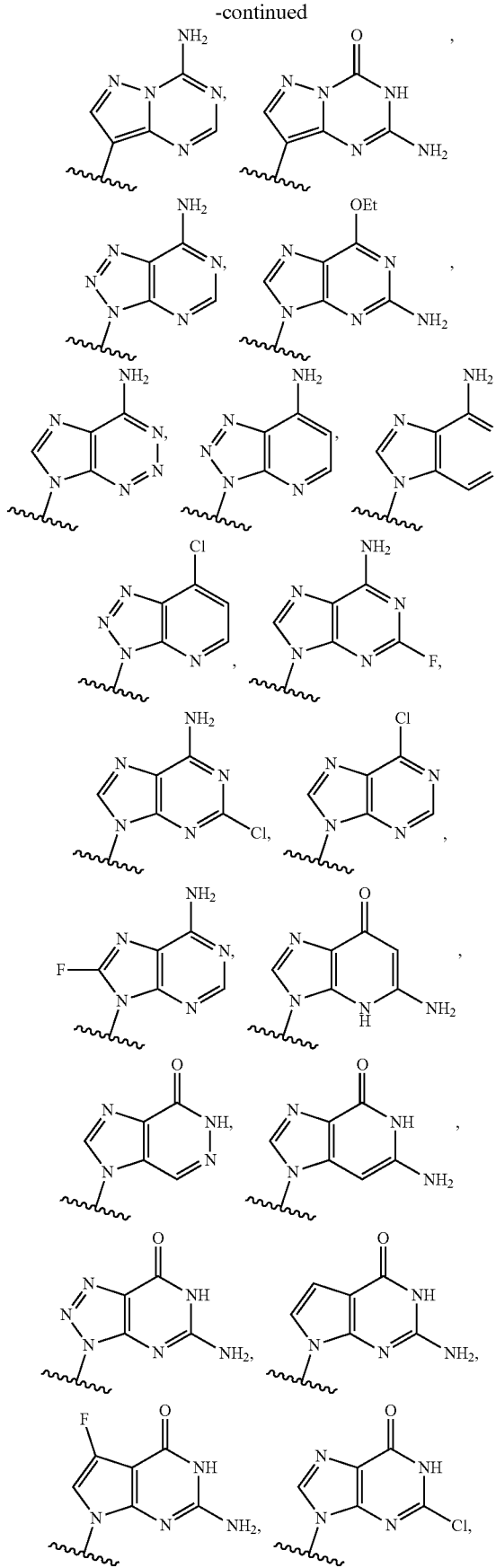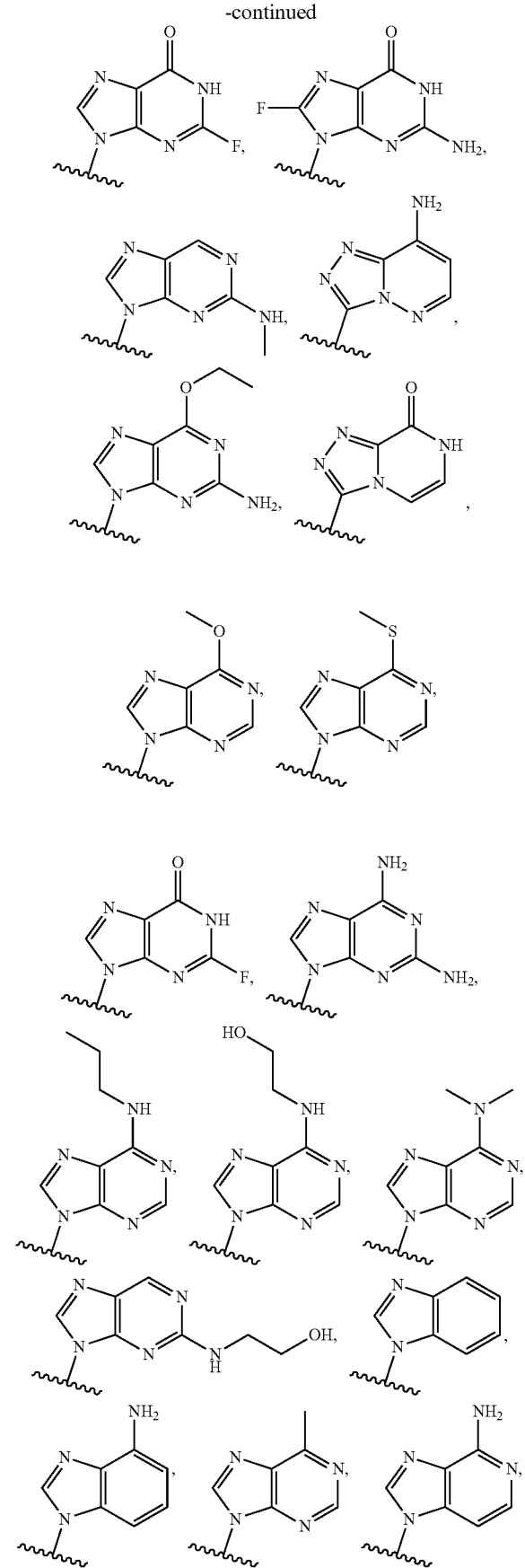

-continued

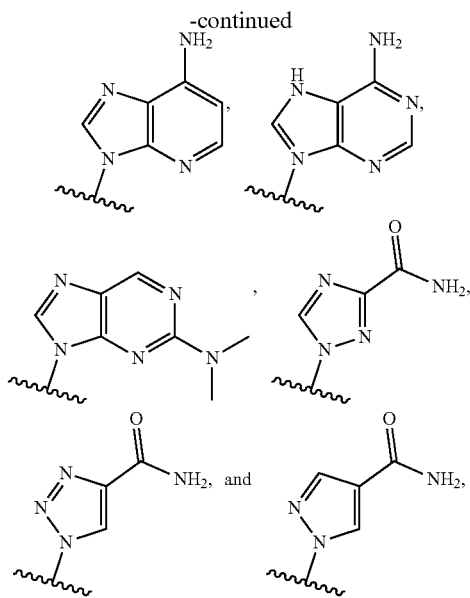

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $NH(C_{3-6}$ cycloalkyl)$_2$; Y and $Y^a$ are each independently selected from the group consisting of —O—, —S—, —$SO_2$—, —$CH_2$—, and —$CF_2$—; $X^a$ and $X^{a1}$ are each independently selected from the group consisting of O, C, and S; $X^b$ and $X^{b1}$ are each independently selected from the group consisting of O, C, and S; $X^c$ and $X^{c1}$ are each independently selected from the group consisting of $O^-$, $S^-$, $OR^9$, and $NR^9R^9$; $X^d$ and $X^{d1}$ are each independently selected from the group consisting of O and S; $R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^{3a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{3a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^5$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; each $R^9$ is independently selected from the group consisting of H, $C_1$-$C_{20}$ alkyl,

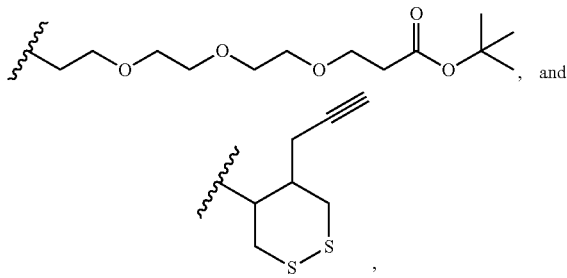

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)OC$_1$-C$_6$ alkyl; optionally R$^{3a}$ and R$^{6a}$ are connected to form —O—C$_1$-C$_6$ alkylene, —O—C$_2$-C$_6$ alkenylene, or —O—C$_2$-C$_6$ alkynylene, such that where R$^{3a}$ and R$^{6a}$ are connected to form —O—C$_1$-C$_6$ alkylene, —O—C$_2$-C$_6$ alkenylene, or —O—C$_2$-C$_6$ alkynylene, said O is bound at the R$^{3a}$ position; optionally R$^{3a}$ and R$^{4a}$ are connected to form C$_1$-C$_6$ alkylene, C$_2$-C$_6$ alkenylene, C$_2$-C$_6$ alkynylene, —O—C$_1$-C$_6$ alkylene, —O—C$_2$-C$_6$ alkenylene, or —O—C$_2$-C$_6$ alkynylene, such that where R$^{3a}$ and R$^{4a}$ are connected to form —O—C$_1$-C$_6$ alkylene, —O—C$_2$-C$_6$ alkenylene, or —O—C$_2$-C$_6$ alkynylene, said O is bound at the R$^{3a}$ position; optionally R$^4$ and R$^5$ are connected to form are connected to form C$_1$-C$_6$ alkylene, C$_2$-C$_6$ alkenylene, C$_2$-C$_6$ alkynylene, —O—C$_1$-C$_6$ alkylene, —O—C$_2$-C$_6$ alkenylene, or —O—C$_2$-C$_6$ alkynylene, such that where R$^4$ and R$^5$ are connected to form —O—C$_1$-C$_6$ alkylene, —O—C$_2$-C$_6$ alkenylene, or —O—C$_2$-C$_6$ alkynylene, said O is bound at the R$^5$ position; optionally R$^5$ and R$^6$ are connected to form —O—C$_1$-C$_6$ alkylene, —O—C$_2$-C$_6$ alkenylene, or —O—C$_2$-C$_6$ alkynylene, such that where R$^5$ and R$^6$ are connected to form —O—C$_1$-C$_6$ alkylene, —O—C$_2$-C$_6$ alkenylene, or —O—C$_2$-C$_6$ alkynylene, said O is bound at the R$^5$ position; optionally R$^7$ and R$^8$ are connected to form C$_1$-C$_6$ alkylene, C$_2$-C$_6$ alkenylene, or C$_2$-C$_6$ alkynylene; and optionally R$^{7a}$ and R$^{8a}$ are connected to form C$_1$-C$_6$ alkylene, C$_2$-C$_6$ alkenylene, or C$_2$-C$_6$ alkynylene.

In specific aspects of this embodiment, when Y and Y$^a$ are each O, X$^a$ and X$^{a1}$ are each O, X$^b$ and X$^{b1}$ are each O, and X$^c$ and X$^{c1}$ are each OH or SH, X$^d$ and X$^{d1}$ are each O, R$^1$ and R$^{1a}$ are each H, R$^2$ is H, R$^6$ and R$^{6a}$ are each H, R$^7$ and R$^{7a}$ are each H, R$^8$ and R$^{8a}$ are each H, and Base$^1$ and Base$^2$ are each selected from the group consisting of

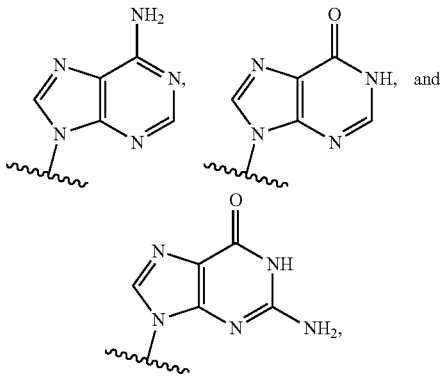

R$^5$ and R$^{3a}$ are not both selected from the group consisting of H, F and OH. That is, when Y and Y$^a$ are each O, X$^a$ and X$^{a1}$ are each O, X$^b$ and X$^{b1}$ are each O, and X$^c$ and X$^{c1}$ are each OH or SH, X$^d$ and X$^{d1}$ are each O, R$^1$ and R$^{1a}$ are each H, R$^2$ is H, R$^6$ and R$^{6a}$ are each H, R$^7$ and R$^{7a}$ are each H, R$^8$ and R$^{8a}$ are each H, and Base$^1$ and Base$^2$ are each selected from the group consisting of

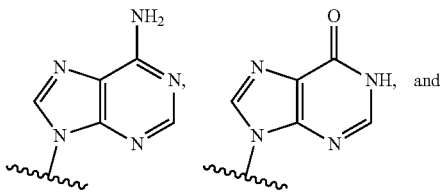

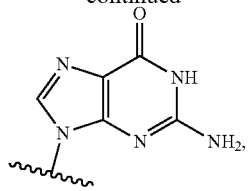

either only one of R$^5$ and R$^{3a}$ is selected from the group consisting of H, F, and OH, or neither R$^5$ and R$^{3a}$ is selected from the group consisting of H, F, and OH. In further instances of these aspects, when Y and Y$^a$ are each O, X$^a$ and X$^{a1}$ are each O, X$^b$ and X$^{b1}$ are each O, and X$^c$ and X$^{c1}$ are each OH, X$^d$ and X$^{d1}$ are each O or S, R$^1$ and R$^{1a}$ are each H, R$^2$ is H, R$^6$ and R$^{6a}$ are each H, R$^7$ and R$^{7a}$ are each H, R$^8$ and R$^{8a}$ are each H, and Base$^1$ and Base$^2$ are each selected from the group consisting of

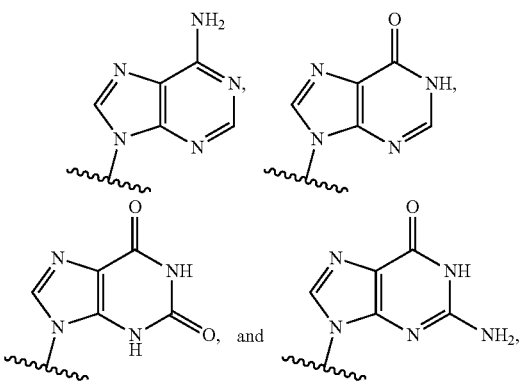

R$^5$ and R$^{3a}$ are not both selected from the group consisting of H, C$_1$-C$_6$ alkyl, C$_2$-C$_6$ alkenyl, C$_2$-C$_6$ alkynyl, where said C$_1$-C$_6$ alkyl, C$_2$-C$_6$ alkenyl and C$_2$-C$_6$ alkynyl are substituted by 0 to 3 substituents selected from the group consisting of F, Cl, Br, I and OH.

In further specific aspects of this embodiment, when Base$^1$ and Base$^2$ are each selected from the group consisting of

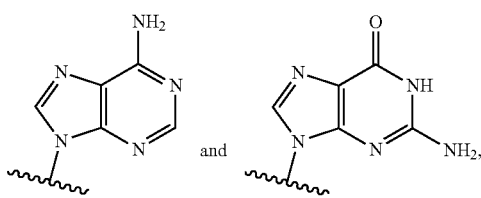 [SMILES: *n1cnc2c(N)ncnc21 ; *n1cnc2c(=O)[nH]c(N)nc21]

and R$^{2a}$ is F and R$^5$ is F, at least one of X$^c$ and X$^{c1}$ is SR$^9$.

In a first aspect of the first embodiment, Base$^1$ and Base$^2$ are each independently selected from the group consisting of

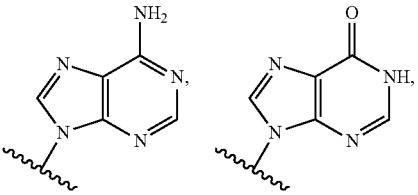

-continued

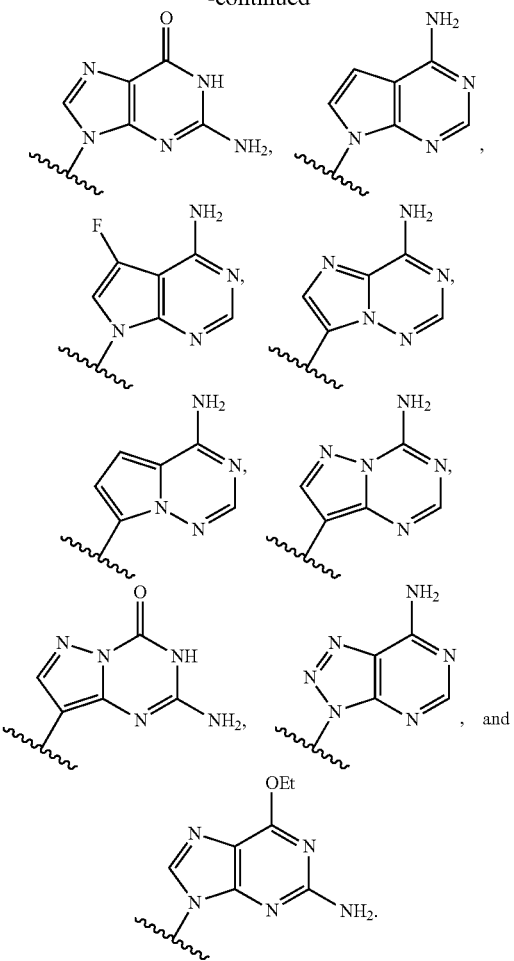

In particular instances, Base¹ and Base² are each independently selected from the group consisting of

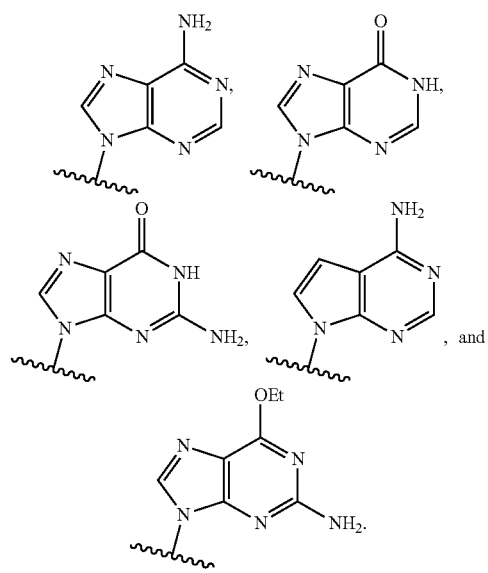

In even more particular instances, Base¹ and Base² are each independently selected from the group consisting of

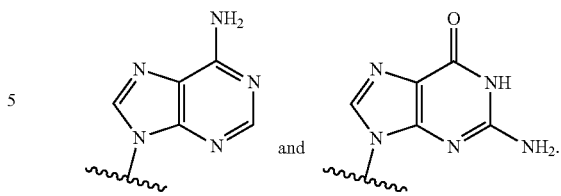

In this aspect, all other groups are as provided in the general formula (II) of the first embodiment above.

In specific aspects of this embodiment, when Y and $Y^a$ are each O and Base¹ and Base² are each selected from the group consisting of


$R^5$ and $R^{3a}$ are not both selected from the group consisting of OH, —O—$C_1$-$C_6$ alkyl, —O—$C_2$-$C_6$ alkenyl, and —O—$C_2$-$C_6$ alkynyl, and where said $R^5$—O—$C_1$-$C_6$ alkyl, —O—$C_2$-$C_6$ alkenyl, and —O—$C_2$-$C_6$ alkynyl and said $R^{3a}$—O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$.

In a second aspect of the first embodiment, Y and $Y^a$ are each independently selected from the group consisting of —O—, —S—, —$SO_2$—, —$CH_2$—, and —$CF_2$—. In this aspect, all other groups are as provided in the general formula (II) of the first embodiment above or in the first aspect described above.

In a third aspect of the first embodiment, $X^a$ and $X^{a1}$ are each independently selected from the group consisting of O and S. In this aspect, all other groups are as provided in the general formula (II) of the first embodiment above or in the first through second aspects described above.

In a fourth aspect of the first embodiment, $X^b$ and $X^{b1}$ are each independently selected from the group consisting of O and S. In this aspect, all other groups are as provided in the general formula (II) of the first embodiment above or in the first through third aspects described above.

In a fifth aspect of the first embodiment, $X^c$ and $X^{c1}$ are each independently selected from the group consisting of $O^-$, $S^-$, $OR^9$, and $NR^9R^9$, where each $R^9$ is independently selected from the group consisting of H, $C_1$-$C_{20}$ alkyl,

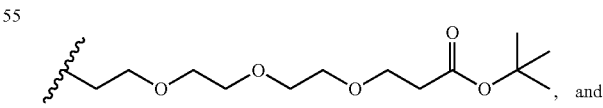

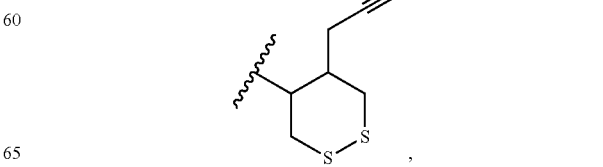

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl. In particular instances, $X^c$ and $X^{c0}$ are each independently selected from the group consisting of $O^-$, $S^-$, said $R^2$ and $R^{2a}$$C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^2$ and $R^{2a}$ are each independently selected from the group consisting of H, F, Cl, Br, I, OH, CN, $N_3$, $CF_3$, $CH_3$, $CH_2OH$, and $CH_2CH_3$. In this aspect, all other groups

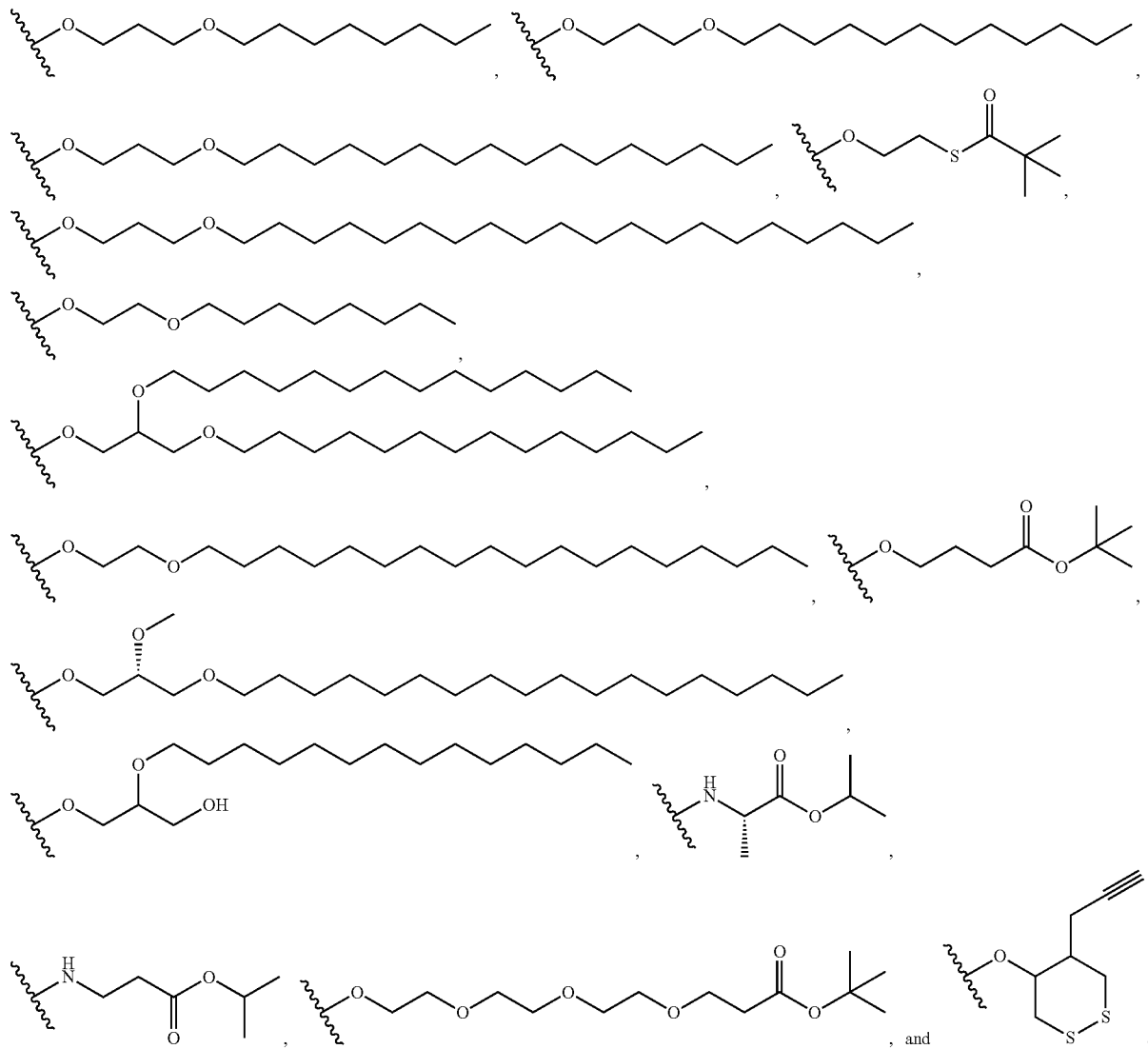

In all instances of this aspect, all other groups are as provided in the general formula (II) of the first embodiment above or in the first through fourth aspects described above.

In a sixth aspect of the first embodiment, $X^d$ and $X^{d1}$ are each independently selected from the group consisting of O and S. In this aspect, all other groups are as provided in the general formula (II) of the first embodiment above or in the first through fifth aspects described above.

In a seventh aspect of the first embodiment, $R^1$ and $R^{1a}$ are each H. In this aspect, all other groups are as provided in the general formula (II) of the first embodiment above or in the first through sixth aspects described above.

In an eighth aspect of the first embodiment, $R^2$ and $R^{2a}$ are each independently selected from the group consisting of H, F, Cl, Br, I, OH, $N_3$, $C_1$-$C_6$ alkyl, and $C_1$-$C_6$ haloalkyl, where are as provided in the general formula (II) of the first embodiment above or in the first through seventh aspects described above.

In a ninth aspect of the first embodiment, $R^{3a}$ is selected from the group consisting H, F, Cl, Br, I, OH, $N_3$, $C_1$-$C_6$ alkyl, and $C_1$-$C_6$ haloalkyl, where said $R^{3a}$$C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^{3a}$ are each independently selected from the group consisting of H, F, Cl, Br, I, OH, CN, $N_3$, $CF_3$, $CH_3$, $CH_2OH$, and $CH_2CH_3$. In this aspect, all other groups are as provided in the general formula (II) of the first embodiment above or in the first through eighth aspects described above.

In a tenth aspect of the first embodiment, $R^4$ and $R^{4a}$ are each independently selected from the group consisting of H, F, Cl, Br, I, OH, $N_3$, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^4$ and $R^{4a}$ are each independently selected from the group consisting of H, F, Cl, Br, I, OH, CN, $N_3$, $CF_3$, $CH_3$, $CH_2OH$, and $CH_2CH_3$. In this aspect, all other groups are as provided in the general formula (II) of the first embodiment above or in the first through ninth aspects described above.

In an eleventh aspect of the first embodiment, $R^5$ is selected from the group consisting of H, F, Cl, Br, I, OH, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^5$ are each independently selected from the group consisting of H, F, Cl, Br, I, OH, CN, $N_3$, $CF_3$, $CH_3$, $CH_2OH$, and $CH_2CH_3$. In this aspect, all other groups are as provided in the general formula (II) of the first embodiment above or in the first through tenth aspects described above.

In a twelfth aspect of the first embodiment, $R^6$ and $R^{6a}$ are each independently selected from the group consisting of H, F, Cl, Br, I, OH, $C_1$-$C_6$ alkyl, $C_2$-$C_6$ alkenyl, and $C_2$-$C_6$ alkynyl.

In this aspect, all other groups are as provided in the general formula (II) of the first embodiment above or in the first through eleventh aspects described above.

In a thirteenth aspect of the first embodiment, $R^7$ and $R^{7a}$ are each H. In this aspect, all other groups are as provided in the general formula (II) of the first embodiment above or in the first through twelfth aspects described above.

In a fourteenth aspect of the first embodiment, $R^8$ and $R^{8a}$ are each H. In this aspect, all other groups are as provided in the general formula (II) of the first embodiment above or in the first through thirteenth aspects described above.

In a fifteenth aspect of the first embodiment, $R^{1a}$ and $R^{3a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^{3a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II) of the first embodiment above or in the first through fourteenth aspects described above.

In a sixteenth aspect of the first embodiment, $R^{2a}$ and $R^{3a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^{3a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II) of the first embodiment above or in the first through fifteenth aspects described above.

In a seventeenth aspect of the first embodiment, $R^{3a}$ and $R^{6a}$ are connected to form —O—$C_1$-$C_6$ alkylene, —O—$C_2$-$C_6$ alkenylene, and —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II) of the first embodiment above or in the first through sixteenth aspects described above.

In an eighteenth aspect of the first embodiment, $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (II) of the first embodiment above or in the first through seventeenth aspects described above.

In a nineteenth aspect of the first embodiment, $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (II) of the first embodiment above or in the first through eighteenth aspects described above.

In a twentieth aspect of the first embodiment, $R^7$ and $R^8$ are connected to form $C_1$-$C_6$ alkylene, $C_2$-$C_6$ alkenylene, or $C_2$-$C_6$ alkynylene. In this aspect, all other groups are as provided in the general formula (II) of the first embodiment above or in the first through nineteenth aspects described above.

In a twenty-first aspect of the first embodiment, $R^{7a}$ and $R^{8a}$ are connected to form $C_1$-$C_6$ alkylene, $C_2$-$C_6$ alkenylene, or $C_2$-$C_6$ alkynylene. In this aspect, all other groups are as provided in the general formula (II) of the first embodiment above or in the first through twentieth aspects described above.

In a twenty-second aspect of the first embodiment, the compound of formula (II) is a compound of formula (IIa):

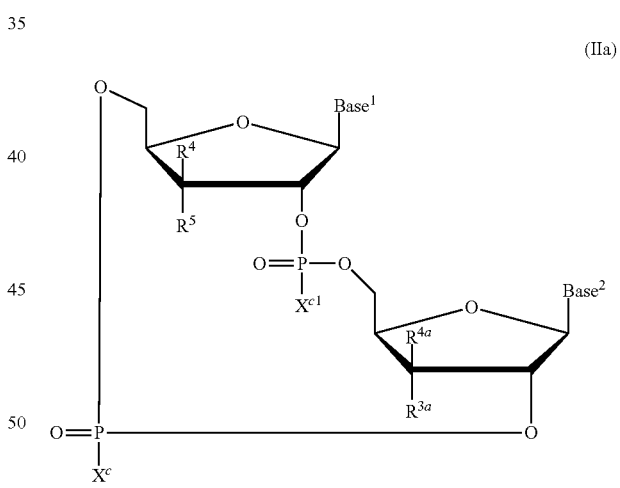

(IIa)

or a pharmaceutically acceptable salt, hydrate, solvate, or prodrug thereof, wherein $Base^1$ and $Base^2$ are each independently selected from the group consisting of

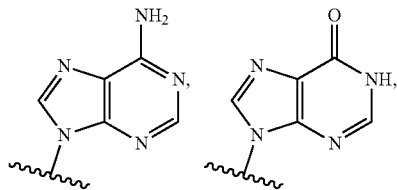

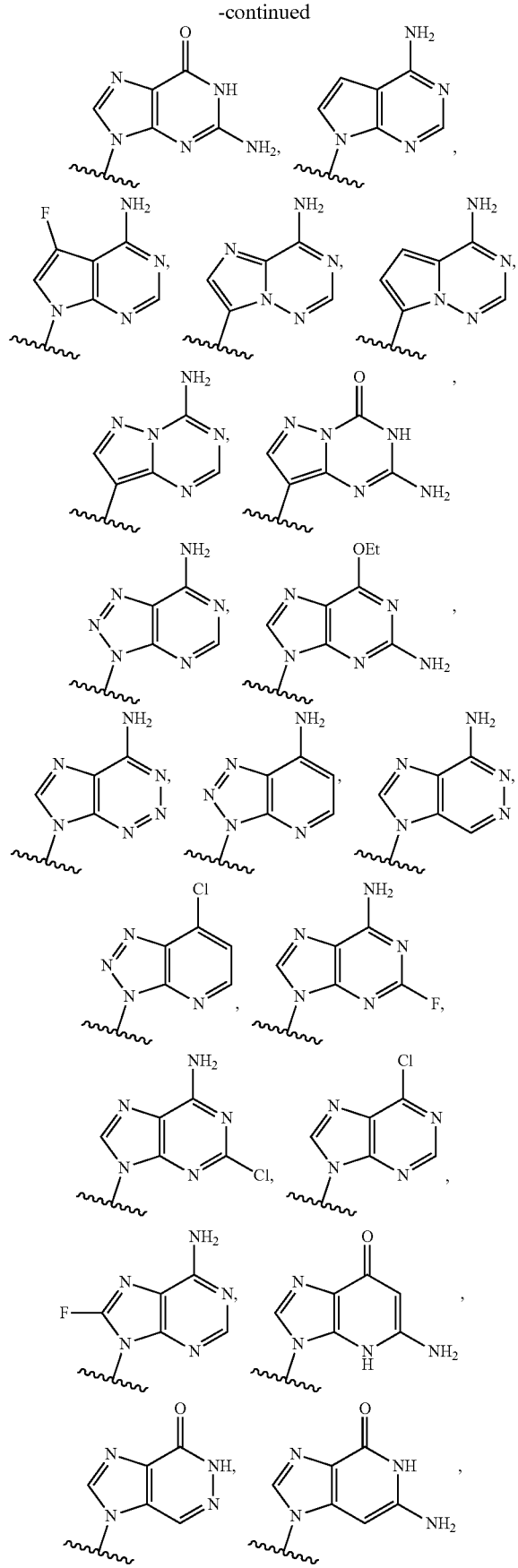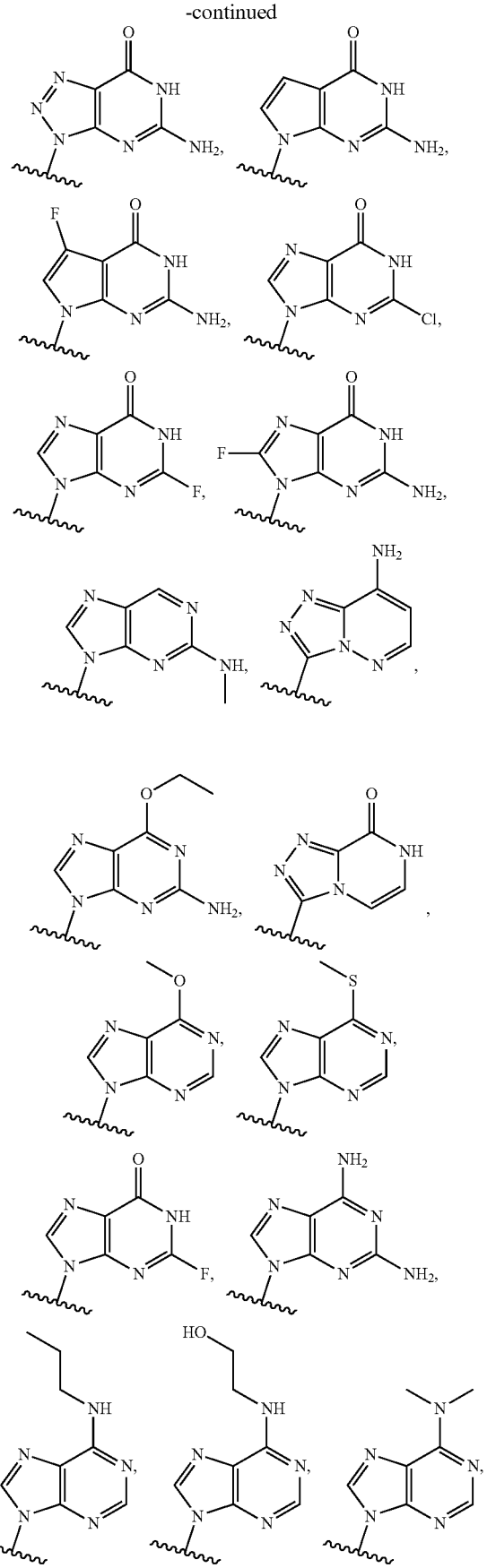

-continued

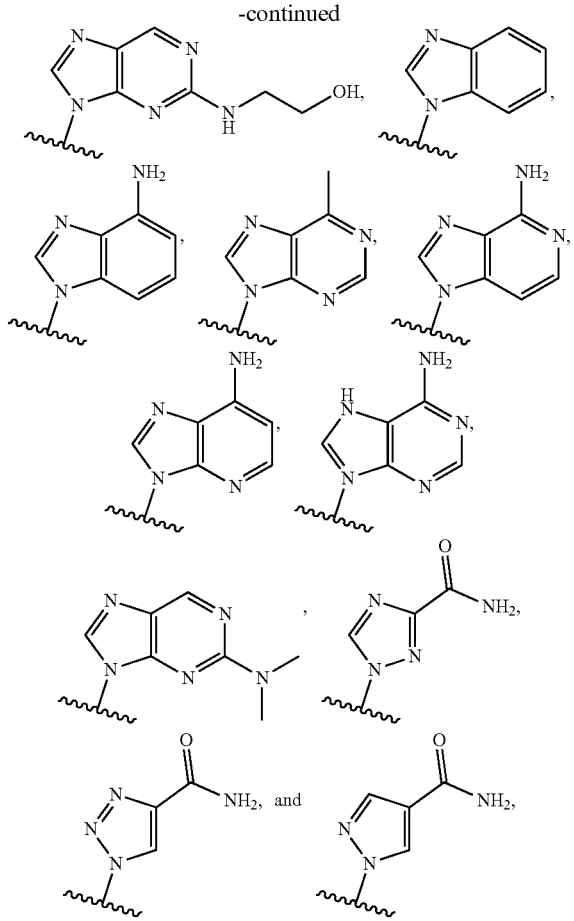

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $NH(C_{3-6}$ cycloalkyl)$_2$; $X^c$ and $X^{c1}$ are each independently selected from the group consisting of $O^-$, $S^-$, $OR^9$, and $NR^9R^9$; $R^{3a}$ is selected from the group consisting of H, F, Cl, Br, I, OH, CN, $N_3$, $C_1$-$C_6$ alkyl, and $C_1$-$C_6$ haloalkyl, where said $R^{3a}$$C_1$-$C_6$ alkyl or $C_1$-$C_6$ haloalkyl are substituted by 0 to 3 substituents selected from the group consisting of F, Cl, Br, I, and OH; $R^4$ and $R^{4a}$ are selected from the group consisting of H, F, Cl, Br, I, OH, CN, $N_3$, $C_1$-$C_6$ alkyl, and $C_1$-$C_6$ haloalkyl, where said $R^4$ $C_1$-$C_6$ alkyl or $C_1$-$C_6$ haloalkyl are substituted by 0 to 3 substituents selected from the group consisting of F, Cl, Br, I, and OH; $R^5$ is selected from the group consisting of H, F, Cl, Br, I, OH, CN, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, and OH; each $R^9$ is independently selected from the group consisting of H, $C_2$-$C_3$ alkyl,

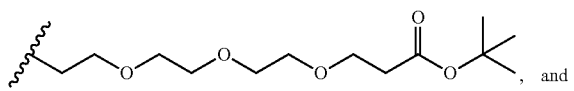, and

-continued

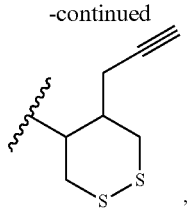

where each $R^9$ $C_2$-$C_3$ alkyl is optionally substituted by 1 to 2 substituents independently selected from the group consisting of OH, —O—$C_1$-$C_{20}$ alkyl, —S—$C(O)C_1$-$C_6$ alkyl, and $C(O)OC_1$-$C_6$ alkyl; optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position; and optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this embodiment, all other groups are as provided in the general formula (II) of the first embodiment above or in the first through twenty-first aspects described above.

A twenty-third aspect of the first embodiment relates to a pharmaceutical composition, said pharmaceutical composition comprising (a) a compound according to any one of general formula (II) of the first embodiment above or in the first through twenty-second aspects described above or a pharmaceutically acceptable salt, hydrate, solvate, or prodrug thereof, and (b) a pharmaceutically acceptable carrier.

A twenty-fourth aspect of the first embodiment relates to methods of inducing an immune response in a subject, comprising administering a therapeutically effective amount of a compound according to any one of general formula (II) of the first embodiment above or in the first through twenty-second aspects described above or a pharmaceutically acceptable salt, hydrate, solvate, or prodrug thereof to the subject.

A twenty-fifth aspect of the first embodiment relates to methods of inducing an immune response in a subject, comprising administering a therapeutically effective amount of a composition according to the twenty-third aspect described above to the subject.

A twenty-sixth aspect of the first embodiment relates to methods of inducing a STING-dependent type I interferon production in a subject, comprising administering a therapeutically effective amount of a compound according to any one of general formula (II) of the first embodiment above or in the first through twenty-second aspects described above or a pharmaceutically acceptable salt, hydrate, solvate, or prodrug thereof to the subject.

A twenty-seventh aspect of the first embodiment relates to methods of inducing a STING-dependent type I interferon production in a subject, comprising administering a therapeutically effective amount of a composition according to the twenty-third aspect described above to the subject.

A twenty-eighth aspect of the first embodiment relates to methods of inducing a STING-dependent cytokine production in a subject, comprising administering a therapeutically effective amount of a compound according to any one of general formula (II) of the first embodiment above or in the first through twenty-second aspects described above or a pharmaceutically acceptable salt, hydrate, solvate, or prodrug thereof to the subject.

A twenty-ninth aspect of the first embodiment relates to methods of inducing a STING-dependent cytokine production in a subject, comprising administering a therapeutically effective amount of a composition according to the twenty-third aspect described above to the subject.

A second embodiment of the disclosure relates to cyclic di-nucleotide compounds of general formula (II'):

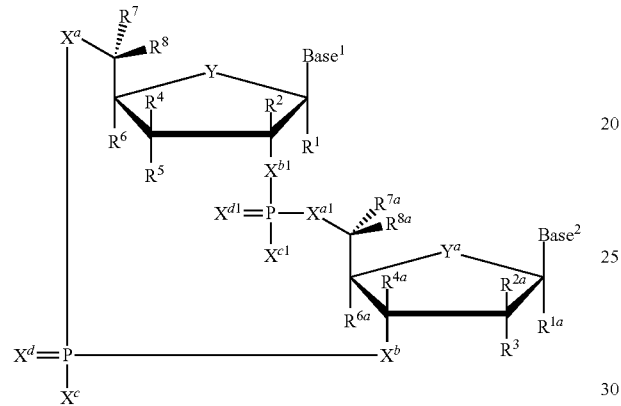

(II')

or a pharmaceutically acceptable salt, hydrate, solvate, or prodrug thereof, wherein Base$^1$ and Base$^2$ are each independently selected from the group consisting of

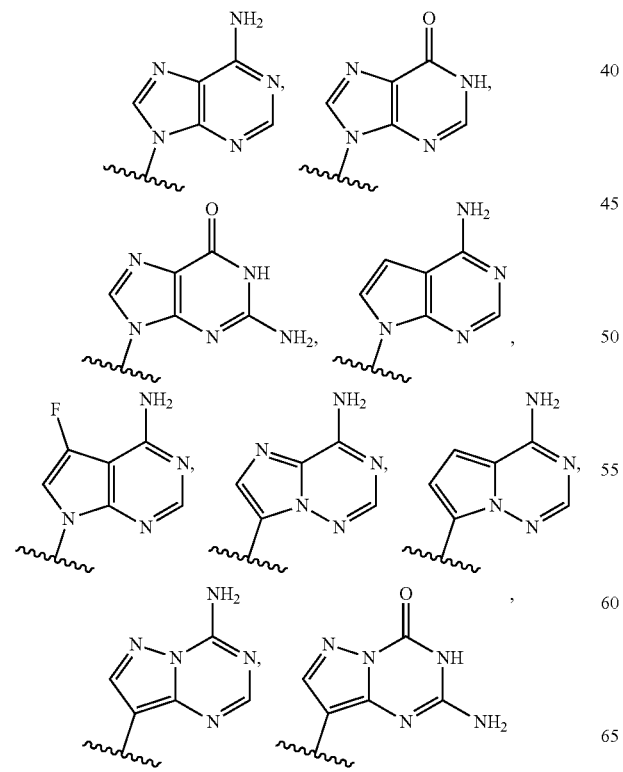

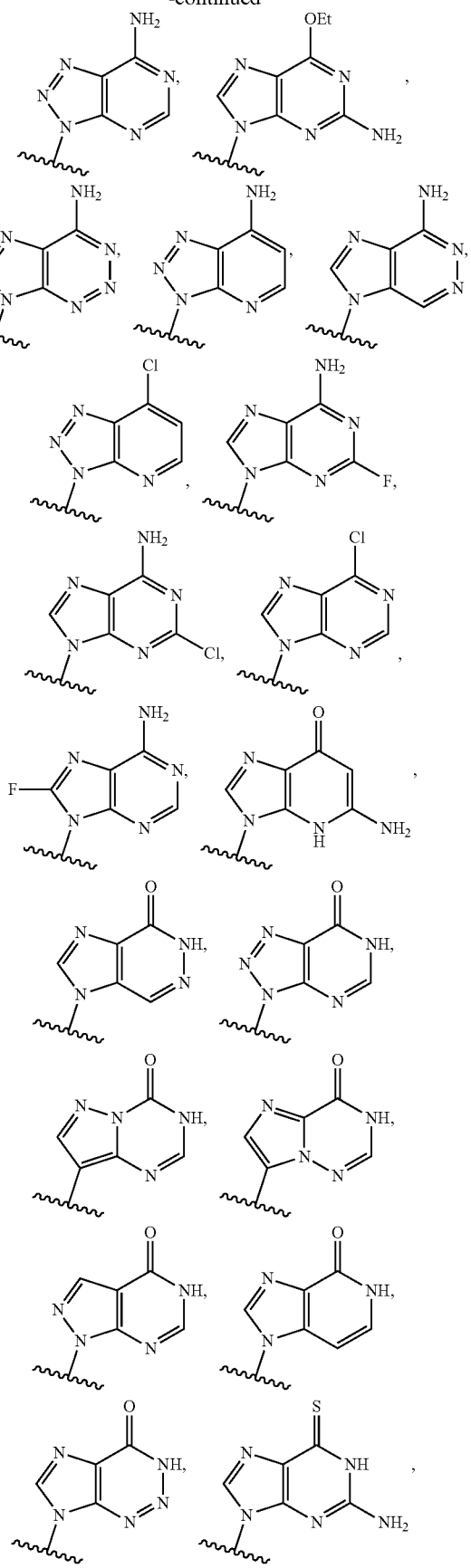

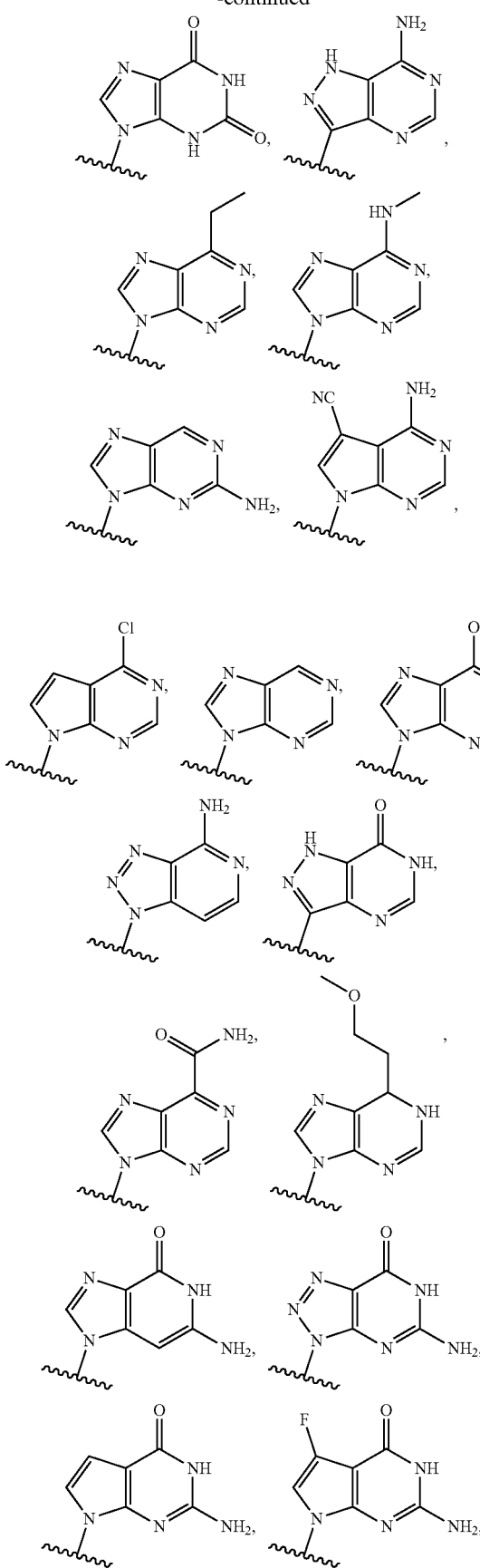
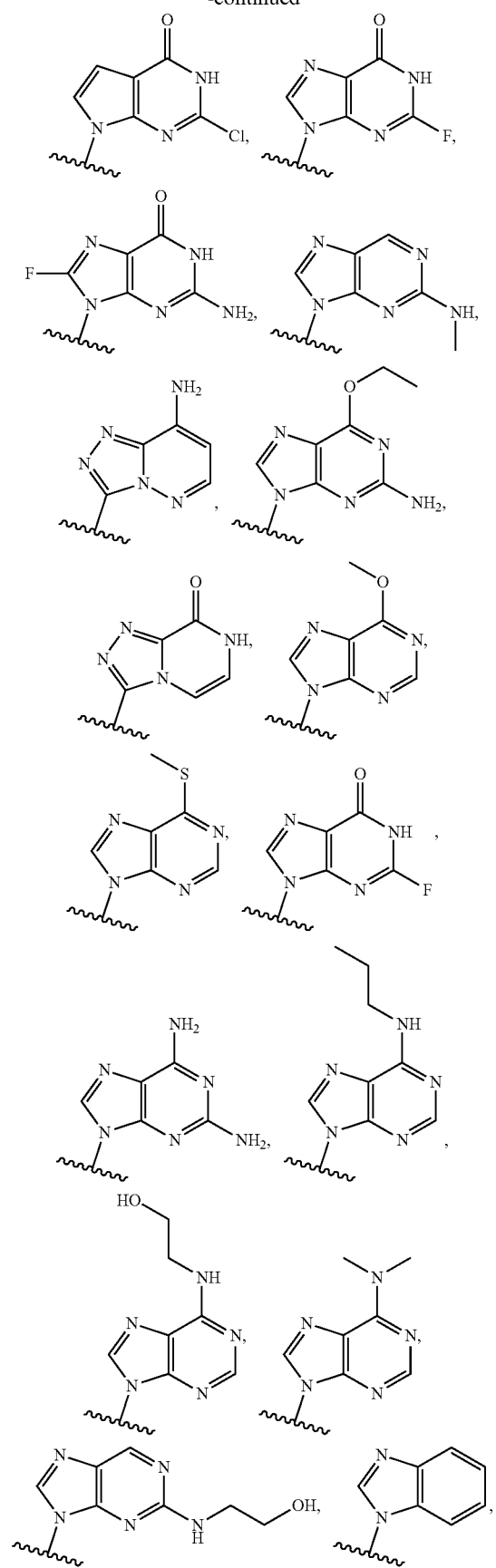

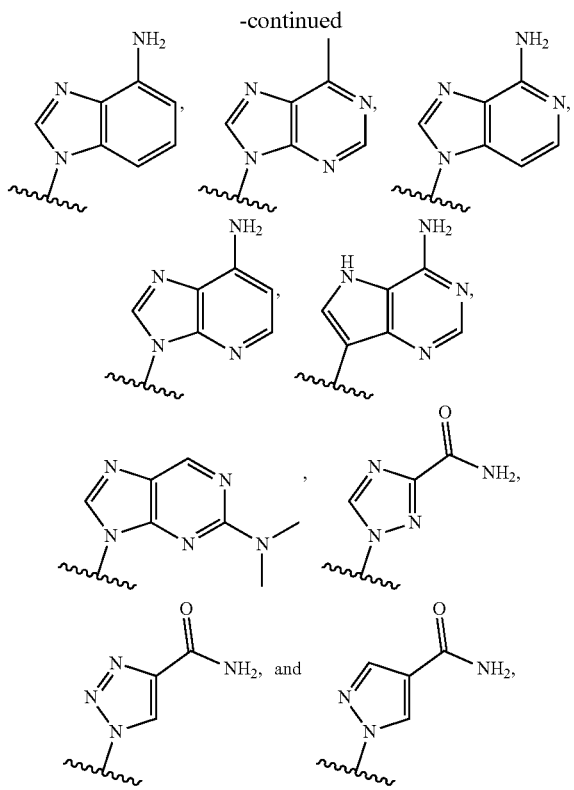

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each independently selected from the group consisting of O, and S; $X^b$ and $X^{b1}$ are each independently selected from the group consisting of O, and S; $X^c$ and $X^{c1}$ are each independently selected from the group consisting of $OR^9$, $SR^9$, and $NR^9R^9$; $X^d$ and $X^{d1}$ are each independently selected from the group consisting of O and S; $R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^{3a}$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{3a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, $NR^9R^9$, and $N_3$; $R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; each $R^9$ is independently selected from the group consisting of H, $C_1$-$C_{20}$ alkyl,

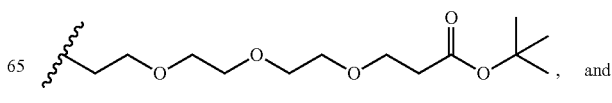, and

-continued

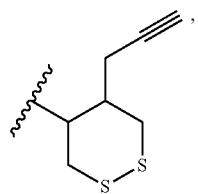

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^{3a}$ and $R^{6a}$ are connected to form —O—$C_1$-$C_6$ alkylene, —O—$C_2$-$C_6$ alkenylene, or —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position; optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position; optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^7$ and $R^8$ are connected to form $C_1$-$C_6$ alkylene, $C_2$-$C_6$ alkenylene, or $C_2$-$C_6$ alkynylene; and optionally $R^{7a}$ and $R^{8a}$ are connected to form $C_1$-$C_6$ alkylene, $C_2$-$C_6$ alkenylene, or $C_2$-$C_6$ alkynylene.

In specific aspects of this embodiment, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

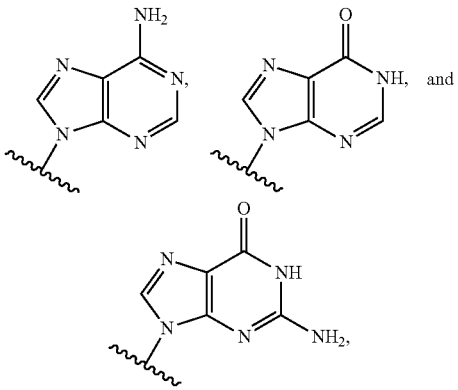

$R^5$ and $R^{3a}$ are not both selected from the group consisting of H, F and OH. That is, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

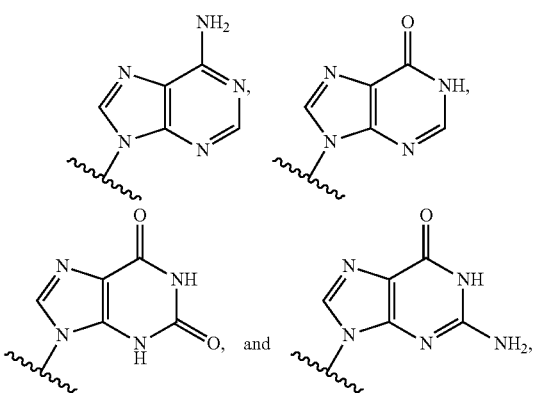

either only one of $R^5$ and $R^{3a}$ is selected from the group consisting of H, F, and OH, or neither $R^5$ and $R^{3a}$ is selected from the group consisting of H, F, and OH. In further instances of these aspects, when Y and $Y^a$ are each O, $X^a$ and $X^{a1}$ are each O, $X^b$ and $X^{b1}$ are each O, and $X^c$ and $X^{c1}$ are each OH, $X^d$ and $X^{d1}$ are each O or S, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

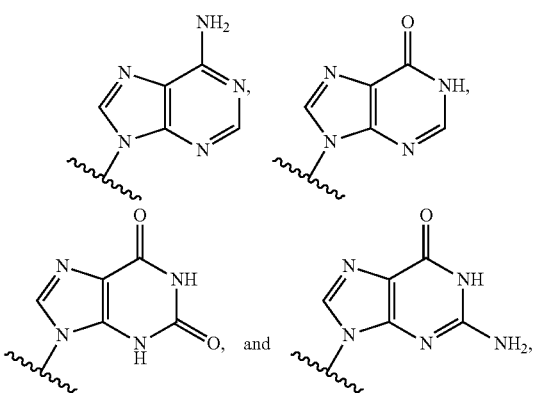

$R^5$ and $R^{3a}$ are not both selected from the group consisting of H, $C_1$-$C_6$ alkyl, $C_2$-$C_6$ alkenyl, $C_2$-$C_6$ alkynyl, where said $C_1$-$C_6$ alkyl, $C_2$-$C_6$ alkenyl and $C_2$-$C_6$ alkynyl are substituted by 0 to 3 substituents selected from the group consisting of F, Cl, Br, I and OH.

In further specific aspects of this embodiment, when Base$^1$ and Base$^2$ are each selected from the group consisting of

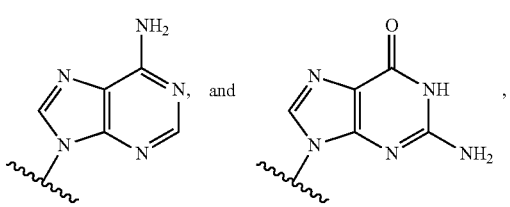 [SMILES: *n1cnc2c(N)ncnc21 ; *n1cnc2c(=O)[nH]c(N)nc21]

and $R^{2a}$ is F and $R^5$ is F, at least one of $X^c$ and $X^{c1}$ is $SR^9$.

In a first aspect of the second embodiment, Base¹ and Base² are each independently selected from the group consisting of

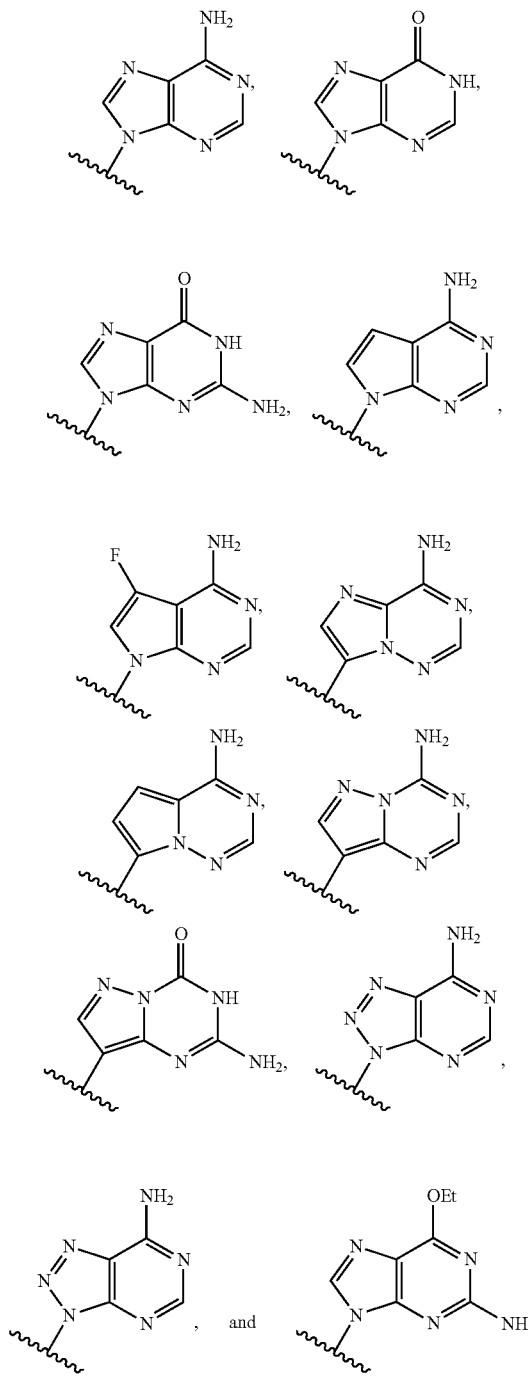

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In particular instances, Base¹ and Base² are each independently selected from the group consisting of

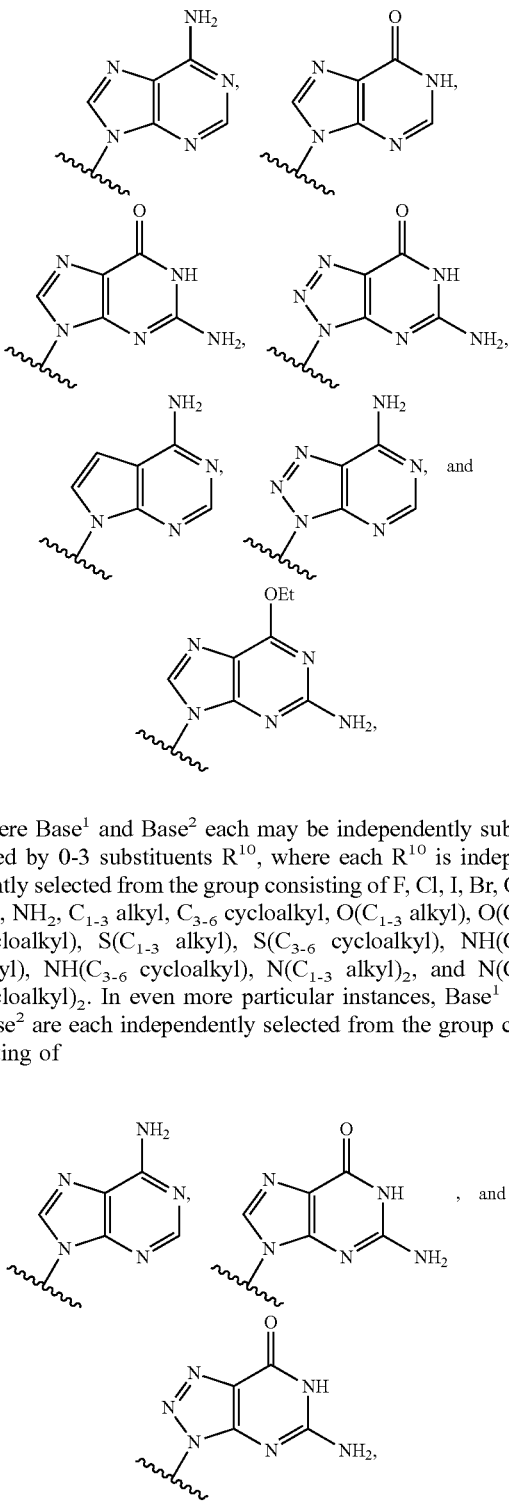

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In even more particular instances, Base¹ and Base² are each independently selected from the group consisting of where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In this aspect, all other groups are as provided in the general formula (II') of the second embodiment above.

In a second aspect of the second embodiment, $X^c$ and $X^{c1}$ are each independently selected from the group consisting of $OR^9$ and $SR^9$, where each $R^9$ is independently selected from the group consisting of H, $C_1$-$C_{20}$ alkyl,

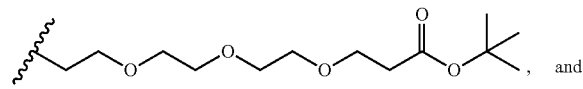, and

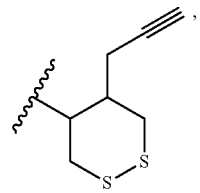, where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl. In particular instances, $X^c$ and $X^{c1}$ are each independently selected from the group consisting of

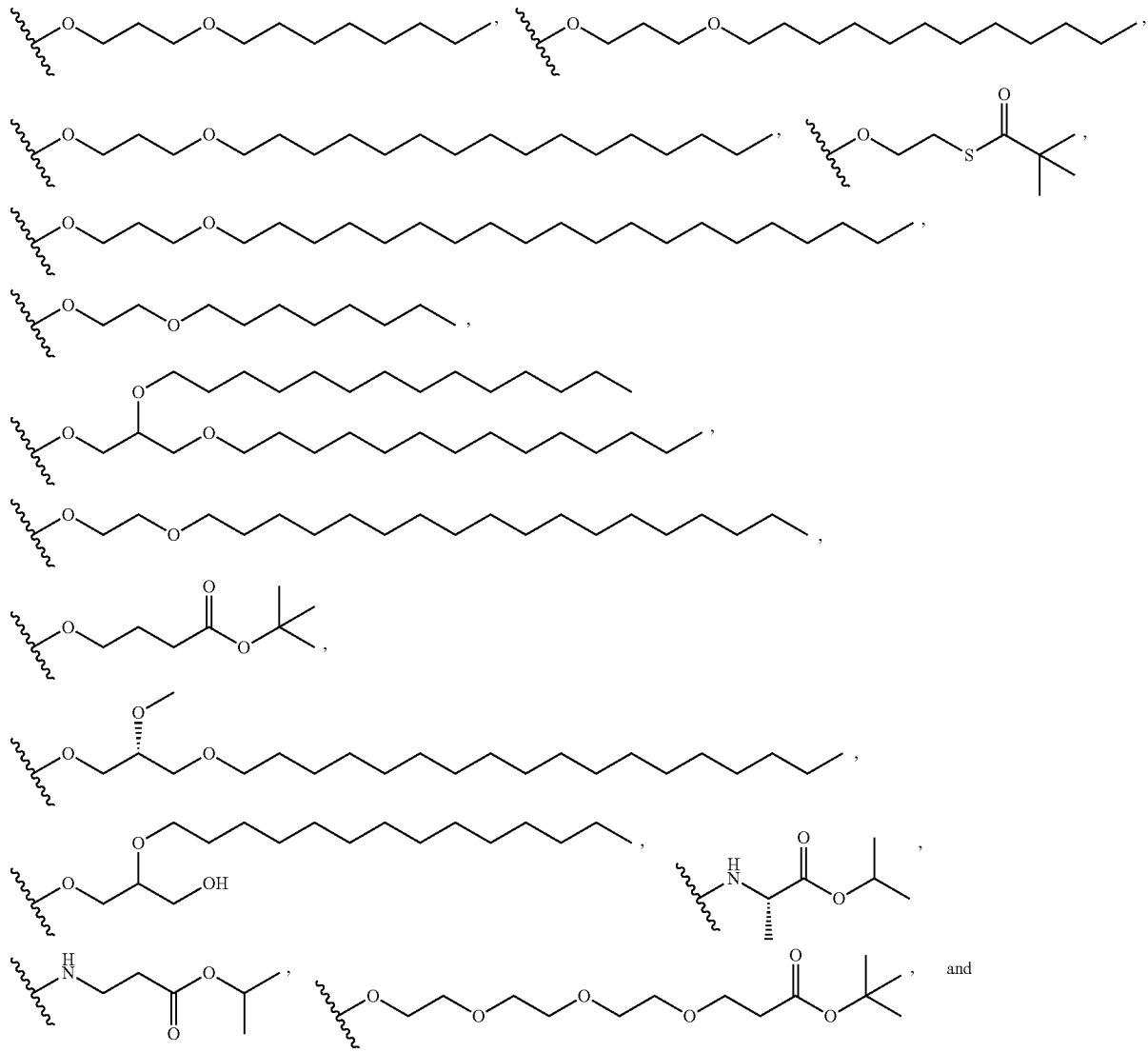

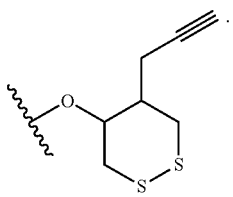

In more particular instances, $X^c$ and $X^{c1}$ are each independently selected from the group consisting of $OR^9$ and $SR^9$. In all instances of this aspect, all other groups are as provided in the general formula (II') of the second embodiment above or in the first aspect described above.

In a third aspect of the second embodiment, $R^1$ and $R^{1a}$ are each H. In this aspect, all other groups are as provided in the general formula (II') of the second embodiment above or in the first through second aspects described above.

In a fourth aspect of the second embodiment, $R^2$ and $R^{2a}$ are each independently selected from the group consisting of H, F, Cl, I, Br, OH, $N_3$, $C_1$-$C_6$ alkyl, and $C_1$-$C_6$ haloalkyl, where said $R^2$ and $R^{2a}C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^2$ and $R^{2a}$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (II') of the second embodiment above or in the first through third aspects described above.

In a fifth aspect of the second embodiment, $R^{3a}$ is selected from the group consisting H, F, Cl, Br, I, OH, CN, $NH_2$, $N_3$, $C_1$-$C_6$ alkyl, and $C_1$-$C_6$ haloalkyl, where said $R^{3a}C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^{3a}$ is selected from the group consisting of H, F, Cl, Br, I, OH, CN, $NH_2$, $N_3$, $CF_3$, $CH_3$, $CH_2OH$, and $CH_2CH_3$. In even more particular instances, $R^{3a}$ is selected from $NH_2$ and $N_3$. In this aspect, all other groups are as provided in the general formula (II') of the second embodiment above or in the first through fourth aspects described above.

In a sixth aspect of the second embodiment, $R^4$ and $R^{4a}$ are each independently selected from the group consisting of H, F, Cl, I, Br, OH, $N_3$, $C_1$-$C_6$ alkyl, and $C_1$-$C_6$ haloalkyl, where said $R^4$ and $R^{4a}C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^4$ and $R^{4a}$ are each independently selected from the group consisting of H, F, Cl, I, Br, OH, CN, $N_3$, $CF_3$, $CH_3$, $CH_2OH$, and $CH_2CH_3$. In even more particular instances, $R^4$ and $R^{4a}$ are each F. In this aspect, all other groups are as provided in the general formula (II') of the second embodiment above or in the first through fifth aspects described above.

In a seventh aspect of the second embodiment, $R^5$ is selected from the group consisting of H, F, Cl, Br, I, OH, $NH_2$, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, $NR^9R^9$, and $N_3$. In particular instances, $R^5$ are each independently selected from the group consisting of H, F, Cl, I, Br, OH, CN, $N_3$, $CF_3$, $CH_3$, $CH_2OH$, and $CH_2CH_3$. In even more particular instances, $R^5$ is selected from $NH_2$ and $N_3$. In this aspect, all other groups are as provided in the general formula (II') of the second embodiment above or in the first through sixth aspects described above.

In an eighth aspect of the second embodiment, $R^6$ and $R^{6a}$ are each independently selected from the group consisting of H, F, Cl, I, Br, OH, $C_1$-$C_6$ alkyl, $C_2$-$C_6$ alkenyl, and $C_2$-$C_6$ alkynyl. In this aspect, all other groups are as provided in the general formula (II') of the second embodiment above or in the first through seventh aspects described above.

In a ninth aspect of the second embodiment, $R^7$ and $R^{7a}$ are each independently selected from the group consisting of H and $C_1$-$C_6$ alkyl. In particular instances, $R^7$ and $R^{7a}$ are each independently selected from the group consisting of H and $CH_3$. In more particular instances, $R^{7a}$ is $CH_3$. In additional instances, $R^7$ and $R^{7a}$ are each H. In this aspect, all other groups are as provided in the general formula (II') of the second embodiment above or in the first through eighth aspects described above.

In a tenth aspect of the second embodiment, $R^8$ and $R^{8a}$ are each independently selected from the group consisting of H and $C_1$-$C_6$ alkyl. In particular instances, $R^8$ and $R^{8a}$ are each independently selected from the group consisting of H and $CH_3$. In more particular instances, $R^{8a}$ is $CH_3$. In additional instances, $R^8$ and $R^{8a}$ are each H. In this aspect, all other groups are as provided in the general formula (II') of the second embodiment above or in the first through ninth aspects described above.

In an eleventh aspect of the second embodiment, $R^{1a}$ and $R^{3a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^{3a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II') of the second embodiment above or in the first through tenth aspects described above.

In a twelfth aspect of the second embodiment, $R^{2a}$ and $R^{3a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^{3a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II') of the second embodiment above or in the first through eleventh aspects described above.

In a thirteenth aspect of the second embodiment, $R^{3a}$ and $R^{6a}$ are connected to form —O—$C_1$-$C_6$ alkylene, —O—$C_2$-$C_6$ alkenylene, and —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position. In this aspect, all other groups are as provided in the general formula (II') of the second embodiment above or in the first through eleventh aspects described above.

In a fourteenth aspect of the second embodiment, $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (II') of the second embodiment above or in the first through eleventh aspects described above.

In a fifteenth aspect of the second embodiment, $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (II') of the second embodiment above or in the first through eleventh aspects described above.

In a sixteenth aspect of the second embodiment, $R^7$ and $R^8$ are connected to form $C_1$-$C_6$ alkylene, $C_2$-$C_6$ alkenylene, or $C_2$-$C_6$ alkynylene. In this aspect, all other groups are as provided in the general formula (II') of the second embodiment above or in the first through eleventh aspects described above.

In a seventeenth aspect of the second embodiment, $R^{7a}$ and $R^{8a}$ are connected to form $C_1$-$C_6$ alkylene, $C_2$-$C_6$ alkenylene, or $C_2$-$C_6$ alkynylene. In this aspect, all other groups are as provided in the general formula (II') of the second embodiment above or in the first through eleventh aspects described above.

In an eighteenth aspect of the second embodiment, Base$^1$ and Base$^2$ are each independently selected from the group consisting of

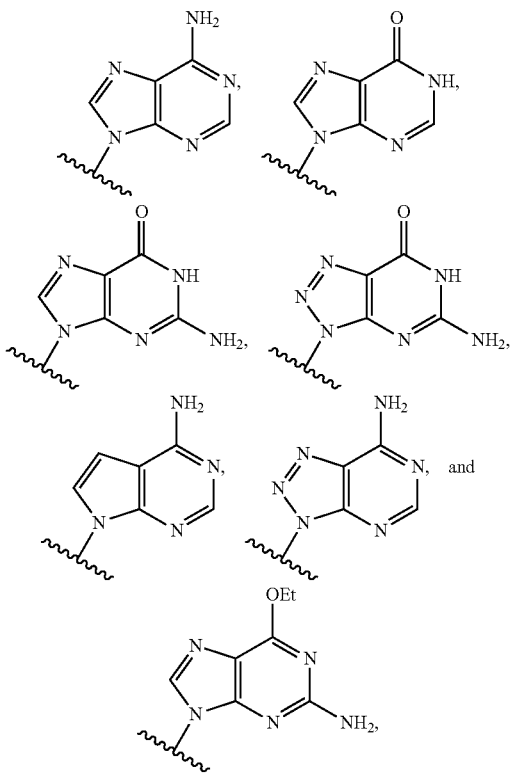

where Base$^1$ and Base$^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each independently selected from the group consisting of O and S; $X^b$ and $X^{b1}$ are each independently selected from the group consisting of O and S; $X^c$ and $X^{c1}$ are each independently selected from the group consisting of $OR^9$, $SR^9$, and $NR^9R^9$; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, Br, I, OH, $N_3$, $C_1$-$C_6$ alkyl, and $C_1$-$C_6$ haloalkyl, where said $R^2$ and $R^{2a}C_1$-$C_6$ alkyl or $C_1$-$C_6$ haloalkyl are substituted by 0 to 3 substituents selected from the group consisting of F, Cl, Br, I, OH, CN, and $N_3$; $R^3$ is selected from the group consisting of H, F, Cl, Br, I, OH, CN, $N_3$, $C_1$-$C_6$ alkyl, and $C_1$-$C_6$ haloalkyl, where said $R^{3a}C_1$-$C_6$ alkyl or $C_1$-$C_6$ haloalkyl are substituted by 0 to 3 substituents selected from the group consisting of F, Cl, Br, I, OH, CN, and $N_3$; $R^4$ and $R^{4a}$ are each independently selected from the group consisting of H, $C_1$-$C_6$ alkyl, and $C_1$-$C_6$ haloalkyl, where said $R^4$ and $R^{4a}C_1$-$C_6$ alkyl or $C_1$-$C_6$ haloalkyl are substituted by 0 to 3 substituents selected from the group consisting of F, Cl, Br, I, OH, CN, and $N_3$; $R^5$ is selected from the group consisting of H, F, Cl, Br, I, OH, $NH_2$, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, $NR^9R^9$, and $N_3$; $R^6$ and $R^{6a}$ are each independently selected from the group consisting of H, F, Cl, Br, I, OH, $C_1$-$C_6$ alkyl, $C_2$-$C_6$ alkenyl, $C_2$-$C_6$ alkynyl, and $C_1$-$C_6$ haloalkyl, where said $R^6$ and $R^{6a}C_1$-$C_6$ alkyl or $C_1$-$C_6$ haloalkyl are substituted by 0 to 3 substituents selected from the group consisting of F, Cl, Br, I, OH, CN, and $N_3$; $R^7$ and $R^{7a}$ are each H; $R^8$ and $R^{8a}$ are each H; each $R^9$ is independently selected from the group consisting of H, $C_2$-$C_3$ alkyl,

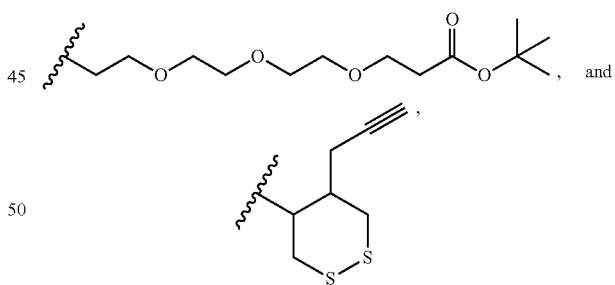

, and where each $R^9$ $C_2$-$C_3$ alkyl is optionally substituted by 1 to 2 substituents independently selected from the group consisting of OH, —O—$C_1$-$C_{20}$ alkyl, —S—$C(O)C_1$-$C_6$ alkyl, and $C(O)OC_1$-$C_6$ alkyl; optionally $R^{3a}$ and $R^{6a}$ are connected to form —O—$C_1$-$C_6$ alkylene, —O—$C_2$-$C_6$ alkenylene, and —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position or optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In specific instances of this aspect in which Y and $Y^a$ are each O and $Base^1$ and $Base^2$ are each selected from the group consisting of

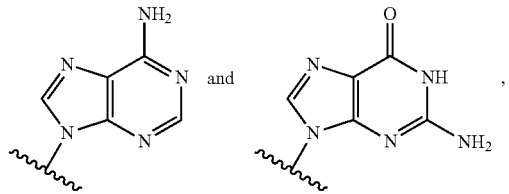 [SMILES: *n1cnc2c(N)ncnc21 ; *n1cnc2c(=O)[nH]c(N)nc21]

$R^5$ and $R^{3a}$ are not both OH. In all instances of this aspect, all other groups are as provided in the general formula (II') of the second embodiment above.

In a nineteenth aspect of the second embodiment, the compound of formula (II') is a compound of formula (II'a):

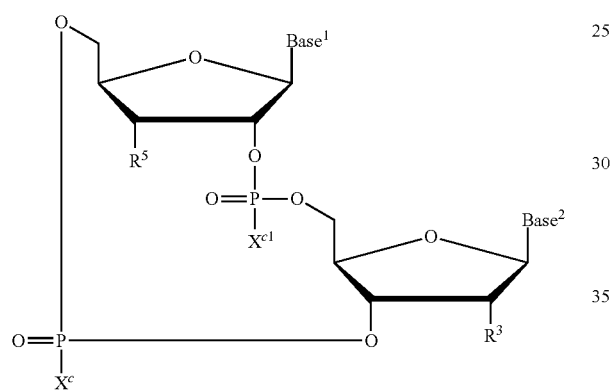

(II'a)

or a pharmaceutically acceptable salt, hydrate, solvate, or prodrug thereof, wherein $Base^1$ and $Base^2$ are each independently selected from the group consisting of

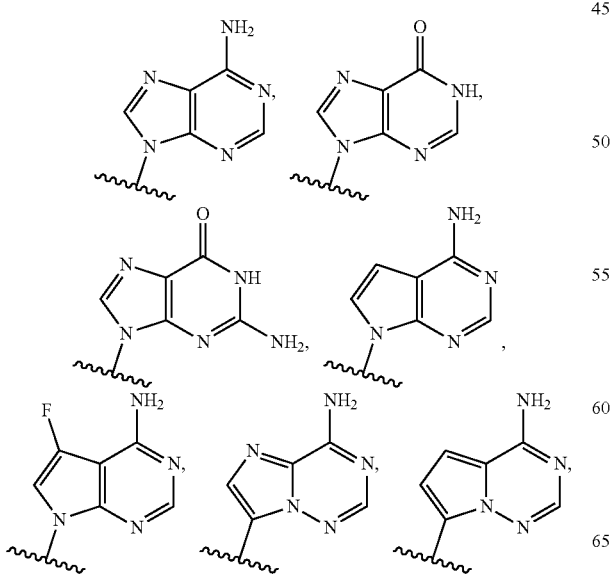

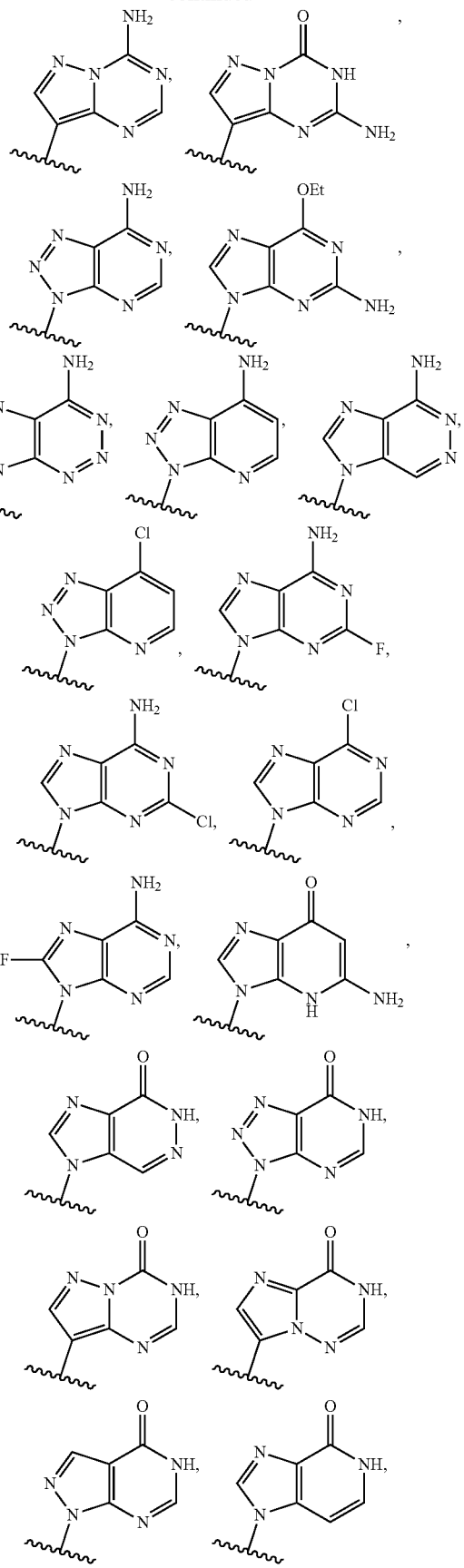

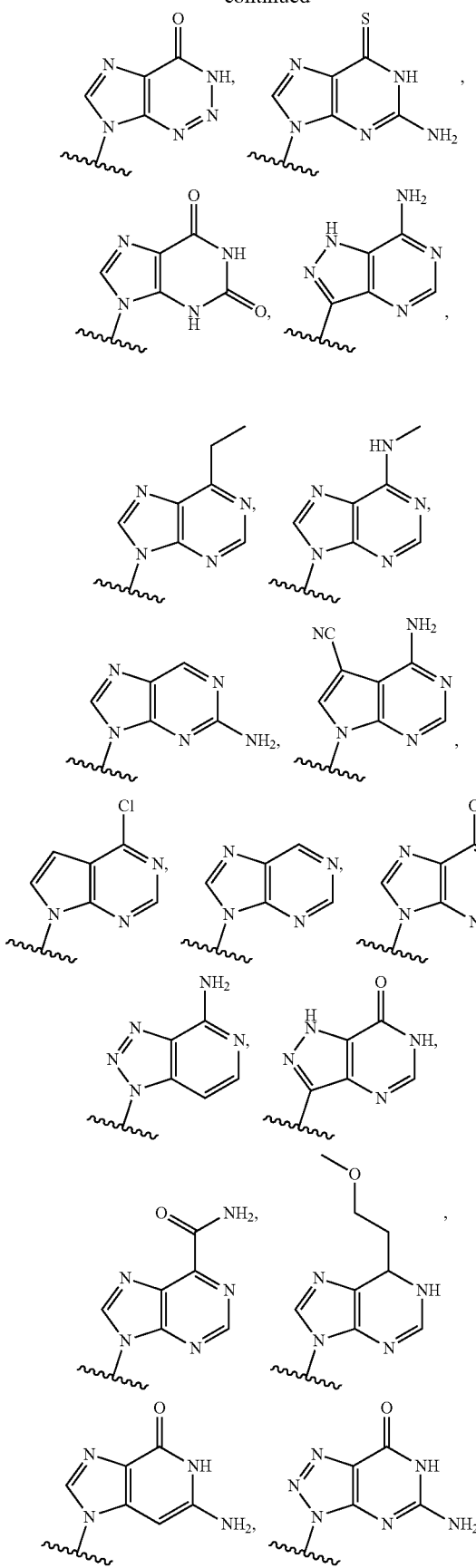

-continued

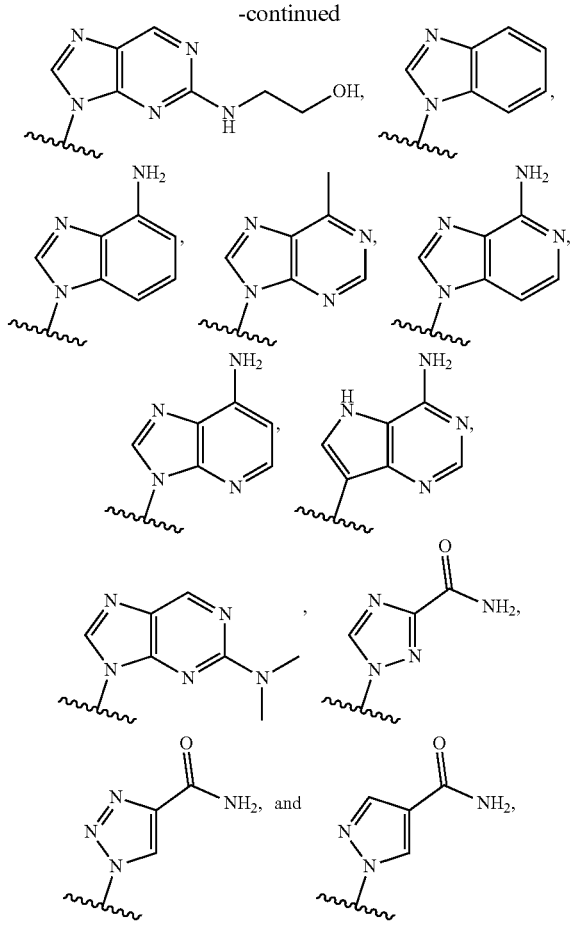

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; $X^c$ and $X^{c1}$ are each independently selected from the group consisting of $OR^9$, $SR^9$, and $NR^9R^9$; $R^{3a}$ is selected from the group consisting of H, F, Cl, Br, I, OH, CN, $NH_2$, $N_3$, $C_1$-$C_6$ alkyl, and $C_1$-$C_6$ haloalkyl, where said $R^{3a}C_1$-$C_6$ alkyl or $C_1$-$C_6$ haloalkyl are substituted by 0 to 3 substituents selected from the group consisting of F, Cl, Br, I, and OH; $R^4$ and $R^{4a}$ are selected from the group consisting of H, F, Cl, Br, I, OH, CN, $N_3$, $C_1$-$C_6$ alkyl, and $C_1$-$C_6$ haloalkyl, where said $R^4$ $C_1$-$C_6$ alkyl or $C_1$-$C_6$ haloalkyl are substituted by 0 to 3 substituents selected from the group consisting of F, Cl, Br, I, and OH; $R^5$ is selected from the group consisting of H, F, Cl, Br, I, OH, CN, $NH_2$, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, and OH; each $R^9$ is independently selected from the group consisting of H, $C_2$-$C_3$ alkyl,

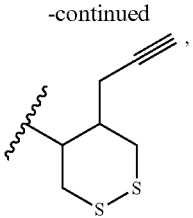

where each $R^9$ $C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^5$ position; and optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In all instances of this aspect, all other groups are as provided in the general formula (II') of the second embodiment above.

A twentieth aspect of the second embodiment relates to a pharmaceutical composition, said pharmaceutical composition comprising (a) a compound according to any one of general formula (II') of the second embodiment above or in the first through nineteenth aspects described above or a pharmaceutically acceptable salt, hydrate, solvate, or prodrug thereof; and (b) a pharmaceutically acceptable carrier.

A twenty-first aspect of the second embodiment relates to methods of inducing an immune response in a subject, comprising administering a therapeutically effective amount of a compound according to any one of general formula (II') of the second embodiment above or in the first through nineteenth aspects described above or a pharmaceutically acceptable salt, hydrate, solvate, or prodrug thereof to the subject.

A twenty-second aspect of the second embodiment relates to methods of inducing an immune response in a subject, comprising administering a therapeutically effective amount of a composition according to the twentieth aspect described above or a pharmaceutically acceptable salt, hydrate, solvate, or prodrug thereof to the subject.

A twenty-third aspect of the second embodiment relates to methods of inducing a STING-dependent type I interferon production in a subject, comprising administering a therapeutically effective amount of a compound according to any one of general formula (II') of the second embodiment above or in the first through nineteenth aspects described above or a pharmaceutically acceptable salt, hydrate, solvate, or prodrug thereof to the subject.

A twenty-fourth aspect of the second embodiment relates to methods of inducing a STING-dependent type I interferon production in a subject, comprising administering a therapeutically effective amount of a composition according to the twentieth aspect described above to the subject.

A twenty-fifth aspect of the second embodiment relates to methods of inducing a STING-dependent cytokine production in a subject, comprising administering a therapeutically effective amount of a compound according to any one of general (II') of the second embodiment above or in the first through nineteenth aspects described above or a pharmaceutically acceptable salt, hydrate, solvate, or prodrug thereof to the subject.

A twenty-sixth aspect of the second embodiment relates to methods of inducing a STING-dependent cytokine production in a subject, comprising administering a therapeutically effective amount of a composition according to the twentieth aspect described above to the subject.

A third embodiment of the disclosure relates to cyclic di-nucleotide compounds of general formula (II"):

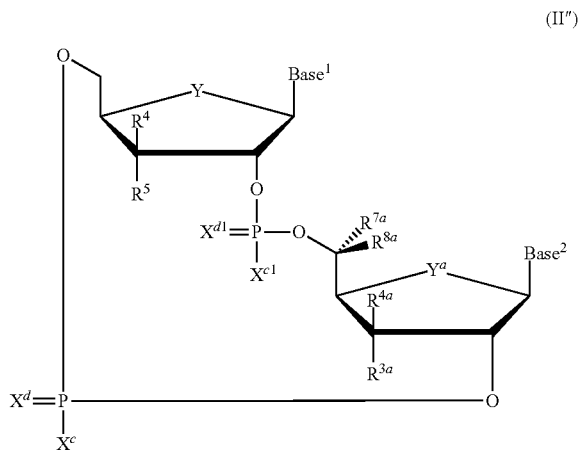

(II")

or a pharmaceutically acceptable salt, hydrate, solvate, or prodrug thereof, wherein Base$^1$ and Base$^2$ are each independently selected from the group consisting of

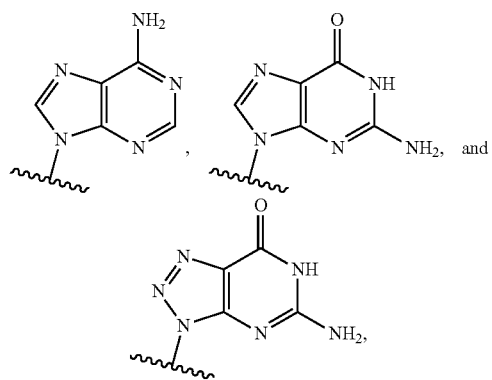

where Base$^1$ and Base$^2$ each may be independently substituted by 0-3 substituents $R^{10}$, where each $R^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; Y and Y$^a$ are each independently selected from the group consisting of —O— and —S—; X$^c$ and X$^{c1}$ are each independently selected from the group consisting of SR$^9$ and OR$^9$; X$^d$ and X$^{d1}$ are each independently selected from the group consisting of O and S; R$^{3a}$ is selected from the group consisting of H, F, OH, CN, NH$_2$, and N$_3$; R$^4$ and R$^{4a}$ are each independently selected from the group consisting of H, F, and OH; R$^5$ is selected from the group consisting of H, F, OH, NH$_2$, and N$_3$; R$^{3a}$ and R$^5$ are not both selected from the group consisting of: OH, C$_1$-C$_6$ alkyl substituted with OH, or C$_1$-C$_6$ haloalkyl substituted with OH; and R$^6$ and R$^{6a}$ are each independently selected from the group consisting of H, F, Cl, Br, I, OH, C$_1$-C$_6$ alkyl, C$_2$-C$_6$ alkenyl, C$_2$-C$_6$ alkynyl, and C$_1$-C$_6$ haloalkyl, where said R$^6$ and R$^{6a}$C$_1$-C$_6$ alkyl or C$_1$-C$_6$ haloalkyl are substituted by 0 to 3 substituents selected from the group consisting of F, Cl, Br, I, OH, CN, and N$_3$; R$^{7a}$ is selected from the group consisting of H and C$_1$-C$_6$ alkyl; R$^{8a}$ is selected from the group consisting of H and C$_1$-C$_6$ alkyl; and each R$^9$ is independently selected from the group consisting of H and C$_1$-C$_3$ alkyl.

In specific aspects of this embodiment, when Y is O, X$^c$ and X$^{c1}$ are each OH or SH, X$^d$ and X$^{d1}$ are each O, R$^{6a}$ is H, and Base$^1$ and Base$^2$ are each selected from the group consisting of

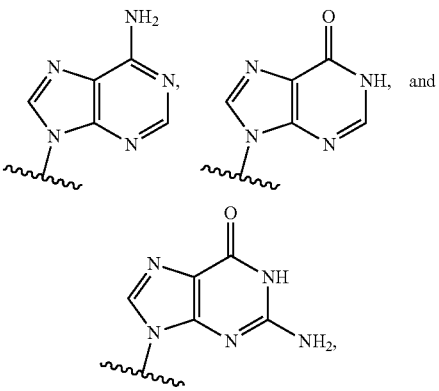

R$^5$ and R$^{3a}$ are not both selected from the group consisting of H, F and OH. That is, when Y is O, X$^c$ and X$^{c1}$ are each OH or SH, X$^d$ and X$^{d1}$ are each O, R$^{6a}$ is H, and Base$^1$ and Base$^2$ are each selected from the group consisting of

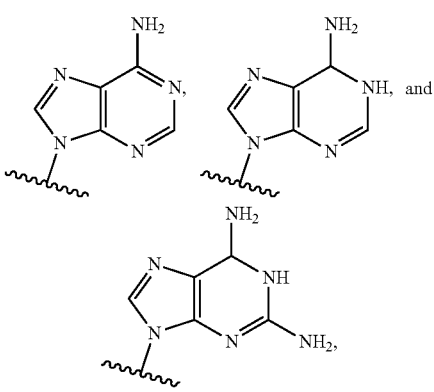

either only one of R$^5$ and R$^{3a}$ is selected from the group consisting of H, F, and OH, or neither R$^5$ and R$^{3a}$ is selected from the group consisting of H, F, and OH. Additionally, in specific instances, when Y and Y$^a$ are each O, X$^a$ and X$^{a1}$ are each O, X$^b$ and X$^{b1}$ are each O, and X$^c$ and X$^{c1}$ are each OH, X$^d$ and X$^{d1}$ are each O or S, R$^1$ and R$^{1a}$ are each H, R$^2$ is H, R$^6$ and R$^{6a}$ are each H, R$^7$ and R$^{7a}$ are each H, R$^8$ and R$^{8a}$ are each H, and Base$^1$ and Base$^2$ are each selected from the group consisting of

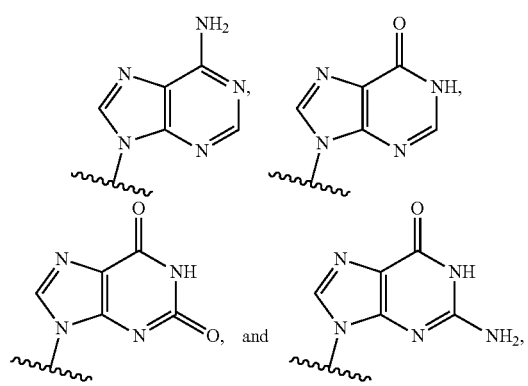

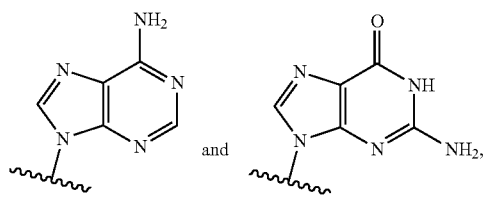 [SMILES: *n1cnc2c(N)ncnc21 ; *n1cnc2c(=O)[nH]c(N)nc21]

$R^5$ and $R^{3a}$ are not both selected from the group consisting of H, $C_1$-$C_6$ alkyl, $C_2$-$C_6$ alkenyl, $C_2$-$C_6$ alkynyl, where said $C_1$-$C_6$ alkyl, $C_2$-$C_6$ alkenyl and $C_2$-$C_6$ alkynyl are substituted by 0 to 3 substituents selected from the group consisting of F, Cl, Br, I and OH.

In further specific aspects of this embodiment, when Base¹ and Base² are each selected from the group consisting of and $R^{2a}$ is F and $R^5$ is F, at least one of $X^c$ and $X^{c1}$ is $SR^9$.

A first aspect of the third embodiment relates to a pharmaceutical composition, said pharmaceutical composition comprising (a) a compound according to any one of general formula (II") of the third embodiment or a pharmaceutically acceptable salt, hydrate, solvate, or prodrug thereof, and (b) a pharmaceutically acceptable carrier.

A second aspect of the third embodiment relates to methods of inducing an immune response in a subject, comprising administering a therapeutically effective amount of a compound according to general formula (II") of the third embodiment above or a pharmaceutically acceptable salt, hydrate, solvate, or prodrug thereof to the subject.

A third aspect of the third embodiment relates to methods of inducing an immune response in a subject, comprising administering a therapeutically effective amount of a composition according to the first aspect described above to the subject.

A fourth aspect of the third embodiment relates to methods of inducing a STING-dependent type I interferon production in a subject, comprising administering a therapeutically effective amount of a compound according general formula (II") of the third embodiment above or a pharmaceutically acceptable salt, hydrate, solvate, or prodrug thereof to the subject.

A fifth aspect of the third embodiment relates to methods of inducing a STING-dependent type I interferon production in a subject, comprising administering a therapeutically effective amount of a composition according to the second aspect described above to the subject.

A sixth aspect of the third embodiment relates to methods of inducing a STING-dependent cytokine production in a subject, comprising administering a therapeutically effective amount of a compound according to general formula (II") of the third embodiment above or a pharmaceutically acceptable salt, hydrate, solvate, or prodrug thereof to the subject.

A seventh aspect of the third embodiment relates to methods of inducing a STING-dependent cytokine production in a subject, comprising administering a therapeutically effective amount of a composition according to the second aspect described above to the subject.

In an additional embodiment, the compound is selected from the group consisting of

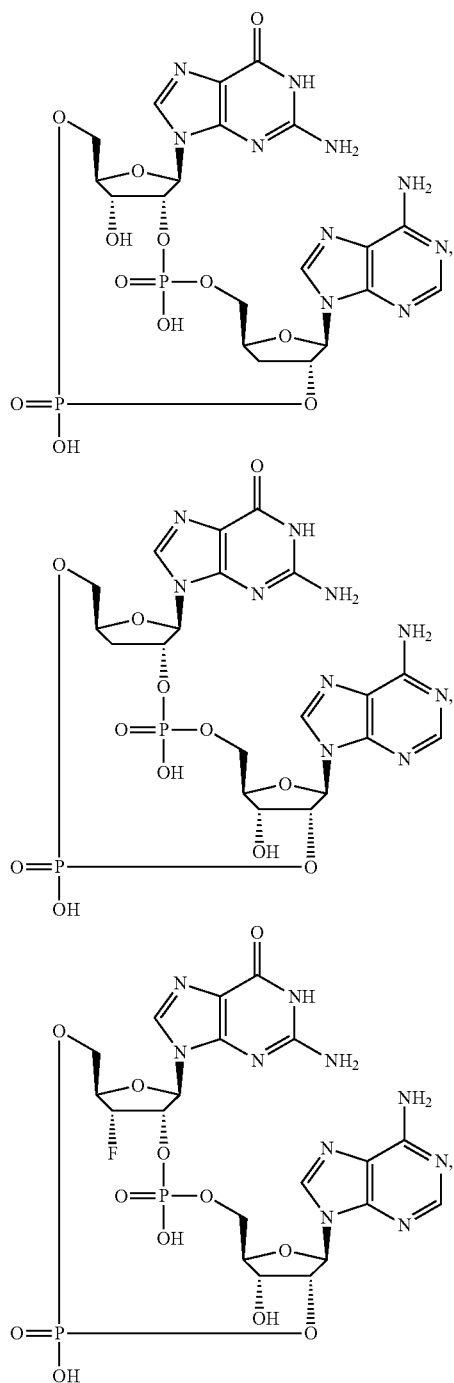

-continued
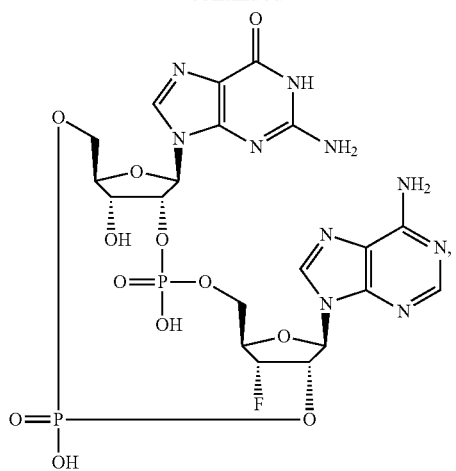
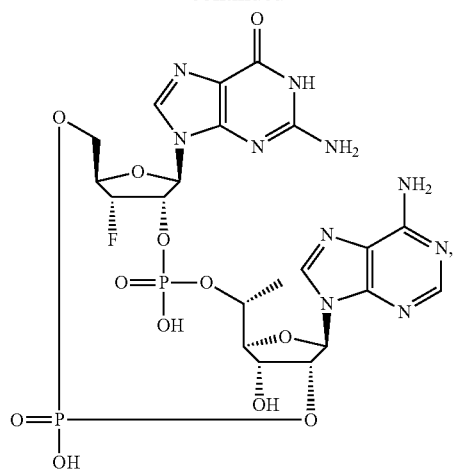
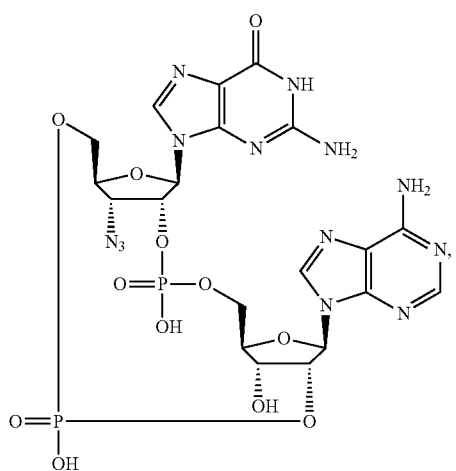 [SMILES: Nc1nc2c(ncn2[C@@H]2O[C@@H]3COP(O)(=S)O[C@@H]4[C@H](N)[C@@H](COP(=O)(O)O[C@@H]2[C@@H]3F)O[C@H]4n2cnc3c(N)ncnc32)c(=O)[nH]1]
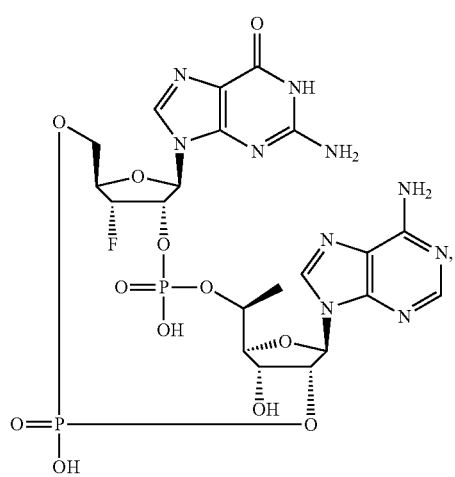
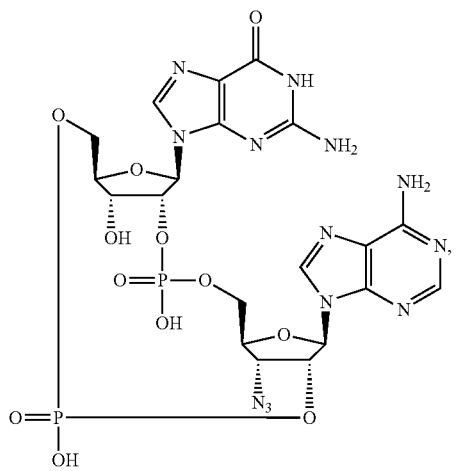
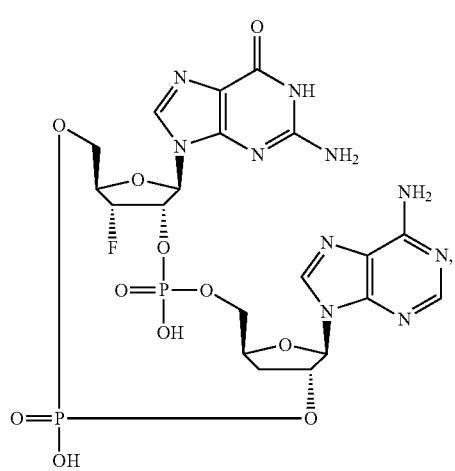

49
-continued
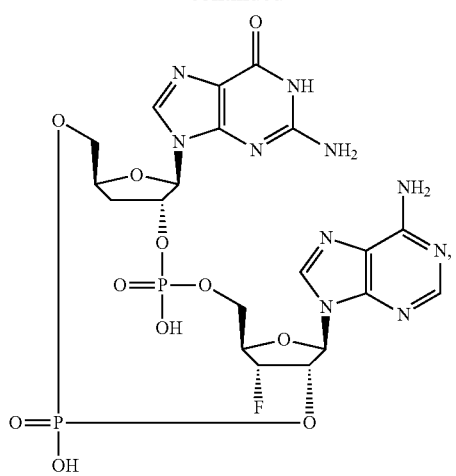
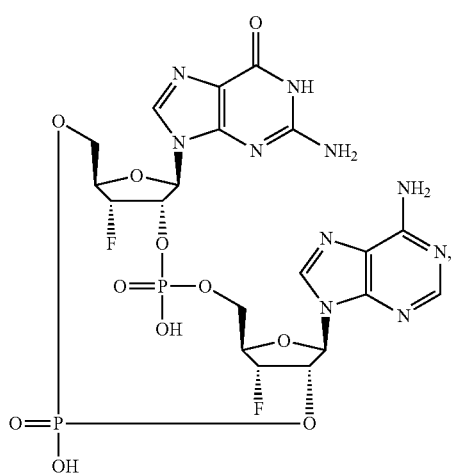
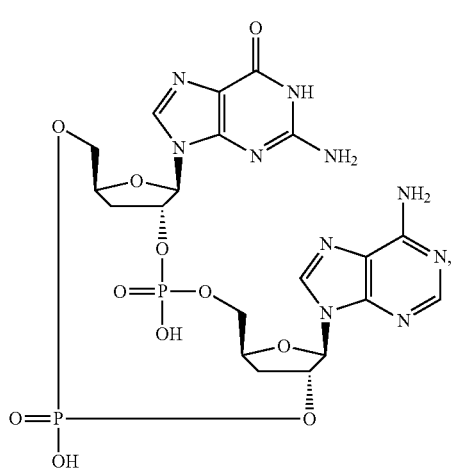
50
-continued
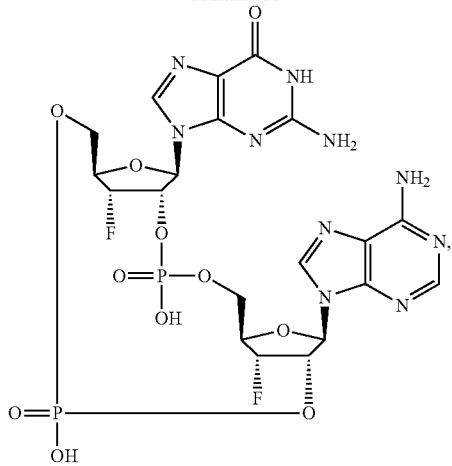
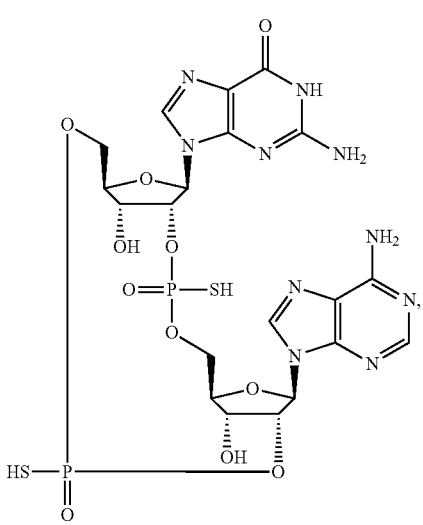
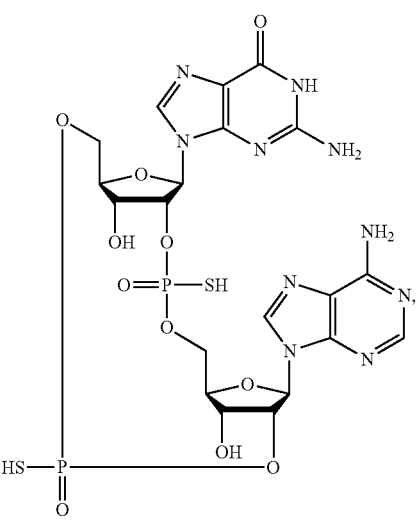

51
-continued
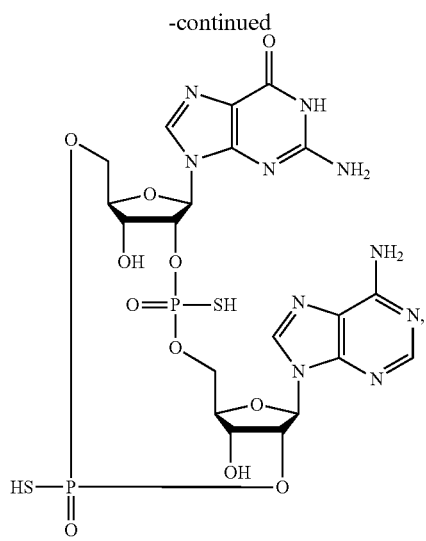
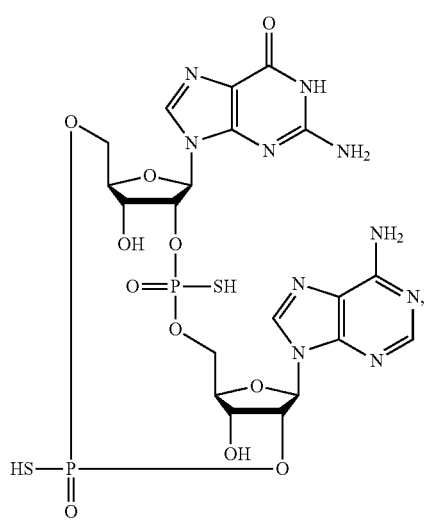
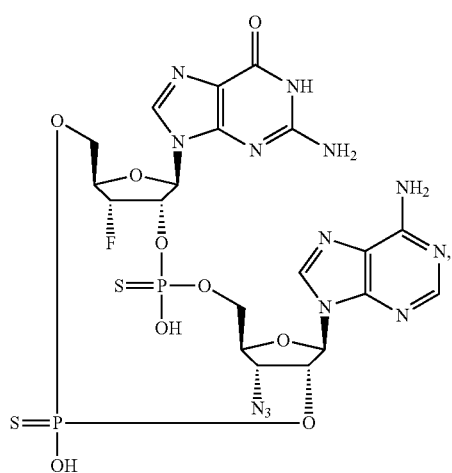
52
-continued
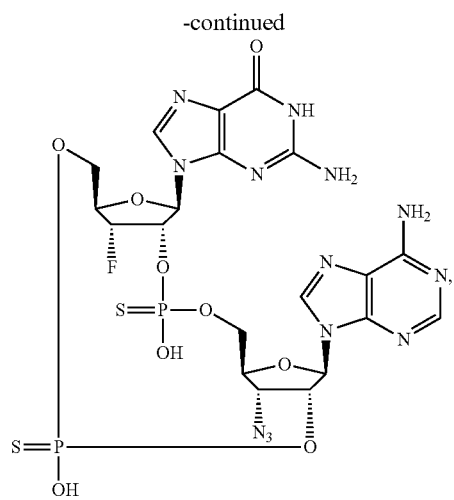
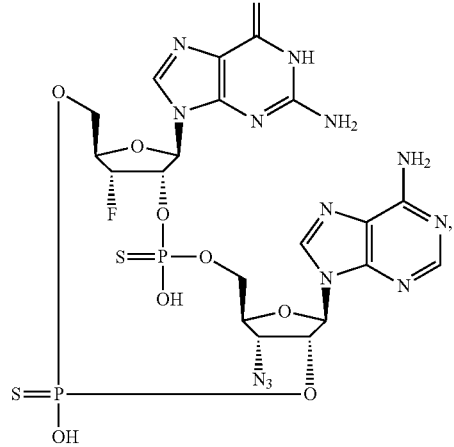
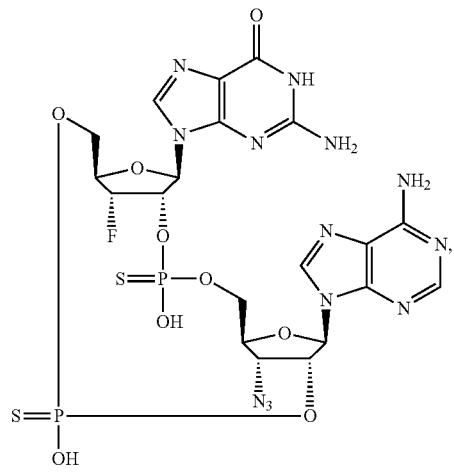

53
-continued
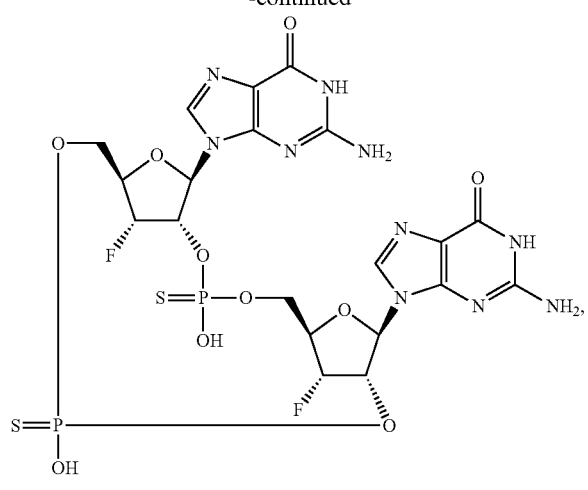
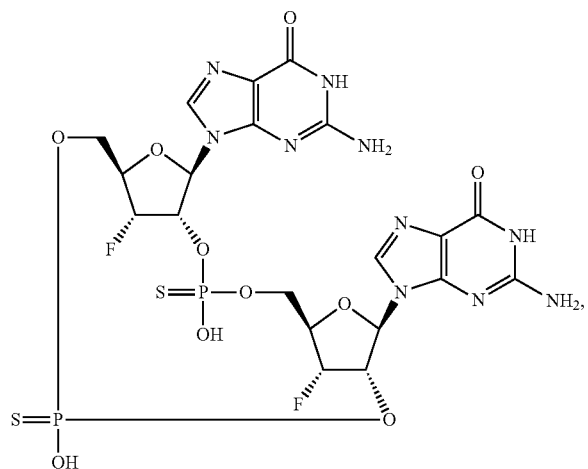
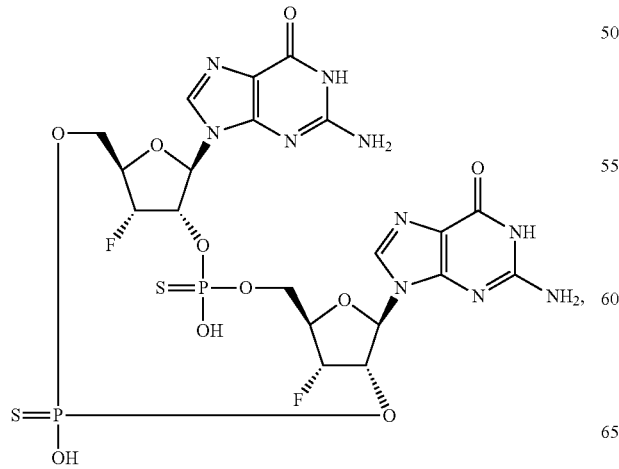
54
-continued
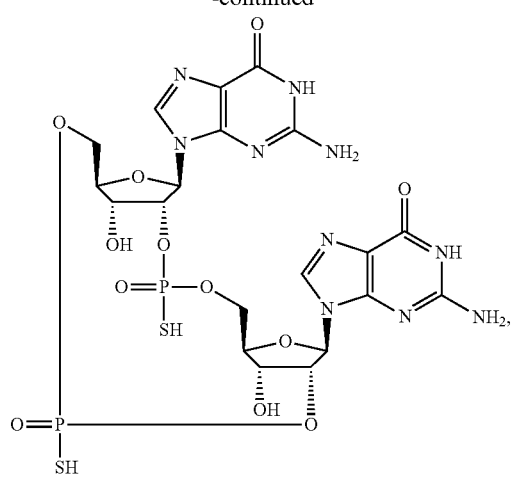
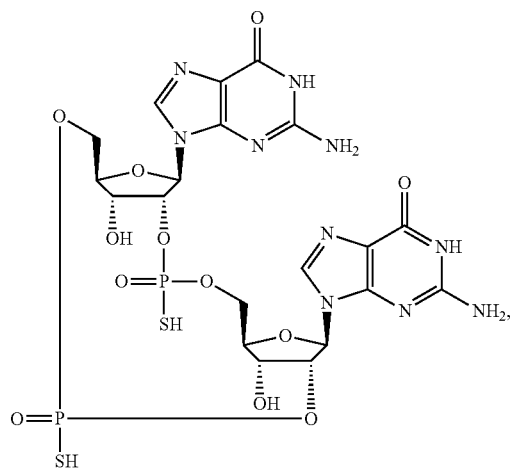
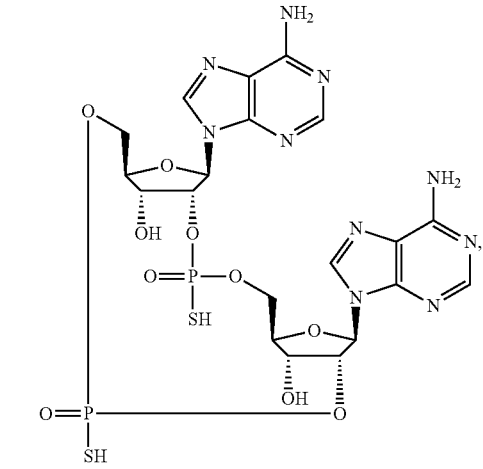

55
-continued
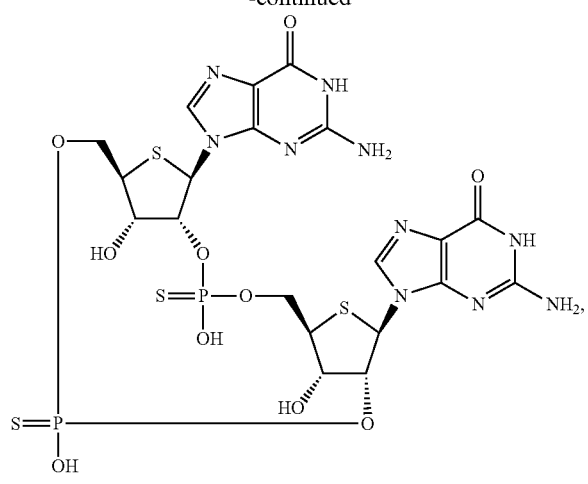
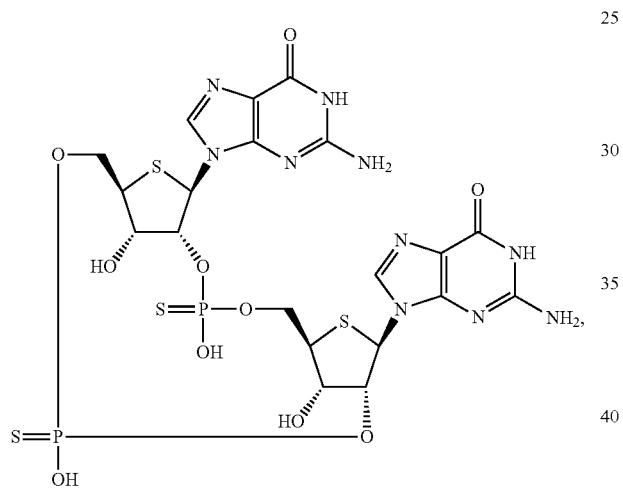
56
-continued
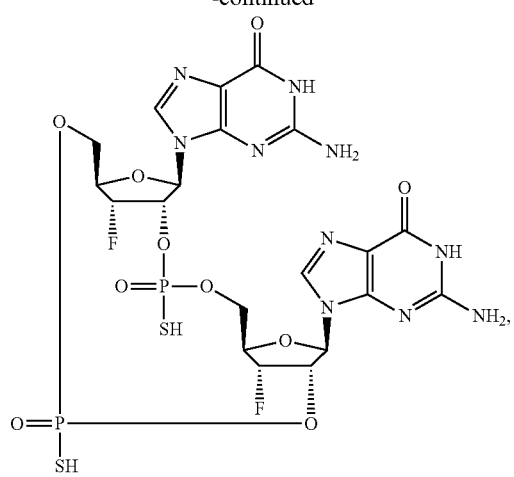
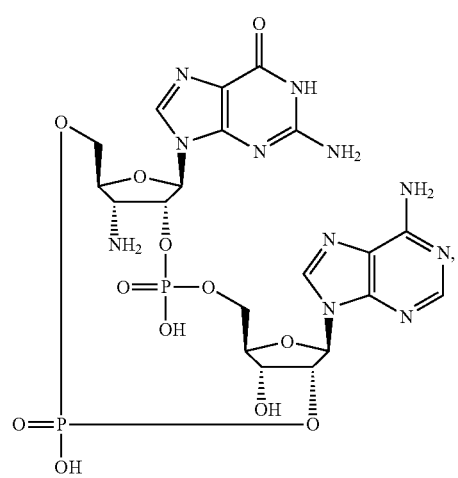
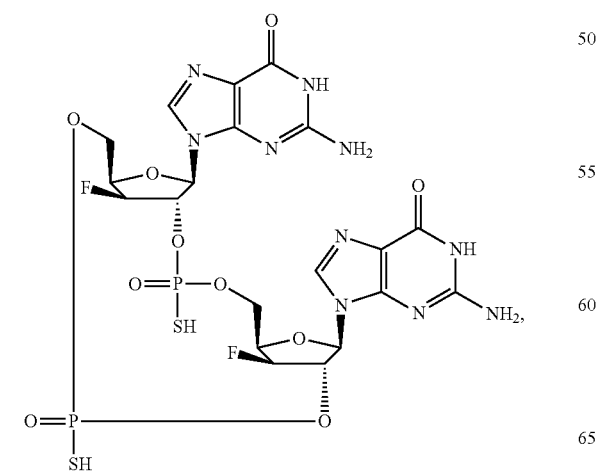
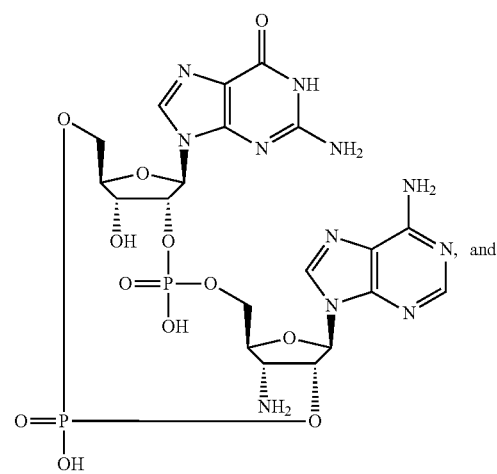
and

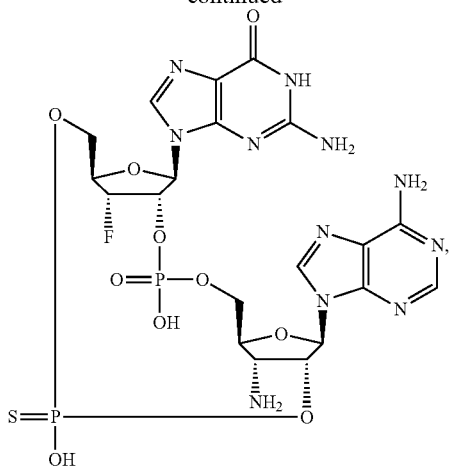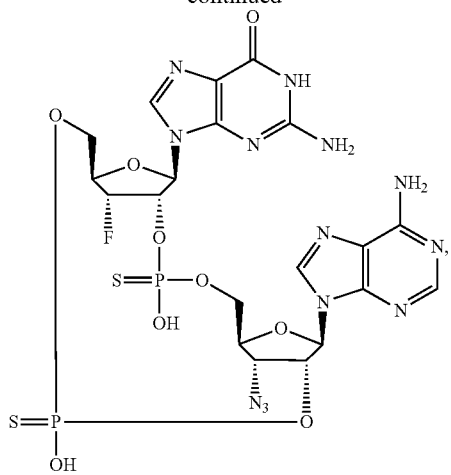
and pharmaceutically acceptable salts, hydrates, solvates, or prodrugs thereof. In particular aspects, the compound is selected from the group consisting of
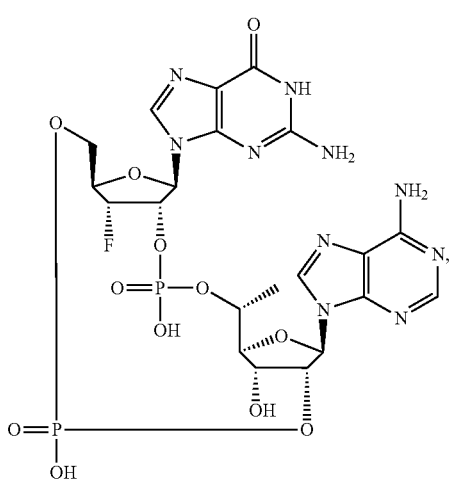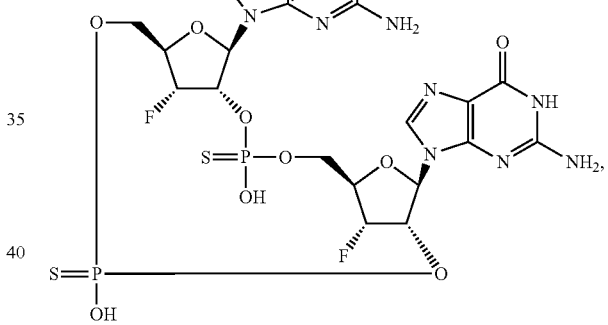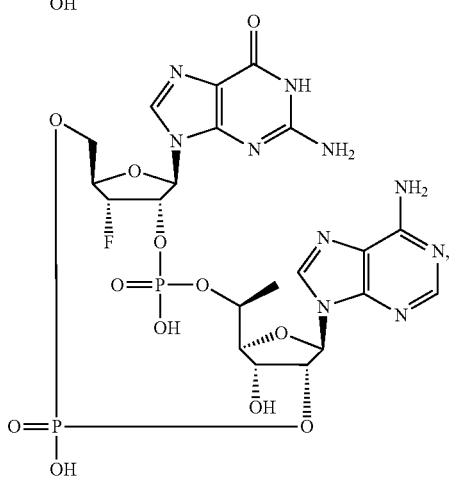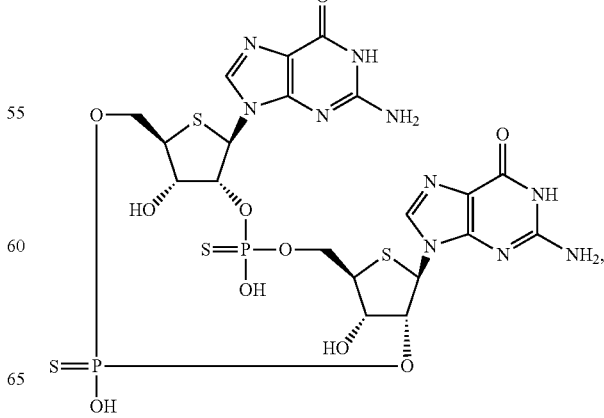

-continued

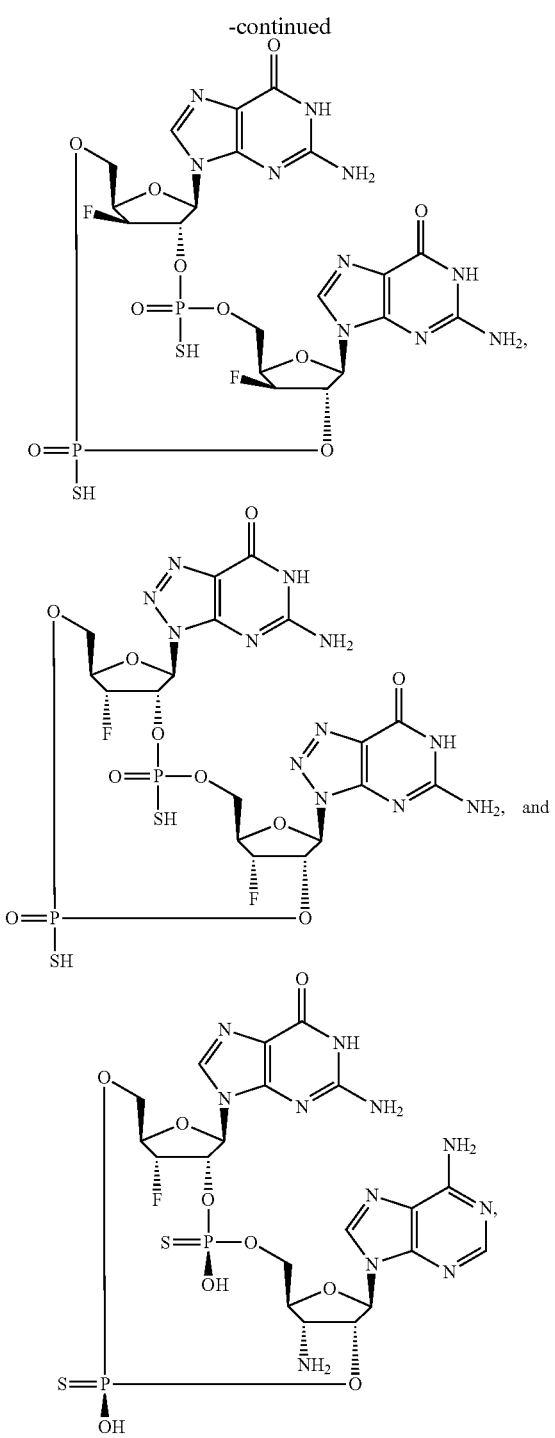

and pharmaceutically acceptable salts, hydrates, solvates, or prodrugs thereof.

In another embodiment, for the compounds of general formula (II), compounds of general formula (II') and compounds of general formula (II"), variables Base$^1$, Base$^2$, Y, Y$^a$, X$^a$, X$^{a1}$, X$^b$, X$^{b1}$, X$^c$, X$^{c1}$, X$^d$, X$^{d1}$, R$^1$, R$^{1a}$, R$^2$, R$^{2a}$, R$^{3a}$, R$^4$, R$^{4a}$, R$^5$, R$^6$, R$^{6a}$, R$^7$, R$^{7a}$, R$^8$, R$^{8a}$, R$^9$, and R$^{10}$ are each selected independently from each other.

In another embodiment of the disclosure, the compound of the disclosure is selected from the exemplary species depicted in Examples 1 through 34 shown below.

Other embodiments of the present disclosure include the following:

(a) A pharmaceutical composition comprising an effective amount of a compound of general formula (II) or a compound of general formula (II'), or a compound of general formula (II"), or a pharmaceutically acceptable salt, hydrate, solvate, or prodrug thereof, and a pharmaceutically acceptable carrier.

(b) The pharmaceutical composition of (a), further comprising a second therapeutic agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (II) or a compound of general formula (II'), or a compound of general formula (II"), or a pharmaceutically acceptable salt, hydrate, solvate, or prodrug thereof, and (ii) a second therapeutic agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the a compound of general formula (II) or compound of general formula (II'), or compound of general formula (II"), or a pharmaceutically acceptable salt, hydrate, solvate, or prodrug thereof, and the second therapeutic agent are each employed in an amount that renders the combination effective for inducing an immune response in a patient.

(e) A method of inducing an immune response in a patient, which comprises administering to the subject an effective amount of a a compound of general formula (II) or a compound of general formula (II'), or a compound of general formula (II"), or a pharmaceutically acceptable salt, hydrate, solvate, or prodrug thereof.

(f) A method of inducing an immune response in a patient, which comprises administering to the subject an effective amount of a composition of (a), a composition of (b) or a combination of (c).

(g) A method of inducing STING-dependent type I interferon production in a patient, which comprises administering to the subject an effective amount of a a compound of general formula (II) or a compound of general formula (II'), or a compound of general formula (II").

(h) A method of inducing STING-dependent type I interferon production in a patient, which comprises administering to the subject an effective amount of a composition of (a), a composition of (b) or a combination of (c).

(i) A method of inducing STING-dependent cytokine production in a patient, which comprises administering to the subject an effective amount of a compound of general formula (II) or a compound of general formula (II'), or a compound of general formula (II"), or a pharmaceutically acceptable salt, hydrate, solvate, or prodrug thereof.

(j) A method of inducing STING-dependent cytokine production in a patient, which comprises administering to the subject an effective amount of a composition of (a), a composition of (b) or a combination of (c).

(k) A method of treating a cell proliferation disorder in a subject, said method comprising administering a therapeutically effective amount of a compound of general formula (II) or a compound of general formula (II'), or a compound of general formula (II"), or a pharmaceutically acceptable salt, hydrate, solvate, or prodrug thereof to the subject;

(l) The method of (k), wherein the cell proliferation disorder is cancer.

(m). A method of treating a cell proliferation disorder in a subject, said method comprising administering a therapeutically effective amount of a pharmaceutical composition of (a), a composition of (b) or a combination of (c) to the subject.

(n) The method of (m), wherein the cell proliferation disorder is cancer.

The present disclosure also includes a compound of the present disclosure for use (i) in, (ii) as a medicament for, or (iii) in the preparation of a medicament for: (a) inducing an immune response in a patient, or (b) inducing a STING-dependent cytokine production in a patient. In these uses, the compounds of the present disclosure can optionally be employed in combination with one or more second therapeutic agents selected from STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

Additional embodiments of the disclosure include the pharmaceutical compositions, combinations and methods set forth in (a)-(n) above and the uses set forth in the preceding paragraph, wherein the compound of the present disclosure employed therein is a compound of one of the embodiments, aspects, classes, sub-classes, or features of the compounds described above. In all of these embodiments, the compound may optionally be used in the form of a pharmaceutically acceptable salt, hydrate, solvate, or prodrug as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (n) above are understood to include all embodiments of the compounds, including such embodiments as result from combinations of embodiments.

The term "subject" (alternatively referred to herein as "patient") as used herein refers to an animal, preferably a mammal, such as a human being, male or female, that has been the object of treatment, observation, or experiment. A subject also refers to one or more of cows, sheep, goats, horses, dogs, cats, rabbits, rats, mice, fish, and birds. In embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the compound of general formula (II), compound of general formula (II'), or compound of general formula (II"), or pharmaceutically acceptable salt, hydrate, solvate, or prodrug thereof, is administered in conjunction with one or more additional therapeutic agents including vaccines intended to stimulate an immune response to one or more predetermined anti-viral compounds, antigens, adjuvants, CTLA-4 and PD-1 pathway antagonists and other immunomodulatory agents, lipids, liposomes, peptides, anti-cancer and chemotherapeutic agents, etc. In certain embodiments, the compound of general formula (II), compound of general formula (II'), or compound of general formula (II"), or a pharmaceutically acceptable salt, hydrate, solvate, or prodrug thereof, is administered in conjunction with one or more additional compositions including vaccines intended to stimulate an immune response to one or more predetermined anti-viral compounds, antigens, adjuvants, CTLA-4 and PD-1 pathway antagonists and other immunomodulatory agents, lipids, liposomes, peptides, anti-cancer and chemotherapeutic agents, etc.

Compounds

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bond.

As used herein, the term "alkenylene" refers to a bivalent straight chain, unsaturated aliphatic hydrocarbon radical having a number of carbon atoms in the specified range and including one or more double bond.

As used herein, the term "alkynyl" refers to a monovalent straight or branched chain, unsaturated aliphatic hydrocarbon radical having a number of carbon atoms in the specified range and including one or more triple bond.

As used herein, the term "alkynylene" refers to a bivalent straight chain, unsaturated aliphatic hydrocarbon radical having a number of carbon atoms in the specified range and including one or more triple bond.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "spirocycle" or "spirocyclic ring" refers to a pendant cyclic group formed by substituents on a single atom. For example, in general formula (II), a spirocycle may be formed by $R^4$ and $R^5$.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of 1%, +2%, +3%, +4%, +5%, +10%, +15%, and +20% and their numerical equivalents.

As used herein, the term "one or more" item includes a single item selected from the list as well as mixtures of two or more items selected from the list.

In the compounds of general formula (II), compounds of general formula (II'), and compounds of general formula (II"), the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general formula (II), compounds of general formula (II'), and compounds of general formula (II"). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within general formula (II) can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (II), compounds of general formula (II'), and compounds of general formula (II"), the compounds are isotopically enriched with deuterium. In aspects of these embodiments, one or more of $R^1$, $R^{1a}$, $R^2$, $R^{2a}$, $R^{3a}$, $R^4$, $R^{4a}$, $R^5$, $R^6$, $R^{6a}$, $R^7$, $R^{7a}$, $R^8$, $R^{8a}$, $R^9$, and $R^{10}$ may be deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry, but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. The separation of a mixture of stereoisomers can be carried out at an intermediate step during the synthesis of a compound of general formula (II), a compound of general formula (II'), and/or a compound of general formula (II"), or it can be done on a final racemic product. Absolute stereochemistry may be determined by X-ray crystallography of crystalline products or crystalline intermediates, which are derivatized, if necessary, with a reagent containing a stereogenic center of known configuration.

Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

Those skilled in the art will recognize that chiral compounds, and in particular sugars, can be drawn in a number of different ways that are equivalent. Those skilled in the art will further recognize that the identity and regiochemical position of the substituents on ribose can vary widely and that the same principles of stereochemical equivalence apply regardless of substituent. Non-limiting examples of such equivalence include those exemplified below.

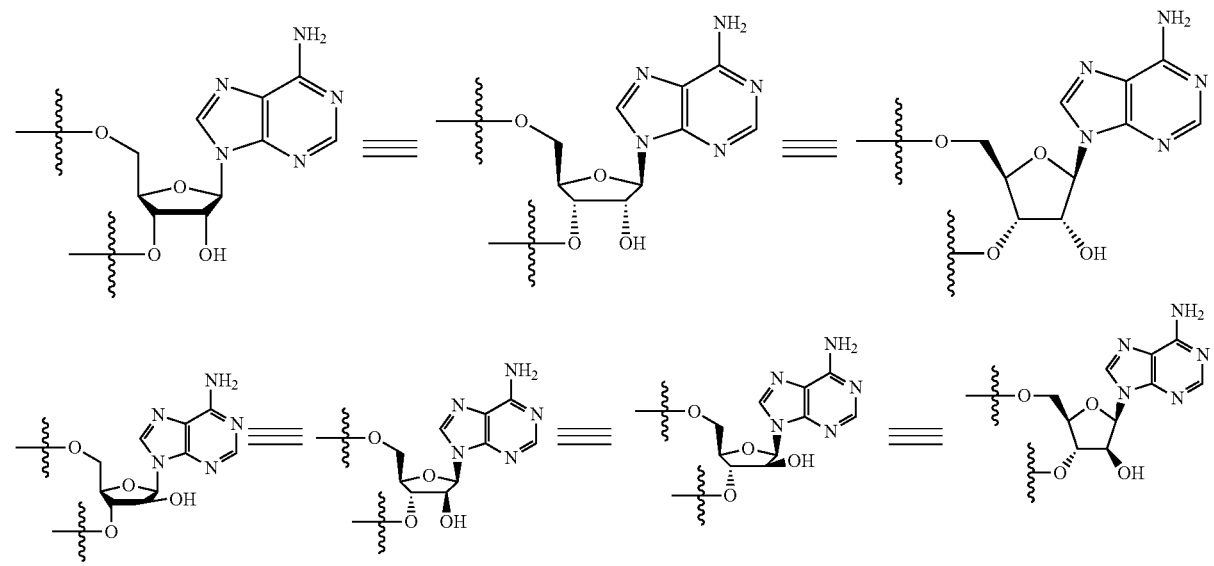

Salts

Compounds described herein having appropriate functional groups can be provided as salts. Examples of such compounds are described herein by reference to possible salts. Such reference is for illustration only. Additional embodiments include salts of any compounds described herein having suitable groups.

Pharmaceutically acceptable salts can be used with compounds for treating patients. Non-pharmaceutical salts may, however, be useful in the preparation of intermediate compounds.

Pharmaceutically acceptable salts are suitable for administration to a patient, preferably, a human. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Methods of Preparing Compounds

Several methods for preparing the compounds of general formula (II), compounds of general formula (II'), and compounds of general formula (II''), or pharmaceutically acceptable salts, hydrates, solvates, or prodrugs thereof, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

One method for the preparation of examples of general formula (II) of the disclosure is detailed in Scheme 3. The sequence starts with modified ribo-nucleoside with a nucleobase of which amino group was appropriately protected with an alkyl or phenyl carbonyl group, and H-phosphonate functionality at 2'-O position. It was treated with modified ribo-nucleoside with a nucleobase of which amino group was appropriately protected with an alkyl or phenyl carbonyl group, a phosphoramidite functionality at 2'-O position and DMTr ether at 5'-O position in acetonitrile. The product was immediately thioated with (E)-N,N-dimethyl-N'-(3-thioxo-3H-1,2,4-dithiazol-5-yl) formimidamide. Then, DMTr ether was removed under acidic condition. Using 2-chloro-5,5-dimethyl-1,3,2-dioxaphosphinane 2-oxide as a coupling reagent, the resulting 5'-hydroxyl group was reacted with 2'-H-phosphonate of fully protected first modified ribonucleoside to give cyclized product. It was immediately thioated with 3H-benzo[c][1,2]dithiol-3-one. Treatment with t-butylamine and methylamine plus fluoride anion in case silyl protection was used provided the desired cyclic dinucleotide diphosphorothioate 3F.

SCHEME 3

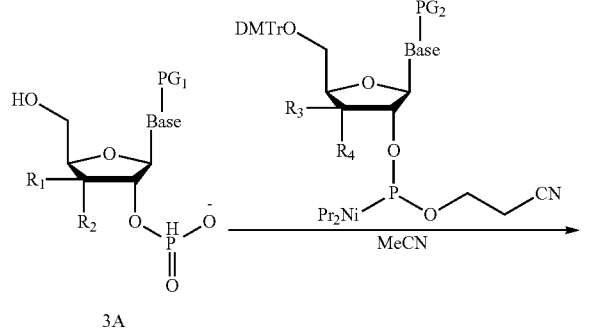

3A

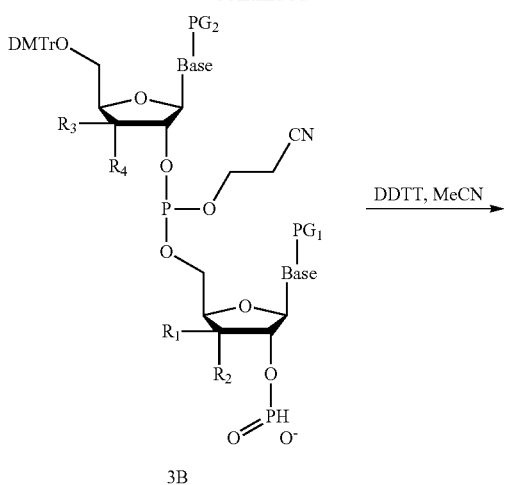

3B

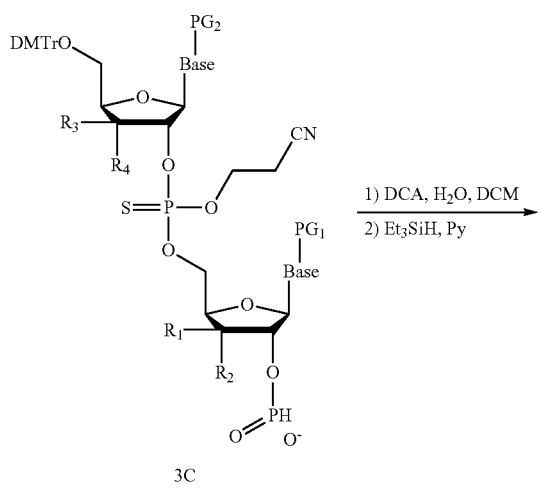

3C

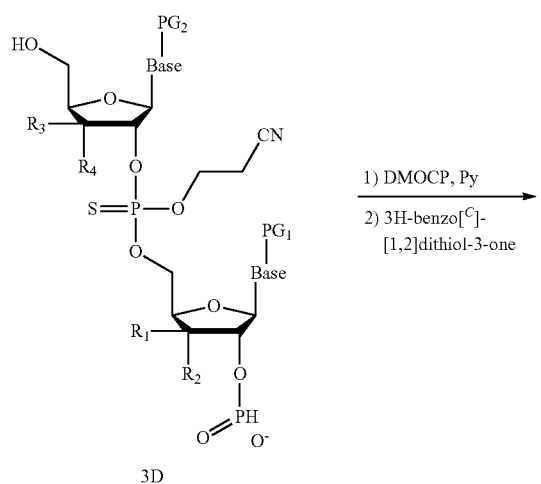

3D

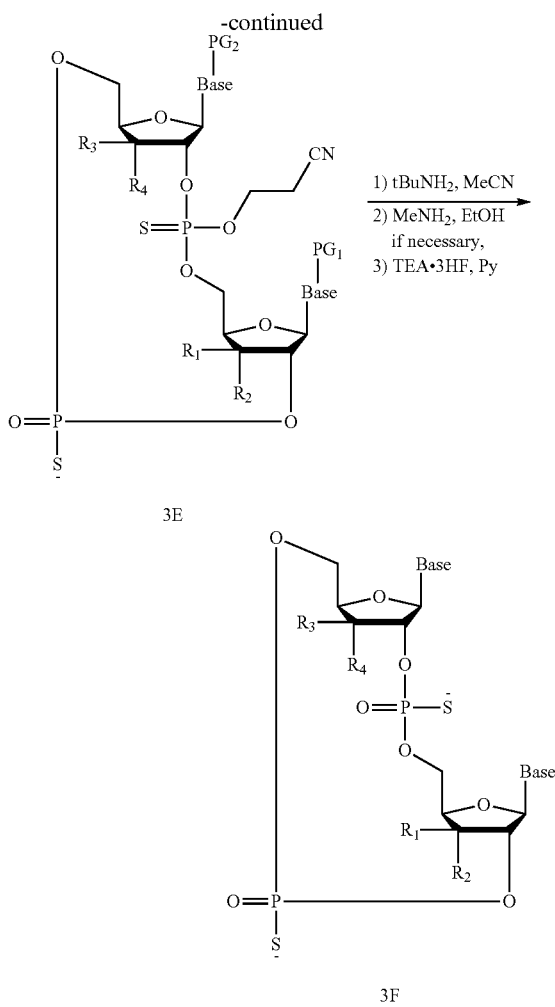

3E

3F

Methods of Use

Compounds described herein having therapeutic applications, such as the compounds of general formula (II), the compounds of general formula (II'), and the compounds of general formula (II"), and the compounds of the Examples 1 through 34, can be administered to a patient for the purpose of inducing an immune response, inducing a STING-dependent cytokine production and/or inducing anti-tumor activity. The term "administration" and variants thereof (e.g., "administering" a compound) means providing the compound to the individual in need of treatment. When a compound is provided in combination with one or more other active agents (e.g., antiviral agents useful for treating HCV infection or anti-tumor agents for treating cancers), "administration" and its variants are each understood to include concurrent and sequential provision of the compound or salt and other agents.

The compounds disclosed herein are STING agonists and inhibitors of viral replication. These compounds are potentially useful in treating diseases or disorders including, but not limited to, cell proliferation disorders, such as cancer.

Cell-proliferation disorders include, but are not limited to, cancer. Examples of such cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, the cancer is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, atypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, the cancer is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, and acute lymphoblastic leukemia.

In one embodiment, the cancer is skin cancer, including melanoma. In another embodiment, the cancer is prostate cancer, breast cancer, thyroid cancer, colon cancer, or lung cancer. In another embodiment, the cancer is sarcoma, including central chondrosarcoma, central and periosteal chondroma, and fibrosarcoma. In another embodiment, the cancer is cholangiocarcinoma.

As used herein, the terms "treatment" and "treating" refer to all processes wherein there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt, hydrate, solvate, or prodrug thereof, and compositions of the foregoing to a subject.

The amount of a compound administered to a subject is an amount sufficient to induce an immune response and/or to induce STING-dependent type I interferon production in the subject. In an embodiment, the amount of a compound can be an "effective amount" or "therapeutically effective amount," wherein the subject compound is administered in an amount that will elicit, respectively, a biological or medical (i.e., intended to treat) response of a tissue, system, animal or human that is being sought by a researcher, veterinarian, medical doctor or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (II), a compound of general formula (II'), or a compound of general formula (II") to a subject in need of treatment thereof. In one embodiment, the cell proliferation disorder is cancer.

In one embodiment, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of general formula (II), compound of general formula (II'), and/or compound of general formula (II"), or a pharmaceutically acceptable salt, hydrate, solvate, or prodrug thereof, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (II), compound of general formula (II'), and/or compound of general formula (II"), or a pharmaceutically acceptable salt, hydrate, solvate, or prodrug thereof, for use in potential treatment to induce an immune response and/or to induce STING-dependent type I interferon production.

In one embodiment, disclosed herein is the use of a compound of general formula (II), compound of general formula (II'), and/or compound of general formula (II"), or a pharmaceutically acceptable salt, hydrate, solvate, or prodrug thereof, in the manufacture of a medicament for the treatment to induce an immune response and/or to induce STING-dependent type I interferon production. In one embodiment, the disease or disorder to be treated is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer, or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The term "composition" as used herein is intended to encompass a dosage form comprising a specified compound in a specified amount, as well as any dosage form which results, directly or indirectly, from combination of a specified compound in a specified amount.

Such term is intended to encompass a dosage form comprising a compound of general formula (II), a compound of general formula (II'), and/or a compound of general formula (II"), or a pharmaceutically acceptable salt, hydrate, solvate, or prodrug thereof, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing a STING-dependent type I interferon production, the compounds, optionally in the form of a salt, hydrate, solvate, or prodrug, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

In one embodiment, disclosed herein is a composition comprising a compound of general formula (II), a compound of general formula (II'), and/or a compound of general formula (II"), or a pharmaceutically acceptable salt thereof, and one or more pharmaceutically acceptable carriers or excipients. The composition may be prepared and packaged in bulk form wherein an effective amount of a compound of the disclosure can be extracted and then given to a subject, such as with powders or syrups. Alternatively, the composition may be prepared and packaged in unit dosage form wherein each physically discrete unit contains an effective amount of a compound of general formula (II), a compound of general formula (II'), and/or a compound of general formula (II").

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the disclosure. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the disclosure are prepared using techniques and methods known to those skilled in the art. Some methods commonly used in the art are described in Remington's Pharmaceutical Sciences (Mack Publishing Company).

In one embodiment, the disclosure is directed to a solid oral dosage form such as a tablet or capsule comprising an effective amount of a compound of the disclosure and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The oral solid dosage form may further comprise a binder. Suitable binders include starch (e.g., corn starch, potato starch, and pregelatinized starch) gelatin, acacia, sodium alginate, alginic acid, tragacanth, guar gum, povidone, and cellulose and its derivatives (e.g., microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant.

Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the disclosure is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the disclosure in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions which may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

The compounds of general formula (II), compounds of general formula (II'), and/or compounds of general formula (II"), or pharmaceutically acceptable salt, hydrate, solvate, or prodrug thereof, may be administered in combination with one or more additional therapeutic agents. In embodiments, one or more a compound of general formula (II), compound of general formula (II'), or compound of general formula (II"), or pharmaceutically acceptable salt, hydrate, solvate, or prodrug thereof, and the one or more additional therapeutic agents may be co-adminstered. The additional therapeutic agent(s) may be administered in a single dosage form with the compound of general formula (II), compound of general formula (II'), or compound of general formula (II"), or pharmaceutically acceptable salt, hydrate, solvate, or prodrug thereof, or the additional therapeutic agent(s) may be administered in separate dosage form(s) from the dosage form containing the compound of general formula (II), compound of general formula (II'), or compound of general formula (II"), or pharmaceutically acceptable salt, hydrate, solvate, or prodrug thereof. The additional therapeutic agent(s) may be one or more agents selected from the group consisting of STING agonist compounds, anti-viral compounds, antigens, adjuvants, anti-cancer agents, CTLA-4, LAG-3 and PD-1 pathway antagonists, lipids, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the compounds of general formula (II), compounds of general formula (II'), or compounds of general formula (II") and one or more additional therapeutic agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as combinations may include a composition comprising a compound of general formula (II), compound of general formula (II'), or compound of general formula (II"), or pharmaceutically acceptable salt, hydrate, solvate, or prodrug thereof, and one or more other active agent(s) together in the same pharmaceutical composition, or may include a composition comprising a compound of general formula (II), compound of general formula (II'), or compound of general formula (II"), or pharmaceutically acceptable salt, hydrate, solvate, or prodrug thereof, and a composition comprising one or more other therapeutic agent(s) in separate form, e.g. in the form of a kit or in any form designed to enable separate administration either concurrently or on separate dosing schedules.

The weight ratio of a compound disclosed herein to a second active agent may be varied and will depend upon the effective dose of each agent. Generally, an effective dose of each will be used. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s). In one embodiment, this disclosure provides a composition comprising a compound of general formula (II), compound of general formula (II'), or compound of general formula (II"), or pharmaceutically acceptable salt, hydrate, solvate, or prodrug thereof, and at least one other therapeutic agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (II), compound of general formula (II'), or compound of general formula (II"), or pharmaceutically acceptable salt, hydrate, solvate, or prodrug thereof. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (II), compound of general formula (II'), or compound of general formula (II"), or pharmaceutically acceptable salt, hydrate, solvate, or prodrug thereof, for treating a cell proliferation disorder, wherein the medicament is prepared for administration with another active agent. The disclosure also provides the use of another active agent for treating a cell proliferation disorder, wherein the medicament is administered with a compound of general formula (II).

The disclosure also provides the use of a compound of general formula (II), compound of general formula (II'), or compound of general formula (II"), or pharmaceutically acceptable salt, hydrate, solvate, or prodrug thereof, for treating a cell proliferation disorder, wherein the patient has previously (e.g., within 24 hours) been treated with another active agent. The disclosure also provides the use of another therapeutic agent for treating a cell proliferation disorder, wherein the patient has previously (e.g., within 24 hours) been treated with a compound of general formula (II), compound of general formula (II'), or compound of general formula (II"), or pharmaceutically acceptable salt, hydrate, solvate, or prodrug thereof. The second agent may be applied a week, several weeks, a month, or several months after the administration of a compound disclosed herein.

STING agonist compounds that may be used in combination with the compounds of general formula (II), compounds of general formula (II'), and compounds of general formula (II") disclosed herein include but are not limited to cyclic di-nucleotide compounds.

Anti-viral compounds that may be used in combination with the compounds of general formula (II), compounds of general formula (II'), and compounds of general formula (II") disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the compounds of general formula (II), compounds of general formula (II'), and compounds of general formula (II") disclosed herein include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions.

Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants.

CLTA-4 and PD-1 pathways are important negative regulators of immune response. Activated T-cells upregulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (II) disclosed herein include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488, 802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the comounds of general formula (II), compounds of general formula (II'), and compounds of general formula (II"), or pharmaceutically acceptable salts, hydrates, solvates, or prodrugs thereof include, but are not limited to, arsenic trioxide (sold under the tradename TRISENOX®), asparaginase (also known as L-asparaginase, and *Erwinia* L-asparaginase, sold under the tradenames ELSPAR® and KIDROLASE®).

Chemotherapeutic agents that may be used in combination with the compounds of general formula (II), compounds of general formula (II'), and compounds of general formula (II"), or pharmaceutically acceptable salts, hydrates, solvates, or prodrugs thereof, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-tbutylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-amino-propanoate, also known as BMS-582664), motesanib (N-(2, 3-dihydro-3,3-dimethyl-1H-indol-6-yl)-2-[(4-pyridinylmethyl)amino]-3-pyridinecarboxamide, and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea (sold under the tradenames HYDREA®, DROXIA™ and MYLOCEL™), fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®).

Activity: STING Biochemical [3H]cGAMP Competition Assay

The individual compounds described in the Examples herein are defined as STING agonists by demonstrating binding to the STING protein with an $EC_{50}$ of 20 uM or less in the STING Biochemical [3H]cGAMP Competition Assay and demonstrating interferon production with a 20% or greater luminescence induction at 30 uM in the IFN-β secretion in the THP1 cell assay.

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

Abbreviations $^1$H-NMR Proton nuclear magnetic resonance spectroscopy
$^{19}$F-NMR $^{19}$F nuclear magnetic resonance spectroscopy
$^{31}$P-NMR $^{31}$P nuclear magnetic resonance spectroscopy
Å Angstrom
$A^{Bz}$ 6-N-benzoyladenine
aq Aqueous
Ar Argon
ATP Adenosine 5'-triphosphate
Bz Benzoyl
CD$_3$OD Deuterium-enriched methyl alcohol, deuterium-enriched methanol
CHCl$_3$ Trichloromethane
Ci Curie, a non-standard unit of radioactivity; 1 Ci=3.7× $10^{10}$Bq, where Bq is Becquerel, the SI unit of radioactivity, equivalent to 1 disintegration per second (dps)
CO$_2$ Carbon dioxide
d Doublet
d Day(s)
D$_2$O Deuterium-enriched water
DCA Dichloroacetic acid
DCM, CH$_2$Cl$_2$ Dichloromethane
ddd Doublet of doublet of doublet
ddt Doublet of doublet of triplet
DDTT (E)-N,N-dimethyl-N'-(3-thioxo-3H-1,2,4-dithiazol-5-yl)formimidamide
DMA N,N-dimethylacetamide
DMF N,N-dimethylformamide
DMOCP 2-chloro-5,5-dimethyl-1,3,2-dioxaphosphineane 2-oxide
DMSO Dimethyl sulfoxide
DMTr 4,4'-dimethoxytrityl
DMTrCl 4,4'-dimethoxytrityl chloride
dq Doublet of quartet
$EC_{50}$ half maximal effective concentration, concentration of a drug, antibody or toxicant that induces a response halfway between the baseline and maximum after a specified exposure time
eq Equivalents
ES Electron spray
Et Ethyl
Et$_2$O Diethyl ether
Et$_3$SiH Triethylsilane
EtOAc Ethyl acetate
EtOH Ethyl alcohol, ethanol
g Gram
GTP Guanosine 5'-triphosphate
h Hour
H$_2$O Water
HEPES 2-[4-(2-hydroxyethyi)piperazin-1-yl]ethanesulfonnic acid, a zwitterionic organic chemical buffering agent
hept Heptet
Hex Hexanes
HF-Pyr Hydrogen fluoride-pyridine complex
HPLC High performance liquid chromatography
Hz Hertz
ITP Inosine 5'-triphosphate
J NMR Coupling constant
LCMS Liquid chromatography-mass spectroscopy
m Multiplet
M Molar, moles per liter
mCi Millicurie
Me Methyl
MeCN, ACN Acetonitrile
MeNH$_2$ Methylamine
mg Milligram
MgCl$_2$ Magnesium chloride
MHz Megahertz
min Minute(s)
mL, ml Milliliter
mM Millimole per liter
mmol Millimole
MOI Multiplicity of infection
MPLC Medium pressure liquid chromatography
MTBE Methyl t-butyl ether, methyl tertiary butyl ether
Na$_2$SO$_4$ Sodium sulfate
NaCl Sodium chloride
NaHCO$_3$ Sodium bicarbonate
NaHSO$_3$ Sodium bisulfite
NaOH Sodium hydroxide ng Nanogram(s)
NH$_4$HCO$_3$ Ammonium bicarbonate
NH$_4$OH Ammonium hydroxide
nL Nanoliter
nm Nanometer
nM Nanomolar
P$_2$O$_5$ Phosphorus pentoxide
Prep-HPLC Preparative high performance liquid chromatography
Py Pyridine
q Quartet
RPM, rpm Revolutions per minute
RT, rt Room temperature, approximately 25° C.
s Singlet
sat Saturated
t Triplet
TBS t-Butyldimethylsilyl
TMA Trimethylamine
TEA, Et$_3$N Triethylamine
TFA Trifluoroacetic acid
THF Tetrahydrofuran
TLC Thin layer chromatography
TMSCl Trimethylsilyl chloride
T$_R$ Retention time
TrisCl Tris(hydroxymethyl)aminomethane hydrochloride
v/v Volume/volume
λ$_{em}$ Emission wavelength
λ$_{ex}$ Excitation wavelength
μg Microgram
L, uL Microliter
M, uM Micromolar Preparation 1: N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

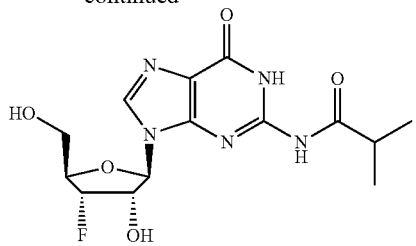

Step 1: N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide

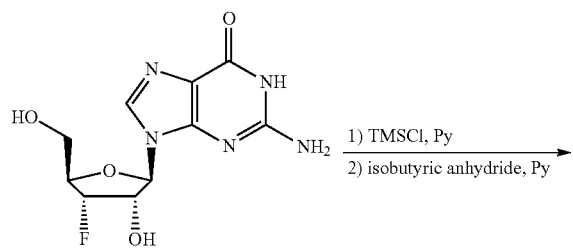

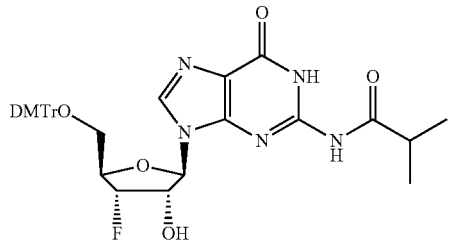

To a suspension of 2-amino-9-((2R,3S,4S,5R)-4-fluoro-3-hydroxy-5-(hydroxymethyl)tetrahydrofuran-2-yl)-1,9-dihydro-6H-purin-6-one (Carbosynth catalog # ND10826, 1.50 g, 5.26 mmol) in pyridine (30 mL) at 0-5° C. was added TMSCl (2.86 g, 26.3 mmol), and the mixture was stirred at rt for 30 min. Then, isobutyric anhydride (2.50 g, 15.8 mmol) was added dropwise, and it was stirred for an additional 2 h. Then, MeOH (5.3 mL) was added. After 5 min, NH$_4$OH (10.5 mL) was added dropwise, and stirring was continued for 30 min. The reaction mixture was concentrated under reduced pressure, and MeOH (2 mL) in CH$_2$Cl$_2$ (18 mL) was added to the residue. Insolubles were filtered off, and the filtrate was concentrated and purified by flash column chromatography with 2-10% MeOH in CH$_2$Cl$_2$ to give the product. LCMS (ES, m/z): 356.1 [M+H]$^+$. $^1$H-NMR: (400 MHz, DMSO-d$_6$): δ 12.11 (s, 1H), 11.68 (s, 1H), 8.28 (s, 1H), 5.98 (d, J=6.1 HZ, 1H), 5.85 (d, J=8.0 HZ, 1H), 5.24 (t, J=5.4 HZ, 1H), 5.14 (d, J=4.1 HZ, 0.5H), 5.01 (d, J=4.2 HZ, 0.5H), 4.87-4.69 (m, 1H), 4.26 (t, J=4.4 HZ, 0.5H), 4.19 (t, J=4.4 HZ, 0.5H), 3.61 (t, J=4.9 HZ, 2H), 2.77 (hept, J=6.8 HZ, 1H), 1.13 (d, J=6.7 HZ, 6H). $^{19}$F-NMR: (376 MHz, DMSO-d$_6$): δ −197.5 (s).

Step 2: N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

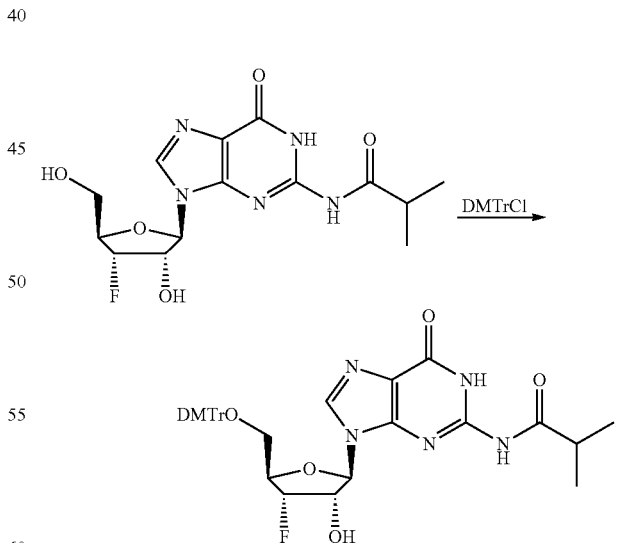

N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide (1.30 g, 3.66 mmol) was co-evaporated with pyridine (3×10 mL) and re-dissolved in pyridine (26 mL). To the solution at 0-5° C. was added DMTrCl (1.36 g, 4.02 mmol). It was stirred at rt for 3 h and then concentrated.

CH$_2$Cl$_2$ (40 mL, with 1% Et$_3$N) was added, and it was washed with sat aq NaHCO$_3$ (15 mL), water (10 mL) and brine (10 mL). The organic solution was dried (Na$_2$SO$_4$), concentrated and purified by silica gel column chromatography using 0-10% MeOH in CH$_2$Cl$_2$ (1% Et$_3$N) to give the product. LCMS (ES, m/z): 656.2 [M−H]$^−$. $^1$H-NMR: (400 MHz, DMSO-d$_6$): δ 12.10 (s, 1H), 11.61 (s, 1H), 8.14 (s, 1H), 7.40-7.31 (m, 2H), 7.31-7.19 (m, 7H), 6.89-6.78 (m, 4H), 6.08 (d, J=6.1 Hz, 1H), 5.87 (d, J=7.3 Hz, 1H), 5.23 (dd, J=4.1, 1.8 Hz, 1H), 5.10 (d, J=4.4 Hz, 1H), 4.96 (dq, J=22.4, 5.9 Hz, 1H), 4.30 (dt, J=26.1, 4.6 Hz, 1H), 3.74 (d, J=1.1 Hz, 6H), 3.39 (dd, J=10.6, 5.7 Hz, 1H), 3.22 (dd, J=10.6, 3.8 Hz, 1H), 2.76 (p, J=6.8 Hz, 1H), 1.13 (d, J=6.8 Hz, 6H). $^{19}$F-NMR: (376 MHz, DMSO-d$_6$): δ −198.1 (s, 1F).

Preparation 2: (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite

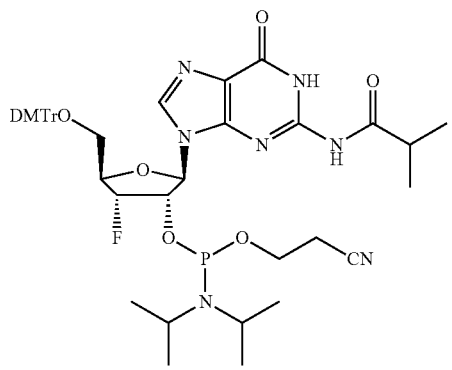

Step 1: (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite

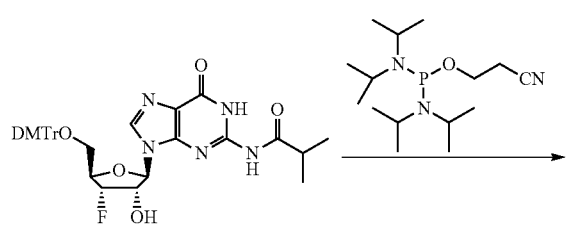

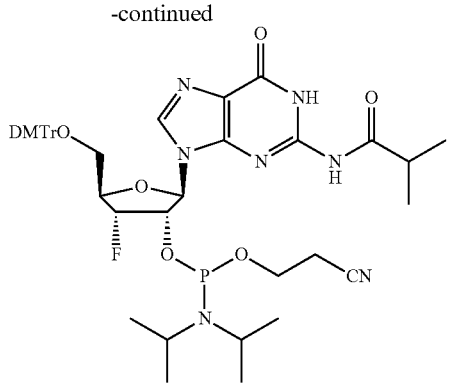

To a mixture of N-(9-((2R,3S,4S,5R)-5-((bis(4-methoxyphenyl)(phenyl)methoxy)-methyl)-4-fluoro-3-hydroxytetrahydrofuran-2-yl)-6-oxo-6,9-dihydro-1H-purin-2-yl)-isobutyramide (2.1 g, 3.19 mmol) in MeCN (30 mL) under Ar was added pyridine trifluoroacetate (0.678 g, 3.51 mmol), followed by 3-((bis(diisopropylamino)phosphino)oxy)-propanenitrile (1.16 g, 3.83 mmol) in MeCN (2 mL), which was added dropwise with stirring at 0° C. over 10 min. Then, the mixture was stirred at 20° C. for 5 h. TLC/LCMS indicated complete conversion to desired product. The resulting mixture was diluted with a solution of 2% TEA in CHCl$_3$ (300 mL) and washed successively with aq NaHCO$_3$ (3×100 mL), H$_2$O (2×100 mL) and brine (2×100 ml). The organic layer was dried over anhydrous Na$_2$SO$_4$ and concentrated. The crude residue was purified by flash column chromatography with 10% DCM in EtOAc/hexane (2/3) to give crude product. The residue was dissolved in CHCl$_3$ (20 mL) and precipitated in hexane (500 mL). The precipitate was filtered, and the residue was washed successively with H$_2$O (2×100 mL), and brine (2×100 ml). The organic layer was dried over anhydrous Na$_2$SO$_4$ and concentrated. The residue was dissolved in MTBE (20 mL) and precipitated in hexane (500 mL). The precipitate was filtered to yield the title compound. LCMS (ES, m/z): 856.9 [M−H]$^−$. $^1$H NMR (400 MHz, DMSO-d$_6$) δ 12.07 (s, 1H), 11.55 (s, 1H), 8.08 (d, J=4.2 Hz, 1H), 7.38-7.16 (m, 10H), 6.83 (ddd, J=8.9, 6.2, 2.1 Hz, 5H), 5.99 (t, J=6.8 Hz, 1H), 5.19-5.12 (m, 1H), 4.39 (d, J=5.2 Hz, 1H), 3.71 (s, 8H), 3.59-3.35 (m, 3H), 3.26 (dd, J=10.3, 3.5 Hz, 1H), 2.79-2.66 (m, 2H), 1.26-1.00 (m, 18H), 0.88-0.70 (m, 4H). $^{19}$F NMR (376 MHz, DMSO-d$_6$) δ −195.78, −197.06. $^{31}$P NMR (162 MHz, DMSO-d$_6$) δ 151.57, 151.53, 151.37, 151.33.

Preparation 3: N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide

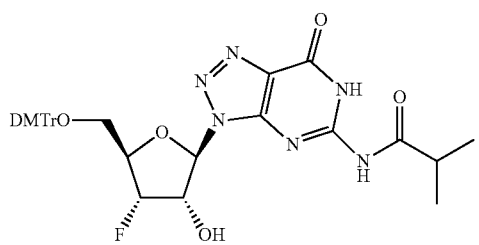

Step 1: ((2R,3R,4S,5R)-5-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate

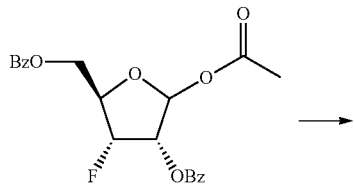

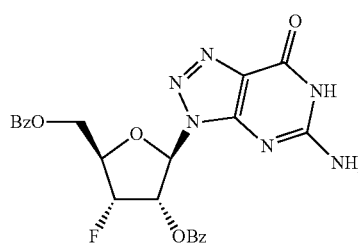

To a suspension of 8-azaguanine (5.14 g, 33.8 mmol) in anhydrous $CH_3CN$ (100 mL) at rt was added dropwise (E)-trimethylsilyl N-(trimethylsilyl)acetimidate (16.53 mL, 67.6 mmol) then the mixture was stirred at 70° C. for 2 h. The reaction was cooled to rt and a solution of ((2R,3R,4S)-5-acetoxy-4-(benzoyloxy)-3-fluorotetrahydrofuran-2-yl)methyl benzoate (6.8 g, 16.90 mmol) in anhydrous $CH_3CN$ (20 mL) was added followed by dropwise addition of tin(IV) chloride (67.6 mL, 67.6 mmol). The homogeneous solution was stirred at 70° C. for 2 h. The reaction was cooled to rt and concentrated. The residue was dissolved in EtOAc (1000 mL) and neutralized by pouring into saturated aq $NaHCO_3$ (500 mL). The organic layer was separated, and the aq layer was extracted with EtOAc (4×500 mL). The organic layers were combined and washed with water (3×700 mL), brine, dried over anhydrous sodium sulfate, filtered, and concentrated to afford title compound without further purification. LCMS (ES, m/z): 495.3 $[M+H]^+$.

Step 2: ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate

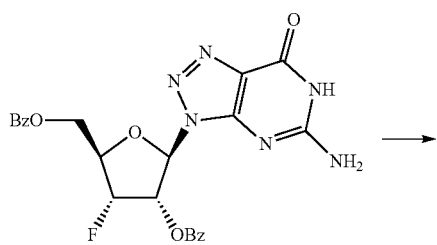

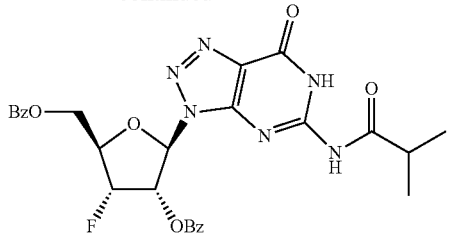

To a solution of ((2R,3R,4S,5R)-5-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate (8 g, 16.18 mmol) from Step 1 in anhydrous DMA (40 mL) at rt was added dropwise isobutyric anhydride (4.02 mL, 24.27 mmol). The mixture was stirred at 140° C. for 4 h. The reaction was cooled and diluted with EtOAc (600 mL), washed with sat aq $NH_4Cl$ (4×500 mL), brine, dried over anhydrous sodium sulfate, filtered and concentrated. The crude product was purified by MPLC (220 g silica gel, eluting with a gradient of 100% hexanes to 100% ethyl acetate) to afford ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate. LCMS (ES, m/z): 565.3 $[M+H]^+$.

Step 3: N-(3-((2R,3S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide

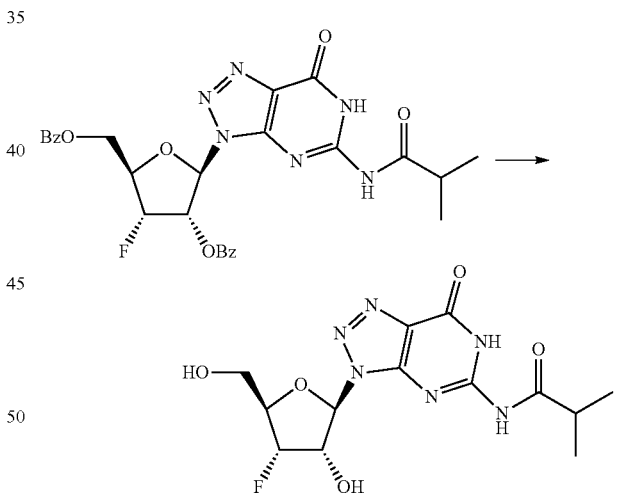

To a solution of ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate (6 g, 10.63 mmol) in THF (20 mL), $CH_3OH$ (16 mL), and water (4 mL) at 0° C. was added 5N aq NaOH (4.89 mL, 24.45 mmol) and stirred for 1 h. The reaction was neutralized with formic acid (1.223 mL, 31.9 mmol). The solvent was removed, and the residue was purified by MPLC (120 g silica gel, eluting with a gradient of 100% $CH_2Cl_2$ to 20% $CH_3OH/CH_2Cl_2$) to afford N-(3-((2R,3S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide. LCMS (ES, m/z): 357.2 $[M+H]^+$.

Step 4: N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide

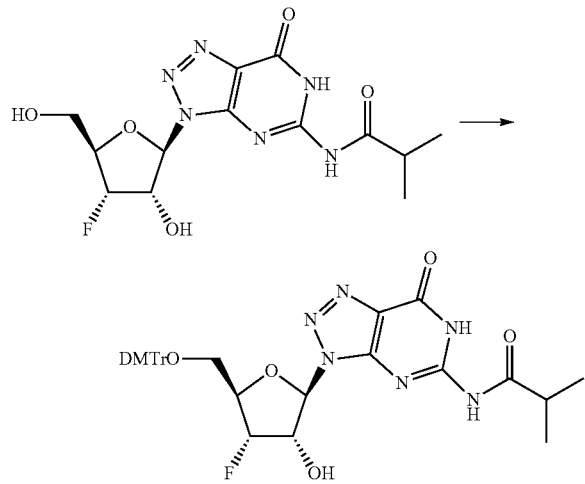

To a solution of N-(3-((2R,3S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide (3 g, 8.42 mmol) in anhydrous pyridine (40 mL) at 0° C. was added 4,4'-dimethoxytrityl chloride (3.42 g, 10.10 mmol). The ice bath was removed, and the reaction mixture was allowed to reach RT and was stirred for 2 h. The mixture was diluted with EtOAc (400 mL), washed with sat aq NaHCO$_3$ (100 mL), water (3×100 mL), brine, and dried over anhydrous sodium sulfate, filtered and concentrated. The crude product was purified by MPLC (120 g silica gel, eluting with a gradient of 100% CH$_2$Cl$_2$ to 15% CH$_3$OH/CH$_2$CH$_2$ to afford N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide. LCMS (ES, m/z): 659.3 [M+H]$^+$.

Preparation 4: 9-{5-O-[bis(4-methoxyphenyl)(phenyl)methyl]-3-deoxy-3-fluoro-β-D-xylofuranosyl}-2-[(2-methylpropanoyl)amino]-1,9-dihydro-6H-purin-6-one

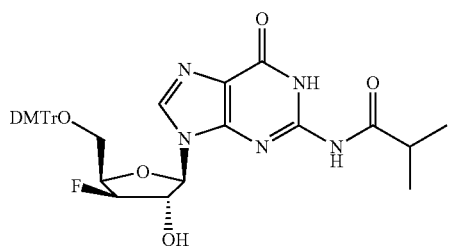

The title compound was prepared according to published procedures (*Tetrahedron Letters*, 1989, 30(24), 3171-3174).

Preparation 5: (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

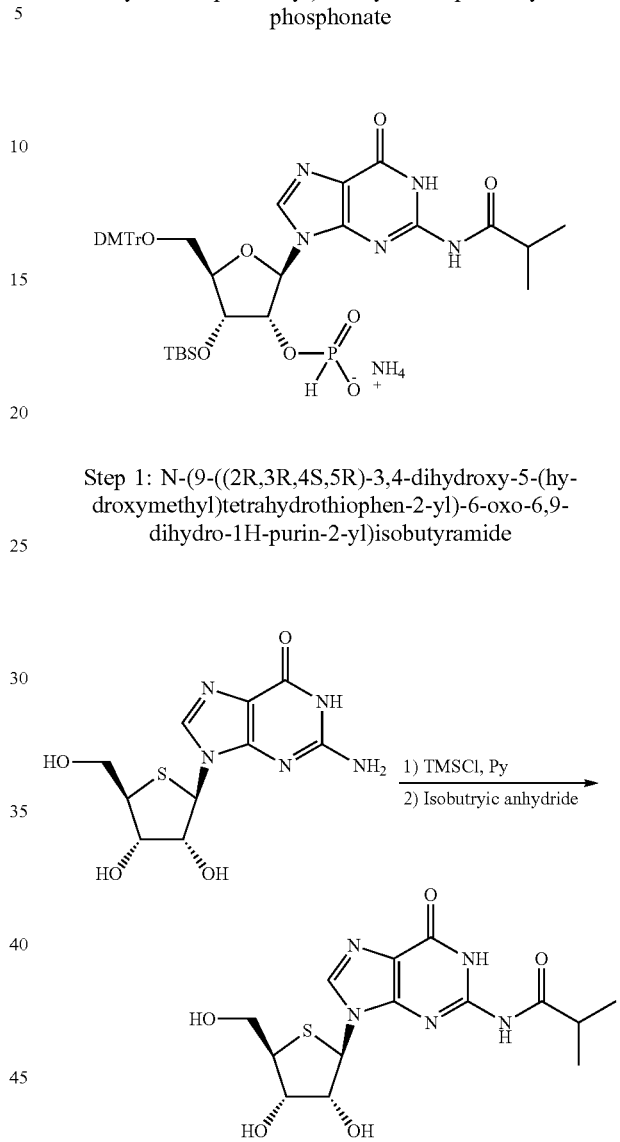

Step 1: N-(9-((2R,3R,4S,5R)-3,4-dihydroxy-5-(hydroxymethyl)tetrahydrothiophen-2-yl)-6-oxo-6,9-dihydro-1H-purin-2-yl)isobutyramide 2-amino-9-((2R,3R,4S,5R)-3,4-dihydroxy-5-(hydroxymethyl)tetrahydrothiophen-2-yl)-1,9-dihydro-6H-purin-6-one (1.7 g, 5.7 mmol) was co-evaporated with pyridine (3×5 mL) and then re-dissolved in pyridine (34 mL). To the mixture at 0° C. was added chlorotrimethylsilane (4.32 g, 39.8 mmol) dropwise. It was stirred at rt for 1 h and then cooled to 0° C. again. Isobutyric anhydride (1.348 g, 8.52 mmol) was added dropwise, and it was stirred at rt for 3 h. It was quenched by the addition of water (8.5 mL). After 5 min, NH$_4$OH (ca. 29%, 17 mL) was added, and the mixture was stirred for 30 min. It was concentrated and purified by column chromatography and eluted with 1 to 30% MeOH in CH$_2$Cl$_2$ to give the product. LCMS (ES, m/z): 396.9 [M+H]$^+$. $^1$H-NMR (400 MHz, DMSO-d$_6$): δ 9.52 (br s, 2H), 8.39 (s, 1H), 5.79 (d, J=7.1 Hz, 1H), 5.59 (s, 1H), 5.40 (s, 1H), 5.22 (s, 1H), 4.55 (d, J=6.7 Hz, 1H), 4.21 (s, 1H), 3.77 (t, J=9.3 Hz, 1H), 3.61 (s, 1H), 3.30 (dt, J=6.4, 3.3 Hz, 1H), 2.78 (p, J=6.9 Hz, 1H), 1.13 (d, J=6.8 Hz, 6H).

Step 2: N-(9-((2R,3R,4S,5R)-5-((bis(4-methoxyphenyl)(phenyl)methoxy)methyl)-3,4-dihydroxytetrahydrothiophen-2-yl)-6-oxo-6,9-dihydro-1H-purin-2-yl)isobutyramide

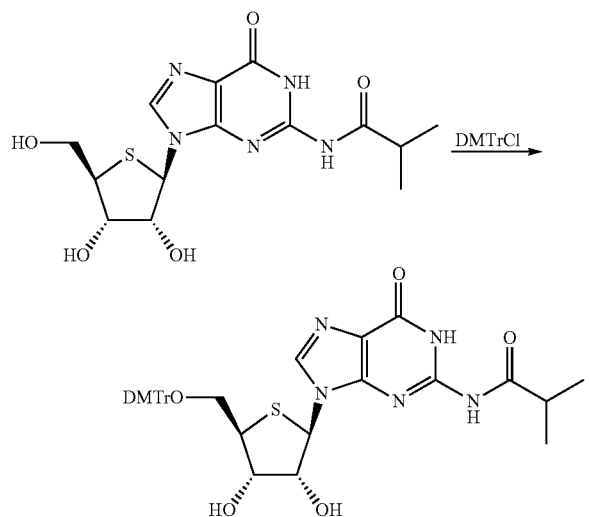

To a mixture of N-(9-((2R,3R,4S,5R)-3,4-dihydroxy-5-(hydroxymethyl)-tetrahydrothiophen-2-yl)-6-oxo-6,9-dihydro-1H-purin-2-yl)isobutyramide (480 mg, 1.299 mmol) in pyridine (10 mL) was added 4,4'-(chloro(phenyl)methylene)-bis(methoxybenzene) (484 mg, 1.43 mmol). It was stirred at rt for 16 h and then concentrated. The crude was purified by column chromatography on silica gel and eluted with 1 to 30% MeOH in CH$_2$Cl$_2$ (containing 1% Et$_3$N) to give the product. LCMS (ES, m/z): 672.2 [M+H]$^+$. $^1$H-NMR (400 MHz, DMSO-d$_6$+D$_2$O): δ 8.08 (s, 1H), 7.39 (d, J=7.2 Hz, 2H), 7.32 (t, J=7.6 Hz, 2H), 7.26 (dt, J=9.1, 3.3 Hz, 5H), 6.94-6.87 (m, 4H), 5.75 (d, J=5.9 Hz, 1H), 4.39 (dd, J=5.9, 3.5 Hz, 1H), 4.14 (t, J=3.9 Hz, 1H), 3.74 (s, 6H), 3.49-3.37 (m, 2H), 3.33 (dd, J=14.5, 7.3 Hz, 1H), 2.87-2.67 (m, 1H), 1.11 (dd, J=6.8, 1.6 Hz, 6H).

Step 3: N-(9-((2R,3R,4S,5R)-5-((bis(4-methoxyphenyl)(phenyl)methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis(4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide

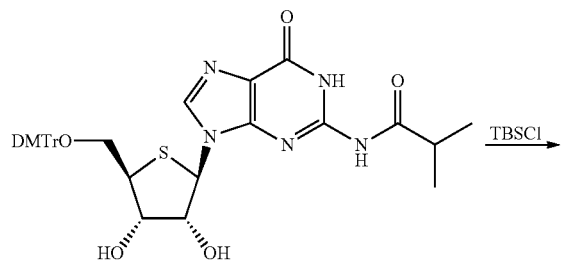

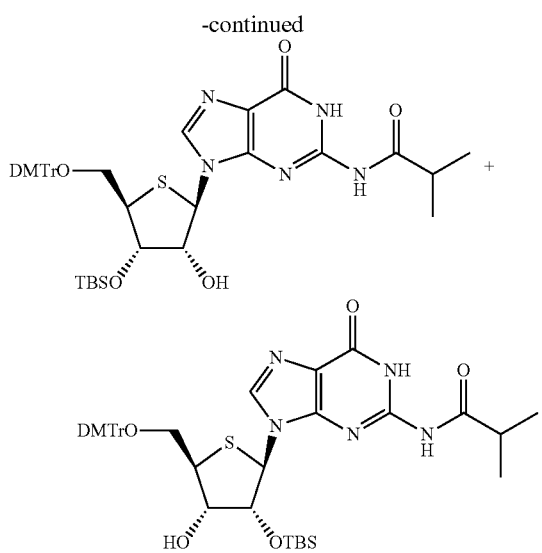

To a solution of N-(9-((2R,3R,4S,5R)-5-((bis(4-methoxyphenyl)(phenyl)-methoxy)methyl)-3,4-dihydroxytetrahydrothiophen-2-yl)-6-oxo-6,9-dihydro-1H-purin-2-yl)isobutyramide (580 mg, 0.863 mmol) in DMF (5 mL) at rt was added 1H-imidazole (147 mg, 2.16 mmol) and tert-butylchlorodimethylsilane (156 mg, 1.04 mmol). After 6 h, the mixture was diluted with EtOAc (50 mL) and washed with sat aq NaHCO$_3$ (2×20 mL) and brine (20 mL). It was dried (Na$_2$SO$_4$), concentrated, and purified by reverse phase (C18) chromatography and eluted with 0 to 95% ACN in water to give the products. LCMS (ES, m/z): 786.3 [M+H]$^+$.

Step 4: (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phenyl phosphonate and (2R,3S,4R,5R)-2-((bis(4-methoxyphenyl)(phenyl)methoxy)methyl)-4-((tert-butyldimethylsilyl)oxy)-5-(2-isobutyramido-6-oxo-1,6-dihydro-9H-purin-9-yl)tetrahydrothiophen-3-yl phenyl phosphonate

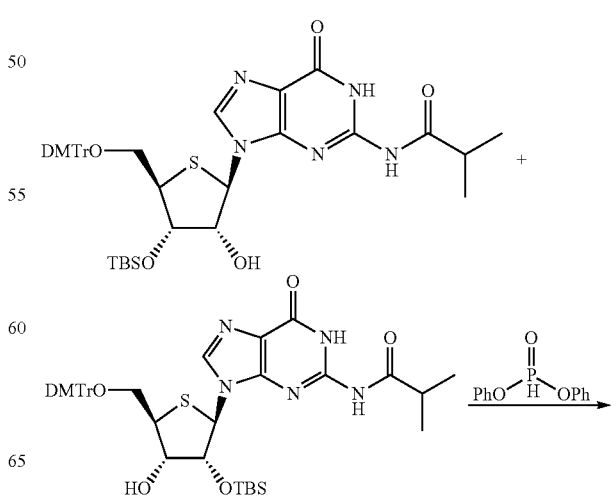

-continued

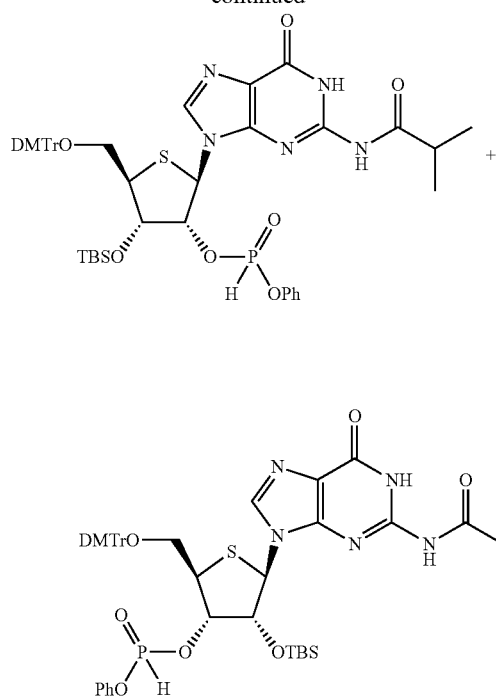

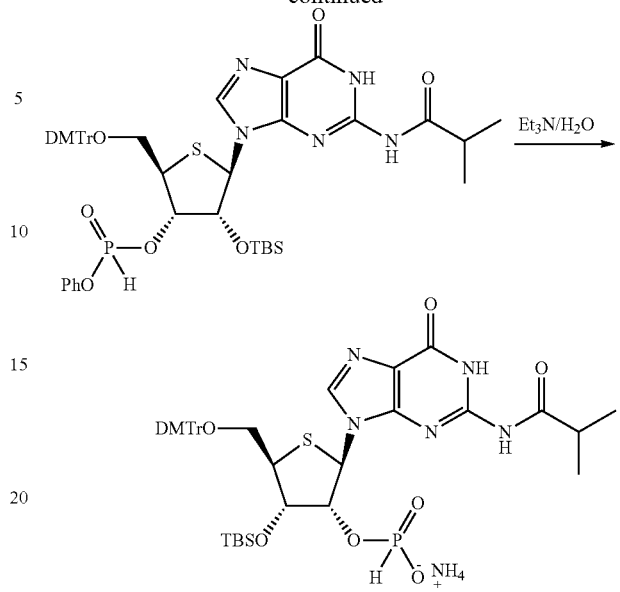

To a solution of a mixture of N-(9-((2R,3R,4S,5R)-5-((bis(4-methoxyphenyl)(phenyl)-methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis(4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide (220 mg, 0.280 mmol) in pyridine (2 mL) at 0° C. was added diphenyl phosphonate (98 mg, 0.420 mmol). The resulting mixture was stirred at rt for 20 min. It was used in the reaction step without purification. LCMS (ES, m/z): 926.2 [M+H]$^+$.

Step 5: ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

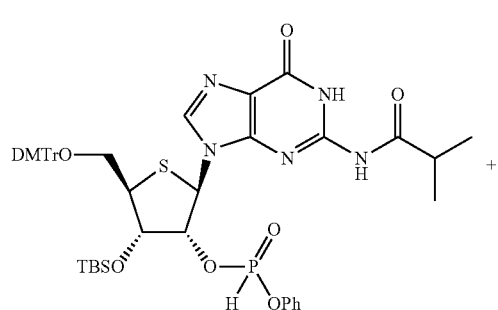

To the reaction mixture from Step 4 at 0° C. was added Et$_3$N (0.28 mL, 2.0 mmol) and water (0.28 mL). It was stirred at rt for 30 min. It was concentrated, and the residue was partitioned between CH$_2$Cl$_2$ (40 mL) and aq NaHCO$_3$ (5%, 30 mL). The organic layer was washed with aq NaHCO$_3$ (5%, 2×30 mL), dried (Na$_2$SO$_4$), concentrated and purified by silica gel column chromatography using 0-10% MeOH in CHCl$_3$ containing 1% Et$_3$N to give a mixture. The mixture was further purified by Prep-HPLC (XBridge Shield RP 18 OBD Column, 19×150 mm) and eluted with 46 to 79% ACN in aq NH$_4$HCO$_3$ (10 mM) over 7 min to give the product. LCMS (ES, m/z): 850.2 [M+H]$^+$. $^1$H-NMR (400 MHz, CD$_3$OD): δ 8.18 (s, 1H), 7.68 (s, 0.5H), 7.59-7.49 (m, 2H), 7.45-7.36 (m, 4H), 7.37-7.30 (m, 2H), 7.28-7.22 (m, 1H), 6.95-6.87 (m, 4H), 6.16-6.07 (m, 2H), 4.88-4.87 (m, 1H), 4.69 (dd, J=7.3, 3.3 Hz, 1H), 3.81 (s, 6H), 3.51 (dd, J=4.9, 1.9 Hz, 2H), 3.37 (s, 1H), 2.67 (p, J=6.9 Hz, 1H), 1.21 (dd, J=6.9, 0.9 Hz, 6H), 0.77 (s, 9H), 0.01 (s, 3H), −0.28 (s, 3H). $^{31}$P-NMR (162 MHz, DMSO-d$_6$): δ −0.74 (s, 1P).

Preparation 6: 9-{3-azido-5-O-[bis(4-methoxyphenyl)(phenyl)methyl]-3-deoxy-3-D-ribofuranosyl}-2-[(2-methylpropanoyl)amino]-1,9-dihydro-6H-purin-6-one

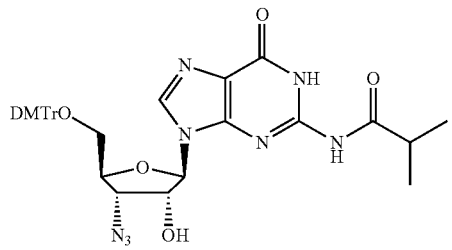

The title compound was prepared according to published procedures (*Nucleosides, Nucleotides & Nucleic Acids* 2005, 24(10-12), 1707-1727).

Preparation 7: 9-{3-azido-5-O-[bis(4-methoxyphenyl)(phenyl)methyl]-3-deoxy-β-D-ribofuranosyl}-N-(phenylcarbonyl)-9H-purin-6-amine

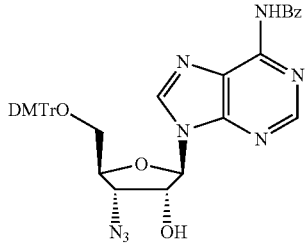

The title compound was prepared according to published procedures (*Bulletin of the Korean Chemical Society* 2004, 25(2), 243-248 and *Nucleosides, Nucleotides & Nucleic Acids* 2005 24(10-12), 1707-1727).

Preparation 8: (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl hydrogen phosphonate

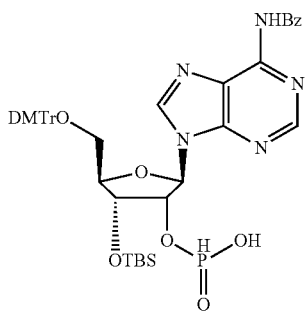

The title compound was prepared according to published procedures (*Tetrahedron*, 1992, 48(15), 3209-3226).

The Preparations below were used as shown or were further modified through additional synthetic manipulations analogous to those described in Preparations 1-9.

Preparation 9: (2R,3R,4S,5R)-2-(6-amino-9H-purin-9-yl)-5-((R)-1-hydroxyethyl)tetrahydrofuran-3,4-diol

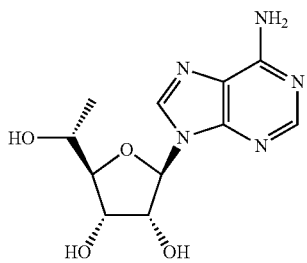 [SMILES: C[C@@H](O)[C@H]1O[C@@H](n2cnc3c(N)ncnc32)[C@H](O)[C@@H]1O]

The title compound was prepared according to published procedures (*Bioorganicheskaya Khimiya* 1989, 15(7), 969-975).

Preparation 10: (2R,3R,4S,5R)-2-(6-amino-9H-purin-9-yl)-5-((S)-1-hydroxyethyl)tetrahydrofuran-3,4-diol

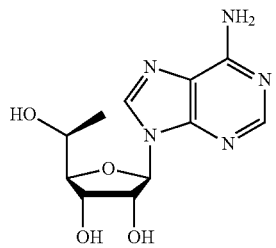

The title compound was prepared according to published procedures (*Bioorganicheskaya Khimiya* 1989, 15(7), 969-975).

Preparation 11: (2R,3S,4R,5R)-2-(6-amino-9H-purin-9-yl)-4-fluoro-5-(hydroxymethyl)tetrahydrofuran-3-ol

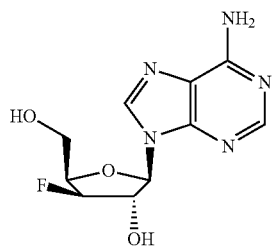 [SMILES: Nc1ncnc2c1ncn2[C@@H]1O[C@H](CO)[C@H](F)[C@H]1O]

The title compound was prepared according to published procedures (Bioorganic & Medicinal Chemistry, 2004, 12, 475-487).

Preparation 12: N-(9-((1S,3R,4R,5S)-4-hydroxy-1-(hydroxymethyl)-2,6-dioxabicyclo[3.2.0]heptan-3-yl)-6-oxo-6,9-dihydro-1H-purin-2-yl)isobutyramide

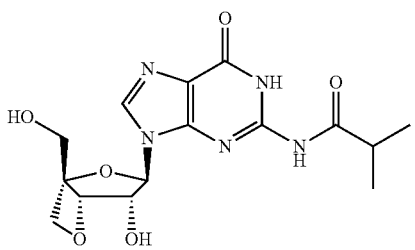 [SMILES: CC(C)C(=O)Nc1nc2c(ncn2[C@@H]2O[C@@]3(CO)CO[C@H]3[C@H]2O)c(=O)[nH]1]

The title compound was prepared according to published procedures (*Tetrahedron*, 2002, 58, 3039-3049).

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular

EXAMPLES

Example 1: 2-amino-9-[(1R,6R,8R,9R,14S,16R,18R)-16-(6-amino-9H-purin-9-yl)-3,11,18-trihydroxy-3,11-dioxido-2,4,7,10,12,15-hexaoxa-3,11-diphosphatricyclo[12.2.1.1⁶,⁹]octadec-8-yl]-1,9-dihydro-6H-purin-6-one

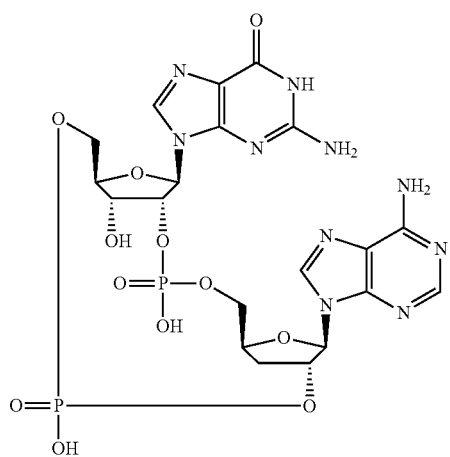 [SMILES: Nc1nc2c(ncn2[C@@H]2O[C@@H]3COP(=O)(O)O[C@@H]4C[C@@H](COP(=O)(O)O[C@@H]2[C@@H]3O)O[C@H]4n2cnc3c(N)ncnc32)c(=O)[nH]1]

Step 1: N-(9-((2R,3R,5S)-3-hydroxy-5-(hydroxymethyl)tetrahydrofuran-2-yl)-9H-purin-6-yl)benzamide

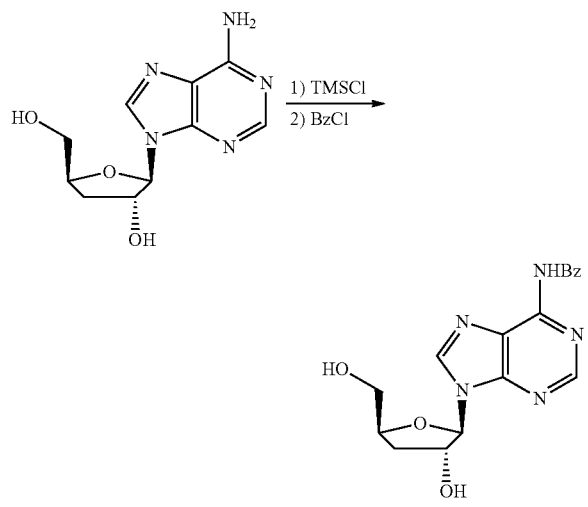

To a suspension of 3'-deoxyadenosine (2.5 g, 10 mmol) in pyridine (40 mL) at 0° C. was added chlorotrimethylsilane (5.43 g, 50.0 mmol). The mixture was stirred at rt for 30 min. Then, the reaction mixture was cooled to 0° C., and benzoyl chloride (2.11 g, 15.0 mmol) was added dropwise. The reaction mixture was stirred at rt for 6 h. Then, water (10 mL) and NH$_4$OH (ca 29%, 20 mL) were added, and the mixture was stirred at rt for 15 min. It was concentrated and purified by silica gel column chromatography using 0-10% MeOH in CH$_2$Cl$_2$ to give the product. LCMS (ES, m/z): 354.0 [M−H]⁻. ¹H-NMR (400 MHz, DMSO-d$_6$): δ 11.21 (s, 1H), 8.77 (s, 1H), 8.75 (s, 1H), 8.13-8.00 (m, 2H), 7.66 (t, J=7.3 Hz, 1H), 7.56 (t, J=7.6 Hz, 2H), 6.06 (d, J=1.9 Hz, 1H), 5.79 (d, J=4.1 Hz, 1H), 5.11 (t, J=5.4 Hz, 1H), 4.67 (dp, J=5.1, 2.6 Hz, 1H), 4.43 (ddt, J=9.5, 6.8, 3.7 Hz, 1H), 3.75 (ddd, J=12.0, 5.4, 3.3 Hz, 1H), 3.57 (ddd, J=12.1, 5.5, 3.9 Hz, 1H), 2.31 (ddd, J=13.2, 9.2, 5.6 Hz, 1H), 1.96 (ddd, J=13.1, 6.1, 2.6 Hz, 1H).

Step 2L N-(9-((2R,3R,5S)-5-((bis(4-methoxyphenyl)(phenyl)methoxy)methyl)-3-hydroxytetrahydrofuran-2-yl)-9H-purin-6-yl)benzamide

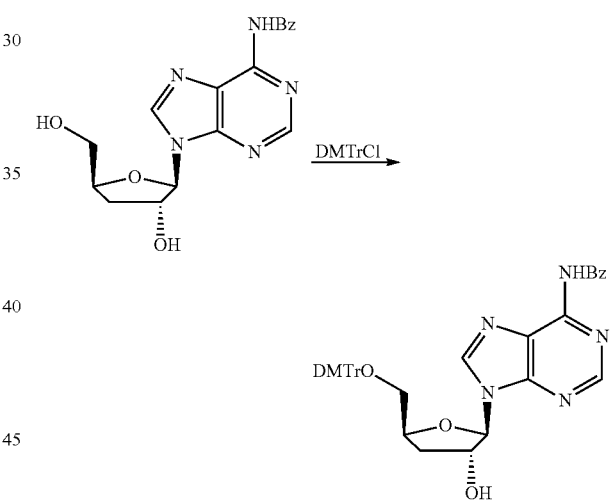

N-(9-((2R,3R,5S)-3-hydroxy-5-(hydroxymethyl)tetrahydrofuran-2-yl)-9H-purin-6-yl)benzamide (1.43 g, 4.02 mmol) was co-evaporated with pyridine (3×10 mL) and re-dissolved in pyridine (4 mL). To the mixture at 0° C. was added DMTrCl (1.50 g, 4.43 mmol), and it was stirred at rt for 17 h. Then, the mixture was concentrated, and the residue was purified by silica gel column chromatography and eluted with 0-10% MeOH in CH$_2$Cl$_2$ (1% Et$_3$N) to give the product. LCMS (ES, m/z): 658.1 [M+H]⁺. ¹H-NMR (400 MHz, CD$_3$OD): δ 8.72 (s, 1H), 8.58 (s, 1H), 8.10 (dd, J=7.3, 1.7 Hz, 2H), 7.72-7.65 (m, 1H), 7.59 (dd, J=8.4, 7.0 Hz, 2H), 7.45-7.39 (m, 2H), 7.33-7.17 (m, 7H), 6.87-6.78 (m, 4H), 6.18 (d, J=1.4 Hz, 1H), 5.01-4.93 (m, 1H), 4.70 (dd, J=8.5, 5.0 Hz, 1H), 3.76 (s, 6H), 3.44 (dd, J=10.6, 2.9 Hz, 1H), 3.38 (dd, J=10.7, 4.7 Hz, 1H), 2.55 (ddd, J=13.5, 9.9, 5.4 Hz, 1H), 2.14-2.06 (m, 1H).

Step 3: (2R,3R,5S)-2-(6-benzamido-9H-purin-9-yl)-5-((bis(4-methoxyphenyl)(phenyl)methoxy)-methyl)tetrahydrofuran-3-yl phosphonate Step 4: (2R,3R,5S)-2-(6-benzamido-9H-purin-9-yl)-5-(hydroxymethyl)tetrahydrofuran-3-yl phosphonate

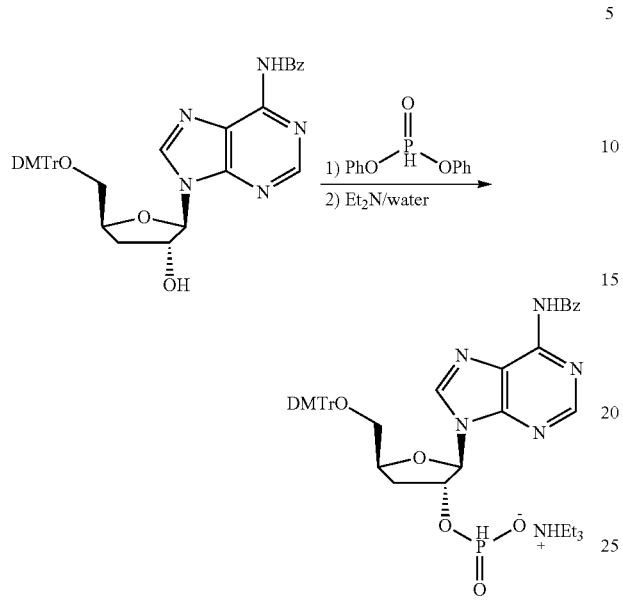

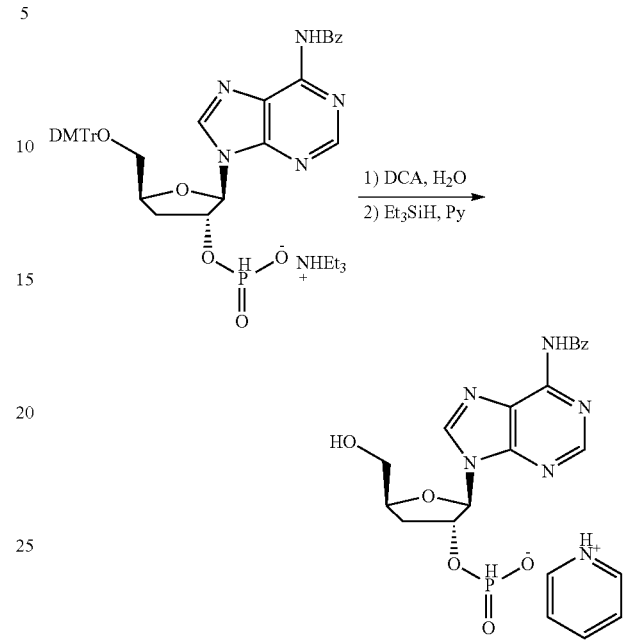

To a solution of N-(9-((2R,3R,5S)-5-((bis(4-methoxyphenyl)(phenyl)methoxy)methyl)-3-hydroxytetrahydrofuran-2-yl)-9H-purin-6-yl)benzamide (0.43 g, 0.65 mmol) in pyridine (3 mL) at rt was added diphenyl phosphonate (1.06 g, 4.55 mmol). After 15 min, water (0.15 mL) and Et$_3$N (0.15 mL) were added, and it was stirred for 15 min. Then, the solution was concentrated, and the residue was partitioned between CH$_2$Cl$_2$ (15 mL with 1% Et$_3$N) and aq NaHCO$_3$ (5%, 10 mL). The organic layer was washed with aq NaHCO$_3$ (5%, 2×10 mL), dried (Na$_2$SO$_4$), concentrated, and purified by silica gel column chromatography using 0-10% MeOH in CH$_2$Cl$_2$ (1% Et$_3$N) to give the product. LCMS (ES, m/z): 722.1 [M+H]$^+$. $^1$H-NMR (400 MHz, CD$_3$OD): δ 8.70 (s, 1H), 8.60 (s, 1H), 8.19-8.04 (m, 2H), 7.75-7.64 (m, 1.5H), 7.59 (t, J=7.6 Hz, 2H), 7.43-7.34 (m, 2H), 7.34-7.12 (m, 7H), 6.79 (dd, J=9.0, 7.3 Hz, 4H), 6.36 (d, J=1.3 Hz, 1H), 6.13 (s, 0.5H), 5.59-5.45 (m, 1H), 4.70 (dd, J=9.2, 4.9 Hz, 1H), 3.77 (d, J=2.8 Hz, 6H), 3.44-3.36 (m, 2H), 3.11 (q, J=7.3 Hz, 12H), 2.87-2.71 (m, 1H), 2.34 (dd, J=13.5, 5.9 Hz, 1H), 1.28 (t, J=7.3 Hz, 18H). $^{31}$P-NMR (162 MHz, CD$_3$OD): δ 3.15 (s), 0.89 (s).

To a solution of (2R,3R,5S)-2-(6-benzamido-9H-purin-9-yl)-5-((bis(4-methoxyphenyl) (phenyl)methoxy)methyl)tetrahydrofuran-3-yl phosphonate (480 mg, 0.58 mmol) in CH$_2$Cl$_2$ (8.7 mL) at rt were added water (0.104 mL, 5.8 mmol) and dichloroacetic acid in CH$_2$Cl$_2$ (0.6M, 8.7 mL, 5.2 mmol). It was stirred at rt for 15 min. Then, triethylsilane (10 mL) was added, and stirring was continued for additional 2 h. To the reaction was added pyridine (7 mL), and it was concentrated to give a crude product, which was used in the next step without purification. LCMS (ES, m/z): 420.3 [M+H]$^+$.

Step 5: (2R,3R,5S)-2-(6-benzamido-9H-purin-9-yl)-5-(((((2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl)oxy)(2-cyanoethoxy)phosphanyl)oxy)methyl)tetrahydrofuran-3-yl phosphonate

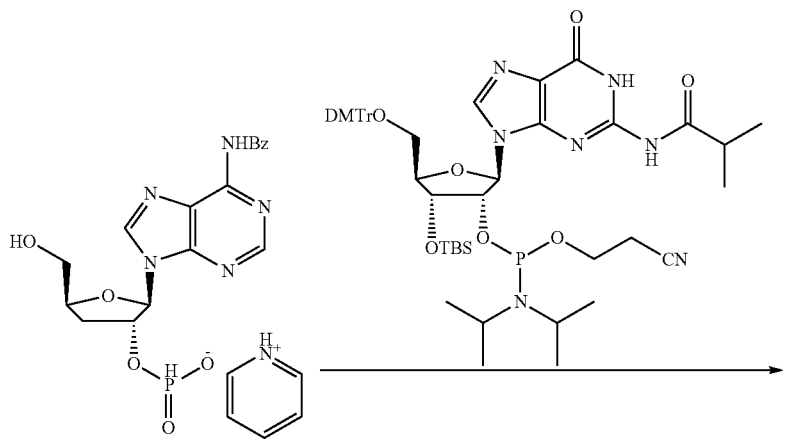

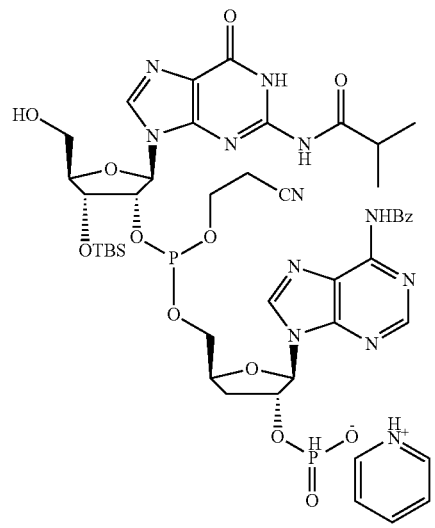

The crude from Step 4 was co-evaporated with ACN (3×5 mL), re-dissolved in ACN (3 mL) under Ar, and dried by adding activated 4 Å molecular sieve (150 mg). (2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) diisopropylphosphoramidite (0.711 g, 0.733 mmol) was co-evaporated with ACN (3×5 mL), re-dissolved in ACN (3 mL), and dried by adding activated 4 Å molecular sieve (150 mg). After 30 min, it was added to the previously prepared mixture containing (2R,3R,5S)-2-(6-benzamido-9H-purin-9-yl)-5-(hydroxymethyl)tetrahydrofuran-3-yl phosphonate. It was stirred at rt for 20 min. The reaction mixture was used in the next reaction step without purification. LCMS (ES, m/z): 984.1 [M+H]$^+$.

Step 6: (2R,3R,5S)-2-(6-benzamido-9H-purin-9-yl)-5-(((((((2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl)oxy)(2-cyanoethoxy)phosphoryl)oxy)methyl)tetrahydrofuran-3-yl hydrogen phosphonate

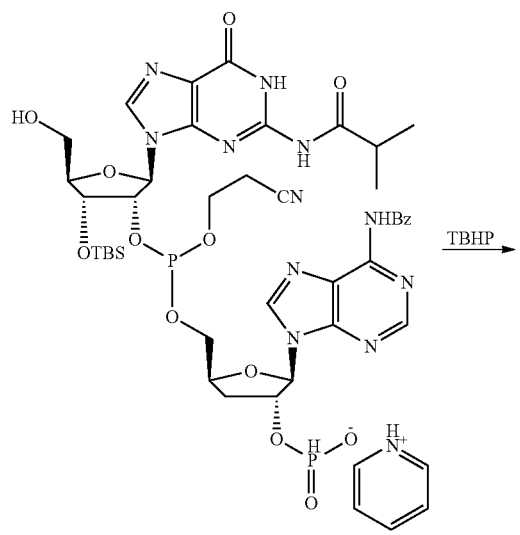

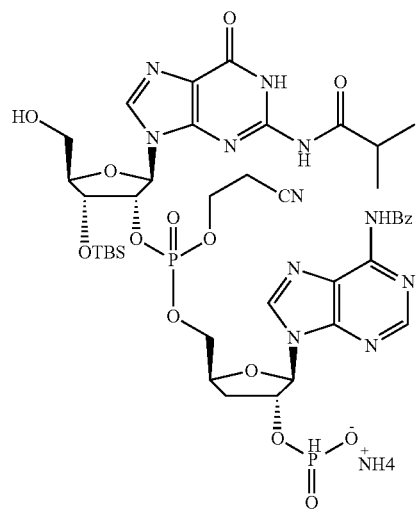

To the reaction mixture at rt from Step 5 was added tert-butyl hydroperoxide in decane solution (5.5M, 0.32 mL, 1.7 mmol) over 2 min, and the resulting mixture was stirred for 1 h. Then, it was cooled at 0° C., and treated with a solution of Na$_2$S$_2$O$_3$.5H$_2$O (500 mg) in H$_2$O (5 mL). Insolubles were filtered off, and the filtrate was concentrated and purified by reverse phase (C18) chromatography and eluted with 0 to 95% ACN in aq NH$_4$HCO$_3$ (5 mM) to give the product. LCMS (ES, m/z): 1002.0 [M+H]$^+$. $^{31}$P-NMR (162 MHz, CD$_3$OD): δ 3.27-3.22 (m), −2.31~−2.51 (m).

101

Step 7: (1R,6R,8R,9R,14S,16R,18R)-16-(6-benzamido-9H-purin-9-yl)-18-((tert-butyldimethylsilyl)oxy)-11-(2-cyanoethoxy)-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 11-oxide

102

Step 8: (1R,6R,8R,9R,14S,16R,18R)-16-(6-benzamido-9H-purin-9-yl)-18-((tert-butyldimethylsilyl)oxy)-11-(2-cyanoethoxy)-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 3,11-dioxide

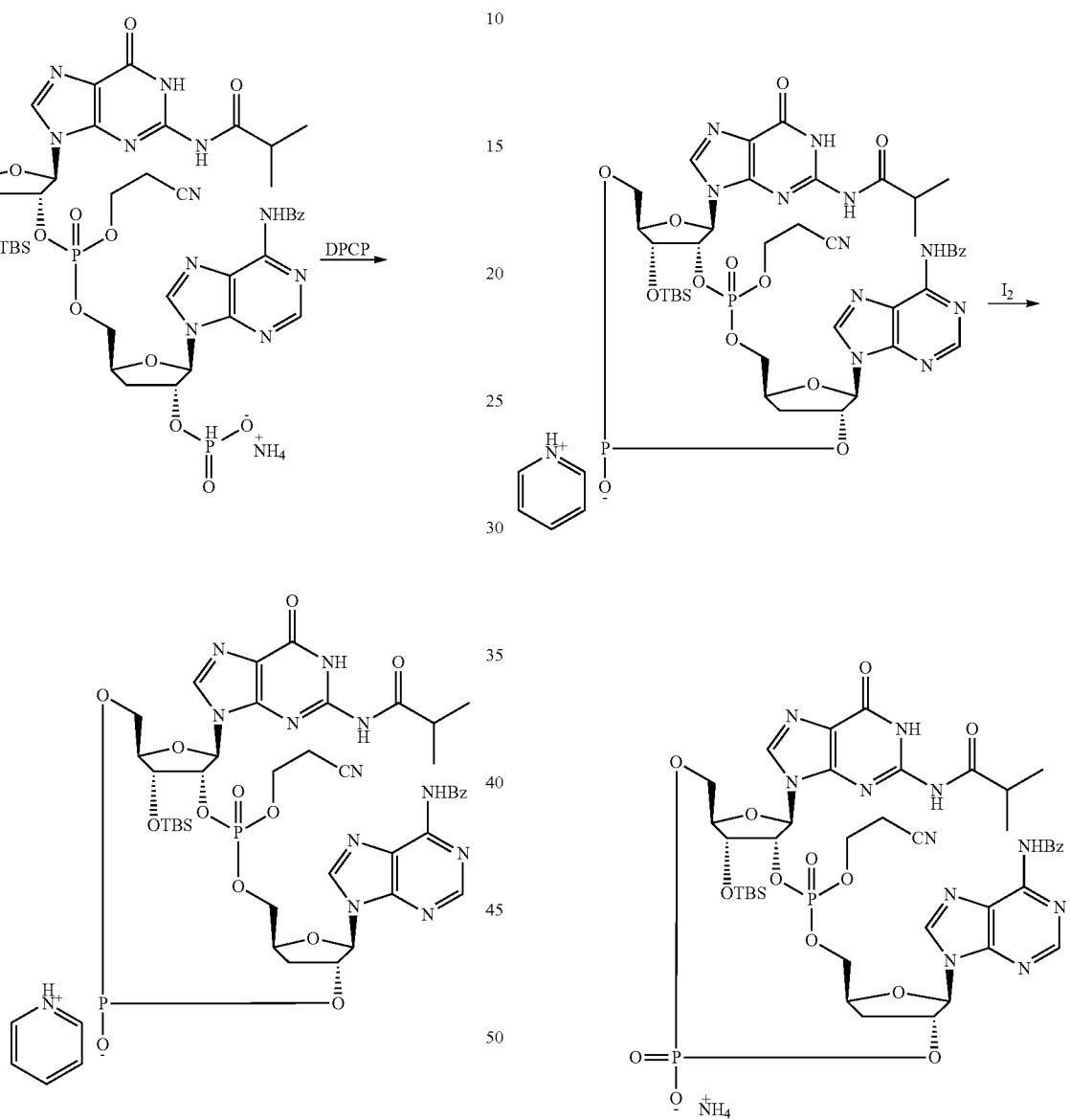

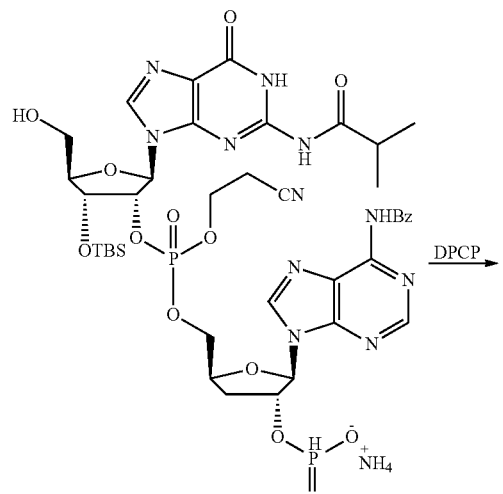

(2R,3R,5S)-2-(6-benzamido-9H-purin-9-yl)-5-(((((2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl)oxy)(2-cyanoethoxy)phosphoryl)oxy)methyl)tetrahydrofuran-3-yl hydrogen phosphonate, ammonia salt (170 mg, 0.17 mmol) was co-evaporated with pyridine (4×3 mL) and then, dissolved in CH$_2$Cl$_2$ (12 mL). This solution was then added to diphenyl phosphorochloridate (0.7 mL, 3.4 mmol) in pyridine (12 mL) at −40° C. over 20 min. The resulting mixture was maintained at the same temperature for 20 min. The reaction mixture was used in the next reaction step directly. LCMS (ES, m/z): 984.2 [M+H]$^+$.

To the mixture from Step 7 at 0° C. was added I$_2$ in pyridine/water (3%, 9/1, 2.5 mL) over 5 min. It was stirred at rt for 30 min. Then, the reaction mixture was slowly poured into a solution of Na$_2$S$_2$O$_3$.5H$_2$O (650 mg) in water (10 mL). After 5 min, the mixture was concentrated. The residue was purified by reverse phase (C18) chromatography and eluted with 0 to 95% ACN in aq NH$_4$HCO$_3$ (5 mM) to give the product. LCMS (ES, m/z): 1000.3 [M+H]$^+$. $^{31}$P-NMR (162 MHz, CD$_3$OD): δ −0.73, −1.32 (2 s, 1P), −1.60, −3.96 (2 s, 1P).

Step 9: (1R,6S,8R,9R,14R,16R,17R)-16-(2-amino-6-oxo-1,6-dihydro-9H-purin-9-yl)-8-(6-amino-9H-purin-9-yl)-17-((tert-butyldimethylsilyl)oxy)-2,4,7,10,12,15-hexaoxa-3,11-diphosphatricyclo[12.2.2.1⁶,⁹]octadecane-3,11-bis(olate) 3,11-dioxide Step 10: 2-amino-9-((1R,6R,8R,9R,14S,16R,18R)-16-(6-amino-9H-purin-9-yl)-3,11,18-trihydroxy-3,11-dioxido-2,4,7,10,12,15-hexaoxa-3,11-diphosphatricyclo[12.2.1.1⁶,⁹]octadecan-8-yl)-1,9-dihydro-6H-purin-6-one

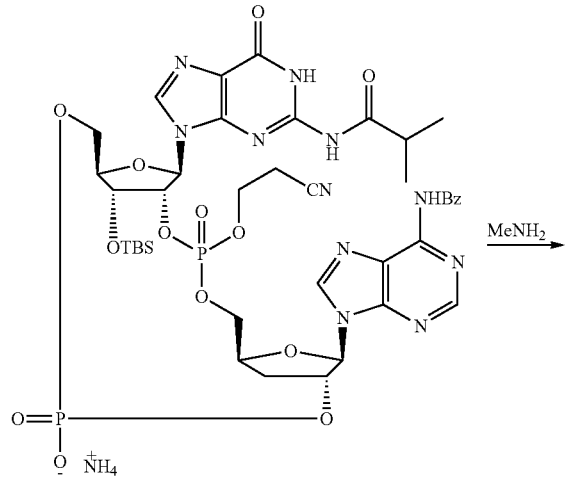

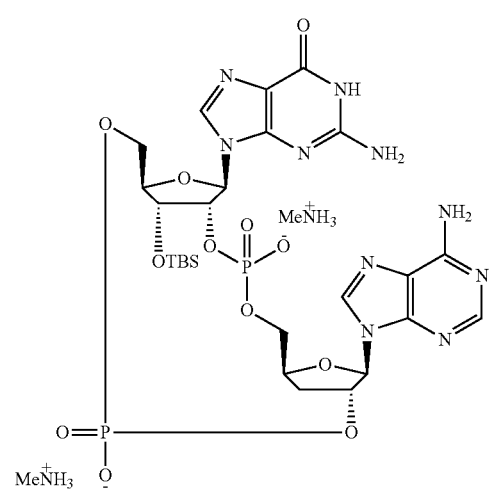

(1R,6R,8R,9R,14S,16R,18R)-16-(6-benzamido-9H-purin-9-yl)-18-((tert-butyldimethylsilyl)oxy)-11-(2-cyanoethoxy)-8-(2-isobutyramido-6-oxo-1,6-dihydro-9H-purin-9-yl)-2,4,7,10,12,15-hexaoxa-3,11-diphosphatricyclo[12.2.1.1⁶,⁹]octadecan-3-olate 3,11-dioxide (120 mg, 0.12 mmol) was dissolved in a solution of MeNH₂ in EtOH (30%, 12 mL), and it was stirred at rt for 6 h. The solution was concentrated, and the residue was used in the next step without purification. LCMS (ES, m/z): 773.3 [M+H]⁺.

The crude from Step 9 was suspended in pyridine (2.5 mL), and triethylamine (1.2 g, 12 mmol) and triethylamine trihydrofluoride (482 mg, 3.0 mmol) were added. The mixture was heated at 50° C. for 6 h. Then, it was concentrated and purified by prep-HPLC (T3 Prep Column, 19×250 mm) and eluted with 0 to 12% ACN in aq NH₄HCO₃ (50 mM) to give the product. LCMS (ES, m/z): 657.0 [M−H]⁻. ¹H-NMR (400 MHz, D₂O): δ 8.16 (s, 1H), 8.07 (s, 1H), 7.79 (s, 1H), 6.08 (d, J=7.0 Hz, 1H), 5.93 (d, J=8.3 Hz, 1H), 5.31-5.24 (m, 2H), 4.69-4.59 (m, 2H), 4.39 (s, 1H), 4.16-4.09 (m, 1H), 4.08-3.98 (m, 3H), 2.70 (q, J=10.9, 10.3 Hz, 1H), 2.53 (dd, J=13.1, 7.1 Hz, 1H). ³¹P-NMR (162 MHz, D₂O): δ −0.79 (s), −1.94 (s).

Examples 2 through 8, as shown in Table 1 below, were prepared according to procedures analogous to those outlined in Example 1 above using the appropriate monomers, described as Preparations or as obtained from commercial sources, in the coupling step.

TABLE 1

| Ex. | Structure | Name | Mass [M − H] |
|---|---|---|---|
| 2 | 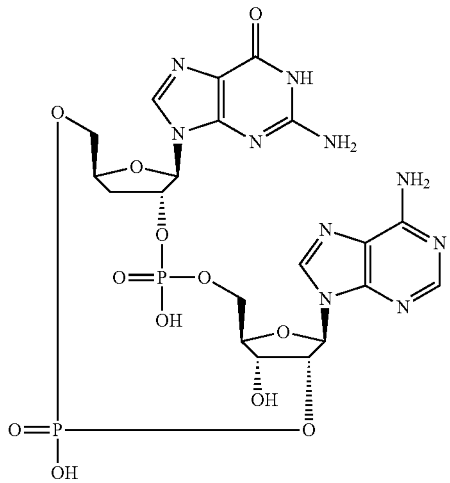 [SMILES: Nc1nc2c(ncn2[C@@H]2O[C@@H]3COP(=O)(O)O[C@@H]4[C@H](O)[C@@H](COP(=O)(O)O[C@@H]2C3)O[C@H]4n2cnc3c(N)ncnc32)c(=O)[nH]1] | 2-amino-9-[(1R,6S,8R,9R,14R,16R,17R)-16-(6-amino-9H-purin-9-yl)-3,11,17-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 657 |
| 3 | 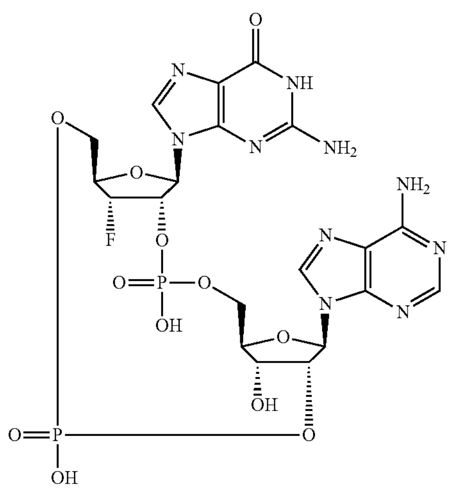 [SMILES: [N-]=[N+]=N[C@H]1[C@H]2OP(=O)(O)OC[C@H]3O[C@@H](n4cnc5c(N)ncnc54)[C@H](OP(=O)(O)OC[C@H]1O[C@H]2n1cnc2c(=O)[nH]c(N)nc21)[C@@H]3O] | 2-amino-9-[(1R,6R,8R,9S,14R,16R,17R,18R)-16-(6-amino-9H-purin-9-yl)-18-fluoro-3,11,17-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 675 |
| 4 | 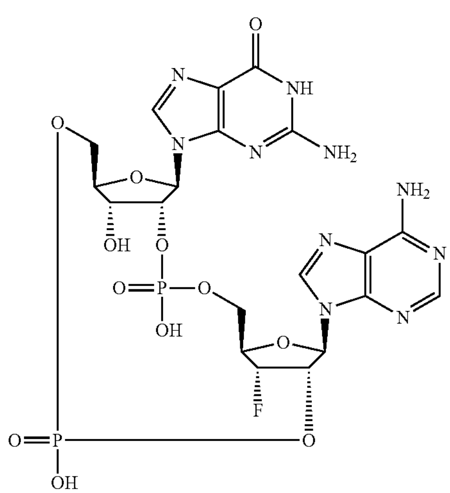 | 2-amino-9-[(1S,6R,8R,9R,14R,16R,17R,18R)-16-(6-amino-9H-purin-9-yl)-17-fluoro-3,11,18-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 675 |

TABLE 1-continued
| Ex. | Structure | Name | Mass [M − H] |
|---|---|---|---|
| 5 | 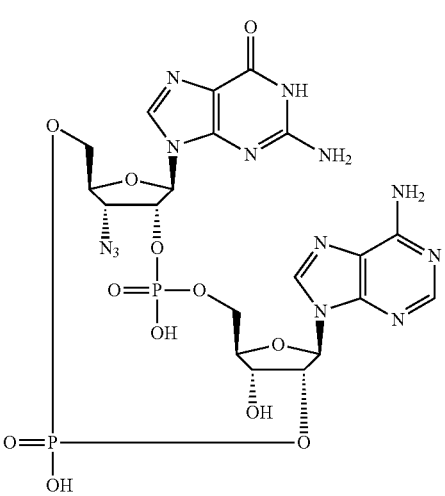 | 2-amino-9-[(1R,6S,8R,9R,14R,16R,17R,18R)-16-(6-amino-9H-purin-9-yl)-18-azido-3,11,17-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 698 |
| 6 | 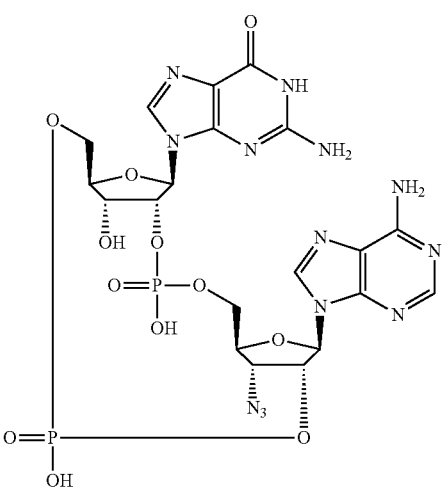 | 2-amino-9-[(1R,6R,8R,9R,14S,16R,17R,18R)-16-(6-amino-9H-purin-9-yl)-17-azido-3,11,18-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 698 |

TABLE 1-continued

| Ex. | Structure | Name | Mass [M − H] |
|---|---|---|---|
| 7 | 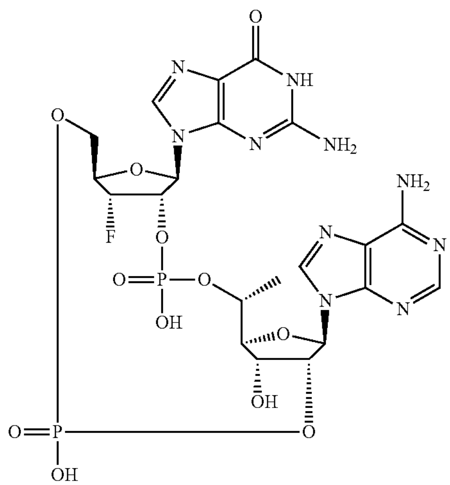 [SMILES: C[C@H]1OP(=O)(O)O[C@@H]2[C@H](F)[C@@H](COP(=O)(O)O[C@@H]3[C@H](O)[C@@H]1O[C@H]3n1cnc3c(N)ncnc31)O[C@H]2n1cnc2c(=O)[nH]c(N)nc21] | 2-amino-9-[(1R,6R,8R,9S,13R,14S,16R,17R,18R)-16-(6-amino-9H-purin-9-yl)-18-fluoro-3,11,17-trihydroxy-13-methyl-3,11-dioxido-2,4,7,10,12,15-hexaoxa-3,11-diphosphatricyclo[12.2.1.1 6,9]octadec-8-yl]-1,9-dihydro-6H-purin-6-one | 689 |
| 8 | 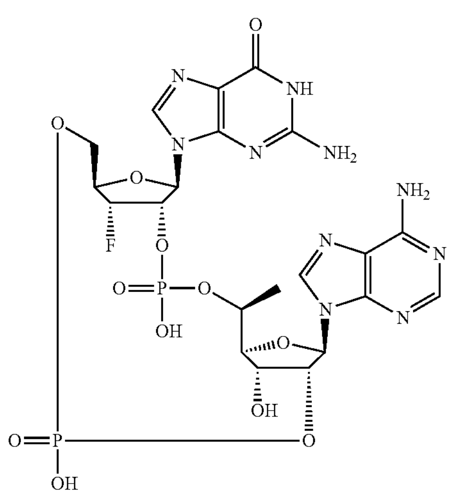 [SMILES: C[C@@H]1OP(=O)(O)O[C@@H]2[C@H](F)[C@@H](COP(=O)(O)O[C@@H]3[C@H](O)[C@@H]1O[C@H]3n1cnc3c(N)ncnc31)O[C@H]2n1cnc2c(=O)[nH]c(N)nc21] | 2-amino-9-[(1R,6R,8R,9S,13S,14S,16R,17R,18R)-16-(6-amino-9H-purin-9-yl)-18-fluoro-3,11,17-trihydroxy-13-methyl-3,11-dioxido-2,4,7,10,12,15-hexaoxa-3,11-diphosphatricyclo[12.2.1.1 6,9]octadec-8-yl]-1,9-dihydro-6H-purin-6-one | 689 |

Example 9: 2-amino-9-[(1R,6R,8R,9S,14S,16R,18R)-16-(6-amino-9H-purin-9-yl)-18-fluoro-3,11-dihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one
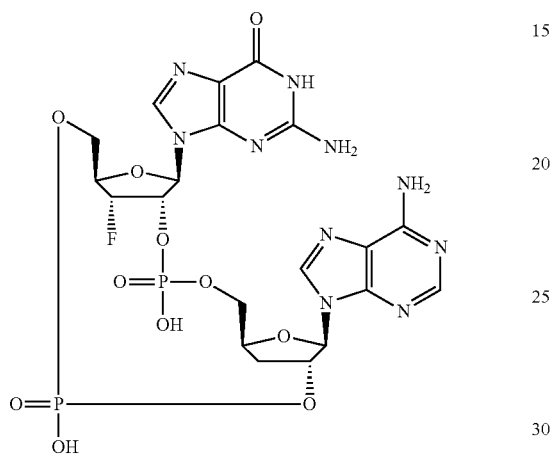
Step 1: (2R,3R,5S)-2-(6-benzamido-9H-purin-9-yl)-5-((((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphanyl)oxy)methyl)tetrahydrofuran-3-yl phosphonate
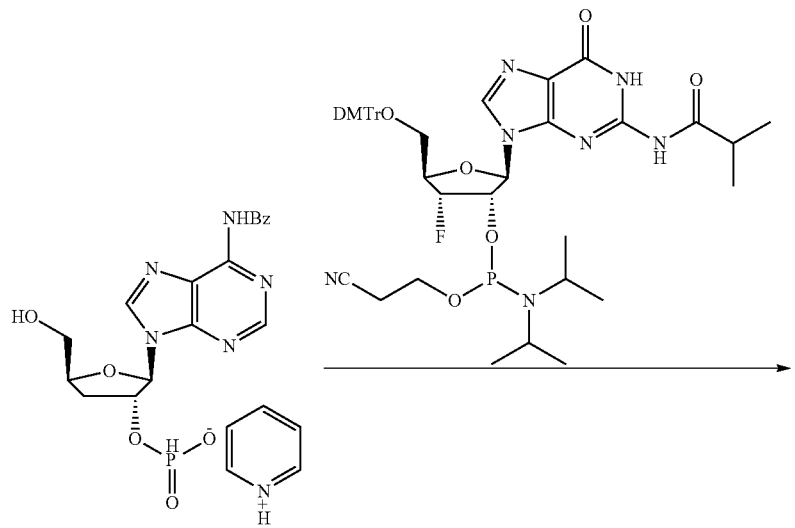

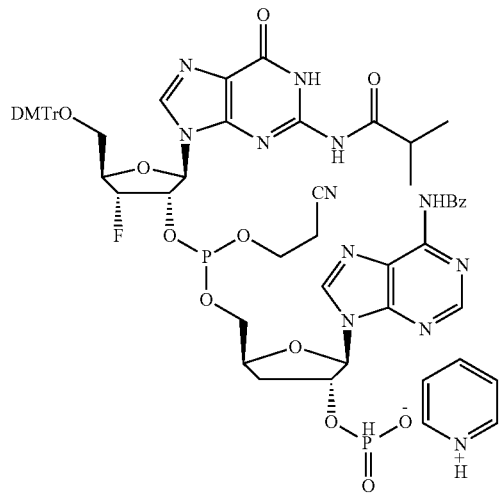

(2R,3S,4R,5R)-5-((bis(4-methoxyphenyl)(phenyl)
methoxy)methyl)-4-fluoro-2-(2-isobutyramido-6-oxo-1,6-
dihydro-9H-purin-9-yl)tetrahydrofuran-3-yl (2-cyanoethyl)
diisopropylphosphoramidite (0.25 g, 0.30 mmol) was co-
evaporated with ACN (3×3 mL), re-dissolved in ACN (3
mL) under Ar, and dried by adding activated 4 Å molecular
sieve (50 mg). Crude (2R,3R,5S)-2-(6-benzamido-9H-pu-
rin-9-yl)-5-(hydroxymethyl)-tetrahydrofuran-3-yl phospho-
nate (0.5 g, ~0.3 mmol, with excess pyridinium 2,2-dichlo-
roacetate salt) was co-evaporated with ACN (3×5 mL),
re-dissolved in ACN (5 mL), and dried by adding activated
4 Å molecular sieve (50 mg). After 30 min, it was added to
the previously prepared mixture containing (2R,3S,4R,5R)-
5-((bis(4-methoxyphenyl)(phenyl)methoxy)methyl)-4-
fluoro-2-(2-isobutyramido-6-oxo-1,6-dihydro-9H-purin-9-
yl)tetrahydrofuran-3-yl (2-cyanoethyl)
diisopropylphosphoramidite. The resulting mixture was
stirred at rt for 30 min. The reaction mixture was used for the
next step without purification. LCMS (ES, m/z): 1174.3
[M−H]⁻.

Step 2: (2R,3R,5S)-2-(6-benzamido-9H-purin-9-yl)-
5-(((((2R,3S,4R,5R)-5-((bis(4-methoxyphenyl)(phe-
nyl)methoxy)methyl)-4-fluoro-2-(2-isobutyramido-
6-oxo-1,6-dihydro-9H-purin-9-yl)tetrahydrofuran-3-
yl)oxy)(2-cyanoethoxy)phosphoryl)oxy)methyl)-
tetrahydrofuran-3-yl phosphonate

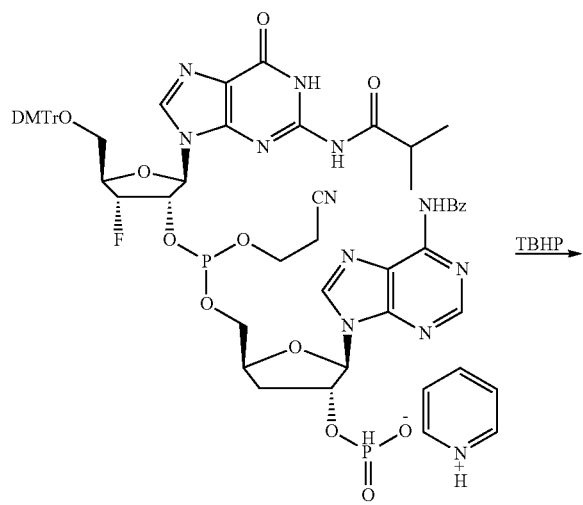

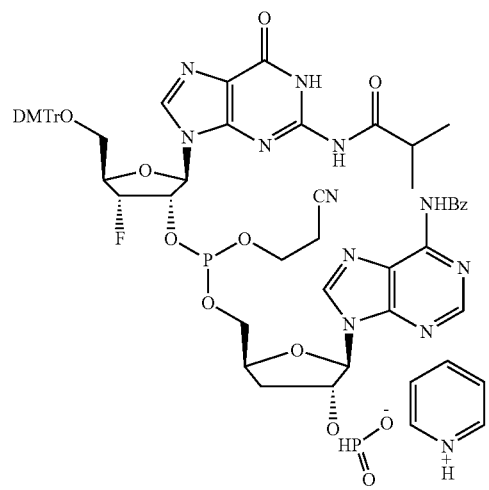

To the reaction mixture from Step1 at rt was added
tert-butyl hydroperoxide in decane (5.5M, 0.191 mL, 1.05
mmol) over 1 min, and the resulting mixture was stirred for
1 h. Then, it was cooled in an ice bath, and treated with a
solution of $Na_2S_2O_3 \cdot 5H_2O$ (400 mg) in water (5 mL). The
solids formed were filtered off, and the filtrate was concen-
trated under reduced pressure to give the crude product.
LCMS (ES, m/z): 1190.3 [M−H]⁻.

Step 3: (2R,3R,5S)-2-(6-benzamido-9H-purin-9-yl)-5-((((2-cyanoethoxy)(((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphoryl)oxy)tetrahydrofuran-3-yl phosphonate Step 4: (1R,6R,8R,9S,14S,16R,18R)-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo[12.2.1.1^{6,9}]octadecan-3-olate 11-oxide

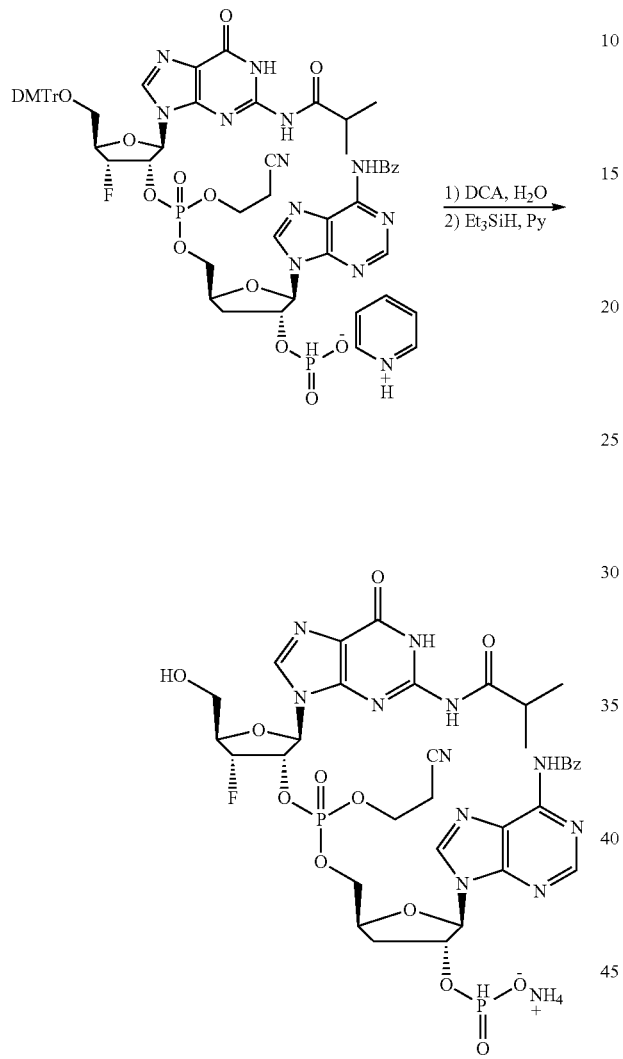

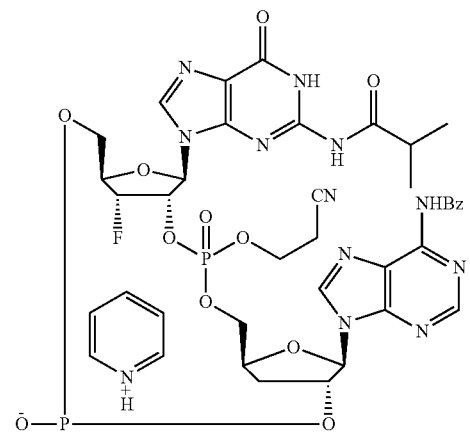

To a solution of the crude from Step 2 in CH$_2$Cl$_2$ (4.5 mL) at rt was added water (54 mg, 3.0 mmol) and 2,2-dichloroacetic acid in CH$_2$Cl$_2$ (0.6M, 4.50 mL, 2.70 mmol) over 2 min, and the resulting mixture was stirred for 10 min. Then, triethylsilane (10 mL) was added, and stirring was continued for 1 h. Pyridine (0.9 mL) was added, and the mixture was stirred for 10 min. It was concentrated and purified by reverse phase (AQ C18) chromatography and eluted with 0 to 95% ACN in aq NH$_4$HCO$_3$ (0.04%) to give the product. LCMS (ES, m/z): 890.2 [M+H]$^+$. $^1$H-NMR (400 MHz, CD$_3$OD): δ 8.74 (2 s, 1H), 8.50 (2 s, 1H), 8.30 (2 s, 1H), 8.16-8.08 (m, 2H), 7.72-7.64 (m, 1.5H), 7.59-7.56 (m, 2H), 6.34 (s, 0.5H), 6.27-6.09 (m, 2H), 5.62-5.19 (m, 3H), 4.69 (m, 1H), 4.47-4.25 (m, 3H), 4.23-4.03 (m, 2H), 3.79 (m, 2H), 2.87-2.78 (m, 1H), 2.78-2.66 (m, 2H), 2.39 (m, 1H), 1.27-1.16 (m, 6H). $^{31}$P-NMR: (162 MHz, CD$_3$OD): δ 3.14 (s, 1P); −2.96, −3.05 (2 s, 1P).

To pyridine (10 mL) at −40° C. under Ar was added diphenyl phosphorochloridate (484 mg, 1.80 mmol) and a solution of (2R,3R,5S)-2-(6-benzamido-9H-purin-9-yl)-5-((((2-cyanoethoxy) (((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphoryl)oxy)methyl) tetrahydrofuran-3-yl phosphonate (80 mg, 0.090 mmol, co-evaporated with pyridine 3×3 mL) in CH$_2$Cl$_2$ (10 mL) dropwise over 20 min. The resulting mixture was stirred at −40° C. for 40 min. It was used in the next reaction step without purification. LCMS (ES, m/z): 872.2 [M+H]$^+$.

Step 5: (1R,6R,8R,9S,14S,16R,18R)-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 3,11-dioxide Step 6: 2-amino-9-((1R,6R,8R,9S,14S,16R,18R)-16-(6-amino-9H-purin-9-yl)-18-fluoro-3,11-dihydroxy-3,11-dioxido-2,4,7,10,12,15-hexaoxa-3,11-diphosphatricyclo[12.2.1.1$^{6,9}$]octadecan-8-yl)-1,9-dihydro-6H-purin-6-one

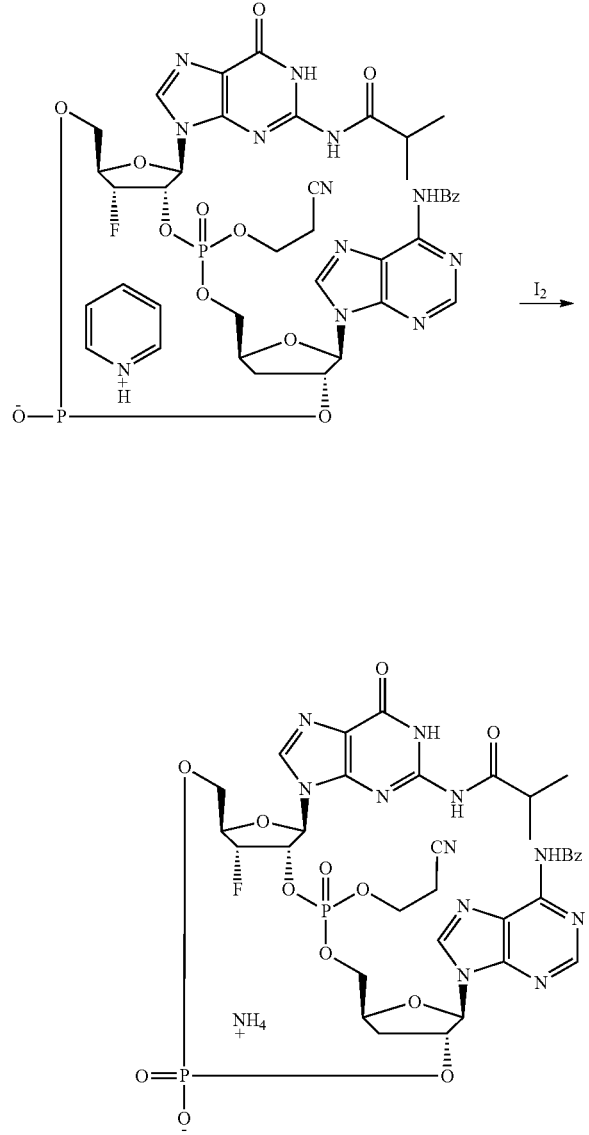

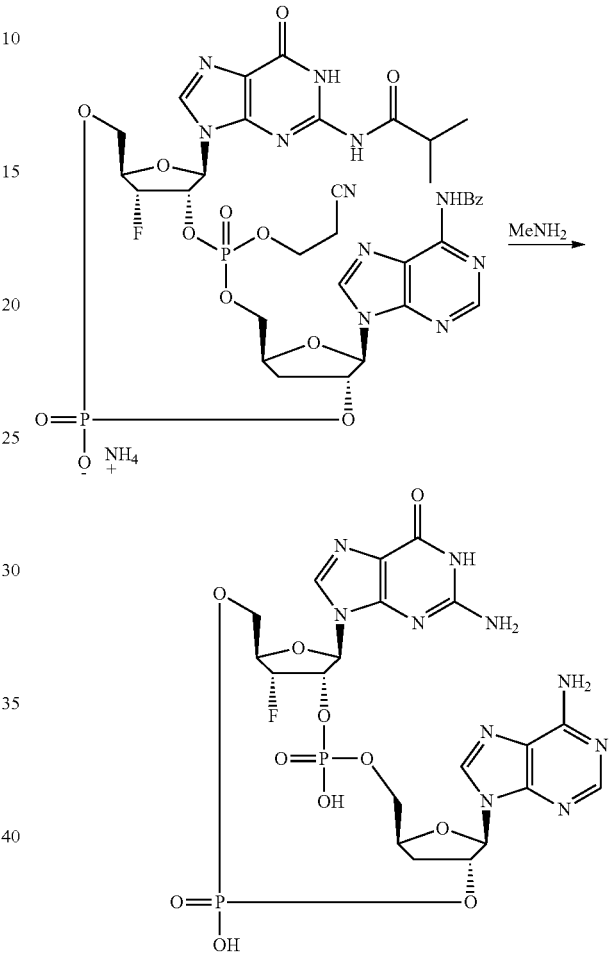

To the reaction mixture from Step 4 at rt was added I$_2$ in pyridine/water (3%, 9/1, 3 mL) dropwise over 5 min, and the mixture was stirred for 1 h. Then, the reaction mixture was cooled in an ice bath, and Na$_2$S$_2$O$_3$.5H$_2$O (0.3 g) in water (1 mL) was added. After 5 min, the reaction mixture was concentrated, and the residue was purified by reverse phase (C18) chromatography and eluted with 0 to 95% ACN in aq NH$_4$HCO$_3$ (5 mM) to give the product. LCMS (ES, m/z): 888.1 [M+H]$^+$.

(1R,6R,8R,9S,14S,16R,18R)-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 3,11-dioxide (240 mg, 0.11 mmol) was dissolved in MeNH$_2$ in EtOH (30%, 10 mL), and it was stirred at rt for 3 h. Then, it was concentrated and purified by Prep-HPLC (T3 Prep Column, 19 mm×250 mm) and eluted with ACN in aq NH$_4$HCO$_3$ (50 mM) to give the product. LCMS (ES, m/z): 659.1 [M−H]$^−$. $^1$H-NMR (400 MHz, D$_2$O): δ 8.12 (s, 1H), 8.08 (s, 1H), 7.81 (s, 1H), 6.10 (d, J=6.9 Hz, 1H), 6.03 (d, J=8.4 Hz, 1H), 5.56 (d, J=3.4 Hz, 0.5H), 5.49-5.40 (m, 1H), 5.37 (dd, J=8.3, 4.4 Hz, 0.5H), 5.21 (q, J=8.2 Hz, 1H), 4.70-4.62 (m, 2H), 4.28-4.17 (m, 1H), 4.17-4.03 (m, 3H), 2.76 (q, J=10.8, 10.4 Hz, 1H), 2.54 (dd, J=13.1, 7.0 Hz, 1H). $^{31}$P-NMR (162 MHz, D$_2$O): δ −1.45 (s), −2.13 (s).

Examples 10 through 13, as shown in Table 2 below, were prepared according to procedures analogous to those outlined in Example 9 above using the appropriate monomers, described as Preparations or as obtained from commercial sources, in the coupling step.

TABLE 2

| Ex. | Structure | Name | Mass [M − H] |
|---|---|---|---|
| 10 | 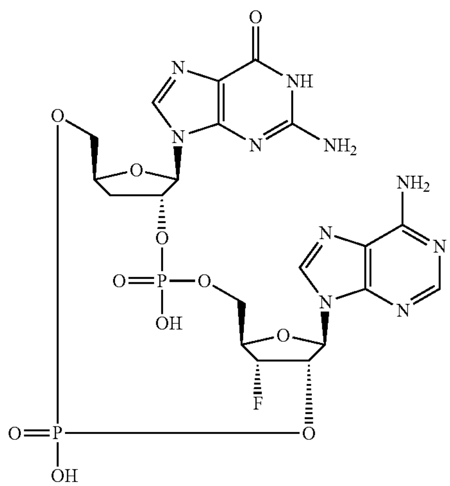 [SMILES: Nc1nc2c(ncn2[C@@H]2O[C@@H]3COP(=O)(O)O[C@@H]4[C@H](F)[C@@H](COP(=O)(O)O[C@@H]2C3)O[C@H]4n2cnc3c(N)ncnc32)c(=O)[nH]1] | 2-amino-9-[(1S,6S,8R,9R,14R,16R,17R)-16-(6-amino-9H-purin-9-yl)-17-fluoro-3,11-dihydroxy-3,11-dioxido-2,4,7,10,12,15-hexaoxa-3,11-diphosphatricyclo[12.2.1.1⁶,⁹]octadec-8-yl]-1,9-dihydro-6H-purin-6-one | 659 |
| 11 | 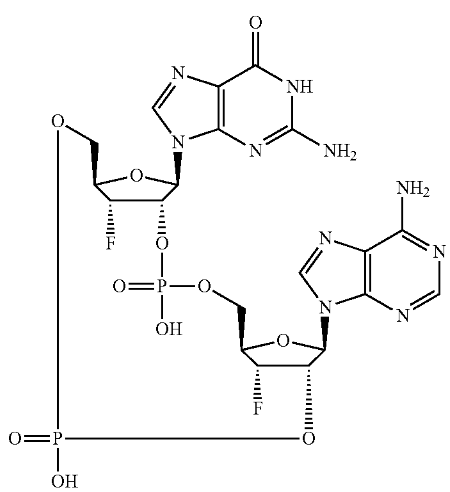 [SMILES: Nc1nc2c(ncn2[C@@H]2O[C@@H]3COP(=O)(O)O[C@@H]4[C@H](F)[C@@H](COP(=O)(O)O[C@@H]2[C@@H]3F)O[C@H]4n2cnc3c(N)ncnc32)c(=O)[nH]1] | 2-amino-9-[(1S,6R,8R,9S,14R,16R,17R,18R)-16-(6-amino-9H-purin-9-yl)-17,18-difluoro-3,11-dihydroxy-3,11-dioxido-2,4,7,10,12,15-hexaoxa-3,11-diphosphatricyclo[12.2.1.1⁶,⁹]octadec-8-yl]-1,9-dihydro-6H-purin-6-one | 677 |
| 12 | 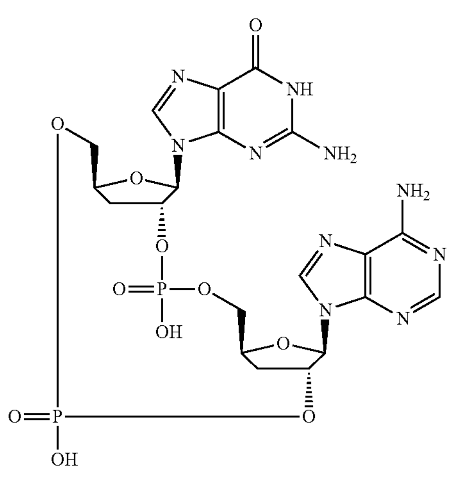 [SMILES: Nc1nc2c(ncn2[C@@H]2O[C@@H]3COP(=O)(O)O[C@@H]4C[C@@H](COP(=O)(O)O[C@@H]2C3)O[C@H]4n2cnc3c(N)ncnc32)c(=O)[nH]1] | 2-amino-9-[(1R,6S,8R,9R,14S,16R)-16-(6-amino-9H-purin-9-yl)-3,11-dihydroxy-3,11-dioxido-2,4,7,10,12,15-hexaoxa-3,11-diphosphatricyclo[12.2.1.1⁶,⁹]octadec-8-yl]-1,9-dihydro-6H-purin-6-one | 641 |

TABLE 2-continued

| Ex. | Structure | Name | Mass [M − H] |
|---|---|---|---|
| 13 | 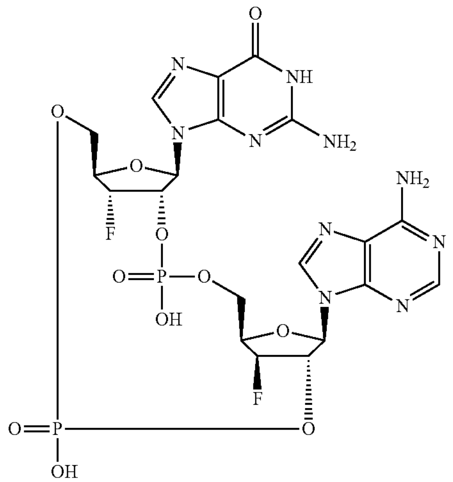 [SMILES: Nc1nc2c(ncn2[C@@H]2O[C@@H]3COP(=O)(O)O[C@@H]4[C@@H](F)[C@@H](COP(=O)(O)O[C@@H]2[C@@H]3F)O[C@H]4n2cnc3c(N)ncnc32)c(=O)[nH]1] | 2-amino-9-[(1S,6R,8R,9S,14R,16R,17S,18R)-16-(6-amino-9H-purin-9-yl)-17,18-difluoro-3,11-dihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 677 |

Example 14: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one (Diastereomer 1)

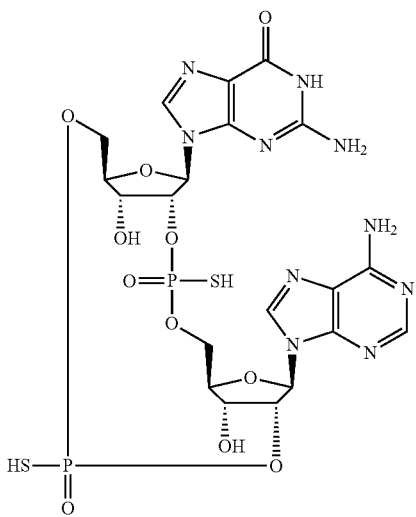 [SMILES: Nc1nc2c(ncn2[C@@H]2O[C@@H]3COP(=O)(S)O[C@@H]4[C@H](O)[C@@H](COP(=O)(S)O[C@@H]2[C@@H]3O)O[C@H]4n2cnc3c(N)ncnc32)c(=O)[nH]1]

Step 1: (2R,3R,4R,5R)-2-(6-benzamido-9H-purin-9-yl)-4-((tert-butyldimethylsilyl)oxy)-5-(hydroxymethyl)tetrahydrofuran-3-yl phosphonate

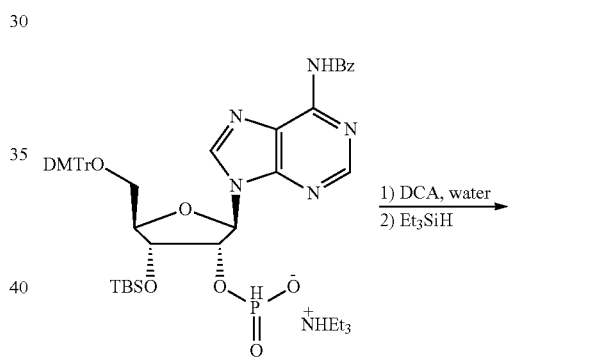

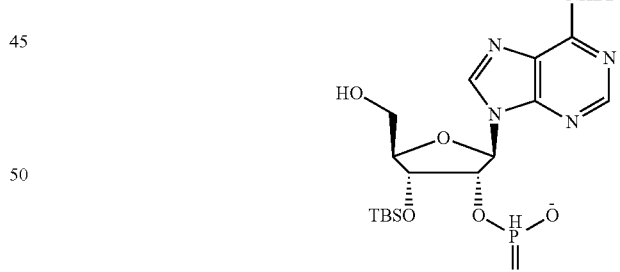

To a solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl phosphonate (0.47 g, 0.51 mmol) in CH$_2$Cl$_2$ (8 mL) at rt was added dichloroacetic acid in CH$_2$Cl$_2$ (0.56M, 8.0 mL, 4.5 mmol). After stirring for 30 min, triethylsilane (2 mL) was added, and stirring was continued for 1.5 h. Pyridine (0.7 mL) was added, and it was concentrated to give crude product, which was used in the next step without purification. LCMS (ES, m/z): 550.2 [M+H]$^+$.

Step 2: (2R,3R,4R,5R)-2-(6-benzamido-9H-purin-9-yl)-5-((((((2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl)oxy)(2-cyanoethoxy)phosphanyl)oxy)methyl)-4-((tert-butyldimethylsilyl)oxy)tetrahydrofuran-3-yl phosphonate

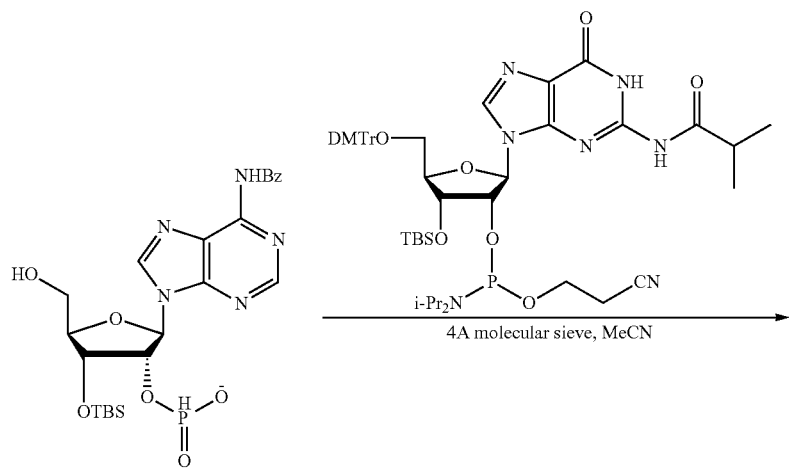

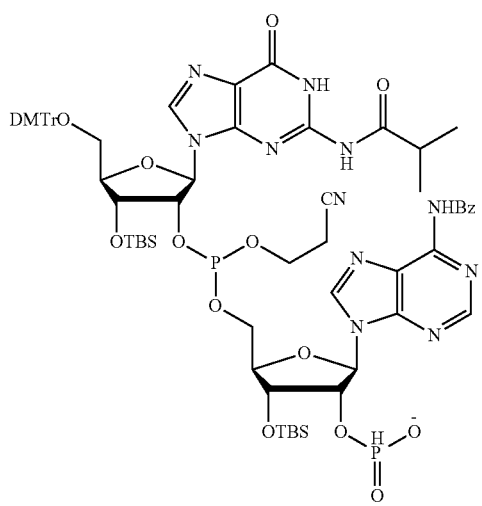

To a stirred solution of (2R,3R,4R,5R)-2-(6-benzamido-9H-purin-9-yl)-4-((tert-butyldimethylsilyl)oxy)-5-(hydroxymethyl)tetrahydrofuran-3-yl phosphonate (1.28 g, 2.32 mmol) in MeCN (10 ml) under Ar was added activated 4 Å molecular sieve (50 mg), and the mixture was stirred at RT over 3 h. (2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) diisopropylphosphoramidite (2.93 g, 3.02 mmol) was co-evaporated with dry MeCN (three times, 5 mL each) and then re-dissolved in MeCN (10 mL) and dried by adding activated 4 Å molecular sieve (50 mg). After 30 min, the solution containing phosphoramidite was transferred into the solution of the dried phosphonate and activated 4 Å molecular sieve by syringe under Ar. After 10 min, the desired product was observed by LCMS and TLC. The reaction mixture was used for the next reaction step directly. LC-MS: (ES, m/z) 1418.57 [M+H]$^+$.

Step 3: (2R,3R,4R,5R)-2-(6-benzamido-9H-purin-9-yl)-5-((((((2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl)oxy)(2-cyanoethoxy)phosphorothioyl) oxy)methyl)-4-((tert-butyldimethylsilyl)oxy)tetrahydrofuran-3-yl phosphonate Step 4: (2R,3R,4R,5R)-2-(6-benzamido-9H-purin-9-yl)-4-((tert-butyldimethylsilyl)oxy)-5-((((((2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl)oxy)(2-cyanoethoxy)phosphorothioyl)oxy)methyl)tetrahydrofuran-3-yl phosphonate

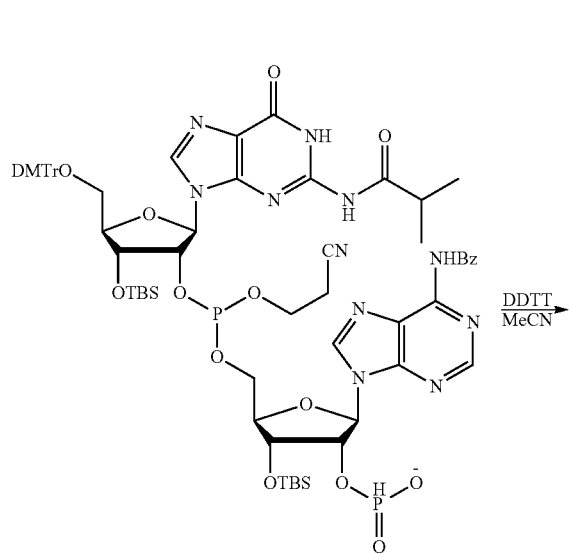

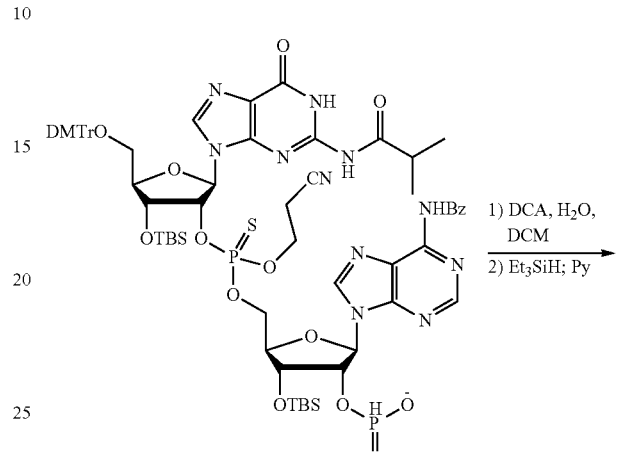

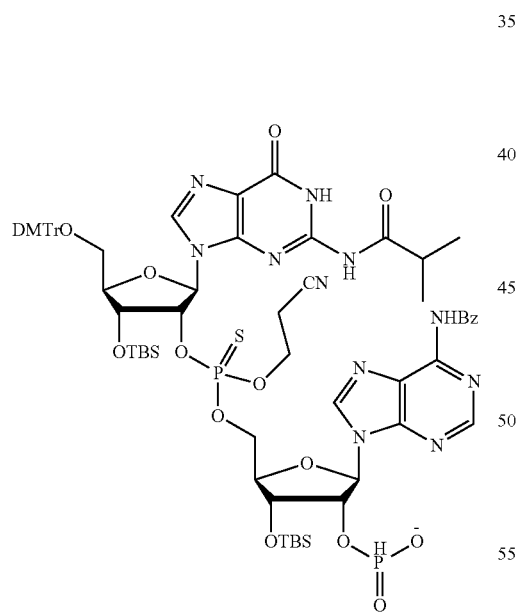

To the reaction mixture containing the crude product of the previous step was added (E)-N,N-dimethyl-N-(3-thioxo-3H-1,2,4-dithiazol-5-yl)formimidamide (0.525 g, 2.56 mmol) in one portion, and the resulting mixture was stirred at RT for 30 min. TLC and LCMS indicated completion of reaction. The reaction mixture was concentrated under reduced pressure and was used in the next step without purification. LCMS (ES, m/z): 1450.64 [M+H]$^+$.

To a solution of the product of Step 3 (2.04 g, 1.4 mmol) in DCM (20 ml) and H$_2$O (0.254 ml, 14.08 mmol) was added 2,2-dichloroacetic acid (1.60 g, 12.39 mmol) in DCM (6% DCA in DCM). The resulting solution was stirred at RT for 30 min. TLC/LCMS indicated completion of the reaction. Then, Et$_3$SiH (10 ml) was added. The resulting solution was stirred for 2 h at RT. Then, pyridine (0.64 g) was added. The resulting solution was concentrated under reduced pressure and was used for the next step without purification. LCMS (ES, m/z): 1148.27 [M+H]$^+$.

127

Step 5: (1R,6R,8R,9R,14R,16R,17R,18R)-17,18-bis{[tert-butyl(dimethyl)silyl]oxy}-11-(2-cyanoethoxy)-8-{2-[(2-methylpropanoyl)amino]-6-oxo-1,6-dihydro-9H-purin-9-yl}-16-{6-[(phenylcarbonyl)amino]-9H-purin-9-yl}-2,4,7,10,12,15-hexaoxa-3,11-diphosphatricyclo[12.2.1.1$^{6,9}$]octadecan-3-olate 11-sulfide

128

Step 6: Diastereomers (1R,6R,8R,9R,14R,16R,17R,18R)-17,18-bis{[tert-butyl(dimethyl)silyl]oxy}-11-(2-cyanoethoxy)-8-{2-[(2-methylpropanoyl)amino]-6-oxo-1,6-dihydro-9H-purin-9-yl}-16-{6-[(phenylcarbonyl)amino]-9H-purin-9-yl}-2,4,7,10,12,15-hexaoxa-3,11-diphosphatricyclo[12.2.1.1$^{6,9}$]octadecane-3-thiolate 3-oxide 11-sulfide (AA1) and (1R,6R,8R,9R,14R,16R,17R,18R)-17,18-bis{[tert-butyl(dimethyl)silyl]oxy}-11-(2-cyanoethoxy)-8-{2-[(2-methylpropanoyl)amino]-6-oxo-1,6-dihydro-9H-purin-9-yl}-16-{6-[(phenylcarbonyl)amino]-9H-purin-9-yl}-2,4,7,10,12,15-hexaoxa-3,11-diphosphatricyclo[12.2.1.1$^{6,9}$]octadecane-3-thiolate 3-oxide 11-sulfide (AA2)

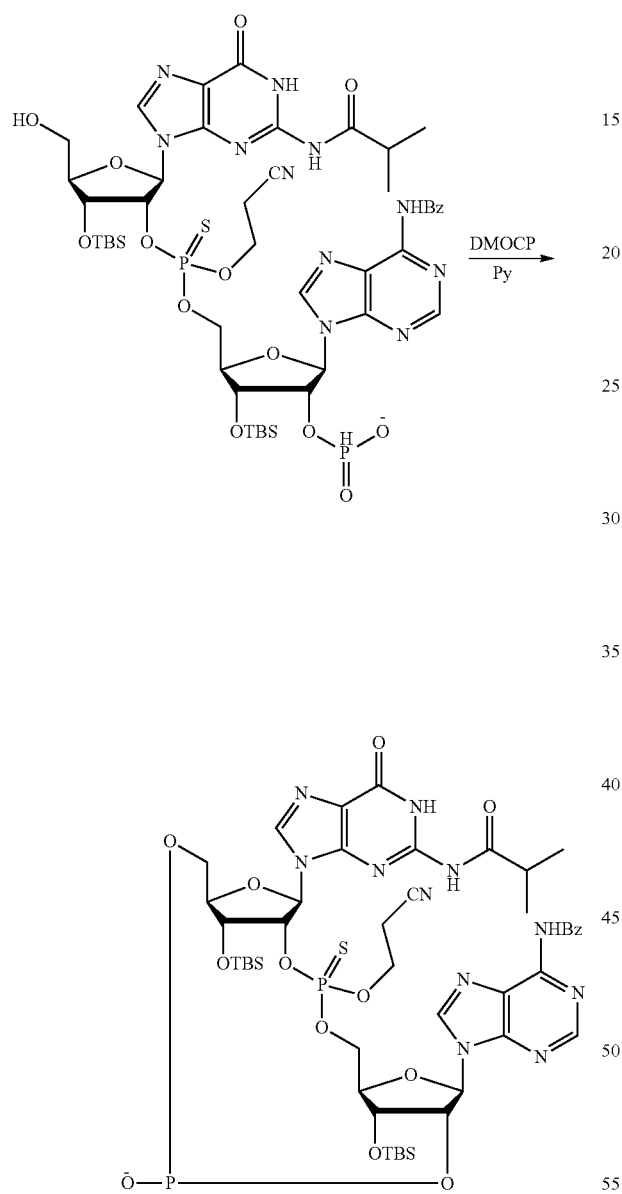

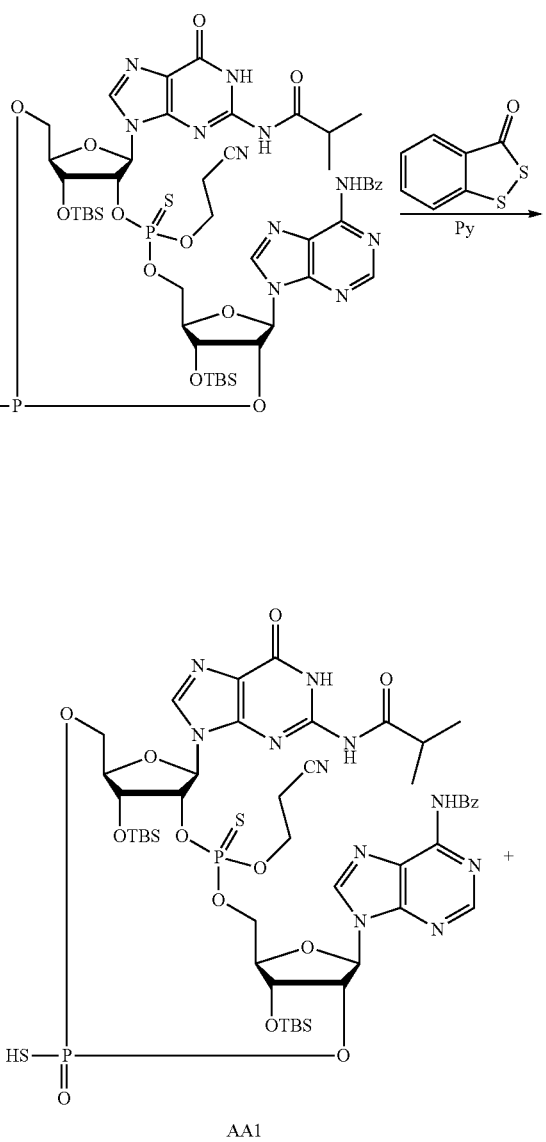

AA1

The crude sample from Step 4 (600 mg, 0.523 mmol) was co-evaporated with dry pyridine (2 mL each, three times) and then re-dissolved in dry pyridine (6 ml). To the solution under Ar, was added 2-chloro-5,5-dimethyl-1,3,2-dioxaphosphinane 2-oxide (338 mg, 1.830 mmol) at RT in one portion. After 30 min, the desired product was observed from LCMS as major product. The reaction mixture was used in the next step directly. LCMS (ES, m/z): 1130.26 [M+H]$^+$.

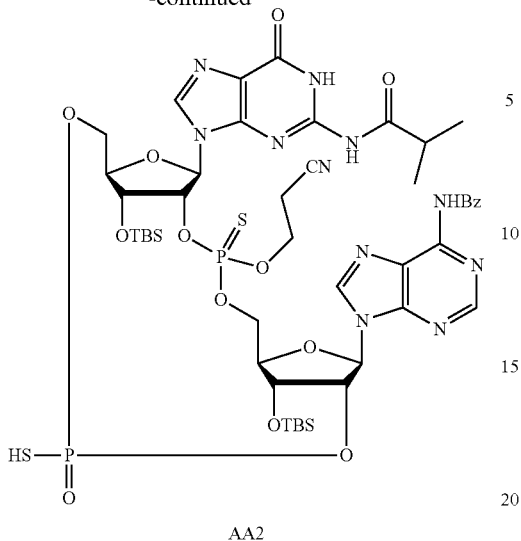

AA2

To the solution from Step 5 was added H₂O (0.329 mL, 18.3 mmol) and 3H-benzo[c][1,2]dithiol-3-one (147 mg, 0.874 mmol). The resulting mixture was stirred at RT for 40 min. TLC and LCMS indicated completion of the reaction. The reaction mixture was poured into aq NaHCO₃ (2.7 g NaHCO₃ in 100 mL H₂O) and stirred for 5 min. The resulting mixture was extracted with EtOAc (30 ml×3), and the organic layers were combined. It was concentrated and was purified by preparative TLC developed with 100 MeOH in DCM to give the desired products AA1 ($R_f$=0.5) and AA2 ($R_f$=0.3). AA1: LCMS (ES, m/z): 1162.32 [M+H]⁺. AA2: LCMS (ES, m/z): 1162.32 [M+H]⁺.

Step 7: Diastereomers (1R,6R,8R,9R,14R,16R,17R,18R)-17,18-bis{[tert-butyl(dimethyl)silyl]oxy}-8-{2-[(2-methylpropanoyl)amino]-6-oxo-1,6-dihydro-9H-purin-9-yl}-16-{6-[(phenylcarbonyl)amino]-9H-purin-9-yl}-2,4,7,10,12,15-hexaoxa-3,11-diphosphatricyclo[12.2.1.1⁶,⁹]octadecane-3,11-bis(thiolate) 3,11-dioxide (BB1) and (1R,6R,8R,9R,14R,16R,7R,18R)-17,18-bis{[tert-butyl(dimethyl)silyl]oxy}-8-{2-[(2-methylpropanoyl)amino]-6-oxo-1,6-dihydro-9H-purin-9-yl}-16-{6-[(phenylcarbonyl)amino]-9H-purin-9-yl}-2,4,7,10,12,15-hexaoxa-3,11-diphosphatricyclo[12.2.1.1⁶,⁹]octadecane-3,11-bis(thiolate) 3,11-dioxide (BB2)

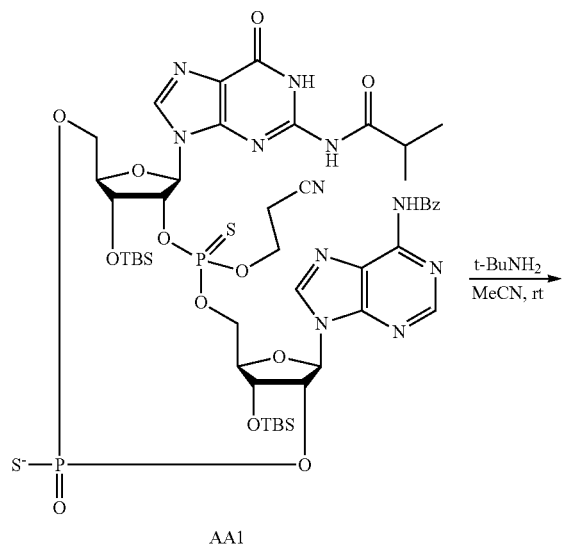

AA1

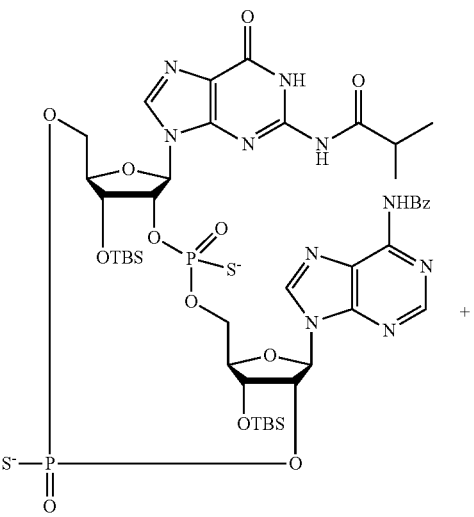

BB1

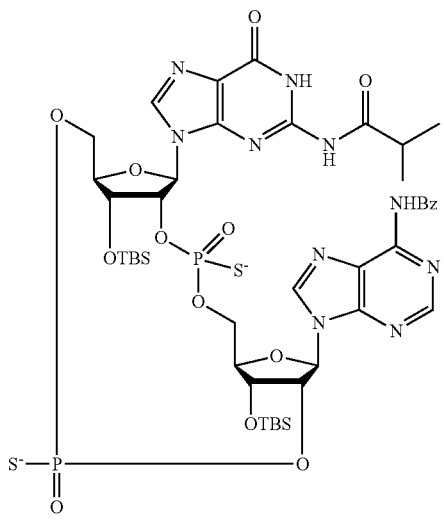

BB2

To a solution of crude Compound AA1 (300 mg, 0.258 mmol) from the previous step in MeCN (1.3 ml) under Ar was added 2-methylpropan-2-amine (1.29 ml, 12.17 mmol), and the resulting mixture was stirred for 30 min. After the reaction completed, the volatile components were removed under reduced pressure. The residue was purified by reverse phase prep-HPLC (X-Bridge BEH130 Prep C18) and eluted with 30 to 70% MeCN in aq NH₄HCO₃ (10 mM) over 8 min to give compound diastereomers BB1 ($T_R$=7.57 min) and BB2 ($T_R$=5.77 min). BB1: LCMS (ES, m/z): 1109.26 [M+H]⁺. BB2: LCMS (ES, m/z): 1109.26 [M+H]⁺.

Step 8: 2-amino-9-[(1R,6R,8R,9R,14R,16R,17R,18R)-16-(6-amino-9H-purin-9-yl)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1⁶,⁹]octadec-8-yl]-1,9-dihydro-6H-purin-6-one Step 8: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1⁶,⁹]octadec-8-yl]-1,9-dihydro-6H-purin-6-one

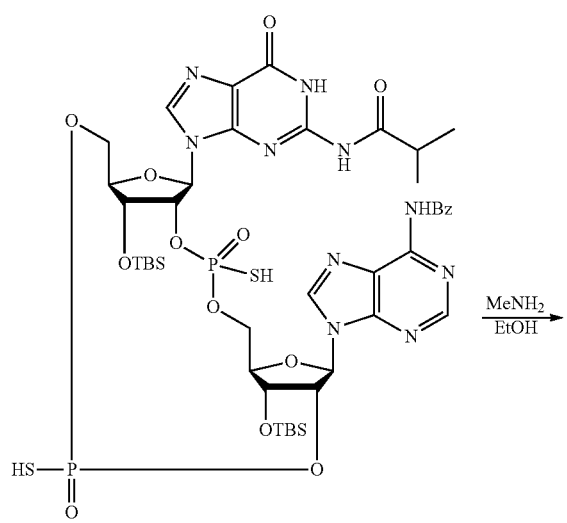

To a solution of Compound BB1 from Step 7 (81 mg, 0.073 mmol) in EtOH (3 ml), 30% methylamine (909 mg, 29.3 mmol) was added. The resulting solution was stirred for 3 h. LCMS indicated completion of reaction. It was concentrated and used directly for the next step. LCMS (ES, m/z): 935.06 [M+H]⁺.

To the crude product from Step 8 (68 mg, 0.073 mmol) in pyridine (1 ml) were added TEA (737 mg, 7.29 mmol) and trimethylamine trihydrofluoride (587 mg, 3.64 mmol). The resulting mixture was stirred at 50° C. After 5 h, LCMS indicated completion of the reaction. Volatile components were evaporated under reduced pressure. The residue was purified by reverse phase prep-HPLC and eluted with aq NH₄HCO₃ (50 mM) over 1 min to give the desired product. LCMS (ES, m/z): 705.10 [M−H]⁻. H-NMR (400 MHz, D₂O): δ 8.11 (s, 1H), 8.07 (s, 1H), 7.77 (s, 1H), 6.23 (d, J=8 Hz, 1H), 5.94 (d, J=8.4 Hz, 1H), 5.24 (m, 1H), 5.18 (m, 1H), 4.89 (d, J=4 Hz, 1H), 4.84 (d, J=4 Hz, 1H), 4.52 (d, J=3.6 Hz, 1H), 4.45 (d, J=3.6 Hz, 1H), 4.36 (m, 2H), 4.04 (m, 2H). ³¹P-NMR (121 MHz, D₂O, ppm): δ 52.01 (s, 1P), 50.97 (s, 1P).

Example 15: 2-amino-9-[(1R,6R,8R,9R,14R,16R, 17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one (Diastereomer 2)

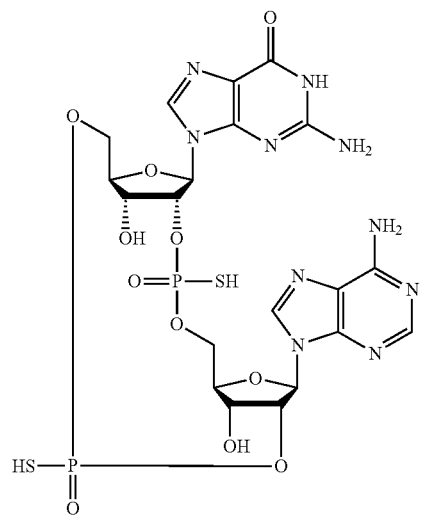

Step 1: 2-amino-9-[(1R,6R,8R,9R,14R,16R,17R, 18R)-16-(6-amino-9H-purin-9-yl)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one

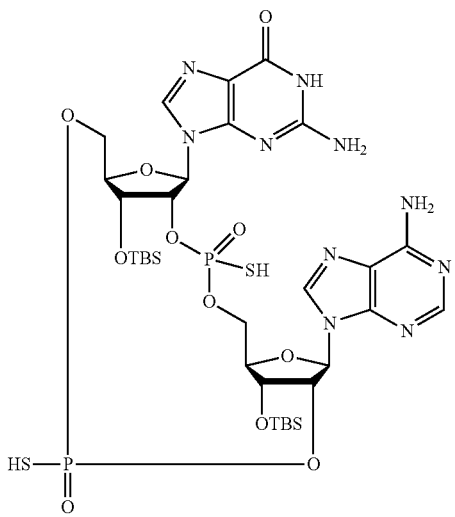

To a solution of Compound BB2 from Example 14, Step 7 (76 mg, 0.069 mmol) in EtOH (3 ml), was added 30% methylamine (85 mg, 27.5 mmol). The resulting solution was stirred for 3 h. LCMS indicated completion of reaction. The solution was concentrated and used directly for the next step. LCMS (ES, m/z): 935.06 [M+H]$^+$.

Step 2: 2-amino-9-[(1R,6R,8R,9R,14R,16R,17R, 18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one

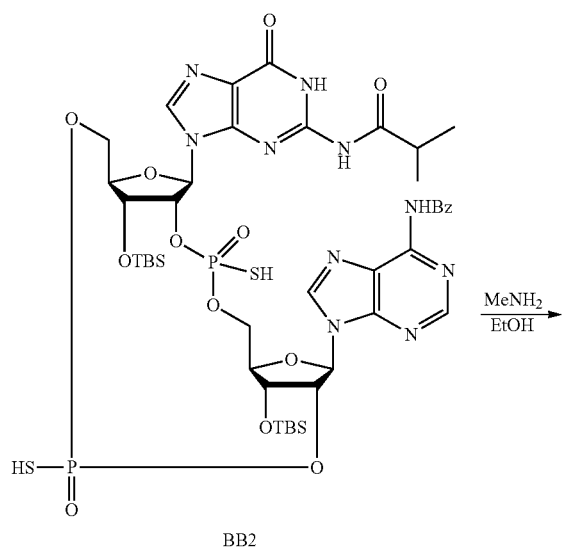

BB2

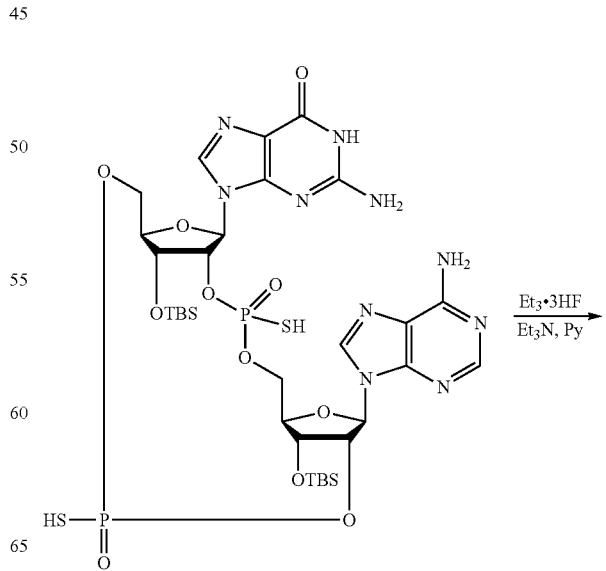

-continued

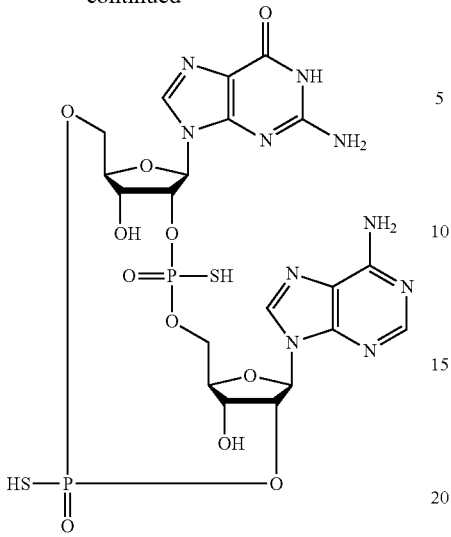

To the crude product from Step 1 (64 mg, 0.069 mmol) in pyridine (1 ml) were added TEA (694 mg, 6.86 mmol) and trimethylamine trihydrofluoride (553 mg, 3.43 mmol). The resulting mixture was stirred at 50° C. After 5 h, LCMS indicated completion of the reaction. Volatile components were evaporated under reduced pressure. The residue was purified by reverse phase prep-HPLC (X-Bridge BEH130 Prep C18) and eluted with 75 to 90% MeCN in aq NH$_4$HCO$_3$ (50 mM) over 13 min to give the desired product. LCMS (ES, m/z): 705.10 [M−H]$^−$. H-NMR (400 MHz, D$_2$O): δ 8.46 (s, 1H), 8.08 (s, 1H), 7.79 (s, 1H), 6.22 (d, J=8 Hz, 1H), 5.90 (d, J=8 Hz, 1H), 5.30 (m, 1H), 5.17 (m, 1H), 4.84 (d, J=3.6 Hz, 1H), 4.55 (d, J=3.6 Hz, 1H), 4.48 (s, 1H), 4.42 (s, 1H), 4.33 (d, J=7.2 Hz, 1H), 4.13 (m, 2H), 4.03 (d, J=11.6 Hz, 1H). $^{31}$P-NMR (121 MHz, D$_2$O, ppm): δ 56.18 (s, 1P), 51.21 (s, 1P).

Example 16: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one (Diastereomer 3)

Step 1: Diastereomers N-{9-[(1R,6R,8R,9R,14R,16R,17R,18R)-17,18-bis{[tert-butyl(dimethyl)silyl]oxy}-16-{2-[(2-methylpropanoyl)amino]-6-oxo-1,6-dihydro-9H-purin-9-yl}-3,11-dioxido-3,11-disulfanyl-2,4,7,10,12,15-hexaoxa-3,11-diphosphatricyclo[12.2.1.1$^{6,9}$]-octadec-8-yl}-9H-purin-6-yl benzamide (BB3) and N-{9-[(1R,6R,8R,9R,14R,16R,17R,18R)-17,18-bis{[tert-butyl(dimethyl)silyl]oxy}-16-{2-[(2-methylpropanoyl)amino]-6-oxo-1,6-dihydro-9H-purin-9-yl}-3,11-dioxido-3,11-disulfanyl-2,4,7,10,12,15-hexaoxa-3,11-diphosphatricyclo[12.2.1.1$^{6,9}$]octadec-8-yl]-9H-purin-6-yl}benzamide (BB4)

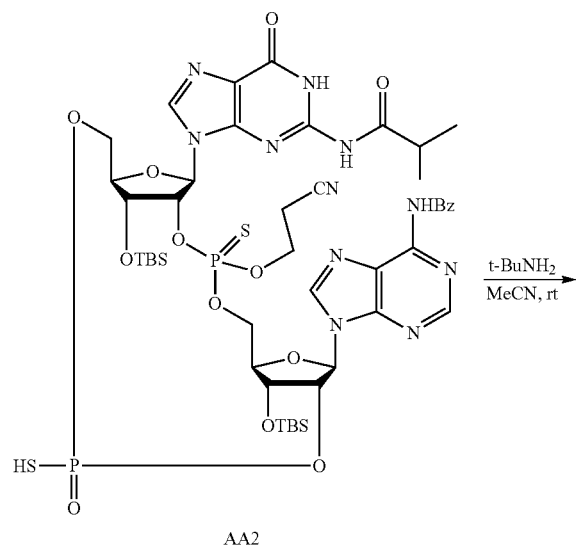

AA2

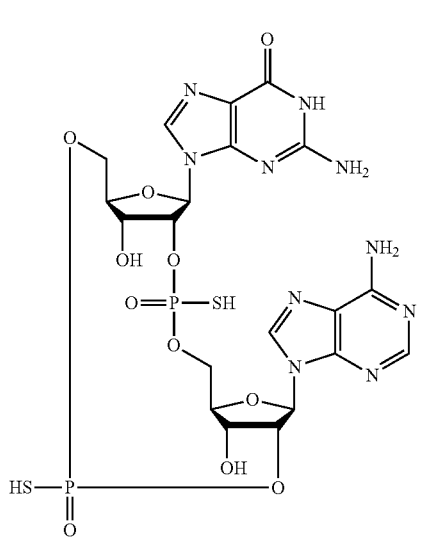 [SMILES: Nc1nc2c(ncn2[C@@H]2O[C@@H]3COP(=O)(S)O[C@H]4C(O)[C@@H](COP(=O)(S)O[C@H]2C3O)O[C@H]4n2cnc3c(N)ncnc32)c(=O)[nH]1]

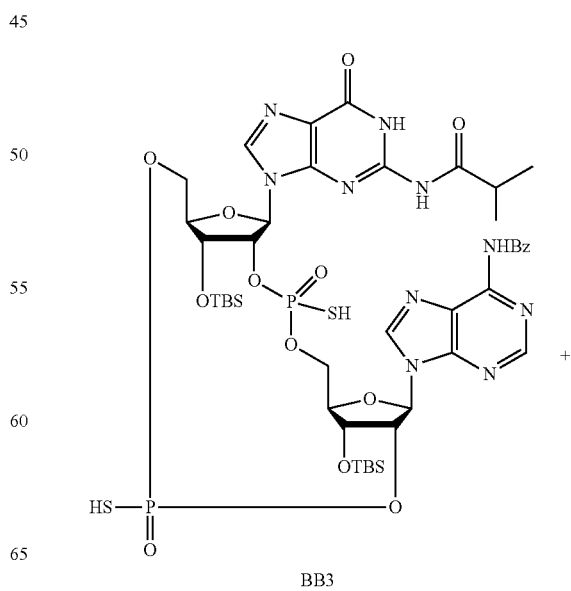

BB3

-continued

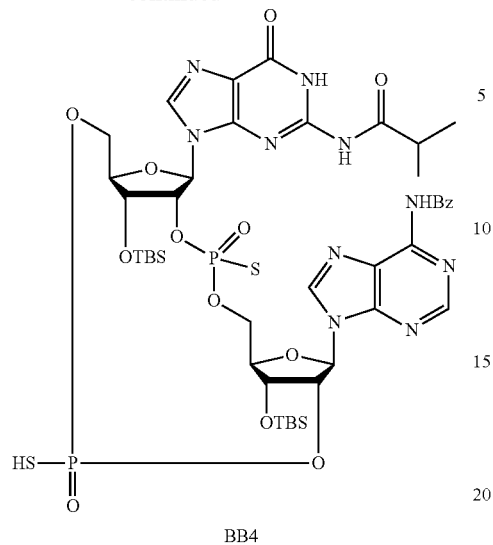

BB4

To a solution of crude AA2 (200 mg, 0.172 mmol) from Example 14, Step 6 in MeCN (0.8 ml) under Ar was added 2-methylpropan-2-amine (0.860 ml, 8.1 mmol), and the resulting mixture was stirred for 30 min. After the reaction has gone to completion, the volatile components were removed under reduced pressure. The residue was purified by reverse phase prep-HPLC and eluted with 10 to 50% MeCN in aq NH$_4$HCO$_3$ (20 mM) over 15 min to give diastereomers BB3 ($T_R$=11.92 min) and BB4 ($T_R$=7.88 min). BB3: LCMS (ES, m/z): 1109.26 [M+H]$^+$. BB4: LCMS (ES, m/z): 1109.26 [M+H]$^+$.

Step 2: 2-amino-9-[(1R,6R,8R,9R,14R,16R,17R,18R)-16-(6-amino-9H-purin-9-yl)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one -continued To a solution of Compound BB3 from the previous step (61 mg, 0.055 mmol) in EtOH (2.5 ml), 30% methylamine (684 mg, 22.0 mmol) was added. The resulting solution was stirred for 3 h. LCMS indicated completion of reaction, and the product was concentrated and used directly for the next step. LCMS (ES, m/z): 935.06 [M+H]$^+$.

Step 3: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1$^{6,9}$]octadec-8-yl]-1,9-dihydro-6H-purin-6-one

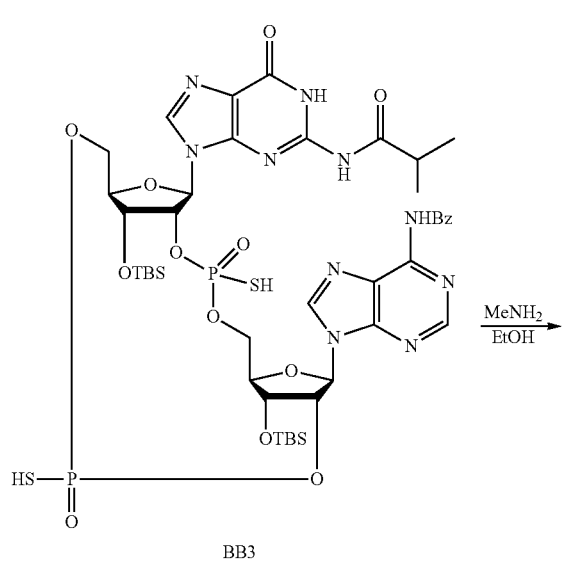

BB3

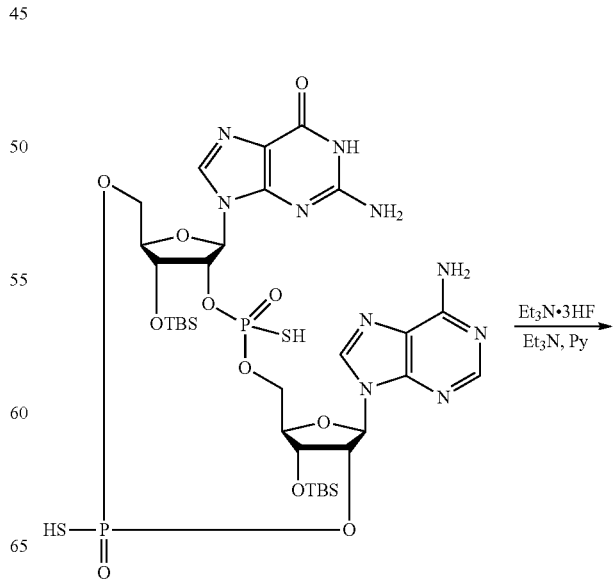

MeNH$_2$ / EtOH →

Et$_3$N·3HF / Et$_3$N, Py →

-continued

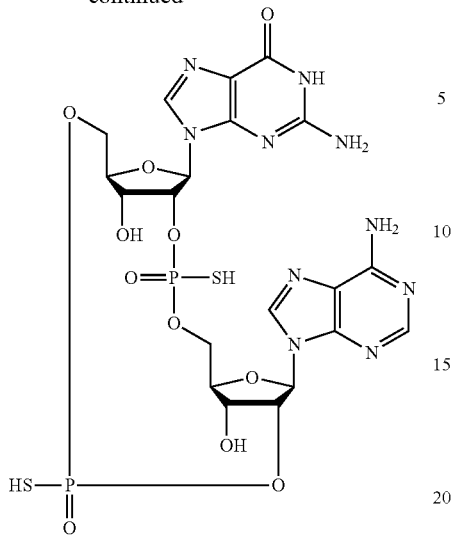

To the crude product from Step 2 (51.5 mg, 0.055 mmol) in pyridine (1 ml) were added TEA (559 mg, 5.52 mmol) and trimethylamine trihydrofluoride (445 mg, 2.76 mmol). The resulting mixture was stirred at 50° C. After 5 h, LCMS indicated completion of the reaction. Volatile components were evaporated under reduced pressure. The residue was purified by reverse phase prep-HPLC (X-Bridge BEH130 Prep C18) and eluted with aq. $NH_4HCO_3$ (50 mM) over 1 min to give the desired product. LCMS (ES, m/z): 705.10 [M−H]⁻. H-NMR (400 MHz, $D_2O$): δ 8.16 (s, 1H), 7.99 (s, 1H), 7.95 (s, 1H), 6.19 (d, J=7.8 Hz, 1H), 5.94 (d, J=8.4 Hz, 1H), 5.17 (m, 2H), 4.77 (d, J=3.3 Hz, 1H), 4.61 (d, J=3.9 Hz, 1H), 4.28-4.49 (m, 3H), 4.03-4.08 (m, 3H). $^{31}$P-NMR (121 MHz, $D_2O$, ppm): δ 55.71 (s, 1P), 52.64 (s, 1P).

Example 17: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1⁶,⁹]octadec-8-yl]-1,9-dihydro-6H-purin-6-one (Diastereomer 4)

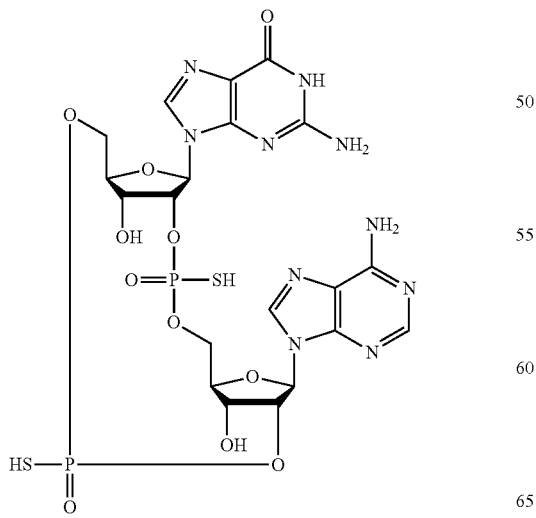

Step 1: 2-amino-9-[(1R,6R,8R,9R,14R,16R,17R,18R)-16-(6-amino-9H-purin-9-yl)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1⁶,⁹]octadec-8-yl]-1,9-dihydro-6H-purin-6-one

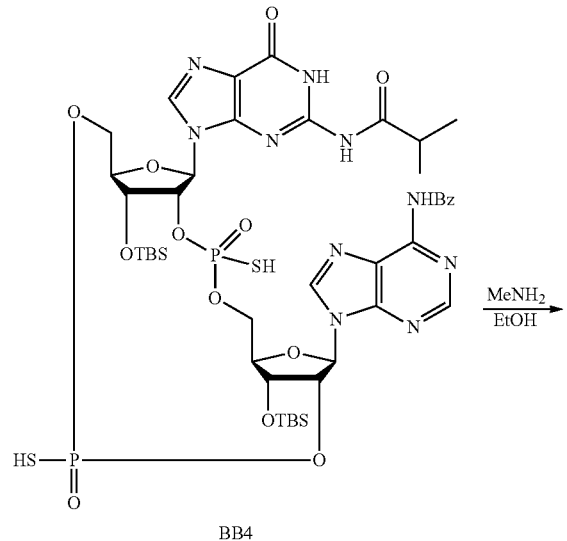

BB4

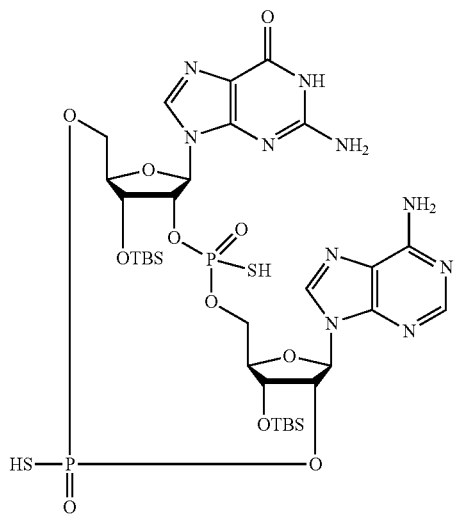

To a solution of Compound BB4 from Example 16, Step 1 (30 mg, 0.027 mmol) in EtOH (1.5 ml), 30% methylamine (337 mg, 10.84 mmol) was added. The resulting solution was stirred for 3 h. LCMS indicated completion of reaction. It was concentrated and used directly for the next step. LCMS (ES, m/z): 935.06 [M+H]⁺.

Step 2: 2-amino-9-[(1R,6R,8R,9R,14R,16R,17R,18R)-16-(6-amino-9H-purin-9-yl)-17,18-dihydroxy-3,11-dioxido-3,11-disulfanyl-2,4,7,10,12,15-hexaoxa-3,11-diphosphatricyclo[12.2.1.1⁶,⁹]octadec-8-yl]-1,9-dihydro-6H-purin-6-one Examples 18, 19, 20, 21: 2-amino-9-[(1R,6R,8R,9S,14S,16R,17R,18R)-16-(6-amino-9H-purin-9-yl)-17-azido-18-fluoro-3,11-dihydroxy-3,11-disulfido-2,4,7,10,12,15-hexaoxa-3,11-diphosphatricyclo[12.2.1.1⁶,⁹]octadec-8-yl]-1,9-dihydro-6H-purin-6-one (Diastereomers 1, 2, 3, and 4)

Diastereomer 1

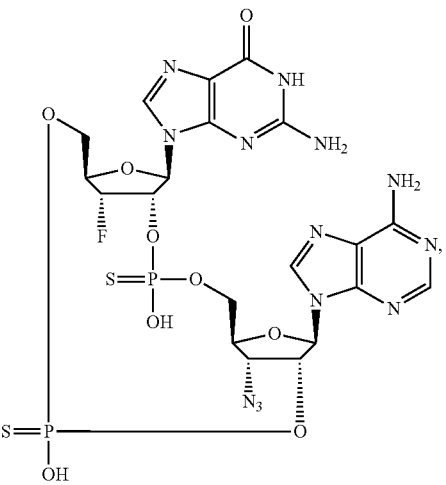

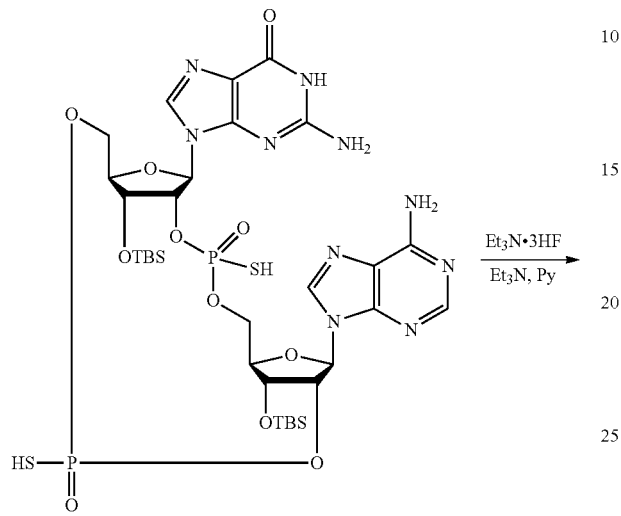

Diastereomer 2

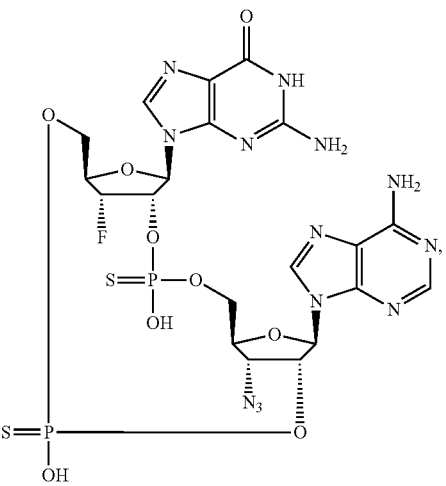

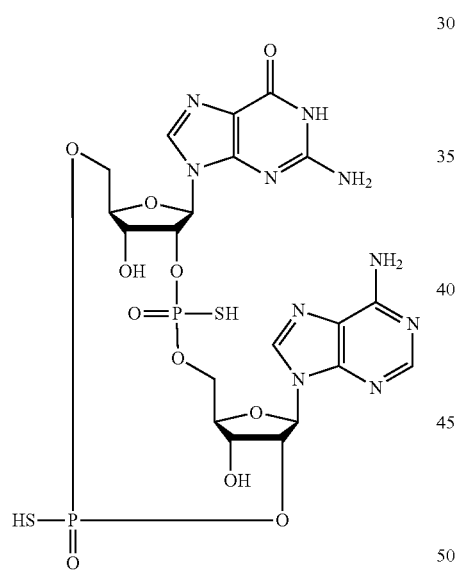

Diastereomer 3

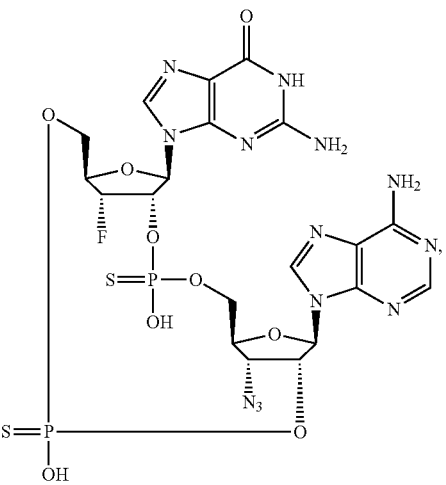

To the crude product from the previous step (25.4 mg, 0.027 mmol) in pyridine (1 ml) were added TEA (275 mg, 2.72 mmol) and trimethylamine trihydrofluoride (219 mg, 1.361 mmol). The resulting mixture was stirred at 50° C. After 5 h, LCMS indicated completion of the reaction.

Volatile components were evaporated under reduced pressure. The residue was purified by reverse phase prep-HPLC (X-Bridge BEH130 Prep C18) and eluted with aq NH$_4$HCO$_3$ (50 mM) over 1 min to give the desired product. LCMS (ES, m/z): 705.10 [M−H]⁻. ¹H NMR (400 MHz, D$_2$O): δ δ 8.73 (s, 1H), 8.16 (s, 1H), 8.12 (s, 1H), 6.23 (d, J=8 Hz, 1H), 5.98 (d, J=8 Hz, 1H), 5.04-5.29 (m, 2H), 4.39-4.59 (m, 6H), 4.06-4.14 (m, 4H). ³¹P-NMR (121 MHz, D$_2$O, ppm): δ 56.91 (s, 1P), 56.33 (s, 1P).

143
-continued

Diastereomer 4

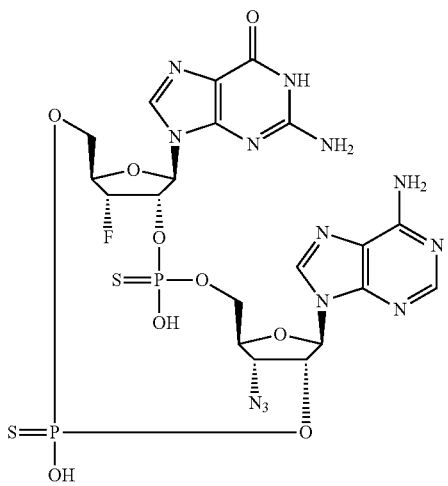

Step 1: (2R,3R,4R,5S)-4-azido-2-(6-benzamido-9H-purin-9-yl)-5-((bis(4-methoxyphenyl)(phenyl)methoxy)methyl)tetrahydrofuran-3-vi phenyl phosphonate

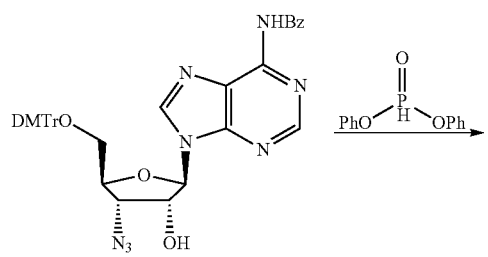

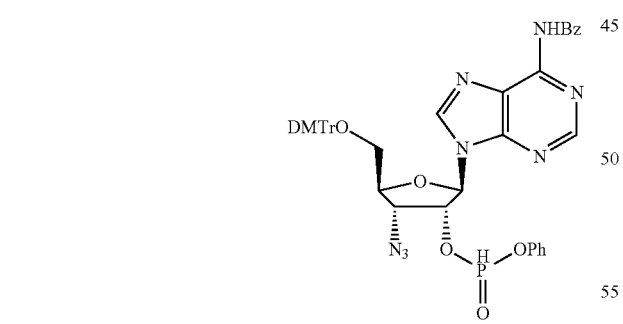

N-(9-((2R,3R,4S,5S)-4-azido-5-((bis(4-methoxyphenyl)(phenyl)methoxy)methyl)-3-hydroxytetrahydrofuran-2-yl)-9H-purin-6-yl)benzamide (957 mg, 1.4 mmol) was co-evaporated with pyridine (3×5 mL) and then re-dissolved in pyridine (7 mL). To the mixture was added diphenyl phosphonate (983.6 mg, 4.2 mmol) dropwise over 2 min. It was stirred for 30 min. The reaction solution was used for the next reaction step without purification. LCMS (ES, m/z): 839.3 [M+H]+.

Step 2: (2R,3R,4R,5S)-4-azido-2-(6-benzamido-9H-purin-9-yl)-5-((bis(4-methoxyphenyl)(phenyl)methoxy)methyl)tetrahydrofuran-3-yl phosphonate

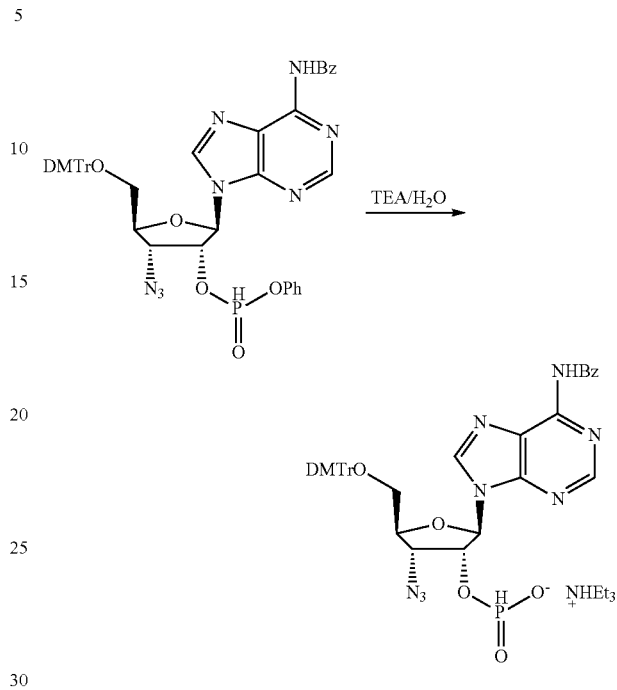

To the reaction mixture from Step 1 at rt was added water (1.4 mL) and Et$_3$N (1.4 mL) dropwise. After 20 min, it was concentrated, and the residue was partitioned between CH$_2$Cl$_2$ (100 mL, with 1% Et$_3$N) and aq NaHCO$_3$ (5%, 40 mL). The organic layer was washed with aq NaHCO$_3$ (5%, 40 mL) and brined (50 mL), dried (Na$_2$SO$_4$), and concentrated. The residue was purified by silica gel chromatography and eluted with 0 to 7.6% MeOH in CH$_2$Cl$_2$ (containing 1% Et$_3$N) to give the product. LCMS (ES, m/z): 763.3 [M+H]+. $^1$H-NMR (400 MHz, CD$_3$OD): δ 8.63 (s, 1H), 8.56 (s, 1H), 8.07 (d, J=7.7 Hz, 2H), 7.77-7.60 (m, 1.5H), 7.54 (t, J=7.6 Hz, 2H), 7.36 (d, J=7.6 Hz, 2H), 7.26-7.14 (m, 7H), 6.77 (dd, J=8.1, 4.4 Hz, 4H), 6.31 (d, J=3.7 Hz, 1H), 6.08 (s, 0.5H), 5.79 (dt, J=9.7, 4.2 Hz, 1H), 4.85-4.78 (m, 1H), 4.26 (q, J=4.3 Hz, 1H), 3.73 (s, 6H), 3.44 (ddd, J=33.6, 10.8, 3.9 Hz, 2H), 3.13 (q, J=7.3 Hz, 7H), 1.26 (t, J=7.3 Hz, 12H). $^{31}$P-NMR (162 MHz, CD$_3$OD): δ 3.14 (s, 1P).

Step 3: (2R,3R,4R,5S)-4-azido-2-(6-benzamido-9H-purin-9-yl)-5-(hydroxymethyl)-tetrahydrofuran-3-yl phosphonate

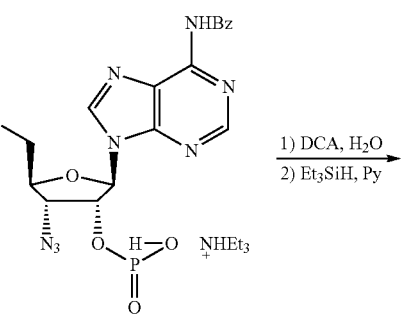

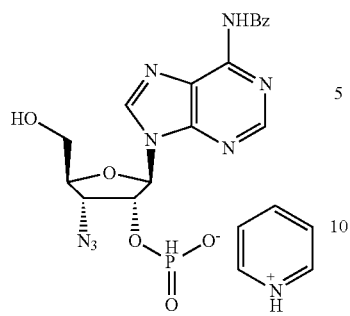

To a solution of (2R,3R,4R,5S)-4-azido-2-(6-benzamido-9H-purin-9-yl)-5-((bis(4-methoxyphenyl)(phenyl)methoxy)methyl)tetrahydrofuran-3-yl phosphonate (811 mg, 0.94 mmol) in CH$_2$Cl$_2$ (9 mL) at rt was added water (0.1 mL) and dichloroacetic acid in CH$_2$Cl$_2$ (0.6M, 11 mL, 6.6 mmol). The mixture was stirred at rt for 10 min. Then, Et$_3$SiH (26.5 mL) was added, and it was stirred further for 1 h. Pyridine (1.28 mL) was added to the reaction, it was concentrated, and the residue was used for next step without purification. LCMS (ES, m/z): 461.1 [M+H]$^+$.

Step 4: (2R,3R,4R,5S)-4-azido-2-(6-benzamido-9H-purin-9-yl)-5-(((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphanyl)oxy)methyl)tetrahydrofuran-3-yl phosphonate

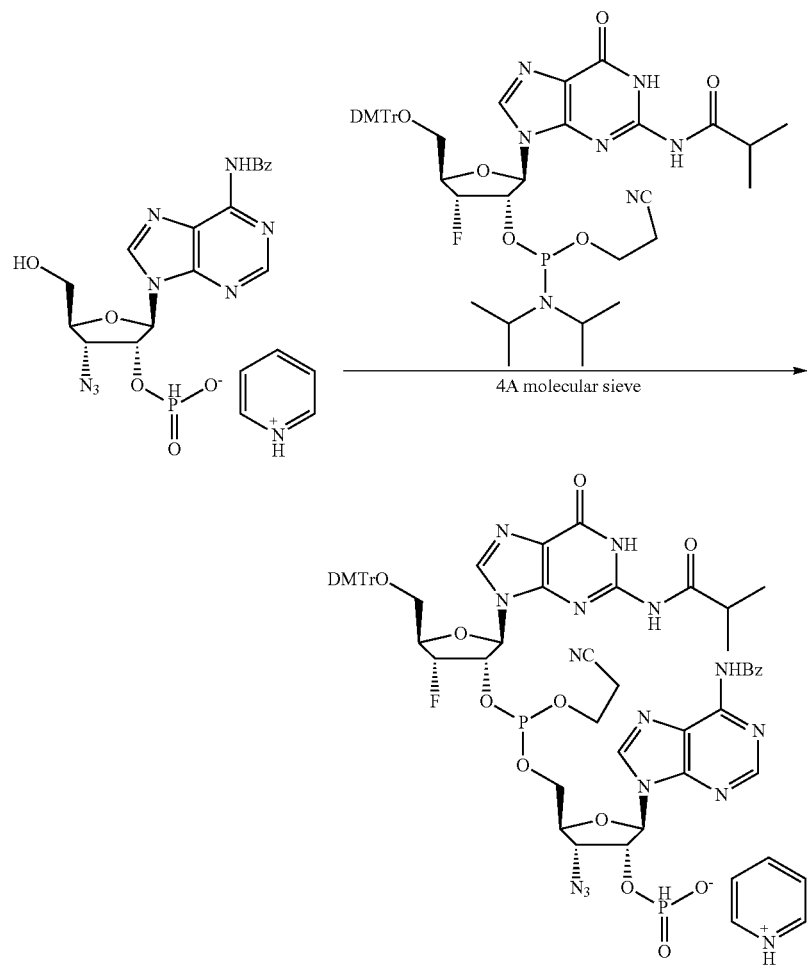

(2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite (887 mg, 1.03 mmol) was co-evaporated with ACN (3×3 mL), re-dissolved in ACN (3 mL) under Ar, and dried by adding activated 4 Å molecular sieve (150 mg). (2R,3R,4R,5S)-4-azido-2-(6-benzamido-9H-purin-9-yl)-5-(hydroxymethyl)tetrahydrofuran-3-yl phosphonate (crude, 2 g, ~0.94 mmol) was co-evaporated with ACN (3×5 mL) and then re-dissolved in ACN (5 mL) under Ar, and dried by adding activated 4 Å molecular sieve (150 mg). After 30 min, it was added to the previously prepared mixture containing (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite. The reaction mixture was used in the next reaction step without purification. LCMS (ES, m/z): 1215.2 [M−H]⁻.

Step 5: (2R,3R,4R,5S)-4-azido-2-(6-benzamido-9H-purin-9-yl)-5-((((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphorothioyl)oxy)methyl)-tetrahydrofuran-3-yl phosphonate

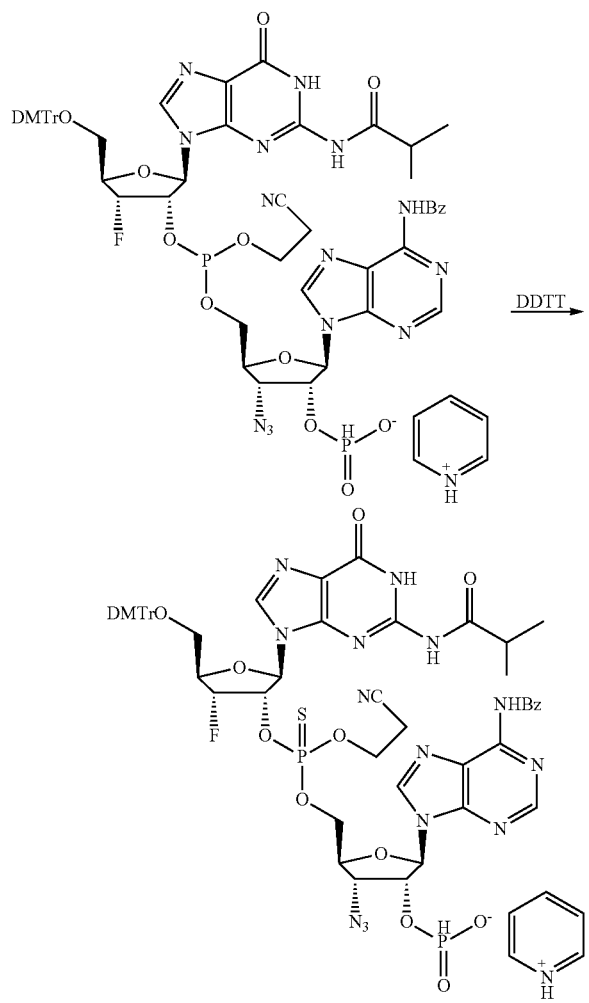

To the mixture from Step 4 at rt was added (E)-N,N-dimethyl-N'-(3-thioxo-3H-1,2,4-dithiazol-5-yl)formimidamide (212 mg, 1.03 mmol), and it was stirred for 30 min. Then, the reaction was concentrated, and the residue was used for the next reaction step without purification. LCMS (ES, m/z): 1247.2 [M−H]⁻.

Step 6: (2R,3R,4R,5S)-4-azido-2-(6-benzamido-9H-purin-9-yl)-5-((((2-cyanoethoxy)-(((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)oxy)methyl)tetrahydrofuran-3-yl phosphonate

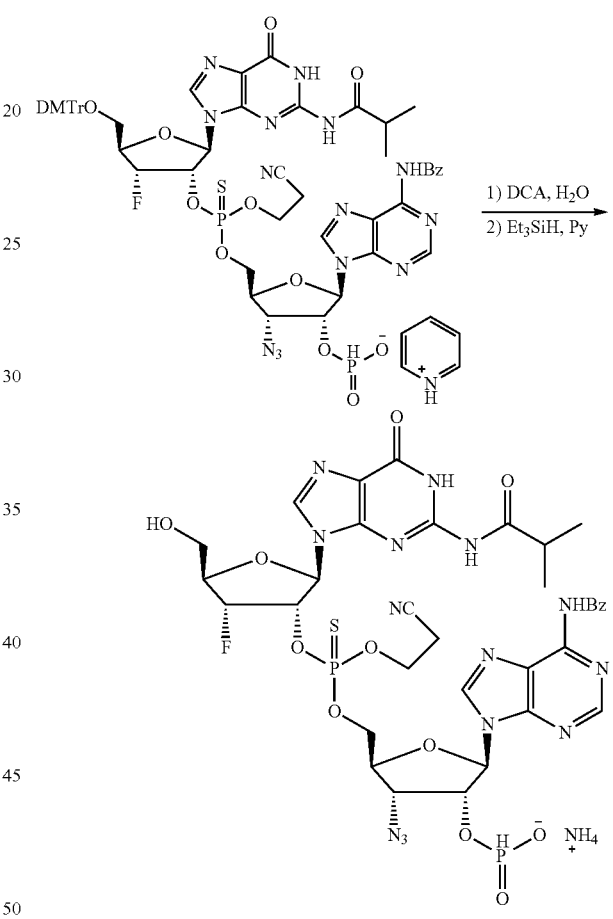

To a solution of (2R,3R,4R,5S)-4-azido-2-(6-benzamido-9H-purin-9-yl)-5-(((((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphorothioyl)oxy)methyl)tetrahydrofuran-3-yl phosphonate (4 g, crude, ~0.94 mmol) in CH₂Cl₂ (9 mL) was added water (0.18 mL) and 2,2-dichloroacetic acid in CH₂Cl₂ (0.6M, 11.0 mL, 6.65 mmol). After 15 min, triethylsilane (26.5 mL) was added, and stirring was continued for additional 2 h. Then, pyridine (1.28 mL) was added, and it was concentrated. The residue was purified by reverse phase chromatography (C18) and eluted with 0 to 95% ACN in aq NH₄HCO₃ (0.04%) to give the product. LCMS (ES, m/z): 947.2 [M+H]⁺. ¹H-NMR (400 MHz, CD₃OD): δ 8.76-8.71 (m, 1H), 8.56, 8.44 (2 s, 1H), 8.33, 8.29 (2 s, 1H), 8.21-8.07 (m, 2H), 7.72-7.63 (m, 1.5H), 7.61-7.55 (m, 2H), 6.37-6.19 (m, 2H), 6.08-5.92 (m, 0.5H), 5.69-5.53 (m, 2H), 5.43-5.24 (m, 1H), 4.76, 4.61 (dt, J=5.4 Hz, 1H), 4.53-4.30 (m, 3H), 4.27-4.21 (m, 3H), 4.12-3.88 (m, 1H), 2.85 (t, J=5.9 Hz, 1H), 2.79-2.55 (m, 3H), 1.27-1.15 (m, 6H). $^{31}$P-NMR (162 MHz, CD$_3$OD): δ 67.98, 67.47 (2 s, 1P); 3.07, 2.96 (2 s, 1P).

Step 7: (1R,6R,8R,9S,14S,16R,17R,18R)-17-azido-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 11-sulfide

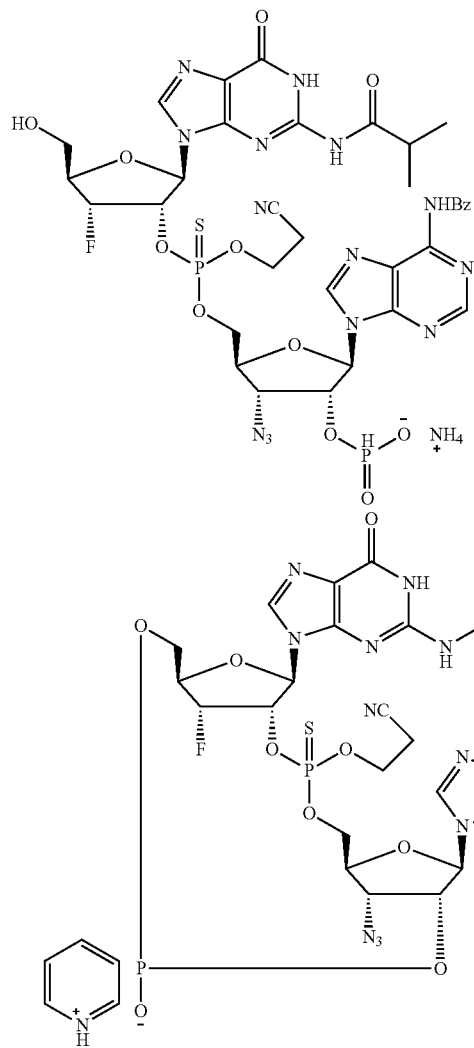

To pyridine (41 mL) under Ar at −40° C. was added diphenyl phosphorochloridate (2.2 g, 8.2 mmol). To the solution at −40° C. was added a solution of (2R,3R,4R,5S)-4-azido-2-(6-benzamido-9H-purin-9-yl)-5-((((2-cyanoethoxy)(((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)-oxy)methyl)tetrahydrofuran-3-yl phosphonate (390 mg, 0.41 mmol, co-evaporated with pyridine 3×5 mL) in CH$_2$Cl$_2$ (41 mL) dropwise over 20 min. It was stirred at −40° C. for 20 min. The reaction mixture was used for the next reaction step immediately without purification. LCMS (ES, m/z): 929.1 [M+H]$^+$.

Step 8: (1R,6R,8R,9S,14S,16R,17R,18R)-17-azido-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecan-3-olate 3,11-disulfide

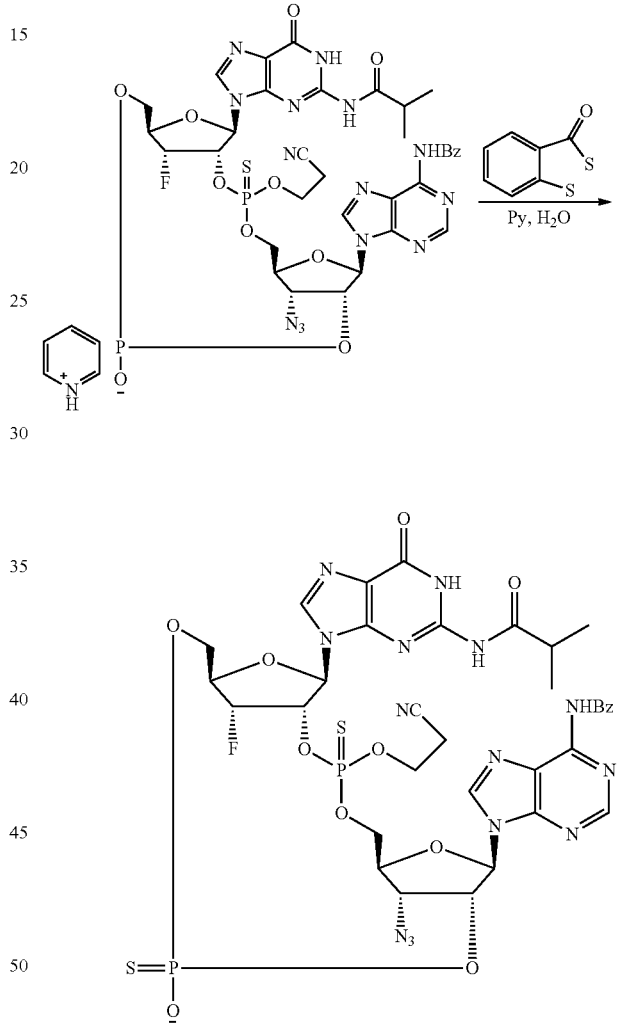

To the reaction mixture from Step 7 at −40° C. was added 3H-benzo[c][1,2]dithiol-3-one (103 mg, 0.615 mmol) and water (117 μl, 6.49 mmol). After stirring at rt for 40 min, the mixture was concentrated under reduced pressure. The residue was purified by reverse phase chromatography (C18) and eluted with 0 to 95% ACN in aq NH$_4$HCO$_3$ (0.04%) to give the product. LCMS (ES, m/z): 961.1 [M+H]$^+$. $^1$H-NMR (400 MHz, CD$_3$OD): δ 8.70-8.05 (m, 5H), 7.80-7.52 (m, 3H), 6.48-6.17 (m, 2H), 5.96-5.67 (m, 2H), 5.67-5.49 (m, 1H), 4.76 (dd, J=26.0, 3.3 Hz, 1H), 4.64-4.23 (m, 6H), 4.23-3.73 (m, 2H), 3.04-2.33 (m, 3H), 1.27-0.82 (m, 6H). $^{31}$P-NMR (162 MHz, CD$_3$OD) δ 64.70-63.97 (m, 1P), 54.94, 54.31 (2 s).

Step 9: (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1⁶,⁹]octadecane-3,11-bis(olate) 3,11-disulfide (152-9-A), (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1⁶,⁹]octadecane-3,11-bis(olate) 3,11-disulfide (152-9-B), (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1⁶,⁹]octadecane-3,11-bis(olate) 3,11-disulfide (152-9-C), and (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1⁶,⁹]octadecane-3,11-bis(olate) 3,11-disulfide (152-9-D)

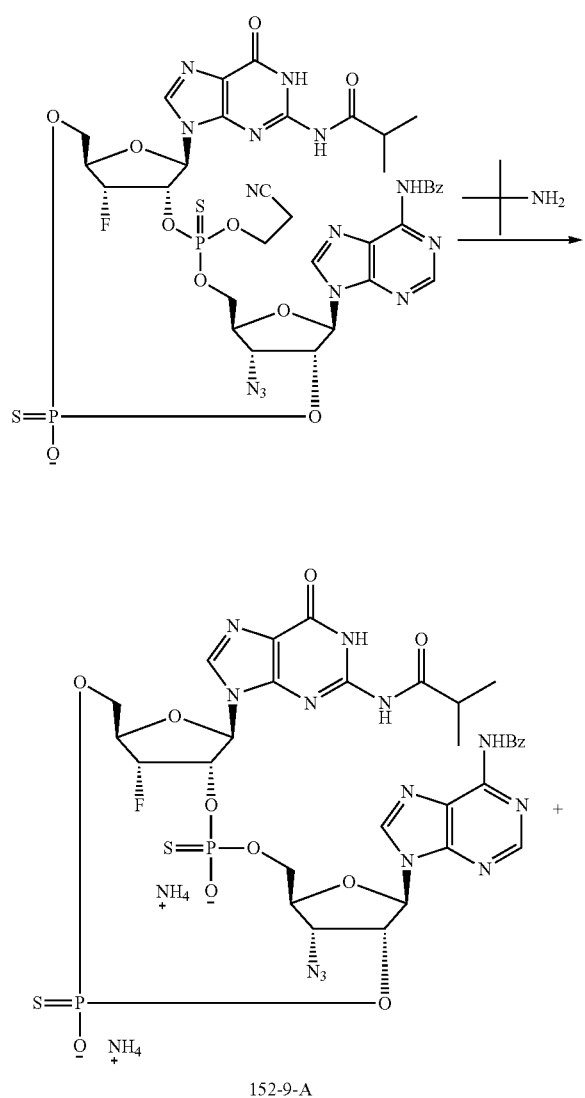

152-9-A

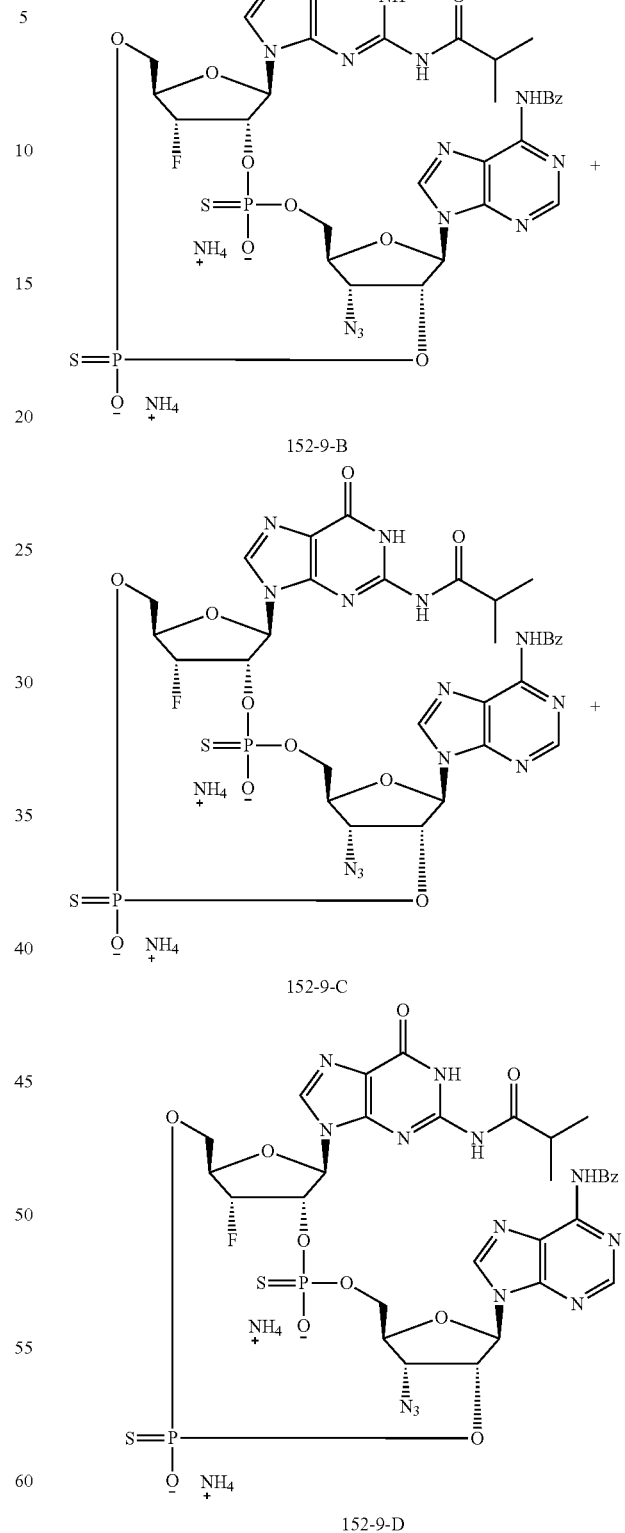

152-9-B 152-9-C 152-9-D

To a suspension of (1R,6R,8R,9S,14S,16R,17R,18R)-17-azido-16-(6-benzamido-9H-purin-9-yl)-11-(2-cyanoethoxy)-18-fluoro-8-(2-isobutyramido-6-oxo-1,6-dihydro-9H-purin-9-yl)-2,4,7,10,12,15-hexaoxa-3,11-diphosphatricyclo

[12.2.1.1$^{6,9}$]octadecan-3-olate 3,11-disulfide (200 mg, 0.2 mmol) in ACN (2 mL) under Ar was added tert-butylamine (2 mL), and the mixture was stirred for 0.5 h. Then, it was concentrated, and the residue was purified by preparative-HPLC (T3 Prep C18 Column, 19 mm×250 mm) and eluted with 18 to 32% ACN in water (0.05% TFA) over 25 min. Fractions with the desired mass were neutralized with NH$_4$OH (25%) and then concentrated to give the following four diastereomeric products:

(1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecane-3,11-bis(olate) 3,11-disulfide (152-9-A). T$_R$: 14.47 min. LCMS (ES, m/z): 908.0 [M+H]$^+$. $^1$H-NMR: (400 MHz, CD$_3$OD): δ 9.36 (s, 1H), 8.98 (s, 1H), 8.75 (s, 1H), 8.15 (d, J=7.6 Hz, 2H), 7.69 (t, J=7.4 Hz, 1H), 7.61 (t, J=7.6 Hz, 2H), 6.42 (d, J=8.2 Hz, 1H), 6.25 (d, J=8.4 Hz, 1H), 5.57 (q, J=7.3, 6.0 Hz, 2H), 5.44 (d, J=3.4 Hz, 1H), 4.71 (d, J=4.9 Hz, 1H), 4.64 (d, J=27.4 Hz, 1H), 4.36-4.28 (m, 3H), 4.24-4.13 (m, 2H), 2.78-2.68 (m, 1H), 1.20 (dd, J=12.0, 6.8 Hz, 6H). $^{31}$P-NMR: (162 MHz, CD$_3$OD): δ 58.64 (s, 1P), 58.19 (s, 1P).

(1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecane-3,11-bis(olate) 3,11-disulfide (152-9-B). T$_R$: 15.80 min. LCMS (ES, m/z): 908.0 [M+H]$^+$. $^1$H-NMR: (400 MHz, CD$_3$OD): δ 9.26 (s, 1H), 8.67 (s, 1H), 8.38 (s, 1H), 8.21-8.09 (m, 2H), 7.70-7.62 (m, 1H), 7.58 (dd, J=8.3, 6.8 Hz, 2H), 6.36 (d, J=8.3 Hz, 1H), 6.13 (d, J=8.1 Hz, 1H), 5.63-5.40 (m, 3H), 4.77 (d, J=4.8 Hz, 1H), 4.70-4.56 (m, 1H), 4.29 (t, J=3.6 Hz, 3H), 4.21-4.03 (m, 2H), 2.50-2.39 (m, 1H), 1.07 (d, J=6.9 Hz, 3H), 0.93 (d, J=6.8 Hz, 3H). $^{31}$P-NMR: (162 MHz, CD$_3$OD): δ 58.61 (s, 1P), 55.52 (s, 1P).

(1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecane-3,11-bis(olate) 3,11-disulfide (152-9-C). T$_R$: 17.80 min. LCMS (ES, m/z): 908.0 [M+H]$^+$. $^1$H-NMR: (400 MHz, CD$_3$OD): δ 8.94 (s, 1H), 8.85 (s, 1H), 8.65 (s, 1H), 8.07 (d, J=7.7 Hz, 2H), 7.75-7.49 (m, 3H), 6.32 (d, J=8.1 Hz, 1H), 6.17 (d, J=8.6 Hz, 1H), 5.76-4.60 (m, 7H), 4.35-3.98 (m, 3H), 2.57-2.54 (m, 1H), 1.13 (t, J=7.4 Hz, 6H). $^{31}$P-NMR: (162 MHz, CD$_3$OD): δ 58.33 (s, 1P), 57.18 (s, 1P).

(1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecane-3,11-bis(olate) 3,11-disulfide (152-9-D). T$_R$: 20.97 min). LCMS (ES, m/z): 908.0 [M+H]$^+$. $^1$H-NMR: (400 MHz, CD$_3$OD): δ 8.85 (s, 1H), 8.66 (s, 1H), 8.41 (s, 1H), 8.20-8.10 (m, 2H), 7.70-7.62 (m, 1H), 7.57 (dd, J=8.2, 6.8 Hz, 2H), 6.34 (d, J=8.3 Hz, 1H), 6.13 (d, J=8.4 Hz, 1H), 5.64 (dd, J=53.0, 3.3 Hz, 1H), 5.55-5.38 (m, 2H), 4.80 (d, J=5.1 Hz, 2H), 4.60 (dq, J=26.5, 2.3 Hz, 1H), 4.37-4.25 (m, 2H), 4.24-4.14 (m, 2H), 4.07 (ddd, J=12.2, 5.9, 1.7 Hz, 1H), 2.51 (p, J=6.9 Hz, 1H), 1.07 (d, J=6.8 Hz, 3H), 0.96 (d, J=6.8 Hz, 3H). $^{31}$P-NMR: (162 MHz, CD$_3$OD): δ 56.96 (s, 1P), 55.74 (s, 1P).

Step 10: 2-amino-9-[(1R,6R,8R,9S,14S,16R,17R,18R)-16-(6-amino-9H-purin-9-yl)-17-azido-18-fluoro-3,11-dihydroxy-3,11-disulfido-2,4,7,10,12,15-hexaoxa-3,11-diphosphatricyclo[12.2.1.1$^{6,9}$]octadec-8-yl]-1,9-dihydro-6H-purin-6-one (Diastereomer 1)

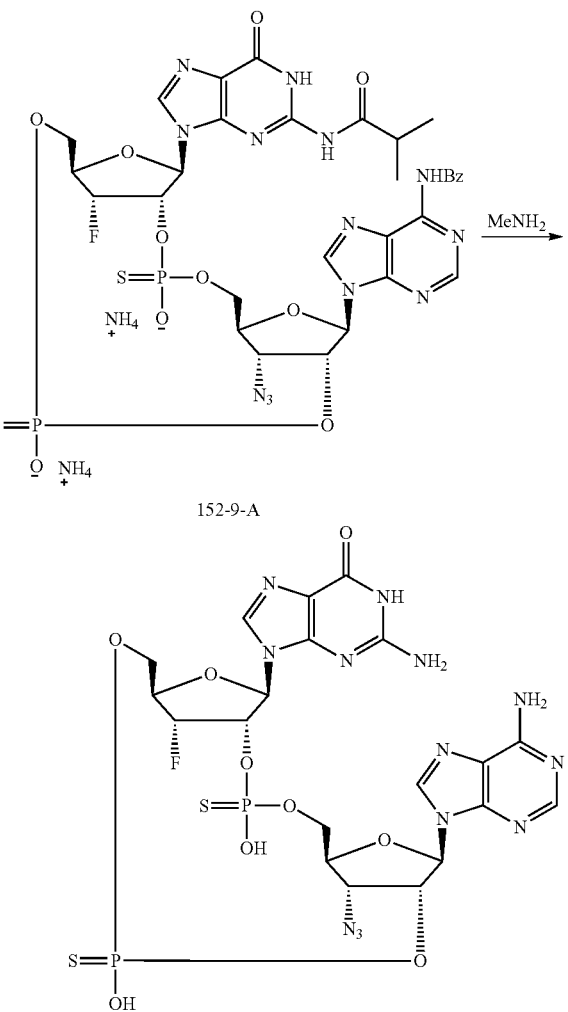

152-9-A (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10,12,15-hexaoxa-3,11-diphosphatricyclo[12.2.1.1$^{6,9}$]octadecane-3,11-bis(olate) 3,11-disulfide (152-9-A)(~300 mg) was dissolved in a solution of MeNH$_2$ in EtOH (30%, 15 mL). The resulting solution was stirred at rt for 3 h. It was concentrated, and the residue was purified by reverse phase (AQ C18) chromatography and eluted with 0 to 95% ACN in aq NH$_4$HCO$_3$ (50 mM) to give the product, Example 18. LCMS (ES, m/z): 732.2 [M−H]$^-$. $^1$H-NMR: (400 MHz, D$_2$O): δ 8.21 (s, 2H), 8.09 (s, 2H), 7.79 (s, 2H), 6.10 (d, J=8.4 Hz, 1H), 5.97 (d, J=8.8 Hz, 1H), 5.67 (dd, J=52.5, 3.5 Hz, 1H), 5.31-5.22 (m, 2H), 4.91 (d, J=5.2 Hz, 1H), 4.75-4.64 (m, 1H), 4.56 (s, 2H), 4.40-4.36 (m, 1H), 4.33-4.28 (m, 1H), 4.12-4.03 (m, 2H). 19F-NMR: (376 MHz, D$_2$O): δ −194.75 (s). $^{31}$P-NMR: (162 MHz, D2O): δ 54.02 (s, 1P), 52.90 (s, 1P).

The other diastereomeric products of Step 9 were each independently treated in an analogous manner to that described immediately above in Step 10 to provide the following products:

Example 19: 2-amino-9-[(1R,6R,8R,9S,14S,16R, 17R,18R)-16-(6-amino-9H-purin-9-yl)-17-azido-18-fluoro-3,11-dihydroxy-3,11-disulfido-2,4,7,10,12,15-hexaoxa-3,11-diphosphatricyclo[12.2.1.1$^{6,9}$]octadec-8-yl]-1,9-dihydro-6H-purin-6-one (Diastereomer 2)

Prepared from (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10, 12,15-hexaoxa-3,11-diphosphatricyclo[12.2.1.1$^{6,9}$] octadecane-3,11-bis(olate) 3,11-disulfide (152-9-B). LCMS (ES, m/z): 732.0 [M–H]$^-$. $^1$H-NMR: (400 MHz, D$_2$O): δ 8.33 (s, 1H), 8.16 (s, 1H), 8.10 (s, 1H), 6.15 (d, J=8.1 Hz, 1H), 6.02 (d, J=8.5 Hz, 1H), 5.61 (dd, J=52.4, 3.5 Hz, 1H), 5.22-5.06 (m, 2H), 4.68-4.61 (m, 2H), 4.44 (s, 1H), 4.32-5-4.27 (m, 1H), 4.19-4.05 (m, 3H). $^{19}$F-NMR: (376 MHz, D$_2$O): δ –195.02 (s). $^{31}$P-NMR: (162 MHz, D$_2$O): δ 55.74 (s, 1P), 54.52 (s, 1P).

Example 20: 2-amino-9-[(1R,6R,8R,9S,14S,16R, 17R,18R)-16-(6-amino-9H-purin-9-yl)-17-azido-18-fluoro-3,11-dihydroxy-3,11-disulfido-2,4,7,10,12,15-hexaoxa-3,11-diphosphatricyclo[12.2.1.1$^{6,9}$]octadec-8-yl]-1,9-dihydro-6H-purin-6-one (Diastereomer 3)

Prepared from (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10, 12,15-hexaoxa-3,11-diphosphatricyclo[12.2.1.1$^{6,9}$] octadecane-3,11-bis(olate) 3,11-disulfide (152-9-C). LCMS (ES, m/z): 732.0 [M–H]$^-$. $^1$H-NMR: (400 MHz, D$_2$O): δ 8.74 (s, 1H), 8.21 (s, 1H), 7.98 (s, 1H), 6.19 (d, J=8.1 Hz, 1H), 6.04 (d, J=8.3 Hz, 1H), 5.42 (dd, J=53.0, 3.6 Hz, 1H), 5.34-5.18 (m, 2H), 4.83 (d, J=5.0 Hz, 1H), 4.67 (d, J=2.4 Hz, 1H), 4.52 (s, 1H), 4.32 (dd, J=9.9, 5.5 Hz, 1H), 4.24-4.07 (m, 3H). $^{19}$F-NMR: (376 MHz, D$_2$O): δ –196.09 (s). $^{31}$P-NMR: (162 MHz, D$_2$O): δ 56.21 (s, 1P), 53.63 (s, 1P).

Example 21: 2-amino-9-[(1R,6R,8R,9S,14S,16R, 17R,18R)-16-(6-amino-9H-purin-9-yl)-17-azido-18-fluoro-3,11-dihydroxy-3,11-disulfido-2,4,7,10,12,15-hexaoxa-3,11-diphosphatricyclo[12.2.1.1$^{6,9}$]octadec-8-yl]-1,9-dihydro-6H-purin-6-one (Diastereomer 4)

Prepared from (1R,6R,8R,9S,14S,16R,17R,18R)-17-azido-16-(6-benzamido-9H-purin-9-yl)-18-fluoro-8-(2-isobutyramido-6-oxo-1,6-dihydro-9H-purin-9-yl)-2,4,7,10, 12,15-hexaoxa-3,11-diphosphatricyclo[12.2.1.1$^{6,9}$] octadecane-3,11-bis(olate) 3,11-disulfide (152-9-D). LCMS (ES, m/z): 732.0 [M–H]$^-$. $^1$H-NMR: (400 MHz, D$_2$O): δ 8.86 (s, 1H), 8.40 (s, 1H), 8.23 (s, 1H), 6.21 (d, J=8.2 Hz, 1H), 6.07 (d, J=8.4 Hz, 1H), 5.52-5.34 (m, 1H), 5.24-5.17 (m, 1H), 5.05-4.97 (m, 1H), 4.67-4.65 (m, 2H), 4.42 (s, 1H), 4.21-4.04 (m, 4H). $^{19}$F-NMR: (376 MHz, D$_2$O): δ –196.43 (s). $^{31}$P-NMR: (162 MHz, D$_2$O): δ 56.80 (s, 1P), 56.65 (s, 1P).

Examples 22 to 24, as shown in Table 3 below, were prepared according to procedures analogous to those outlined in Examples 18 to 21 above using the appropriate monomers, described as Preparations or as obtained from commercial sources, in the coupling step.

TABLE 3

| Ex. | Structure | Name | Mass [M − H]$^-$ |
|---|---|---|---|
| 22 | 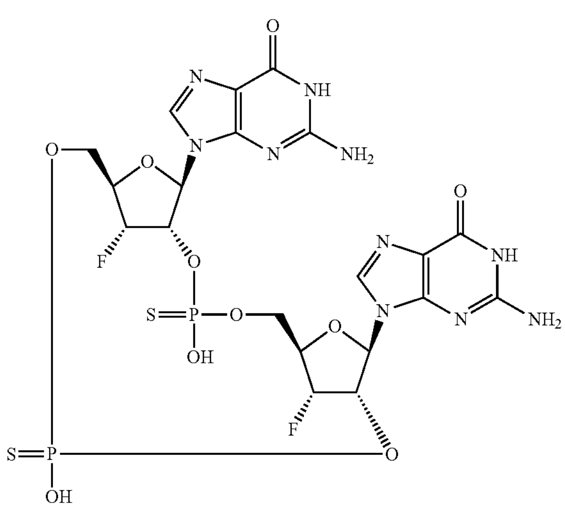 [SMILES: Nc1nc2c(ncn2[C@@H]2O[C@@H]3COP(O)(=S)O[C@@H]4[C@H](F)[C@@H](COP(O)(=S)O[C@@H]2[C@@H]3F)O[C@H]4n2cnc3c(=O)[nH]c(N)nc32)c(=O)[nH]1] | 9,9'-((1S,6R,8R,9S,14R,16R,17R,18R)-17,18-difluoro-3,11-dihydroxy-3,11-disulfido-2,4,7,10,12,15-hexaoxa-3,11-diphosphatricyclo[12.2.1.1$^{6,9}$]octadecane-8,16-diyl)bis(2-amino-1,9-dihydro-6H-purin-6-one) (Diastereomer 1) | 753 |

TABLE 3-continued
| Ex. | Structure | Name | Mass [M − H]⁻ |
|---|---|---|---|
| 23 | 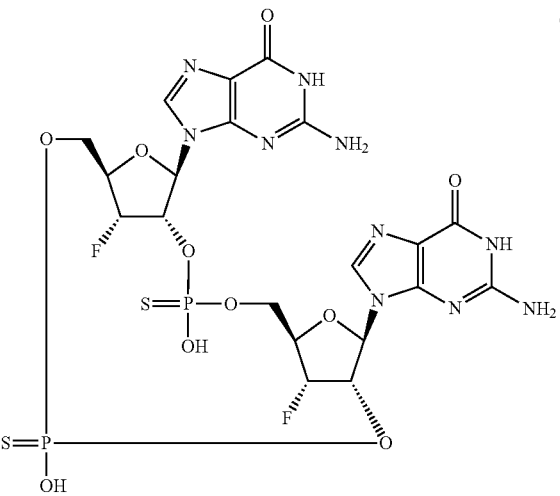 [SMILES: Nc1nc2c(ncn2[C@@H]2O[C@@H]3COP(O)(=S)O[C@@H]4[C@H](F)[C@@H](COP(O)(=S)O[C@@H]2[C@@H]3F)O[C@H]4n2cnc3c(=O)[nH]c(N)nc32)c(=O)[nH]1] | 9,9'-((1S,6R,8R,9S,14R,16R,17R,18R)-17,18-difluoro-3,11-dihydroxy-3,11-disulfido-2,4,7,10,12,15-hexaoxa-3,11-diphosphatricyclo[12.2.1.1$^{6,9}$]octadecane-8,16-diyl)bis(2-amino-1,9-dihydro-6H-purin-6-one) (Diastereomer 2) | 753 |
| 24 | 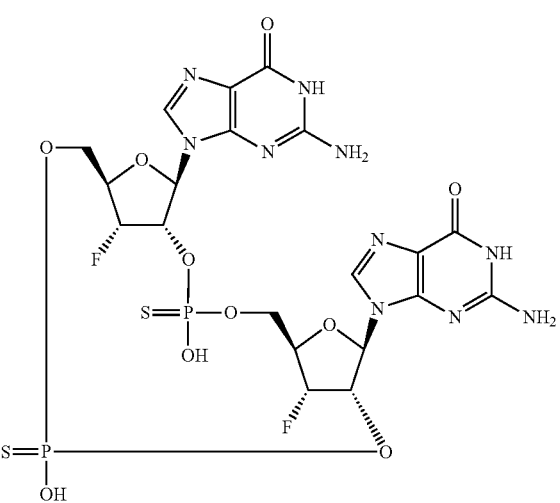 [SMILES: Nc1nc2c(ncn2[C@@H]2O[C@@H]3COP(O)(=S)O[C@@H]4[C@H](F)[C@@H](COP(O)(=S)O[C@@H]2[C@@H]3F)O[C@H]4n2cnc3c(=O)[nH]c(N)nc32)c(=O)[nH]1] | 9,9'-((1S,6R,8R,9S,14R,16R,17R,18R)-17,18-difluoro-3,11-dihydroxy-3,11-disulfido-2,4,7,10,12,15-hexaoxa-3,11-diphosphatricyclo[12.2.1.1$^{6,9}$]octadecane-8,16-diyl)bis(2-amino-1,9-dihydro-6H-purin-6-one) (Diastereomer 3) | 753 |

Examples 25 and 26: 9,9'-[(1R,6R,8R,9R,14R,16R, 17R,18R)-17,18-dihydroxy-3,11-dioxido-3,11-disulfanyl-2,4,7,10,12,15-hexaoxa-3,11-diphosphatricyclo[12.2.1.1⁶,⁹]-octadecane-8,16-diyl]bis(2-amino-1, 9-dihydro-6H-purin-6-one) (Diastereomers 1 and 2)

Step 1: N,N'-{[1R,6R,8R,9R,14R,16R,17R,18R)-17, 18-bis{[tert-butyl(dimethyl)silyl]oxy}-3,11-dioxido-3,11-disulfanyl-2,4,7,10,12,15-hexaoxa-3,11-diphosphatricyclo[12.2.1.1⁶,⁹]octadecane-8,16-diyl]bis(6-oxo-1,6-dihydro-9H-urine-9,2-diyl)}bis(2-methylpropanamide)

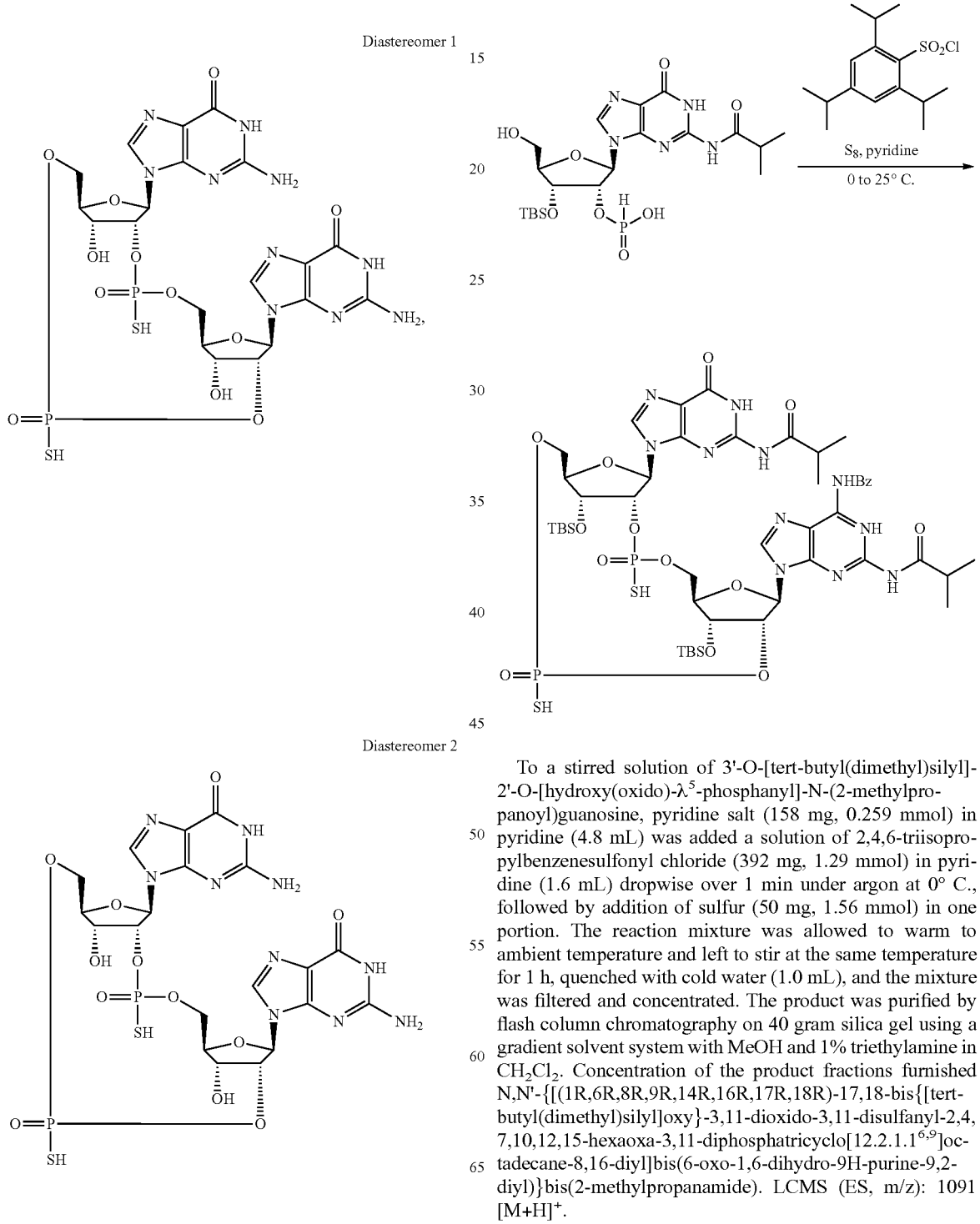

To a stirred solution of 3'-O-[tert-butyl(dimethyl)silyl]-2'-O-[hydroxy(oxido)-λ⁵-phosphanyl]-N-(2-methylpropanoyl)guanosine, pyridine salt (158 mg, 0.259 mmol) in pyridine (4.8 mL) was added a solution of 2,4,6-triisopropylbenzenesulfonyl chloride (392 mg, 1.29 mmol) in pyridine (1.6 mL) dropwise over 1 min under argon at 0° C., followed by addition of sulfur (50 mg, 1.56 mmol) in one portion. The reaction mixture was allowed to warm to ambient temperature and left to stir at the same temperature for 1 h, quenched with cold water (1.0 mL), and the mixture was filtered and concentrated. The product was purified by flash column chromatography on 40 gram silica gel using a gradient solvent system with MeOH and 1% triethylamine in $CH_2Cl_2$. Concentration of the product fractions furnished N,N'-{[(1R,6R,8R,9R,14R,16R,17R,18R)-17,18-bis{[tert-butyl(dimethyl)silyl]oxy}-3,11-dioxido-3,11-disulfanyl-2,4, 7,10,12,15-hexaoxa-3,11-diphosphatricyclo[12.2.1.1⁶,⁹]octadecane-8,16-diyl]bis(6-oxo-1,6-dihydro-9H-purine-9,2-diyl)}bis(2-methylpropanamide). LCMS (ES, m/z): 1091 [M+H]⁺.

Step 2: 9,9'-[(1R,6R,8R,9R,14R,16R,17R,18R)-17, 18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (CC-1) and 9,9'-(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diylbis(2-amino-1,9-dihydro-6H-purin-6-one) (CC-2)

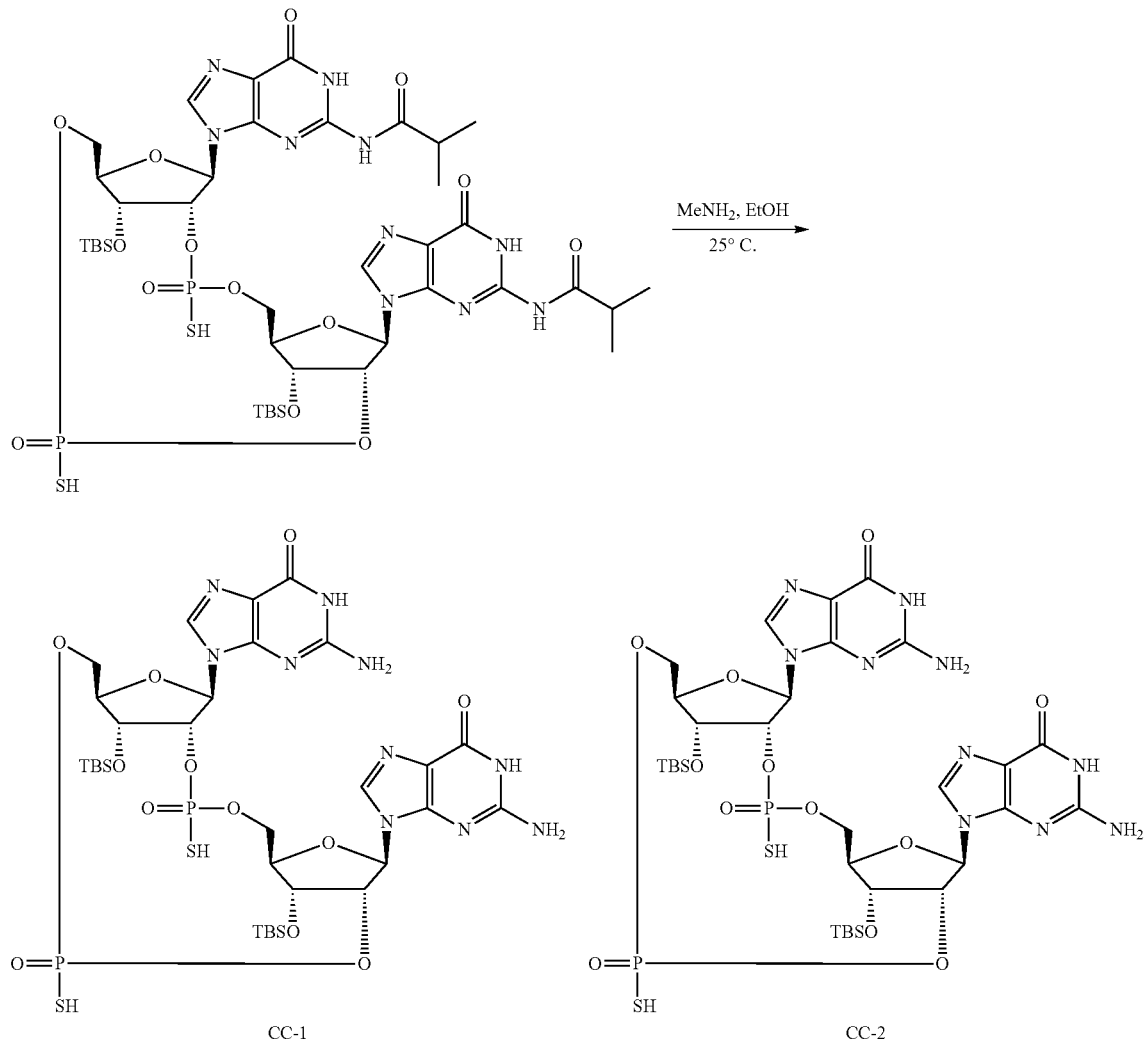

To N,N'-{[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]-octadecane-8,16-diyl]bis(6-oxo-1,6-dihydro-9H-purine-9,2-diyl)}bis(2-methylpropanamide) (167 mg, 0.153 mmol) was added a 33 wt. % methylamine solution in absolute ethanol (1.84 mL, 14.8 mmol), the reaction mixture was left to stir at ambient temperature for 18 h. The reaction mixture was concentrated, and the product was purified by preparative reverse phase HPLC (Waters SunFire C18 OBD Prep Column, 100 Å, 5 μm, 19 mm×150 mm, [Waters Part #186002568]) and eluted with 30 to 100% ACN in water (100 mM triethylammonium acetate) over 15 min. Fractions with the desired mass were collected and then lyophilized to provide two diastereomeric products:

9,9'-[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (Diastereomer 1, CC-1). $T_R$: 11.10 min. LCMS (ES, m/z): 949 [M–H]$^-$.

9,9'-[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (Diastereomer 2, CC-2). $T_R$: 12.00 min. LCMS (ES, m/z): 949 [M–H]$^-$.

Step 3: 9,9'-[(1R,6R,8R,9R,14R,16R,17R,18R)-17,18-dihydroxy-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (Diastereomer 1)

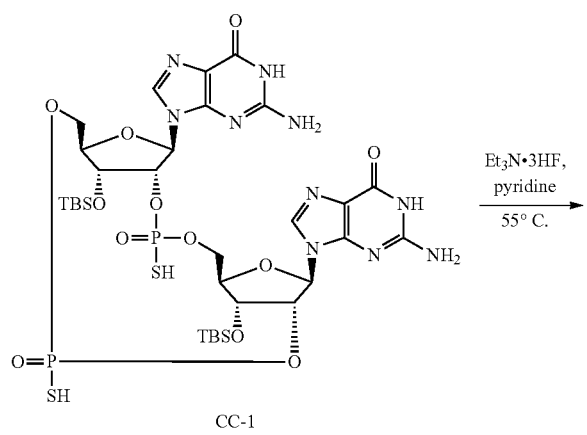

CC-1

To a stirred solution of 9,9'-[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (CC-1, 8 mg, 0.007 mmol) in pyridine (0.6 mL) was added triethylamine (0.36 mL, 2.58 mmol), followed by triethylamine trihydrofluoride (0.12 mL, 0.74 mmol) at ambient temperature. The reaction mixture was heated to 55° C., and left to stir at the same temperature for 22 h. The reaction mixture was cooled to ambient temperature, quenched with 100 mM aq triethylammonium acetate (2.0 mL) at 0° C., and the mixture was filtered and lyophilized. The product was purified using mass-directed reverse phase HPLC with a Waters SunFire C18 OBD Prep Column, 100 Å, 5 µm, 19 mm×150 mm, [Waters Part #186002568] using a gradient solvent system with MeCN and 100 mM aq triethylammonium acetate. Lyophilization of the product fractions furnished Example 25, 9,9'-[(1R,6R,8R,9R,14R,16R,17R,18R)-17,18-dihydroxy-3,11-dioxido-3,11-disulfanyl-2,4,7,10,12,15-hexaoxa-3,11-diphosphatricyclo-[12.2.1.1$^{6,9}$]octadecane-8,16-diyl]bis(2-amino-1,9-dihydro-6H-purin-6-one) (Diastereomer 1). LCMS (ES, m/z): 721 [M−H]$^-$. $^1$H NMR (500 MHz, DMSO-d$_6$): δ 10.54 (s, 1H), 10.53 (s, 1H), 8.98 (s, 1H), 7.59 (s, 1H), 7.56 (s, 1H), 6.43 (s, 2H), 6.37 (s, 2H), 6.17 (s, 1H), 5.91 (s, 1H), 5.89 (s, 1H), 5.24 (s, 1H), 5.01 (t, J=4.0 Hz, 1H), 4.93 (t, J=4.0 Hz, 1H), 4.60 (s, 1H), 4.42 (s, 1H), 4.25 (t, J=8.5 Hz, 1H), 4.20 (s, 2H), 3.92 (m, 1H), 3.85 (d, J=10.6 Hz, 1H), 3.72 (d, J=11.1 Hz, 1H), 3.52 (m, 1H). $^{31}$P NMR: (202 MHz, DMSO-d$_6$): δ 56.2 (s), 47.6 (s).

The other diastereomeric product of Step 2, 9,9'-[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one) (CC-2), was independently treated in an analogous manner to that described immediately above in Step 3 to provide Example 26, 9,9'-[(1R,6R,8R,9R,14R,16R,17R,18R)-17,18-dihydroxy-3,11-dioxido-3,11-disulfanyl-2,4,7,10,12,15-hexaoxa-3,11-diphosphatricyclo-[12.2.1.1$^{6,9}$]-octadecane-8,16-diyl]bis(2-amino-1,9-dihydro-6H-purin-6-one) (Diastereomer 2). LCMS (ES, m/z): 721 [M−H]$^-$. $^1$H NMR (500 MHz, DMSO-d$_6$): δ 10.53 (s, 2H), 7.65 (s, 2H), 6.45 (s, 4H), 5.89 (d, J=8.5 Hz, 2H), 5.30 (s, 2H), 4.93 (t, J=4.0 Hz, 2H), 4.58 (s, 2H), 4.23 (t, J=8.5 Hz, 2H), 4.19 (s, 2H), 3.73 (d, J=11.4 Hz, 2H). $^3$P NMR: (202 MHz, DMSO-d$_6$): δ 47.9 (s).

Example 27, as shown in Table 4 below, was prepared according to procedures analogous to those outlined in Examples 25 and 26 above using the appropriate monomers, described as Preparations or as obtained from commercial sources, in the coupling step.

TABLE 4

| Ex. | Structure | Name | Mass [M − H] |
|---|---|---|---|
| 27 | 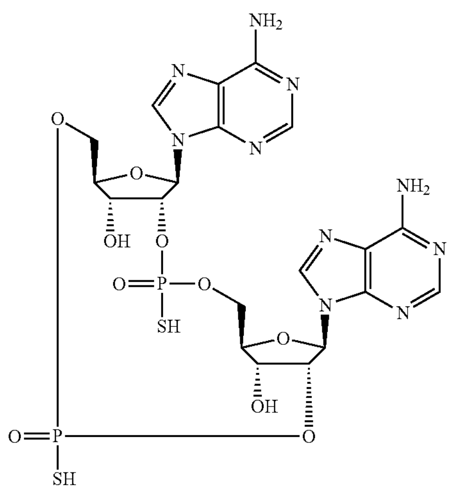 [SMILES: Nc1ncnc2c1ncn2[C@@H]1O[C@@H]2COP(=O)(S)O[C@@H]3[C@H](O)[C@@H](COP(=O)(S)O[C@@H]1[C@@H]2O)O[C@H]3n1cnc2c(N)ncnc21] | (1R,6R,8R,9R,14R,16R,17R,18R)-8,16-bis(6-amino-9H-purin-9-yl)-3,11-disulfanyl-2,4,7,10,12,15-hexaoxa-3,11-diphosphatricyclo[12.2.1.1$^{6,9}$]octadecane-17,18-diol 3,11-dioxide | 689 |

Examples 28 and 29: 9,9'-((1R,6R,8R,9R,14R,16R,17S,18S)-3,11,17,18-tetrahydroxy-3,11-disulfido-2,4,10,12-tetraoxa-7,15-dithia-3,11-diphosphatricyclo[12.2.1.1$^{6,9}$]octadecane-8,16-diyl)bis(2-amino-1,9-dihydro-6H-purin-6-one) (Diastereomers 1 and 2)

Diastereomer 1

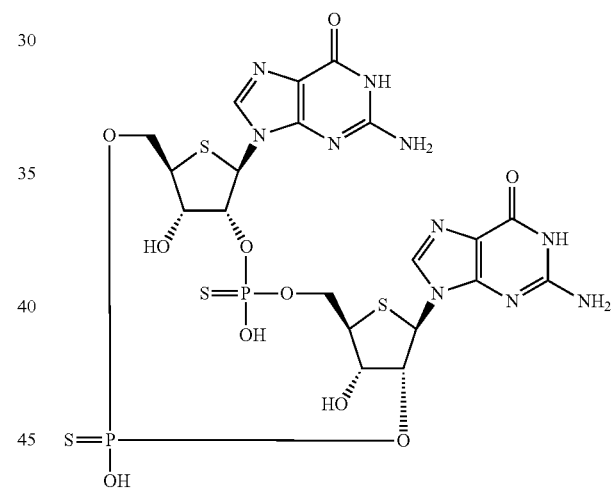

-continued

Diastereomer 2

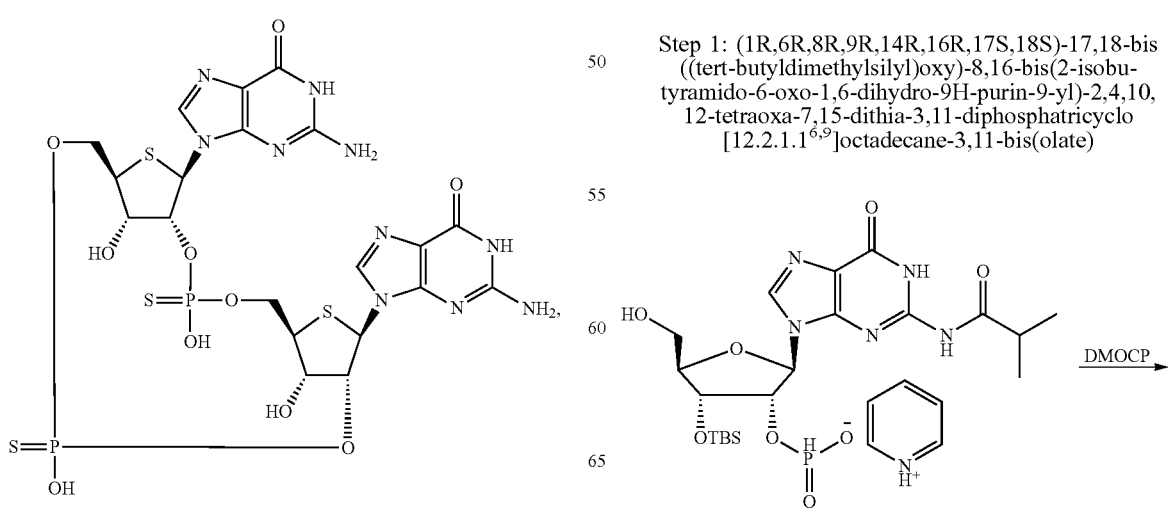

Step 1: (1R,6R,8R,9R,14R,16R,17S,18S)-17,18-bis((tert-butyldimethylsilyl)oxy)-8,16-bis(2-isobutyramido-6-oxo-1,6-dihydro-9H-purin-9-yl)-2,4,10,12-tetraoxa-7,15-dithia-3,11-diphosphatricyclo[12.2.1.1$^{6,9}$]octadecane-3,11-bis(olate)

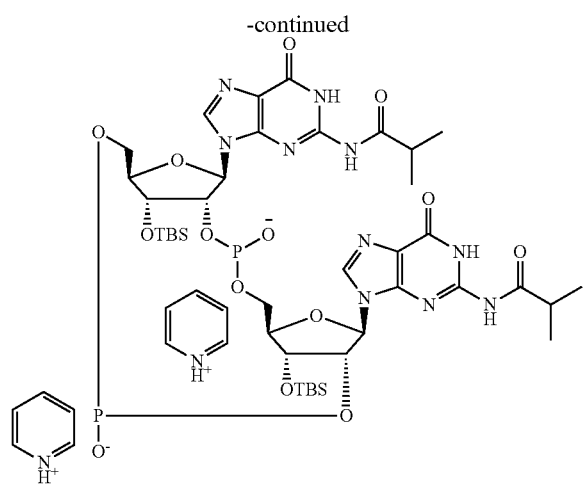

To a solution of (2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl hydrogen phosphonate (300 mg, 0.620 mmol) in pyridine (1 mL) at 0° C. was added 2-chloro-5,5-dimethyl-1,3,2-dioxaphosphinane 2-oxide (2.29 g, 12.4 mmol). The resulting solution was stirred at rt for 1 h. The reaction mixture was used for the next reaction step without purification. LCMS (ES, m/z): 1059.3 [M+H]$^+$.

Step 2: (1R,6R,8R,9R,14R,16R,17S,18S)-17,18-bis((tert-butyldimethylsilyl)oxy)-8,16-bis(2-isobutyramido-6-oxo-1,6-dihydro-9H-purin-9-yl)-2,4,10,12-tetraoxa-7,15-dithia-3,11-diphosphatricyclo[12.2.1.1$^{6,9}$]octadecane-3,11-bis(olate) 3,11-disulfide

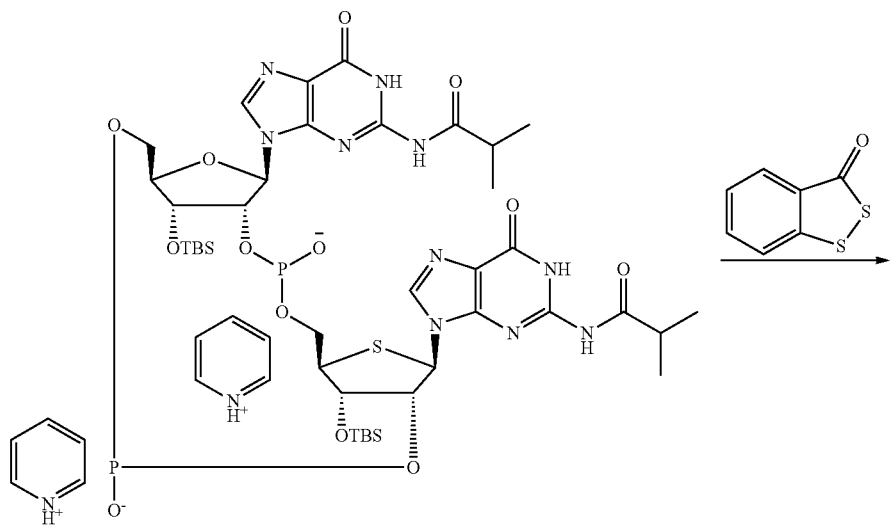

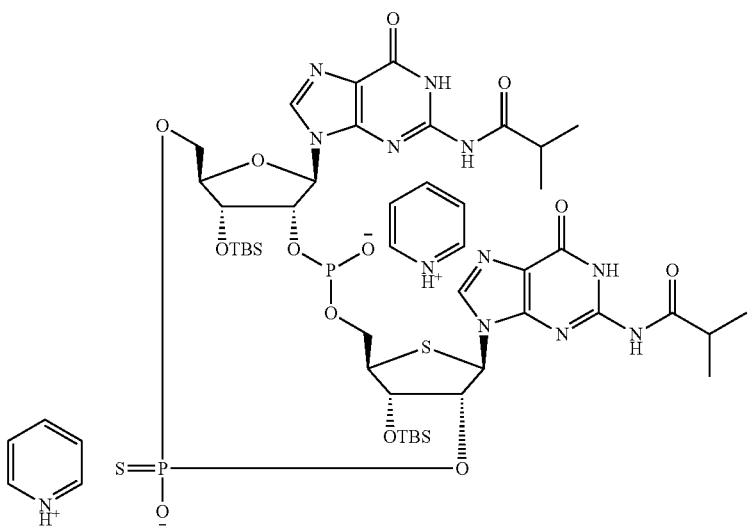

To the solution from Step 1 at rt was added 3H-benzo[c][1,2]dithiol-3-one (0.042 g, 0.25 mmol). The resulting solution was stirred for 0.5 h. Water (0.5 mL) was added to the reaction solution. The mixture was concentrated to give crude product.
Step 3: (1R,6R,8R,9R,14R,16R,17S,18S)-8,16-bis(2-amino-6-oxo-1,6-dihydro-9H-purin-9-yl)-17,18-bis((tert-butyldimethylsilyl)oxy)-2,4,10,12-tetraoxa-7,15-dithia-3,11-diphosphatricyclo[12.2.1.1⁶,⁹]octadecane-3,11-bis(olate) 3,11-disulfide
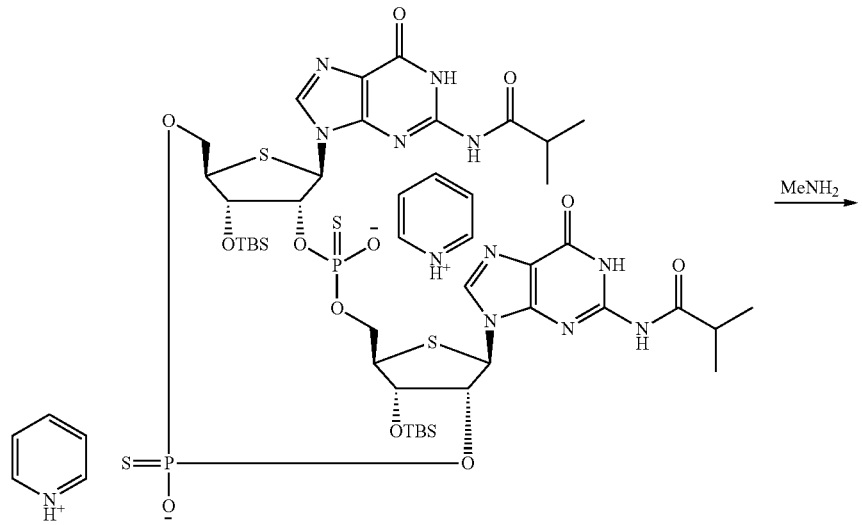
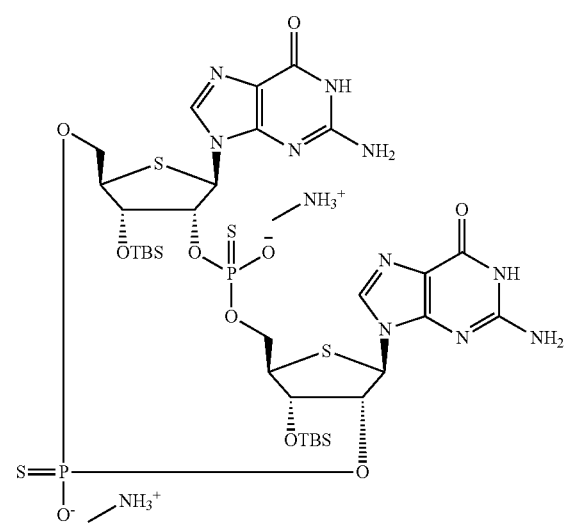

The crude from Step 2 was dissolved in methylamine in ethanol (30%, 6 mL), and it was stirred at rt for 1 h. Then, volatile components were removed under reduced pressure to give crude product.

Step 4: 9,9'-((1R,6R,8R,9R,14R,16R,17S,18S)-3,11,17,18-tetrahydroxy-3,11-disulfido-2,4,10,12-tetraoxa-7,15-dithia-3,11-diphosphatricyclo[12.2.1.1$^{6,9}$]octadecane-8,16-diyl)bis(2-amino-1,9-dihydro-6H-purin-6-one) (Diastereomer1, L-006164026-001J) and 9,9'-((1R,6R,8R,9R,14R,16R,17S,18S)-3,11,17,18-tetrahydroxy-3,11-disulfido-2,4,10,12-tetraoxa-7,15-dithia-3,11-diphosphatricyclo[12.2.1.1$^{6,9}$]octadecane-8,16-diyl)bis(2-amino-1,9-dihydro-6H-purin-6-one) (Diastereomer2, L-006162098-001J)

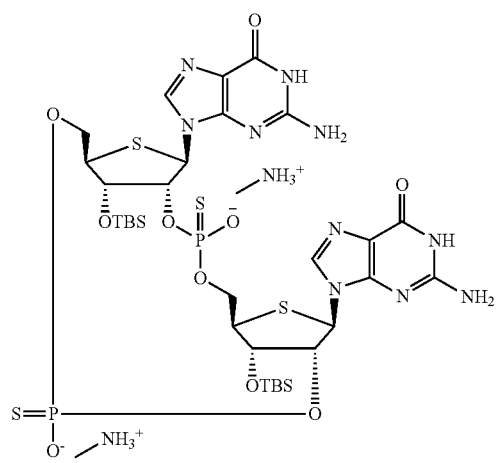

To the crude from Step 3 at rt was added pyridine (2 mL), triethylamine (627 mg, 6.20 mmol) and triethylamine trihydrofluoride (250 mg, 1.55 mmol). The resulting solution was stirred at 60° C. for 16 h. Then, it was cooled to rt, and acetone (30 mL) and Me$_3$SiOEt (2 mL) were added. After 10 min, solids were collected by filtration and washed with acetone (5×5 mL). The solid was purified by Prep-HPLC (Atlantis Prep T3 OBD Column, 19×250 mm) and eluted with 5 to 15% ACN in aq NH$_4$HCO$_3$ (10 mM) over 15 min to give, after concentration, two diastereomeric products.

The first product (T$_R$=9.18 min) was purified further by Prep-HPLC (XBridge Prep Phenyl OBD Column, 19×250 mm) eluting with 3 to 10% ACN in aq NH$_4$HCO$_3$ (10 mM) over 16 min to give Example 28: 9,9'-((1R,6R,8R,9R,14R,16R,17S,18S)-3,11,17,18-tetrahydroxy-3,11-disulfido-2,4,10,12-tetraoxa-7,15-dithia-3,11-diphosphatricyclo[12.2.1.1$^{6,9}$]octadecane-8,16-diyl)bis(2-amino-1,9-dihydro-6H-purin-6-one) (Diastereomer 1, L-006164026-001J): T$_R$: 14.90 min. LCMS (ES, m/z): 755.0 [M+H]$^+$. $^1$H-NMR: (400 MHz, D$_2$O): δ 7.87 (s, 2H), 5.90-5.88 (m, 2H), 5.57-5.55 (m, 4H), 4.70-4.50 (m, 2H), 4.13-4.03 (m, 2H), 3.56-3.49 (m, 2H). $^{31}$P-NMR: (121 MHz, D$_2$O): δ 53.68 (s).

The second product (T$_R$=10.52 min) was purified further by Prep-HPLC (XBridge Prep Phenyl OBD Column, 19×250 mm) eluting with 2 to 7% MECN in aq NH$_4$HCO$_3$ (10 mM) over 16 min to give Example 29: 9,9'-((1R,6R,8R,9R,14R,16R,17S,18S)-3,11,17,18-tetrahydroxy-3,11-disulfido-2,4,10,12-tetraoxa-7,15-dithia-3,11-diphosphatricyclo[12.2.1.1$^{6,9}$]octadecane-8,16-diyl)bis(2-amino-1,9-dihydro-6H-purin-6-one) (Diastereomer 2, L-006162098-001J): T$_R$: 7.87 min. LCMS (ES, m/z): 755.0 [M+H]$^+$. $^1$H-NMR (400 MHz, D$_2$O): δ 7.85 (s, 2H), 5.89-5.88 (m, 2H), 5.52-5.50 (m, 4H), 4.60-4.56 (m, 2H), 4.04-3.98 (m, 2H), 3.59-3.50 (m, 2H). $^{31}$P-NMR: (121 MHz, D$_2$O): δ 57.82 (s), 54.23 (s)

Example 30: 9,9'-[(1S,6R,8R,9S,14R,16R,17S,18S)-17,18-difluoro-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one)

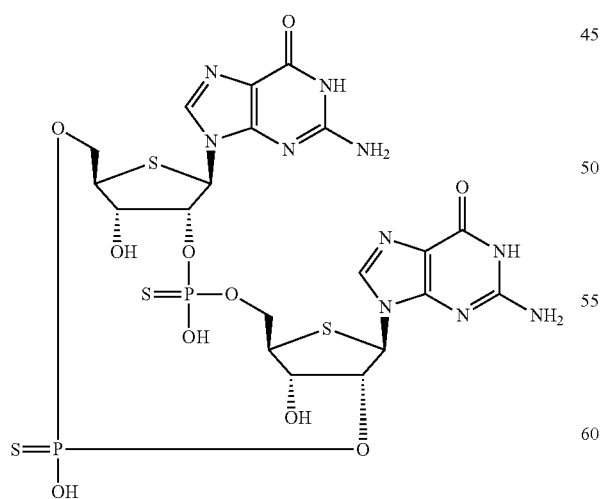

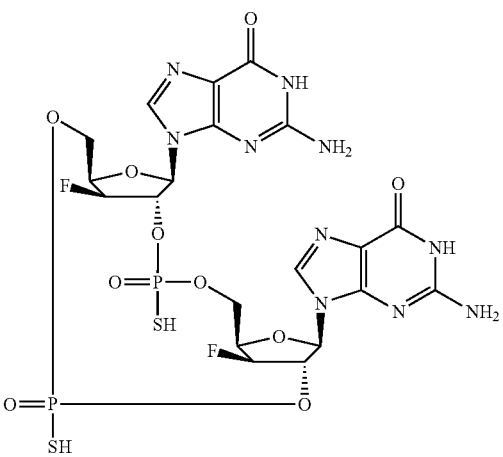 [SMILES: Nc1nc2c(ncn2[C@@H]2O[C@@H]3COP(=O)(S)O[C@@H]4[C@@H](F)[C@@H](COP(=O)(S)O[C@@H]2[C@H]3F)O[C@H]4n2cnc3c(=O)[nH]c(N)nc32)c(=O)[nH]1]

Step 1: N,N'-{[(1S,6R,8R,9S,14R,16R,17S,18S)-17, 18-difluoro-3,11-dioxido-3,11-disulfanyl-2,4,7,10, 12,15-hexaoxa-3,11-diphosphatricyclo[12.2.1.1⁶,⁹] octadecane-8,16-diyl]bis(6-oxo-1,6-dihydro-9H-purine-9,2-diyl)}bis(2-methylpropanamide)

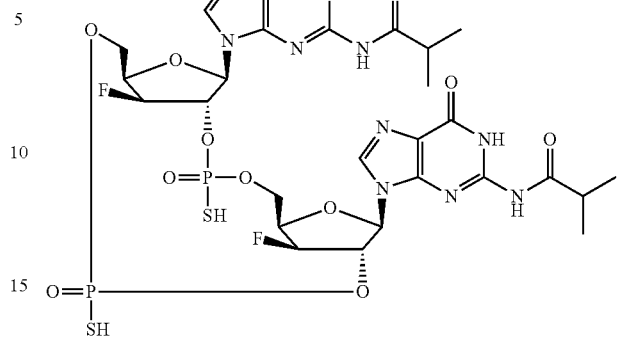

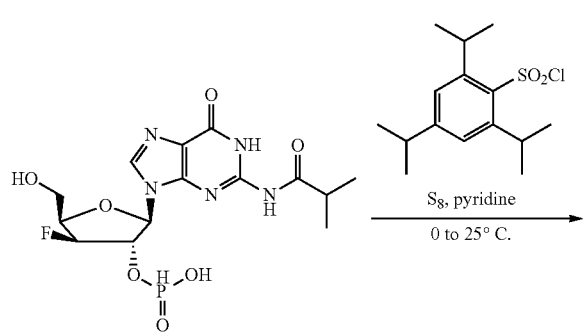

To a stirred solution of 9-{3-deoxy-3-fluoro-2-O-[hydroxy(oxido)-λ⁵-phosphanyl]-b-D-xylofuranosyl}-2-[(2-methylpropanoyl)amino]-1,9-dihydro-6H-purin-6-one, pyridine salt (200 mg, 0.401 mmol) in pyridine (7.5 mL) was added a solution of 2,4,6-triisopropylbenzenesulfonyl chloride (608 mg, 2.01 mmol) in pyridine (2.5 mL) dropwise over 1 min under argon at 0° C., followed by addition of sulfur (77 mg, 2.41 mmol) in one portion. The reaction mixture was allowed to warm to ambient temperature and left to stir at the same temperature for 1 h, quenched with cold water (1.0 mL), and the mixture was filtered and concentrated to furnish crude N,N'-{[(1S,6R,8R,9S,14R, 16R,17S,18S)-17,18-difluoro-3,11-dioxido-3,11-disulfanyl-2,4,7,10,12,15-hexaoxa-3,11-diphosphatricyclo[12.2.1.1⁶,⁹] octadecane-8,16-diyl]bis(6-oxo-1,6-dihydro-9H-purine-9,2-diyl)}bis(2-methylpropanamide), which was used for the next reaction step directly. LCMS (ES, m/z): 867 [M+H]⁺.

Step 2: 9,9'-[(1S,6R,8R,9S,14R,16R,17S,18S)-17, 18-difluoro-3,11-dioxido-3,11-disulfanyl-2,4,7,10, 12,15-hexaoxa-3,11-diphosphatricyclo[12.2.1.1⁶,⁹] octadecane-8,16-diyl]bis(2-amino-1,9-dihydro-6H-purin-6-one)

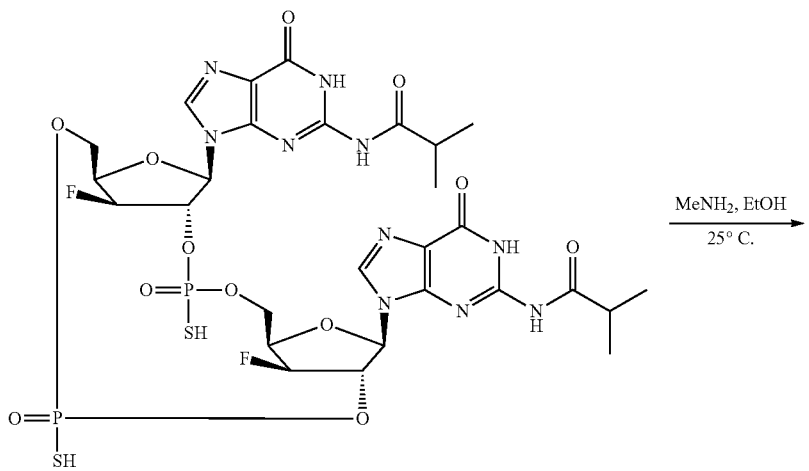

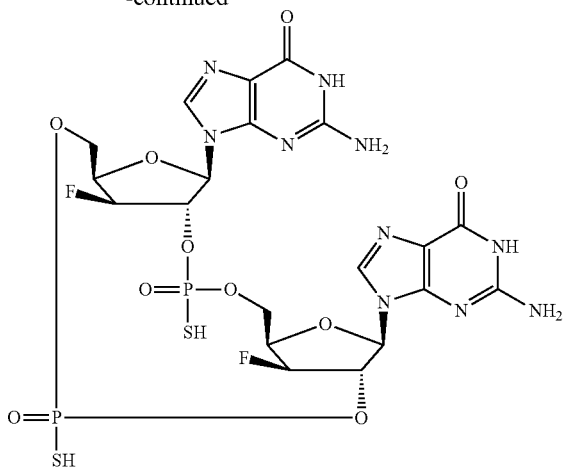

To N,N'-{[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]-octadecane-8,16-diyl]bis(6-oxo-1,6-dihydro-9H-purine-9,2-diyl)}bis(2-methylpropanamide) (214 mg, 0.201 mmol) was added a 33 wt. % methylamine solution in absolute ethanol (2.40 mL, 19.3 mmol), the reaction mixture was left to stir at ambient temperature for 18 h. The reaction mixture was concentrated, and the product was purified using mass-directed reverse phase HPLC with a Waters SunFire C18 OBD Prep Column, 100 Å, 5 m, 19 mm×150 mm, [Waters Part #186002568] using a gradient solvent system with MeCN and 100 mM aq triethylammonium acetate. Lyophilization of the product fractions furnished 9,9'-[(1R,6R,8R,9R,14R,16R,17R,18R)-17,18-bis{[tert-butyl(dimethyl)silyl]oxy}-3,11-dioxido-3,11-disulfanyl-2,4,7,10,12,15-hexaoxa-3,11-diphosphatricyclo[12.2.1.1$^{6,9}$]octadecane-8,16-diyl]bis(2-amino-1,9-dihydro-6H-purin-6-one). LCMS (ES, m/z): 725 [M−H]$^-$. $^1$H NMR (500 MHz, DMSO-d$_6$): δ 10.65 (s, 2H), 7.51 (s, 2H), 6.63 (s, 4H), 6.55 (s, 2H), 5.89 (s, 2H), 5.24 (d, J=50.6 Hz, 2H), 4.99 (t, J=8.8 Hz, 2H), 4.72 (t, J=12.6 Hz, 2H), 4.19 (dd, J=29.5, 7.2 Hz, 2H), 4.19 (s, 2H), 3.96 (m, 2H). $^{31}$P NMR: (202 MHz, DMSO-d$_6$): δ 55.4 (s). $^{19}$F NMR: (470 MHz, DMSO-d$_6$): δ −202.3 (dddd).

Example 31, as shown in Table 5 below, was prepared according to procedures analogous to those outlined in Example 30 above using the appropriate monomers, described as Preparations or as obtained from commercial sources, in the coupling step.

TABLE 5

| Ex. | Structure | Name | Mass [M − H]$^-$ |
|---|---|---|---|
| 31 | 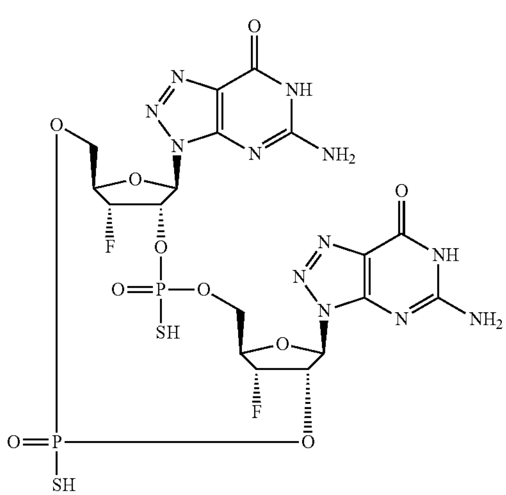 [SMILES: Nc1nc2c(nnn2[C@@H]2O[C@@H]3COP(=O)(S)O[C@@H]4[C@H](F)[C@@H](COP(=O)(S)O[C@@H]2[C@@H]3F)O[C@H]4n2nnc3c(=O)[nH]c(N)nc32)c(=O)[nH]1] | 3,3'-[(1S,6R,8R,9S,14R,16R,17R,18R)-17,18-difluoro-3,11-dioxido-3,11-disulfanyl-2,4,7,10,12,15-hexaoxa-3,11-diphosphatricyclo[12.2.1.1$^{6,9}$]octadecane-8,16-diyl]bis(5-amino-3,6-dihydro-7H-[1,2,3]triazolo[4,5-d]pyrimidin-7-one) | 727 |

Example 32: 2-amino-9-[(1R,6S,8R,9R,14R,16R, 17R,18R)-18-amino-16-(6-amino-9H-purin-9-yl)-3, 11,17-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one

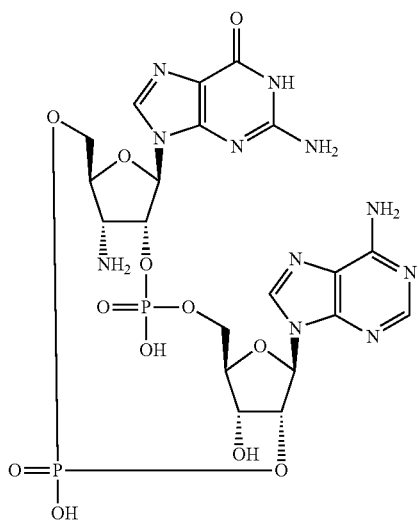 [SMILES: Nc1nc2c(ncn2[C@@H]2O[C@@H]3COP(=O)(O)O[C@@H]4[C@H](O)[C@@H](COP(=O)(O)O[C@@H]2[C@@H]3N)O[C@H]4n2cnc3c(N)ncnc32)c(=O)[nH]1]

Step 1: 2-amino-9-[(1R,6S,8R,9R,14R,16R,17R, 18R)-18-amino-16-(6-amino-9H-purin-9-yl)-3,11, 17-trihydroxy-3,11-dioxido-2,4,7,10,12,15-hexaoxa-3,11-diphosphatricyclo[12.2.1.1$^{6,9}$]-octadec-8-yl]-1, 9-dihydro-6H-purin-6-one

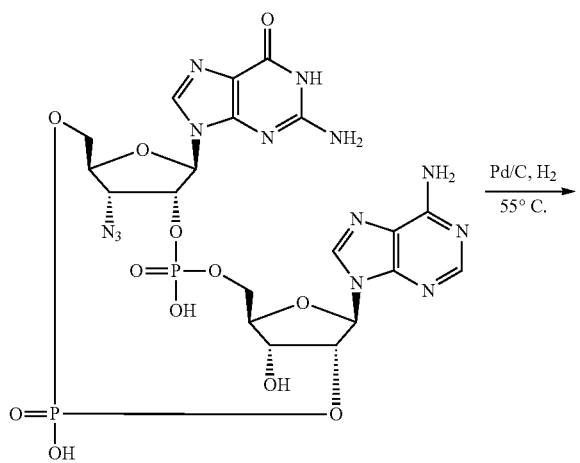

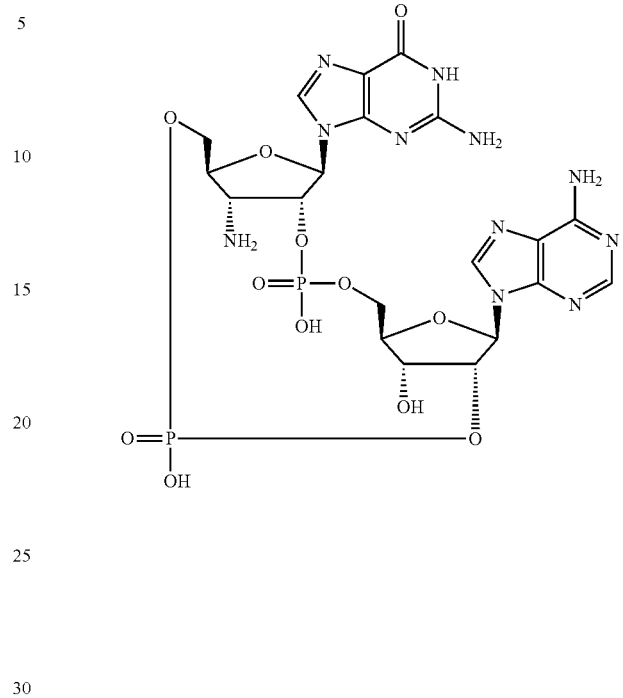

To a stirred solution of 2-amino-9-[(1R,6S,8R,9R,14R, 16R,17R,18R)-16-(6-amino-9H-purin-9-yl)-18-azido-3,11, 17-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one, (4.0 mg, 0.0055 mmol), as prepared in Example 5, in absolute ethanol (1.0 mL) and deionized water (1.0 mL) was added palladium on carbon (1.0 mg, 10 wt. % loading) in one portion under argon at RT. The reaction vessel was then flushed with hydrogen gas and attached to a hydrogen gas balloon. The reaction mixture was left to stir for 48 h, filtered, and concentrated to afford the title compound. LCMS (ES, m/z): 672 [M–H]$^-$. (600 MHz, DMSO-d$_6$) δ 13.40 (s, 1H), 8.12 (s, 1H), 7.99 (s, 1H), 7.74 (s, 1H), 7.36 (br, 2H), 6.43 (br, 2H), 6.14 (d, J=8.3 Hz, 1H), 6.07 (d, J=8.5 Hz, 1H), 5.03 (t, J=6.0 Hz, 1H), 4.89 (dd, J=8.2, 4.1 Hz, 1H), 4.54 (d, J=2.9 Hz, 1H), 4.28 (s, 1H), 4.19 (s, 1H), 4.09 (dd, J=10.5, 5.0 Hz, 1H), 4.07-4.02 (m, 1H), 3.94 (d, J=4.1 Hz, 1H), 3.84 (d, J=11.2 Hz, 1H), 3.76 (d, J=11.2 Hz, 1H). $^{31}$P NMR: (202 MHz, DMSO-d$_6$): δ –1.9 (s), –1.6 (s).

Examples 33 and 34, as shown in Table 5 below, were prepared according to procedures analogous to those outlined in Example 32 above from the starting compound ("St. Cmpd.") specified.

TABLE 5

| Ex. | Structure | Name | Mass [M − H]⁻ | St. Cmpd. |
|---|---|---|---|---|
| 33 | 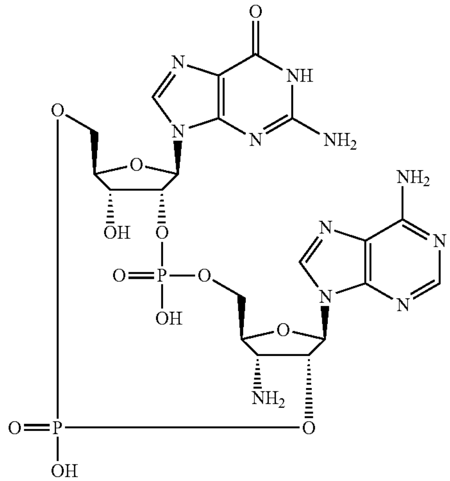 [SMILES: Nc1nc2c(ncn2[C@@H]2O[C@@H]3COP(=O)(O)O[C@@H]4[C@H](N)[C@@H](COP(=O)(O)O[C@@H]2[C@@H]3O)O[C@H]4n2cnc3c(N)ncnc32)c(=O)[nH]1] | 2-amino-9-[(1R,6R,8R,9R,14S,16R,17R,18R)-17-amino-16-(6-amino-9H-purin-9-yl)-3,11,18-trihydroxy-3,11-dioxido-2,4,7,10,12,15-hexaoxa-3,11-diphosphatricyclo[12.2.1.1$^{6,9}$]octadec-8-yl]-1,9-dihydro-6H-purin-6-one | 672 | 6 |

Biological Evaluation

The individual compounds described in the Examples are defined as STING agonists by demonstrating binding to the STING protein with an $EC_{50}$ of 20 uM or less in the STING Biochemical [³H]cGAMP Competition Assay (using either HAQ or wild type (WT) STING) and demonstrating interferon production with a 5% or greater luminescence induction at 30 uM in the IFN-β secretion in the THP1 cell assay. The methods below describe each of these assays.

[³H]-cGAMP Synthesis 2.3 mL of buffer solution containing 80 mM tris Cl, 200 mM $MgCl_2$ and 20 mM NaCl followed by 0.32 mL of a 10 mM aq solution of GTP was added to a plastic 50 mL AMICON tube. A solution of [³H]ATP (21 Ci/mmol, 45 mCi) in 0.5 mL $H_2O$ was then added followed by 1 mL of a 1 mg/mL solution of DNA (Herring testes activator DNA, Sigma, # D6898) and 53 uL of a 47 mM solution of cGAS enzyme. Additional $H_2O$ was added to bring the total volume to 10 mL.

The reaction was stirred for 2 h at 37° C., and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [³H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in ROSETTA™ 2(DE3) Single Competent Cells (Novagen). Affinity purification was carried out using HIS-Select HF Nickel Affinity Gel (Sigma) followed by size exclusion chromatography using a Hi-Load 26/60 SUPERDEX200 prep grade column (GE Healthcare). Fractions were pooled, concentrated, flash frozen in liquid nitrogen and stored at −80° C. until needed for research applications.

Example 35: ³H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (Tni; Expression Systems, cat #94-002F, www.exrpressionsystems.com) overexpressing full-length HAQ STING prepared in-house and tritiated cGAMP ligand also purified in-house.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (1x PBS; Invitrogen # SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control (prepared in-house) was added to the appropriate wells using a Biomek FX. Compound and membrane then preincubated for 60 min at RT to allow compound binding to equilibrate. Following equilibration, 8 nM of [³H] c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TomTec MachIII Cell Harvester equipped with 20 mM HEPES buffer (Fisher Scientific, # BP299500). The filter plates were then dried at 55° C. for 30 min using a pressurized VWR oven before 30 uL of Ultima GoldF scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 μL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of $5\times10^5$ cells/mL to allow for one overnight doubling) in Sf-900II SFM media containing 5 g/mL gentamicin (Invitrogen #15710072). The infected cells were then incubated at 27° C. for 3 d while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 m larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs) according to in-house validated SOP. Cryopreservation media containing Sf-900II SFM media with 10% heat inactivated FBS, 10% DMSO (Sigma # D2650), and 5 g/ml gentamicin was prepared in-house and sterilized through 0.22 μM filter immediately prior to use. P1 cell pellets were resuspended to a density of 2e7 cells/ml and aliquoted into cryovials (1 mL per vial). Cryovials were placed in Mr. Frosty cell freezers O/N at −80° C., and transferred to liquid nitrogen for long term storage the following day. To generate P2 viral stock, 0.5 mL of the P1 viral supernatant was added to 50 mL uninfected Sf21 cells (seeded the day prior to infection at a density of $5\times10^5$ cells/mL to allow for one overnight doubling) in Sf-900II SFM media containing 5 g/mL gentamicin. These cells were incubated at 27° C. for 3 d while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING membranes, P1/P2 BIICs were amplified overnight by adding thawed BIICs to Sf21 cells seeded at a density of $1.0\times10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 m larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0\times10^6$ in cell media (ESF921 SFM containing 5 g/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 μm larger than uninfected cells and viability approximately 80-90%) prior to harvest.

Full-Length STING (HAQ) Membrane Generation

Buffer Stock Reagents:
1) 1 M HEPES pH 7.5, Teknova, Cat # H1035
2) 5 M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (HAQ) prepared above at 5 mL Lysis buffer/g of cell pellet. The pellet was resuspended and dounced twenty times using a Wheaton Dounce Homogenizer to disrupt the cell membrane. Homogenized lysate was then passed through the emulsiflex-C5 microfluidizer at a pressure close to 5000 PSI. The resuspended pellet was centrifuged at 36,000 rpm (100,000×g) in a 45Ti rotor in the ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/500 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length HAQ STING [STING(1-379)R71H, G230A,
H232R, R293Q-GG-AviTag-GS-HRV3C-H158]Amino Acid
Sequence:
                                        (SEQ. ID. No. 1)
MPHSSLHPSIPCPRGHGAQKAALVLLSACLVTLWGLGEPPEHTLRYLVLHL
ASLQLGLLLNGVCSLAEELHHIHSRYRGSYWRTVRACLGCPLRRGALLLLS
IYFYYSLPNAVGPPFTWMLALLGLSQALNILLGLKGLAPAEISAVCEKGNF
NVAHGLAWSYYIGYLRLILPELQARIRTYNQHYNNLLRGAVSQRLYILLPL
DCGVPDNLSMADPNIRFLDKLPQQTADRAGIKDRVYSNSIYELLENGQRAG
TCVLEYATPLQTLFAMSQYSQAGFSREDRLEQAKLFCQTLEDILADAPESQ
NNCRLIAYQEPADDSSFSLSQEVLRHLRQEEKEEVTVGSLKTSAVPSTSTM
SQEPELLISGMEKPLPLRTDFSGGGLNDIFEAQKIEWHEGSLEVLFQGPHH
HHHHHH Full-length HAQ [STING(1-379)R71H, G230A, H232R,
R293Q-GG-AviTag-GS-HRV3C-HIS8/pBAC1] Plasmid DNA
Sequence:
                                        (SEQ. ID. No. 2)
GGAACGGCTCCGCCCACTATTAATGAAATTAAAAATTCCAATTTTAAAAAA
CGCAGCAAGAGAAACATTTGTATGAAAGAATGCGTAGAAGGAAAGAAAAAT
GTCGTCGACATGCTGAACAACAAGATTAATATGCCTCCGTGTATAAAAAAA
ATATTGAACGATTTGAAAGAAAACAATGTACCGCGCGGCGGTATGTACAGG
AAGAGGTTTATACTAAACTGTTACATTGCAAACGTGGTTTCGTGTGCCAAG
TGTGAAAACCGATGTTTAATCAAGGCTCTGACGCATTTCTACAACCACGAC
TCCAAGTGTGTGGGTGAAGTCATGCATCTTTTAATCAAATCCCAAGATGTG
TATAAACCACCAAACTGCCAAAAAATGAAAACTGTCGACAAGCTCTGTCCG
TTTGCTGGCAACTGCAAGGGTCTCAATCCTATTTGTAATTATTGAATAATA
AAACAATTATAAATGCTAAATTTGTTTTTTATTAACGATACAAACCAAACG
CAACAAGAACATTTGTAGTATTATCTATAATTGAAAACGCGTAGTTATAAT
CGCTGAGGTAATATTTAAAATCATTTTCAAATGATTCACAGTTAATTTGCG
ACAATATAATTTTATTTTCACATAAACTAGACGCCTTGTCGTCTTCTTCTT
CGTATTCCTTCTCTTTTTCATTTTTCTCTTCATAAAAATTAACATAGTTAT
TATCGTATCCATATATGTATCTATCGTATAGAGTAAATTTTTTGTTGTCAT
AAATATATATGTCTTTTTTAATGGGGTGTATAGTACCGCTGCGCATAGTTT
TTCTGTAATTTACAACAGTGCTATTTTCTGGTAGTTCTTCGGAGTGTGTTG
CTTTAATTATTAAATTTATATAATCAATGAATTTGGGATCGTCGGTTTTGT
ACAATATGTTGCCGGCATAGTACGCAGCTTCTTCTAGTTCAATTACACCAT
TTTTTAGCAGCACCGGATTAACATAACTTTCCAAAATGTTGTACGAACCGT
TAAACAAAAACAGTTCACCTCCCTTTTCTATACTATTGTCTGCGAGCAGTT
GTTTGTTGTTAAAAATAACAGCCATTGTAATGAGACGCACAAACTAATATC
ACAAACTGGAAATGTCTATCAATATATAGTTGCTGATCAGATCTGATCATG
GAGATAATTAAAATGATAACCATCTCGCAAATAAATAAGTATTTTACTGTT
TTCGTAACAGTTTTGTAATAAAAAAACCTATAAATATAGGATCCATGCCCC
ACTCCAGCCTGCATCCATCCATCCCGTGTCCCAGGGGTCACGGGGCCCAGA
AGGCAGCCTTGGTTCTGCTGAGTGCCTGCCTGGTGACCCTTTGGGGGCTAG
GAGAGCCACCAGAGCACACTCTCCGGTACCTGGTGCTCCACCTAGCCTCCC
TGCAGCTGGGACTGCTGTTAAACGGGGTCTGCAGCCTGGCTGAGGAGCTGC
ACCACATCCACTCCAGGTACCGGGGCAGCTACTGGAGGACTGTGCGGGCCT
GCCTGGGCTGCCCCCTCCGCCGTGGGGCCCTGTTGCTGCTGTCCATCTATT
TCTACTACTCCCTCCCAAATGCGGTCGGCCCGCCCTTCACTTGGATGCTTG
CCCTCCTGGGCCTCTCGCAGGCACTGAACATCCTCCTGGGCCTCAAGGGCC
TGGCCCCAGCTGAGATCTCTGCAGTGTGTGAAAAAGGGAATTTCAACGTGG
CCCATGGGCTGGCATGGTCATATTACATCGGATATCTGCGGCTGATCCTGC
CAGAGCTCCAGGCCCGGATTCGAACTTACAATCAGCATTACAACAACCTGC
TACGGGGTGCAGTGAGCCAGCGGCTGTATATTCTCCTCCCATTGGACTGTG
GGGTGCCTGATAACCTGAGTATGGCTGACCCCAACATTCGCTTCCTGGATA
AACTGCCCCAGCAGACCGCTGACCGTGCTGGCATCAAGGATCGGGTTTACA
GCAACAGCATCTATGAGCTTCTGGAGAACGGGCAGCGGGCGGGCACCTGTG
TCCTGGAGTACGCCACCCCCTTGCAGACTTTGTTTGCCATGTCACAATACA
GTCAAGCTGGCTTTAGCCGGGAGGATAGGCTTGAGCAGGCCAAACTCTTCT
GCCAGACACTTGAGGACATCCTGGCAGATGCCCCTGAGTCTCAGAACAACT
GCCGCCTCATTGCCTACCAGGAACCTGCAGATGACAGCAGCTTCTCGCTGT
CCCAGGAGGTTCTCCGGCACCTGCGGCAGGAGGAAAAGGAAGAGGTTACTG
TGGGCAGCTTGAAGACCTCAGCGGTGCCCAGTACCTCCACGATGTCCCAAG
AGCCTGAGCTCCTCATCAGTGGAATGGAAAAGCCCCTCCCTCTCCGCACGG
ATTTCTCTGGCGGTGGCCTGAACGACATCTTCGAAGCCCAGAAAATCGAAT
GGCATGAAGGCAGCCTGGAAGTGCTGTTCCAGGGCCCACACCACCATCATC
ACCATCACCATTAATGAGCGGCCGCACTCGAGCACCACCACCACCACCACT
AACCTAGGTAGCTGAGCGCATGCAAGCTGATCCGGGTTATTAGTACATTTA
TTAAGCGCTAGATTCTGTGCGTTGTTGATTTACAGACAATTGTTGTACGTA
TTTTAATAATTCATTAAATTTATAATCTTTAGGGTGGTATGTTAGAGCGAA
AATCAAATGATTTTCAGCGTCTTTATATCTGAATTTAAATATTAAATCCTC
AATAGATTTGTAAAATAGGTTTCGATTAGTTTCAAACAAGGGTTGTTTTC
CGAACCGATGGCTGGACTATCTAATGGATTTTCGCTCAACGCCACAAAACT
TGCCAAATCTTGTAGCAGCAATCTAGCTTTGTCGATATTCGTTTGTGTTTT
GTTTTGTAATAAAGGTTCGACGTCGTTCAAAATATTATGCGCTTTTGTATT
TCTTTCATCACTGTCGTTAGTGTACAATTGACTCGACGTAAACACGTTAAA
TAGAGCTTGGACATATTTAACATCGGGCGTGTTAGCTTTATTAGGCCGATT
ATCGTCGTCGTCCCAACCCTCGTCGTTAGAAGTTGCTTCCGAAGACGATTT
TGCCATAGCCACACGACGCCTATTAATTGTGTCGGCTAACACGTCCGCGAT
CAAATTTGTAGTTGAGCTTTTTGGAATTATTTCTGATTGCGGGCGTTTTTG
GGCGGGTTTCAATCTAACTGTGCCCGATTTTAATTCAGACAACACGTTAGA
AAGCGATGGTGCAGGCGGTGGTAACATTTCAGACGGCAAATCTACTAATGG
```

-continued

```
CGGCGGTGGTGGAGCTGATGATAAATCTACCATCGGTGGAGGCGCAGGCGG
GGCTGGCGGCGGAGGCGGAGGCGGAGGTGGTGGCGGTGATGCAGACGGCGG
TTTAGGCTCAAATGTCTCTTTAGGCAACACAGTCGGCACCTCAACTATTGT
ACTGGTTTCGGGCGCCGTTTTTGGTTTGACCGGTCTGAGACGAGTGCGATT
TTTTTCGTTTCTAATAGCTTCCAACAATTGTTGTCTGTCGTCTAAAGGTGC
AGCGGGTTGAGGTTCCGTCGGCATTGGTGGAGCGGGCGGCAATTCAGACAT
CGATGGTGGTGGTGGTGGTGGAGGCGCTGGAATGTTAGGCACGGGAGAAGG
TGGTGGCGGCGGTGCCGCCGGTATAATTTGTTCTGGTTTAGTTTGTTCGCG
CACGATTGTGGGCACCGGCGCAGGCGCCGCTGGCTGCACAACGGAAGGTCG
TCTGCTTCGAGGCAGCGCTTGGGGTGGTGGCAATTCATATTATAATTGGAA
TACAAATCGTAAAAATCTGCTATAAGCATTGTAATTTCGCTATCGTTTACC
GTGCCGATATTTAACAACCGCTCAATGTAAGCAATTGTATTGTAAAGAGAT
TGTCTCAAGCTCGGATCGATCCCGCACGCCGATAACAAGCCTTTTCATTTT
TACTACAGCATTGTAGTGGCGAGACACTTCGCTGTCGTCGAGGTTTAAACG
CTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACT
TATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAA
AAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACT
CACGTTAAGGGATTTTGGTCATGAGATTATCAAAAAGGATCTTCACCTAGA
TCCTTTTAAATTAAAAATGAAGTTTTAAATCAATCTAAAGTATATATGAGT
AAACTTGGTCTGACAGTTACCAATGCTTAATCAGTGAGGCACCTATCTCAG
CGATCTGTCTATTTCGTTCATCCATAGTTGCCTGACTCCCCGTCGTGTAGA
TAACTACGATACGGGAGGGCTTACCATCTGGCCCCAGTGCTGCAATGATAC
CGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCC
AGTCTATTAATTGTTGCCGGGAAGCTAAGTAAGTAGTTCGCCAGTTAATAG
TTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGAC
TGGTGAGTACTCAACCAAGTCATTCTGAGAATAGTGTATGCGGCGACCGAG
TTGCTCTTGCCCGGCGTCAATACGGGATAATACCGCGCCACATAGCAGAAC
TTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAA
CTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTG
AATACTCATACTCTTCCTTTTTCAATATTATTGAAGCATTTATCAGGGTTA
TTGTCTCATGAGCGGATACATATTTGAATGTATTTAGAAAAATAAACAAAT
AGGGGTTCCGCGCACATTTCCCCGAAAAGTGCCACCTGACGCGCCCTGTAG
CGGCGCATTAAGCGCGGCGGGTGTGGTGGTTACGCGCAGCGTGACCGCTAC
ACTTGCCAGCGCCCTAGCGCCCGCTCCTTTCGCTTTCTTCCCTTCCTTTCT
CGCCACGTTCGCCGGCTTTCCCCGTCAAGCTCTAAATCGGGGGCTCCCTTT
AGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCC
TTTGACGTTGGAGTCCACGTTCTTTAATAGTGGACTCTTGTTCCAAACTGG
AACAACACTCAACCCTATCTCGGTCTATTCTTTTGATTTATAAGGGATTTT
GCCGATTTCGGCCTATTGGTTAAAAAATGAGCTGATTTAACAAAAATTTAA
CGCGAATTTTAACAAAATATTAACGTTTACAATTTCCCATTCGCCATTCAG
GCTGCGCAACTGTTGGGAAGGGCGATCGGTGCGGGCCTCTTCGCTATTACG
CCA
```

Certain compounds of the disclosure were evaluated in HAQ STING in vitro binding assay as described above. The following table tabulates the biological data for these compounds as $EC_{50}$ values.

TABLE 6

$^3$H-cGAMP filtration binding assay for HAQ STING

| Compound | $EC_{50}$ (nM) |
| --- | --- |
| Example 1 | 19 |
| Example 2 | 18.2 |
| Example 3 | 3.6 |
| Example 4 | 1.8 |
| Example 5 | <1 |
| Example 6 | 2.3 |
| Example 7 | 45.2 |
| Example 8 | 102 |
| Example 9 | 3.7 |
| Example 10 | 24.4 |
| Example 11 | <1 |
| Example 12 | 673.6 |
| Example 13 | 11.2 |
| Example 14 | 1.9 |
| Example 15 | 23.4 |
| Example 16 | 12.5 |
| Example 17 | 1311 |
| Example 18 | <1 |
| Example 19 | <1 |
| Example 20 | <1 |
| Example 21 | 2.9 |
| Example 25 | <1 |
| Example 26 | <1 |
| Example 27 | 6.6 |

TABLE 6-continued

³H-cGAMP filtration binding assay for HAQ STING

| Compound | $EC_{50}$ (nM) |
| --- | --- |
| Example 32 | 1.9 |
| Example 33 | 1.6 |
| Example 34 | <1 |

Example 36: ³H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (Tni; Expression Systems, cat #94-002F, www.expressionsystems.com) overexpressing full-length WT STING prepared in-house and tritiated cGAMP ligand also purified in-house.

The basic WT STING filtration assay protocol is as follows:

16 nM of [³H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control (prepared in-house) was added to the appropriate wells using a Biomek FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 3) was prepared by diluting concentrated membrane into assay buffer (lx PBS; Invitrogen # SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TomTec MachIII Cell Harvester equipped with 20 mM HEPES buffer (Fisher Scientific, # BP299500). The filter plates were then dried at 55° C. for 30 min using a pressurized VWR oven before 30 uL of Ultima GoldF scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| ³H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 μL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 4) and linearized viral backbone BestBac 2.0] at 27° C. for 5-7 days to generate the P0 viral stock. To generate P1 viral stocks, 0.5 mL of P0 viral supernatant was added to 50 mL uninfected Sf21 cells (seeded the day prior to infection at a density of $5\times10^5$ cells/mL to allow for one overnight doubling) in Sf-900II SFM media containing 5 g/mL gentamicin (Invitrogen #15710072). The infected cells were then incubated at 27° C. for 3 d while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 m larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs) according to in-house validated SOP. Cryopreservation media containing Sf-900II SFM media with 10% heat inactivated FBS, 10% DMSO (Sigma # D2650), and 5 g/ml gentamicin was prepared in-house and sterilized through 0.22 μM filter immediately prior to use. P1 cell pellets were resuspended to a density of 2e7 cells/ml and aliquoted into cryovials (1 mL per vial). Cryovials were placed in Mr. Frosty cell freezers O/N at −80° C., and transferred to liquid nitrogen for long term storage the following day. To generate P2 viral stock, 0.5 mL of the P1 viral supernatant was added to 50 mL uninfected Sf21 cells (seeded the day prior to infection at a density of $5\times10^5$ cells/mL to allow for one overnight doubling) in Sf-900II SFM media containing 5 g/mL gentamicin. These cells were incubated at 27° C. for 3 d while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (WT) Expression

To generate STING membranes, P1/P2 BIICs were amplified overnight by adding thawed BIICs to Sf21 cells seeded at a density of $1.0\times10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 m larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0 \times 10^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 m larger than uninfected cells and viability approximately 80-90%) prior to harvest.

Full-Length STING (WT) Membrane Generation

Buffer Stock Reagents:
1) 1 M HEPES pH 7.5, Teknova, Cat # H1035
2) 5 M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (WT) prepared above at 5 mL Lysis buffer/g of cell pellet. The pellet was resuspended and dounced twenty times using a Wheaton Dounce Homogenizer to disrupt the cell membrane. Homogenized lysate was then passed through the emulsiflex-$C_5$ microfluidizer at a pressure close to 5000 PSI. The resuspended pellet was centrifuged at 36,000 rpm (100,000×g) in a 45Ti rotor in the ultra-high speed centrifuge for 45 min, 4° C. The supernatant was removed. The pellet then was resuspended in wash buffer [(25 mM HEPES pH 7.5, 1 mM $MgCl_2$, 20 mM KCl, 1M NaCl (Complete Protease Inhibitor tab/50 mL)] at a volume of 50 mL/pellet/centrifuge tube. The pellet/Wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/500 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length STING WT [STING(1-379)H232R-gg-AviTag-gs-HRV3C-HIS8] Amino Acid Sequence:
(SEQ. ID. No. 3)
MPHSSLHPSIPCPRGHGAQKAALVLLSACLVTLWGLGEPPEHTLRYLVLH

LASLQLGLLLNGVCSLAEELRHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTGDRAGIKDRVYSNSIYELLEN

GQRAGTCVLEYATPLQTLFAMSQYSQAGFSREDRLEQAKLFCRTLEDILA

DAPESQNNCRLIAYQEPADDSSFSLSQEVLRHLRQEEKEEVTVGSLKTSA

VPSTSTMSQEPELLISGMEKPLPLRTDFSGGGLNDIFEAQKIEWHEGSLE

VLFQGPHHHHHHHH

Full-length WT STING [STING(1-379)H232R-gg-AviTag-gs-HRV3C-HIS8/pBAC1] plasmid sequence:
(SEQ. ID. No. 4)
GGAACGGCTCCGCCCACTATTAATGAAATTAAAAATTCCAATTTTAAAAA

ACGCAGCAAGAGAAACATTTGTATGAAAGAATGCGTAGAAGGAAAGAAAA

ATGTCGTCGACATGCTGAACAACAAGATTAATATGCCTCCGTGTATAAAA

AAAATATTGAACGATTTGAAAGAAAACAATGTACCGCGCGGCGGTATGTA

CAGGAAGAGGTTTATACTAAACTGTTACATTGCAAACGTGGTTTCGTGTG

CCAAGTGTGAAAACCGATGTTTAATCAAGGCTCTGACGCATTTCTACAAC

CACGACTCCAAGTGTGTGGGTGAAGTCATGCATCTTTTAATCAAATCCCA

AGATGTGTATAAACCACCAAACTGCCAAAAAATGAAAACTGTCGACAAGC

TCTGTCCGTTTGCTGGCAACTGCAAGGGTCTCAATCCTATTTGTAATTAT

TGAATAATAAAACAATTATAAATGTCAAATTTGTTTTTTATTAACGATAC

AAACCAAACGCAACAAGAACATTTGTAGTATTATCTATAATTGAAAACGC

GTAGTTATAATCGCTGAGGTAATATTTAAAATCATTTTCAAATGATTCAC

AGTTAATTTGCGACAATATAATTTTATTTTCACATAAACTAGACGCCTTG

TCGTCTTCTTCTTCGTATTCCTTCTCTTTTTCATTTTTCTCTTCATAAAA

ATTAACATAGTTATTATCGTATCCATATATGTATCTATCGTATAGAGTAA

ATTTTTTGTTGTCATAAATATATATGTCTTTTTTAATGGGGTGTATAGTA

CCGCTGCGCATAGTTTTTCTGTAATTTACAACAGTGCTATTTTCTGGTAG

TTCTTCGGAGTGTGTTGCTTTAATTATTAAATTTATATAATCAATGAATT

TGGGATCGTCGGTTTTGTACAATATGTTGCCGGCATAGTACGCAGCTTCT

TCTAGTTCAATTACACCATTTTTTAGCAGCACCGGATTAACATAACTTTC

CAAAATGTTGTACGAACCGTTAAACAAAAACAGTTCACCTCCCTTTTCTA

TACTATTGTCTGCGAGCAGTTGTTTGTTGTTAAAAATAACAGCCATTGTA

ATGAGACGCACAAACTAATATCACAAACTGGAAATGTCTATCAATATATA

GTTGCTGATCAGATCTGATCATGGAGATAATTAAAATGATAACCATCTCG

CAAATAAATAAGTATTTTACTGTTTTCGTAACAGTTTTGTAATAAAAAAA

CCTATAAATATAGGATCCATGCCCCACTCCAGCCTGCATCCATCCATCCC

GTGTCCCAGGGGTCACGGGGCCCAGAAGGCAGCCTTGGTTCTGCTGAGTG

CCTGCCTGGTGACCCTTTGGGGGCTAGGAGAGCCACCAGAGCACACTCTC

CGGTACCTGGTGCTCCACCTAGCCTCCCTGCAGCTGGGACTGCTGTTAAA

CGGGGTCTGCAGCCTGGCTGAGGAGCTGCGCCACATCCACTCCAGGTACC

GGGGCAGCTACTGGAGGACTGTGCGGGCCTGCCTGGGCTGCCCCCTCCGC

CGTGGGGCCCTGTTGCTGCTGTCCATCTATTTCTACTACTCCCTCCCAAA

TGCGGTCGGCCCGCCCTTCACTTGGATGCTTGCCCTCCTGGGCCTCTCGC

AGGCACTGAACATCCTCCTGGGCCTCAAGGGCCTGGCCCCAGCTGAGATC

TCTGCAGTGTGTGAAAAAGGGAATTTCAACGTGGCCCATGGGCTGGCATG

GTCATATTACATCGGATATCTGCGGCTGATCCTGCCAGAGCTCCAGGCCC

GGATTCGAACTTACAATCAGCATTACAACAACCTGCTACGGGGTGCAGTG

-continued

AGCCAGCGGCTGTATATTCTCCTCCCATTGGACTGTGGGGTGCCTGATAA
CCTGAGTATGGCTGACCCCAACATTCGCTTCCTGGATAAACTGCCCCAGC
AGACCGGTGACCGTGCTGGCATCAAGGATCGGGTTTACAGCAACAGCATC
TATGAGCTTCTGGAGAACGGGCAGCGGGCGGGCACCTGTGTCCTGGAGTA
CGCCACCCCCTTGCAGACTTTGTTTGCCATGTCACAATACAGTCAAGCTG
GCTTTAGCCGGGAGGATAGGCTTGAGCAGGCCAAACTCTTCTGCCGGACA
CTTGAGGACATCCTGGCAGATGCCCCTGAGTCTCAGAACAACTGCCGCCT
CATTGCCTACCAGGAACCTGCAGATGACAGCAGCTTCTCGCTGTCCCAGG
AGGTTCTCCGGCACCTGCGGCAGGAGGAAAAGGAAGAGGTTACTGTGGGC
AGCTTGAAGACCTCAGCGGTGCCCAGTACCTCCACGATGTCCCAAGAGCC
TGAGCTCCTCATCAGTGGAATGGAAAAGCCCCTCCCTCTCCGCACGGATT
TCTCTGGCGGTGGCCTGAACGACATCTTCGAAGCCCAGAAAATCGAATGG
CATGAAGGCAGCCTGGAAGTGCTGTTCCAGGGCCCACACCACCATCATCA
CCATCACCATTAATGAGCGGCCGCACTCGAGCACCACCACCACCACCACT
AACCTAGGTAGCTGAGCGCATGCAAGCTGATCCGGGTTATTAGTACATTT
ATTAAGCGCTAGATTCTGTGCGTTGTTGATTTACAGACAATTGTTGTACG
TATTTTAATAATTCATTAAATTTATAATCTTTAGGGTGGTATGTTAGAGC
GAAAATCAAATGATTTTCAGCGTCTTTATATCTGAATTTAAATATTAAAT
CCTCAATAGATTTGTAAAATAGGTTTCGATTAGTTTCAAACAAGGGTTGT
TTTTCCGAACCGATGGCTGGACATCTAATGGATTTTCGCTCAACGCCAC
AAAACTTGCCAAATCTTGTAGCAGCAATCTAGCTTTGTCGATATTCGTTT
GTGTTTTGTTTTGTAATAAAGGTTCGACGTCGTTCAAAATATTATGCGCT
TTTGTATTTCTTTCATCACTGTCGTTAGTGTACAATTGACTCGACGTAAA
CACGTTAAATAGAGCTTGGACATATTTAACATCGGGCGTGTTAGCTTTAT
TAGGCCGATTATCGTCGTCGTCCCAACCCTCGTCGTTAGAAGTTGCTTCC
GAAGACGATTTTGCCATAGCCACACGACGCCTATTAATTGTGTCGGCTAA
CACGTCCGCGATCAAATTTGTAGTTGAGCTTTTTGGAATTATTTCTGATT
GCGGGCGTTTTTGGGCGGGTTTCAATCTAACTGTGCCCGATTTTAATTCA
GACAACACGTTAGAAAGCGATGGTGCAGGCGGTGGTAACATTTCAGACGG
CAAATCTACTAATGGCGGCGGTGGTGGAGCTGATGATAAATCTACCATCG
GTGGAGGCGCAGGCGGGGCTGGCGGCGGAGGCGGAGGCGGAGGTGGTGGC
GGTGATGCAGACGGCGGTTTAGGCTCAAATGTCTCTTTAGGCAACACAGT
CGGCACCTCAACTATTGTACTGGTTTCGGCGCCGTTTTTGGTTTGACCG
GTCTGAGACGAGTGCGATTTTTTTCGTTTCTAATAGCTTCCAACAATTGT
TGTCTGTCGTCTAAAGGTGCAGCGGGTTGAGGTTCCGTCGGCATTGGTGG
AGCGGGCGGCAATTCAGACATCGATGGTGGTGGTGGTGGAGGCGCTG
GAATGTTAGGCACGGGAGAAGGTGGTGGCGGCGGTGCCGCCGGTATAATT
TGTTCTGGTTTAGTTTGTTCGCGCACGATTGTGGGCACCGGCGCAGGCGC
CGCTGGCTGCACAACGGAAGGTCGTCTGCTTCGAGGCAGCGCTTGGGGTG
GTGGCAATTCAATATTATAATTGGAATACAAATCGTAAAAATCTGCTATA

-continued

AGCATTGTAATTTCGCTATCGTTTACCGTGCCGATATTTAACAACCGCTC
AATGTAAGCAATTGTATTGTAAAGAGATTGTCTCAAGCTCGGATCGATCC
CGCACGCCGATAACAAGCCTTTTCATTTTTACTACAGCATTGTAGTGGCG
AGACACTTCGCTGTCGTCGAGGTTTAAACGCTTCCTCGCTCACTGACTCG
CTGCGCTCGGTCGTTCGGCTGCGGCGAGCGGTATCAGCTCACTCAAAGGC
GGTAATACGGTTATCCACAGAATCAGGGGATAACGCAGGAAAGAACATGT
GAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACG
CTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCC
GGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACG
TTAAGGGATTTTGGTCATGAGATTATCAAAAAGGATCTTCACCTAGATCC
TTTTAAATTAAAAATGAAGTTTTAAATCAATCTAAAGTATATATGAGTAA
ACTTGGTCTGACAGTTACCAATGCTTAATCAGTGAGGCACCTATCTCAGC
GATCTGTCTATTTCGTTCATCCATAGTTGCCTGACTCCCCGTCGTGTAGA
TAACTACGATACGGGAGGGCTTACCATCTGGCCCCAGTGCTGCAATGATA
CCGCGAGACCCACGCTCACCGGCTCCAGATTTATCAGCAATAAACCAGCC
AGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTT
AATAGTTTGCGCAACGTTGTTGCCATTGCTACAGGCATCGTGGTGTCACG
CTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGT
TATGGCAGCACTGCATAATTCTCTTACTGTCATGCCATCCGTAAGATGCT
TTTCTGTGACTGGTGAGTACTCAACCAAGTCATTCTGAGAATAGTGTATG
CGGCGACCGAGTTGCTCTTGCCCGGCGTCAATACGGGATAATACCGCGCC
ACATAGCAGAACTTTAAAAGTGCTCATCATTGGAAAACGTTCTTCGGGGC
GAAAACTCTCAAGGATCTTACCGCTGTTGAGATCCAGTTCGATGTAACCC
ACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGG
CGACACGGAAATGTTGAATACTCATACTCTTCCTTTTTCAATATTATTGA
AGCATTTATCAGGGTTATTGTCTCATGAGCGGATACATATTTGAATGTAT

-continued

```
TTAGAAAAATAAACAAATAGGGGTTCCGCGCACATTTCCCCGAAAAGTGC

CACCTGACGCGCCCTGTAGCGGCGCATTAAGCGCGGCGGGTGTGGTGGTT

ACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAG

CTCTAAATCGGGGCTCCCTTTAGGGTTCCGATTTAGTGCTTTACGGCAC

CTCGACCCCAAAAAACTTGATTAGGGTGATGGTTCACGTAGTGGGCCATC

GCCCTGATAGACGGTTTTTCGCCCTTTGACGTTGGAGTCCACGTTCTTTA

ATAGTGGACTCTTGTTCCAAACTGGAACAACACTCAACCCTATCTCGGTC

TATTCTTTTGATTTATAAGGGATTTTGCCGATTTCGGCCTATTGGTTAAA

AAATGAGCTGATTTAACAAAAATTTAACGCGAATTTTAACAAAATATTAA

CGTTTACAATTTCCCATTCGCCATTCAGGCTGCGCAACTGTTGGGAAGGG

CGATCGGTGCGGGCCTCTTCGCTATTACGCCA
```

Certain compounds of the disclosure were evaluated in WT STING in vitro binding assay as described above. The following table tabulates the biological data for these compounds as $EC_{50}$ values.

TABLE 7

$^3$H-cGAMP filtration binding assay for WT STING

| Compound | $EC_{50}$ (nM) |
|---|---|
| Example 14 | 2.4 |
| Example 15 | 102 |
| Example 16 | 35.5 |
| Example 17 | 1090 |
| Example 18 | 0.4 |
| Example 19 | 1 |
| Example 22 | <1 |
| Example 23 | 4 |
| Example 24 | 1.2 |
| Example 25 | 9.5 |
| Example 26 | <1 |
| Example 28 | 13.8 |
| Example 29 | 178 |
| Example 30 | 7348 |
| Example 31 | <1 |
| Example 34 | <1 |

Example 37: IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; 1x non-essential amino acids; Life Technologies, Cat. No. 11140-050). The cell viability and count was ascertained using a Beckman Coulter V-Cell XR cell counter. The cells suspension was centrifuged at 200×g for 5 min at RT. Cells were resuspended to a density of $0.8 \times 10^6$/mL in 37° C. assay medium. Subsequent liquid transfers were performed using either a Matrix electronic multichannel pipette or an Agilent Bravo Automated Liquid Handling Platform.

The assay was started by dispensing 40 μL of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 5 μL of supernatant was transferred into corresponding wells of a white 384-well plate (Perkin Elmer, Cat. No. 6005620). To these supernatant-containing wells was added 10 μL of 5× Anti-Analyte Acceptor beads (50 μg/mL of AlphaLISA HiBlock Buffer) and incubated for 30 min at RT while shaking on an orbital plate shaker. To each well was added 10 μL of 5× Biotinylated Antibody Anti-analyte (5 nM in AlphaLISA HiBlock Buffer) and incubated on an orbital plate shaker for 60 min at RT or overnight at 4° C. To each well was added 25 μL of 2× SA-Donor beads (80 μg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 μM concentration.

TABLE 8

IFN-β secretion in THP1 cell culture (5 h)

| Compound | % Effect at 30 μM relative to 2'3'-cGAMP |
|---|---|
| Example 1 | 121 |
| Example 2 | 123 |
| Example 3 | 150 |
| Example 4 | 104 |
| Example 5 | 145 |
| Example 6 | 166 |
| Example 7 | 59 |
| Example 8 | 36 |
| Example 9 | 115 |
| Example 10 | 87 |
| Example 11 | 131 |
| Example 12 | 50 |
| Example 13 | 128 |
| Example 14 | 150 |
| Example 15 | 132 |
| Example 16 | 147 |
| Example 17 | 38 |
| Example 18 | 118 |
| Example 19 | 122 |
| Example 20 | 144 |
| Example 21 | 10 |
| Example 22 | 129 |
| Example 23 | 135 |
| Example 24 | 84 |

TABLE 8-continued

IFN-β secretion in THP1 cell culture (5 h)

| Compound | % Effect at 30 μM relative to 2'3'-cGAMP |
|---|---|
| Example 25 | 89 |
| Example 26 | 90 |
| Example 27 | 76 |
| Example 28 | 135 |
| Example 29 | 26 |
| Example 30 | 8 |
| Example 31 | 57 |
| Example 32 | 166 |
| Example 33 | 140 |
| Example 34 | 132 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method of inducing STING-dependent type I interferon production in a subject, said method comprising:

(a) administering a therapeutically effective amount of a compound of formula (II) to the subject, wherein the compound of formula (II) is:

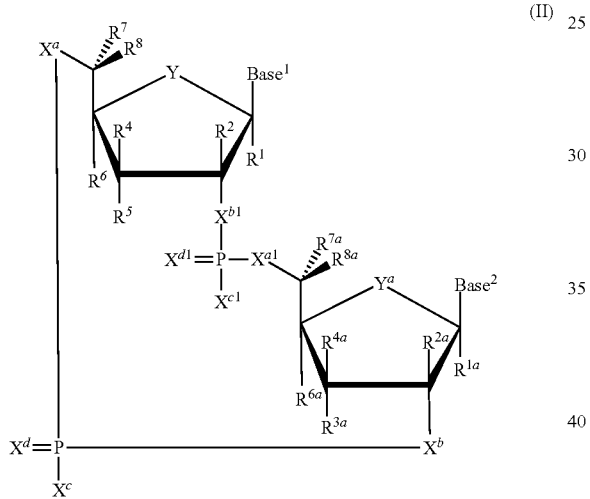

or a pharmaceutically acceptable salt thereof, wherein Base$^1$ and Base$^2$ are each independently selected from the group consisting of

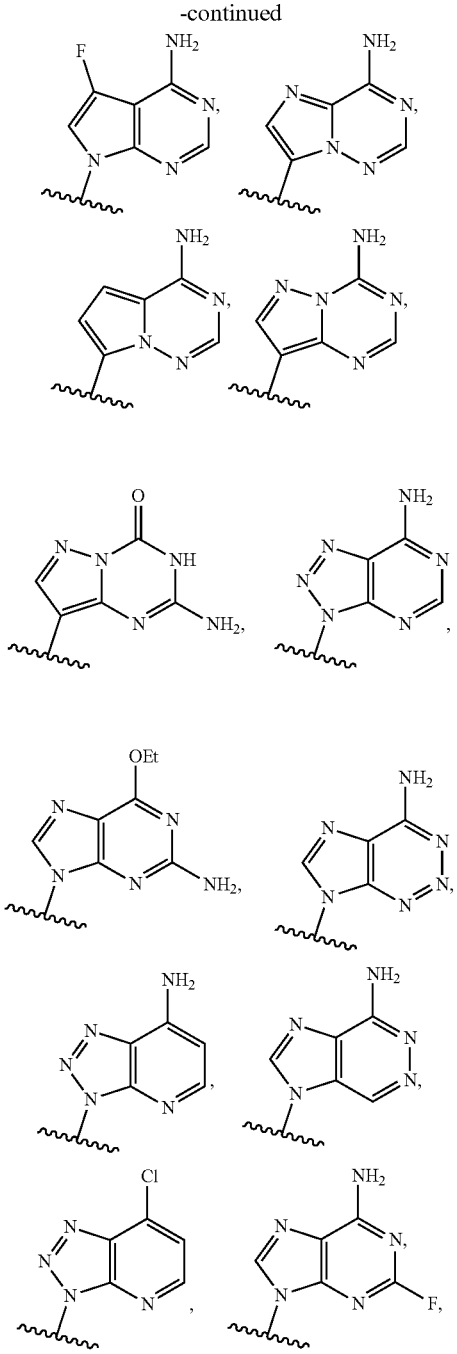

-continued
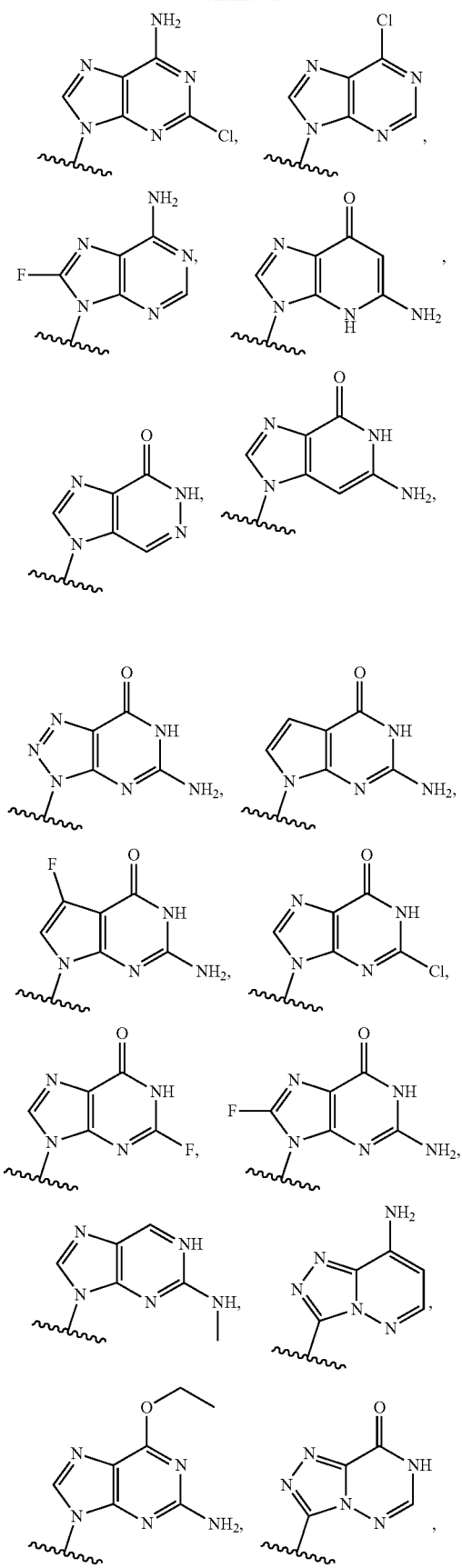
-continued
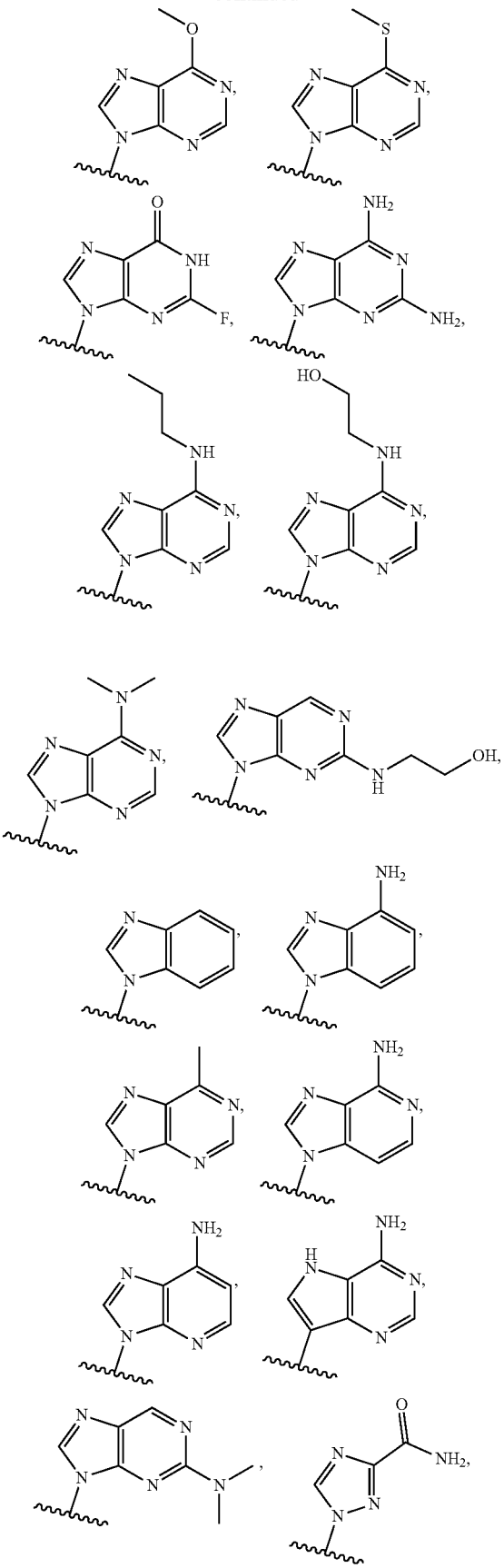

-continued

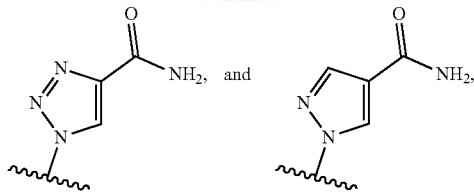 [SMILES: *n1cc(C(N)=O)nn1 ; *n1cc(C(N)=O)cn1]

Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O—, —S—, —$SO_2$—, —$CH_2$—, and —$CF_2$—;

$X^a$ and $X^{a1}$ are each independently selected from the group consisting of O, $CH_2$, and S;

$X^b$ and $X^{b1}$ are each independently selected from the group consisting of O, C, and S;

$X^c$ and $X^{c1}$ are each independently selected from the group consisting of $O^-$, $S^-$, $OR^9$, and $NR^9R^9$;

$X^d$ and $X^{d1}$ are each independently selected from the group consisting of O and S;

$R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_1$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$, $R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^{3a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$, alkenyl, and —O—$C_2$-$C_6$ alkynyl, where said $R^{3a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_3$-$C_6$ alkynyl are substituted by 0 to 3 substituents selected from the group consisting of F, Cl, Br, I, OH, CN, and $N_3$;

$R^5$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_1$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^6$ and $R^{6a}$ are each independently selected from the group consisting of H, F, Cl, Br, I, OH, CN, $N_3$, $C_1$-$C_6$ alkyl, $C_2$-$C_6$, alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_1$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$, alkenyl, and —O—$C_2$-$C_6$ alkynyl are substituted by 0 to 3 substituents selected from the group consisting of F, Cl, Br, I, OH, CN, and $N_3$;

$R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$, haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$, alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

each $R^9$ is independently selected from the group consisting of H, $C_1$-$C_{20}$ alkyl,

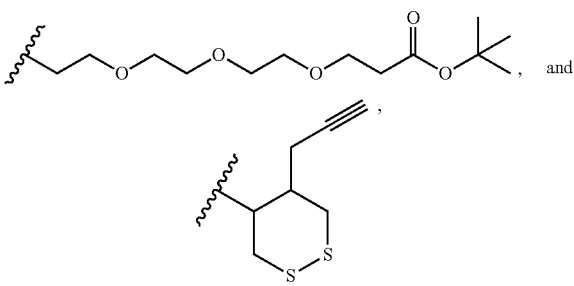

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl;

optionally $R^{3a}$ and $R^{6a}$ are connected to form —O—$C_1$-$C_6$ alkylene, —O—$C_2$-$C_6$ alkenylene, or —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^7$ and $R^8$ are connected to form $C_1$-$C_6$ alkylene, $C_2$-$C_6$ alkenylene, or $C_2$-$C_6$ alkynylene; and optionally $R^{7a}$ and $R^{8a}$ are connected to form $C_1$-$C_6$ alkylene, $C_2$-$C_6$ alkenylene, or $C_2$-$C_6$ alkynylene; and providing that when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

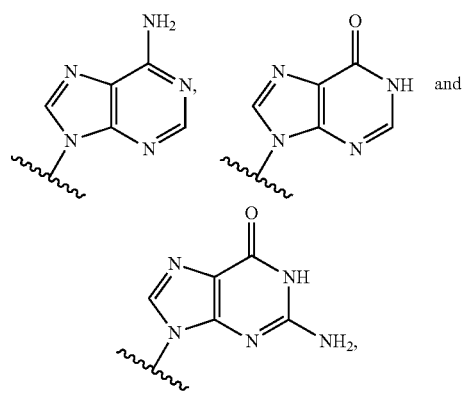

$R^5$ and $R^{3a}$ are not both selected from the group consisting of H, F and OH.

2. A method of inducing STING-dependent type I interferon production in a subject, said method comprising:

(a) administering a therapeutically effective amount of a pharmaceutical composition to the subject, wherein said pharmaceutical composition comprises (a) a compound of formula (II); and (b) a pharmaceutically acceptable carrier, wherein the compound of formula (II) is:

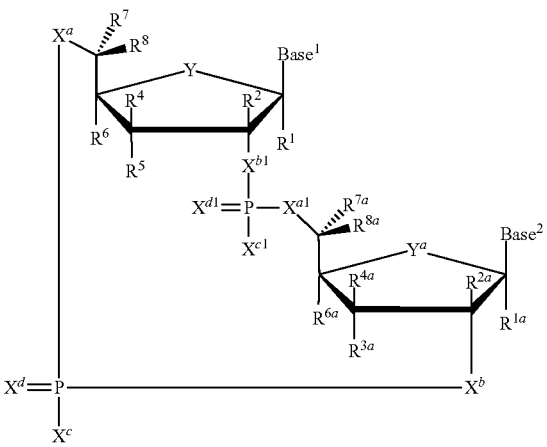

(II)

or a pharmaceutically acceptable salt thereof, wherein Base$^1$ and Base$^2$ are each independently selected from the group consisting of

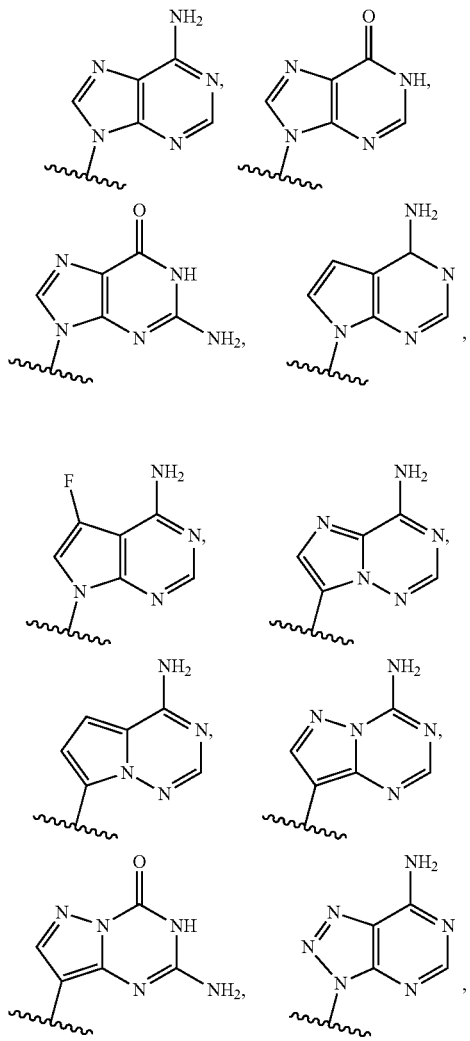

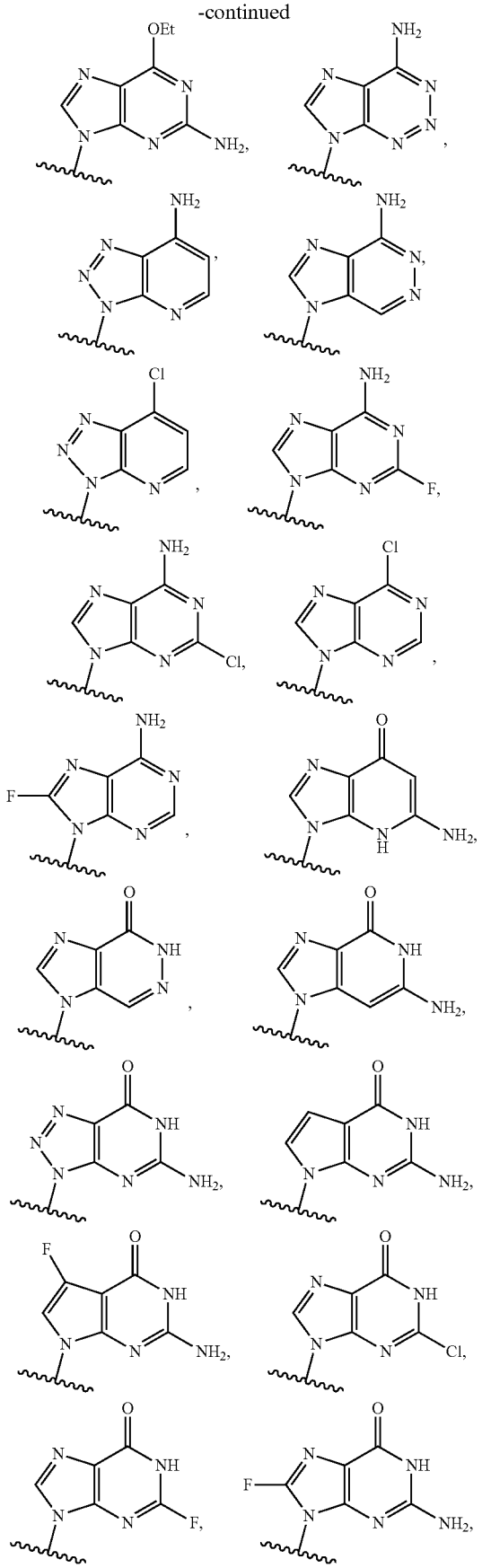
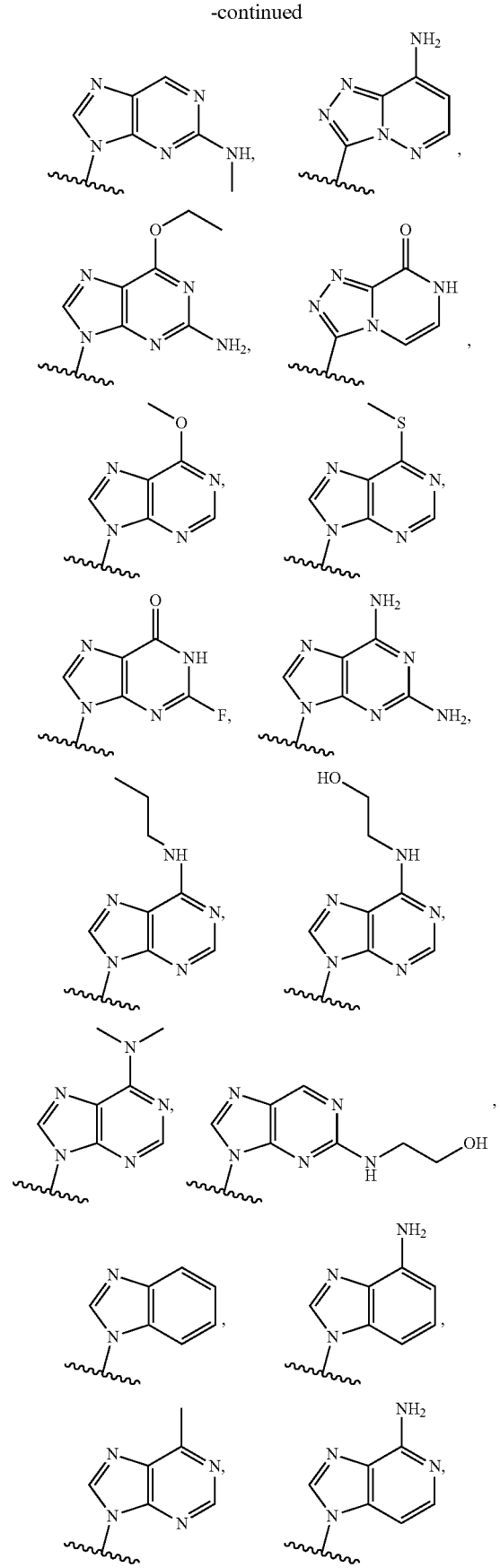

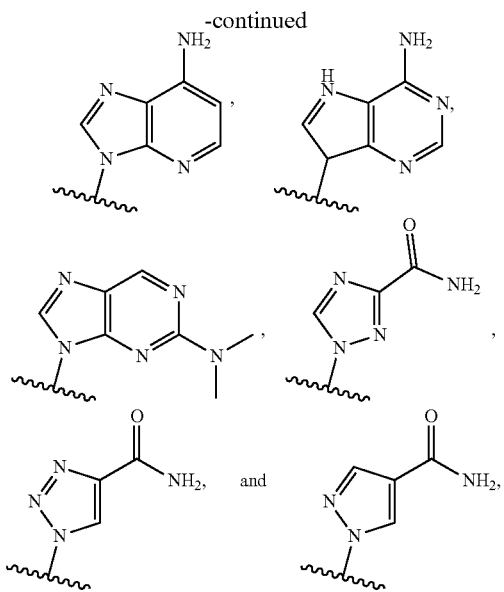

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O—, —S—, —SO$_2$—, —CH$_2$—, and —CF$_2$—;

$X^a$ and $X^{a1}$ are each independently selected from the group consisting of O, CH$_2$, and S;

$X^b$ and $X^{b1}$ are each independently selected from the group consisting of O, C, and S;

$X^c$ and $X^{c1}$ are each independently selected from the group consisting of O⁻, S⁻; $OR^9$, and $NR^9R^9$;

$X^d$ and $X^{d1}$ are each independently selected from the group consisting of O and S;

$R^1$ and $R^{1a}$ are each independently selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_1$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^3$ and $R^{2a}$ are each independently selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^{3a}$ is selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{3a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^4$ and $R^{4a}$ are each independently selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$, haloalkynyl, —O—$C_1$-$C_6$ alkyl, —O—$C_2$-$C_6$ alkenyl, and —O—$C_2$-$C_6$ alkynyl, wherein said $R^4$ and $R^{4a}$ $C_1$-$C_6$ alkyl, $C_2$-$C_6$ alkenyl, —$C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^5$ is selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^6$ and $R^{6a}$ are each independently selected from the group consisting of HL F, Cl, Br, I, OH, CN, N$_3$, $C_1$-$C_6$ alkyl, $C_2$-$C_6$ alkenyl, $C_1$-$C_6$ alkynyl, $C_1$-$C_6$ haloalkyl, $C_2$—O, haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ are substituted by 0 to 3 substituents selected from the group consisting of F, Cl, Br, I, OH, CN, and N$_3$, $R^7$ and $R^{7a}$ are each independently selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

$R^8$ and $R^{8a}$ are each independently selected from the group consisting of H, F, Cl, Br, I, OH, CN, N$_3$, $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_1$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and N$_3$;

each $R^9$ is independently selected from the group consisting of H, $C_1$-$C_{20}$ alkyl,

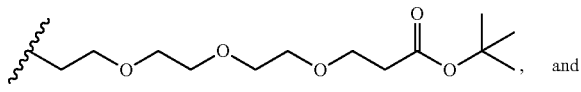, and

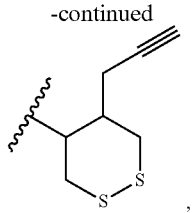

where each $R^9$ $C_1$-$C_{20}$ alkyl is optionally substituted by 0 to 3 substituents independently selected from the group consisting of OH, —O—$C_{20}$ alkyl, —S—C(O)$C_1$-$C_6$ alkyl, and C(O)$C_1$-$C_6$ alkyl;

optionally $R^{3a}$ and $R^{6a}$ are connected to form —O—$C_1$-$C_6$ alkylene, —O—$C_2$-$C_6$ alkenylene, or —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^7$ and $R^8$ are connected to form $C_1$-$C_6$ alkylene, $C_2$-$C_6$ alkenylene, or $C_2$-$C_6$ alkynylene, and optionally $R^{7a}$ and $R^{8a}$ are connected to form $C_1$-$C_6$ alkylene, $C_2$-$C_6$ alkenylene, or $C_2$-$C_6$ alkynylene; and providing that when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

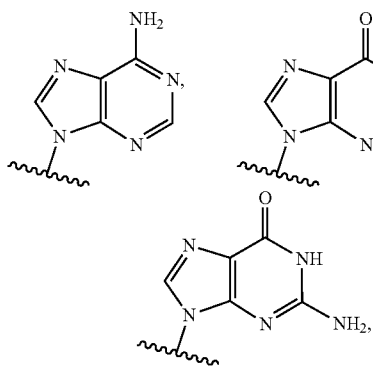

$R^5$ and $R^{3a}$ are not both selected from the group consisting of H, F and OH.

3. A method of inducing STING-dependent type I interferon production in a subject, said method comprising:

(a) administering a therapeutically effective amount of a compound of formula (II') to the subject, wherein the compound of formula (II') is:

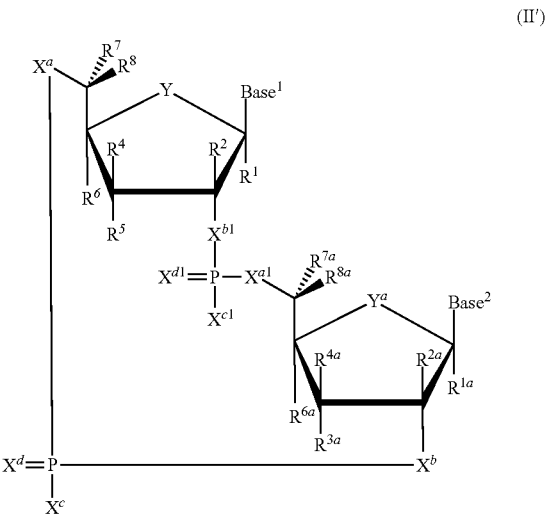

(II')

or a pharmaceutically acceptable salt thereof, wherein Base$^1$ and Base$^2$ are each independently selected from the group consisting of

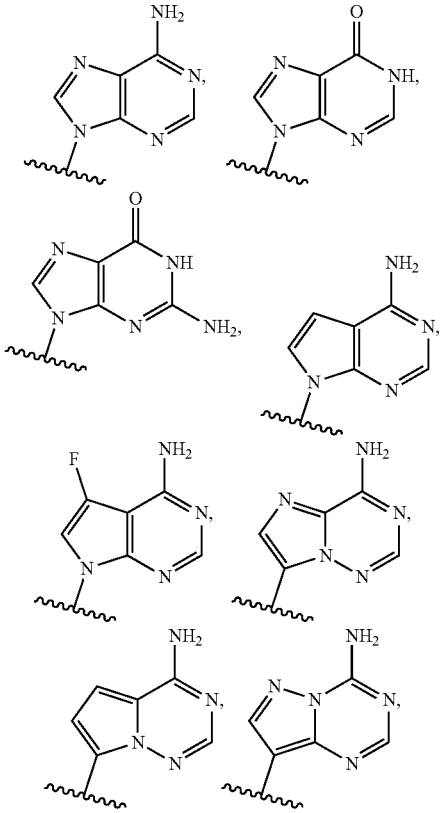

225
-continued
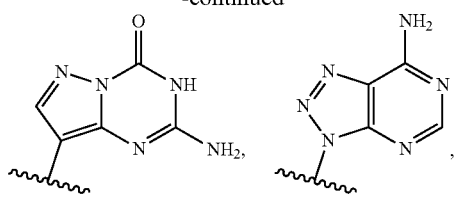
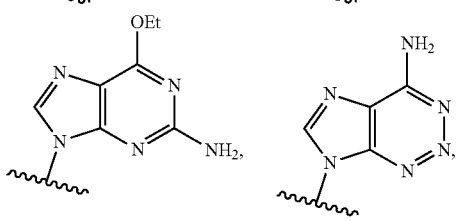
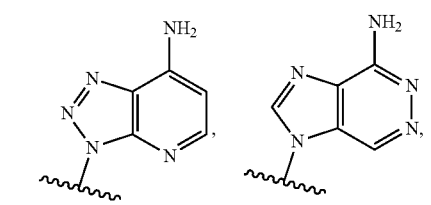
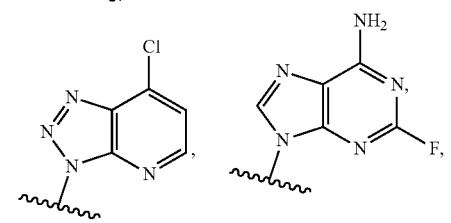
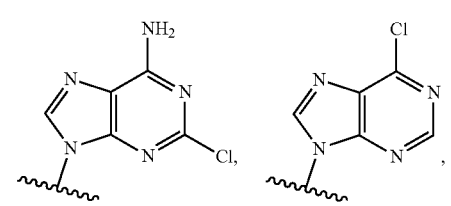
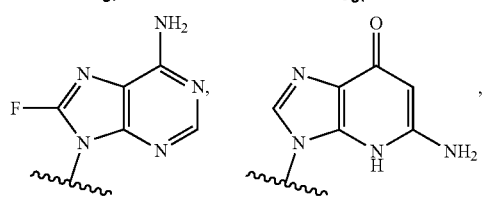
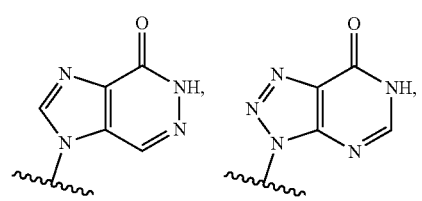
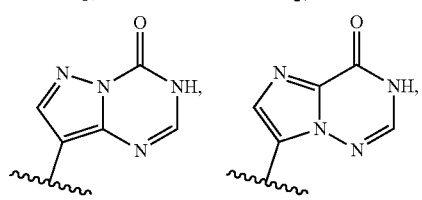
226
-continued
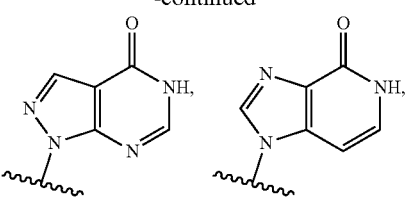
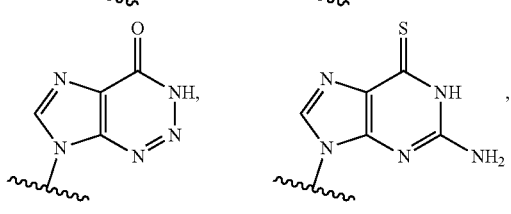
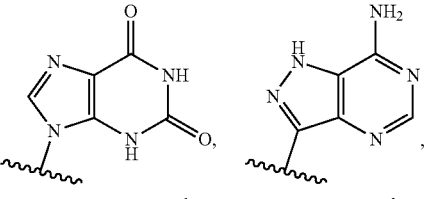
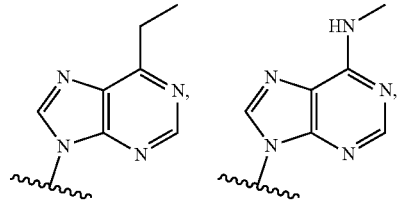
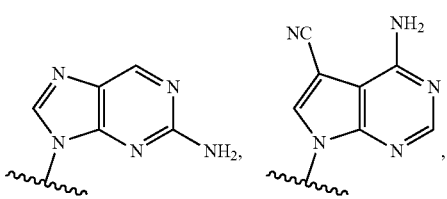
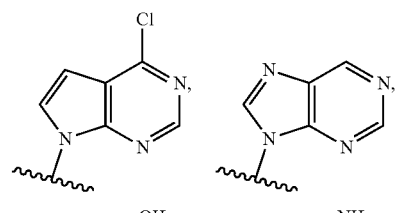
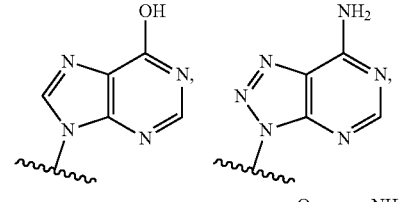
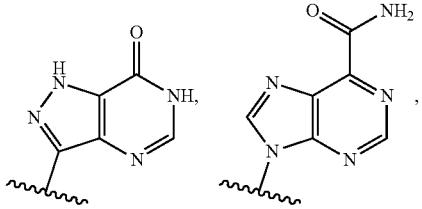

227
-continued
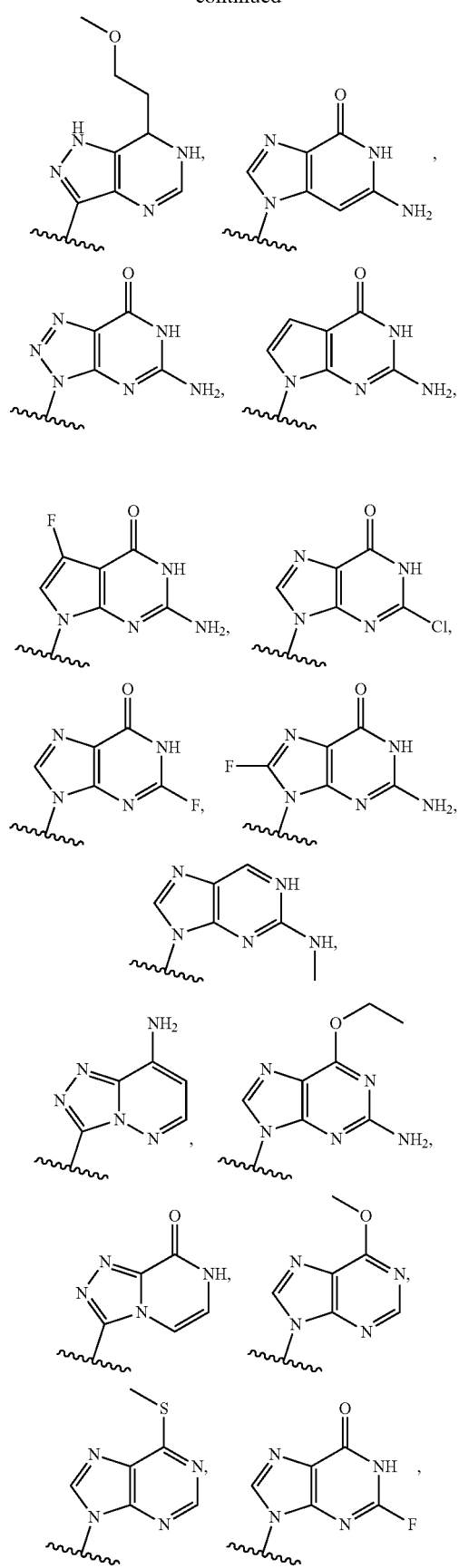
228
-continued
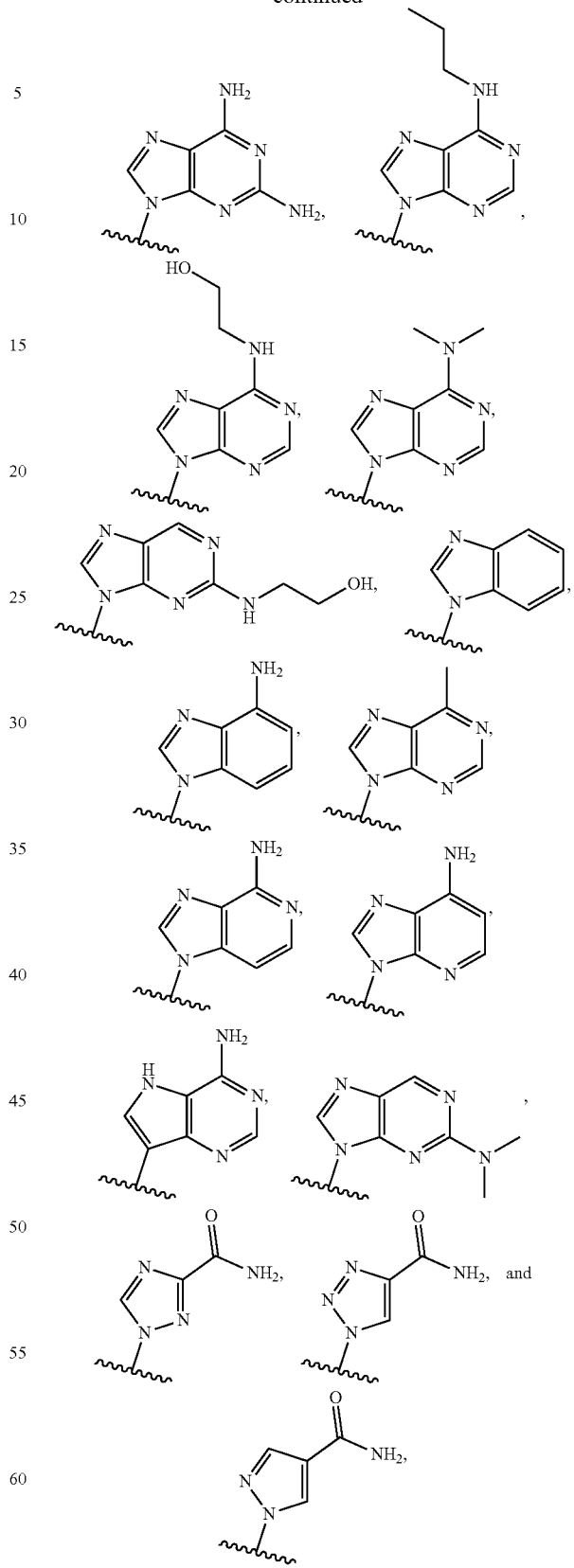
where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O— and —S—;

$X^a$ and $X^{a1}$ are each independently selected from the group consisting of O, and S;

$X^b$ and $X^{b1}$ are each independently selected from the group consisting of O, and S;

$X^c$ and $X^{c1}$ are each independently selected from the group consisting of $OR^9$; $SR^9$, and $NR^9R^9$;

$X^d$ and $X^{d1}$ are each independently selected from the group consisting of O and S;

$R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_1$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^2$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$, $R^{3a}$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{3a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$, $R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_2$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$, alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, $NR^9R^9$, and $N_3$;

$R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl and —O—$C_2$-$C_6$ alkynyl are substituted by 0 to 3 substituents selected from the group consisting of F, Cl, Br, I, OH, CN, and $N_3$;

$R^7$ and $R^{7a}$ are each independently selected from the group consisting of H, F, Cl, Br, I, OH, CN, $N_3$, $C_1$-$C_6$ alkyl, $C_2$-$C_6$ alkenyl $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl and —O—$C_2$-$C_6$ alkynyl, where said $R^7$ and $R^{7a}$ $C_2$-$C_6$ alkyl, $C_2$-$C_6$ alkenyl $C_2$-$C_6$ alkynyl $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^8$ and $R^{8a}$ are each independently selected from the croup consisting of H, F, Cl, Br, I, OH, CN, $N_3$, $C_1$-$C_6$ alkyl, $C_3$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl $C_2$-$C_6$ alkynyl $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl and —O—$C_2$-$C_6$ alkynyl are substituted by 0 to 3 substituents selected from the group consisting of F, Cl, Br, I OH, CN, and $N_3$;

each $R^9$ is independently selected from the group consisting of H, $C_1$-$C_{20}$ alkyl,

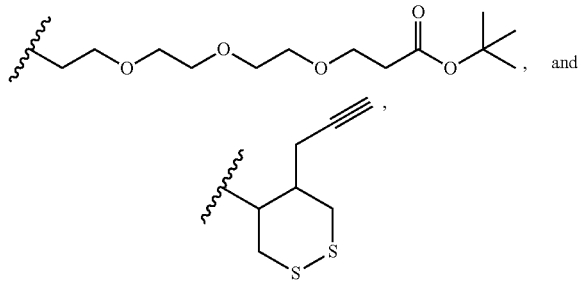

, and where each $R^9$ $C_1$-$C_{20}$ alkyl is optionally substituted by 0 to 3 substituents independently selected from the group consisting of OH, —O—$C_1$-$C_{20}$ alkyl, —S—$C(O)C_1$-$C_6$ alkyl, and $C(O)OC_1$-$C_6$ alkyl;

optionally $R^{3a}$ and $R^{6a}$ are connected to form —O—$C_1$-$C_6$ alkylene, —O—$C_2$-$C_6$ alkenylene, or —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkenylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^7$ and $R^8$ are connected to form $C_1$-$C_6$ alkylene, $C_2$-$C_6$ alkenylene, or $C_2$-$C_6$ alkynylene; and optionally $R^{7a}$ and $R^{8a}$ are connected to form $C_1$-$C_6$ alkylene, $C_2$-$C_6$ alkenylene, or $C_2$-$C_6$ alkynylene; and providing that when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

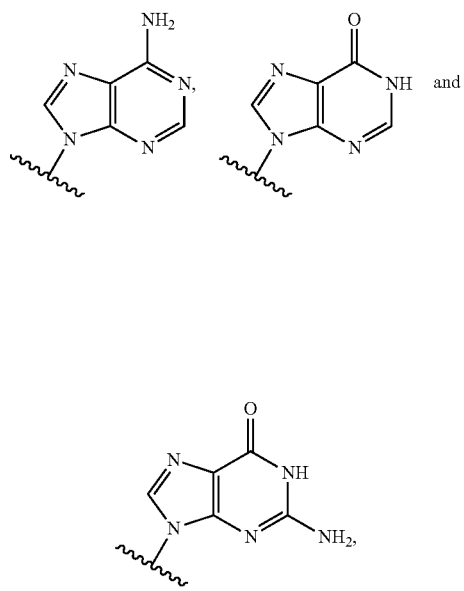

and $R^5$ and $R^{5a}$ are not both selected from the group consisting of H, F and OH.

4. A method of inducing STING-dependent type I interferon production in a subject, said method comprising:
(a) administering a therapeutically effective amount of a pharmaceutical composition to the subject; wherein said pharmaceutical composition comprises (a) a compound of formula (II'); and (b) a pharmaceutically acceptable carrier; wherein the compound of formula (II') is:

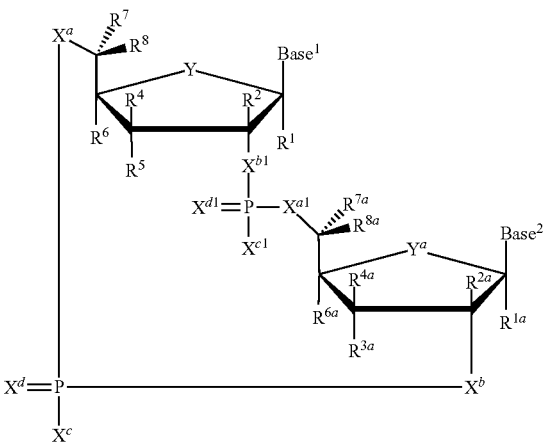

(II')

or a pharmaceutically acceptable salt thereof, wherein
Base$^1$ and Base$^2$ are each independently selected from the group consisting of

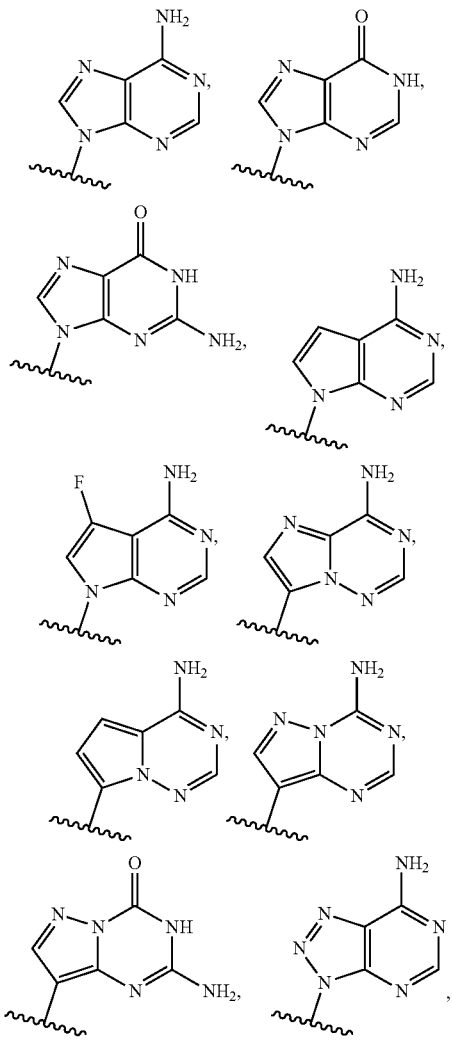

-continued
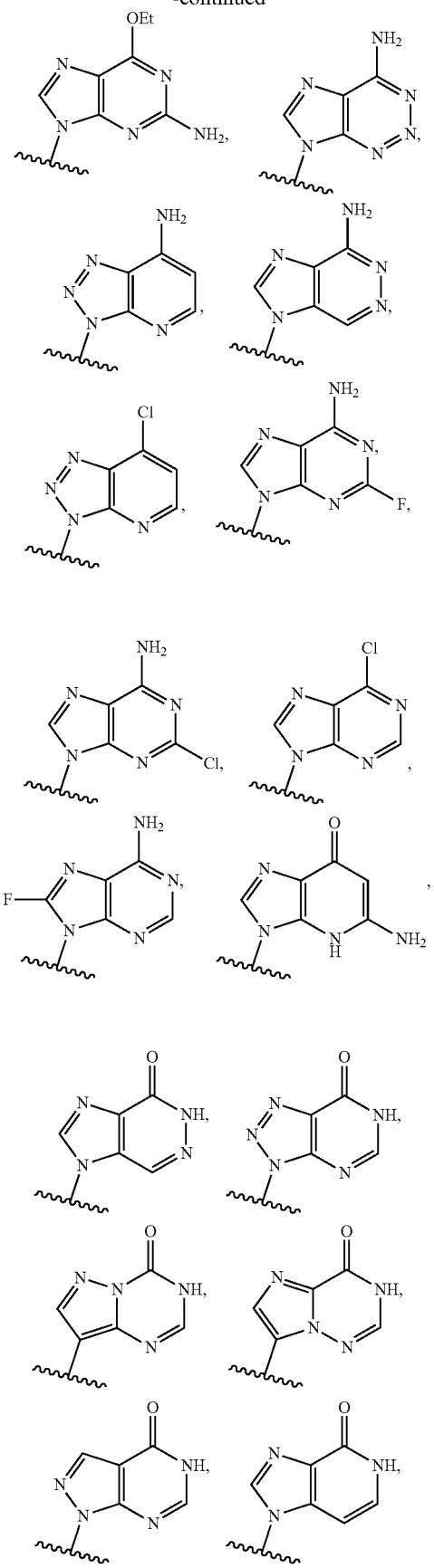
-continued
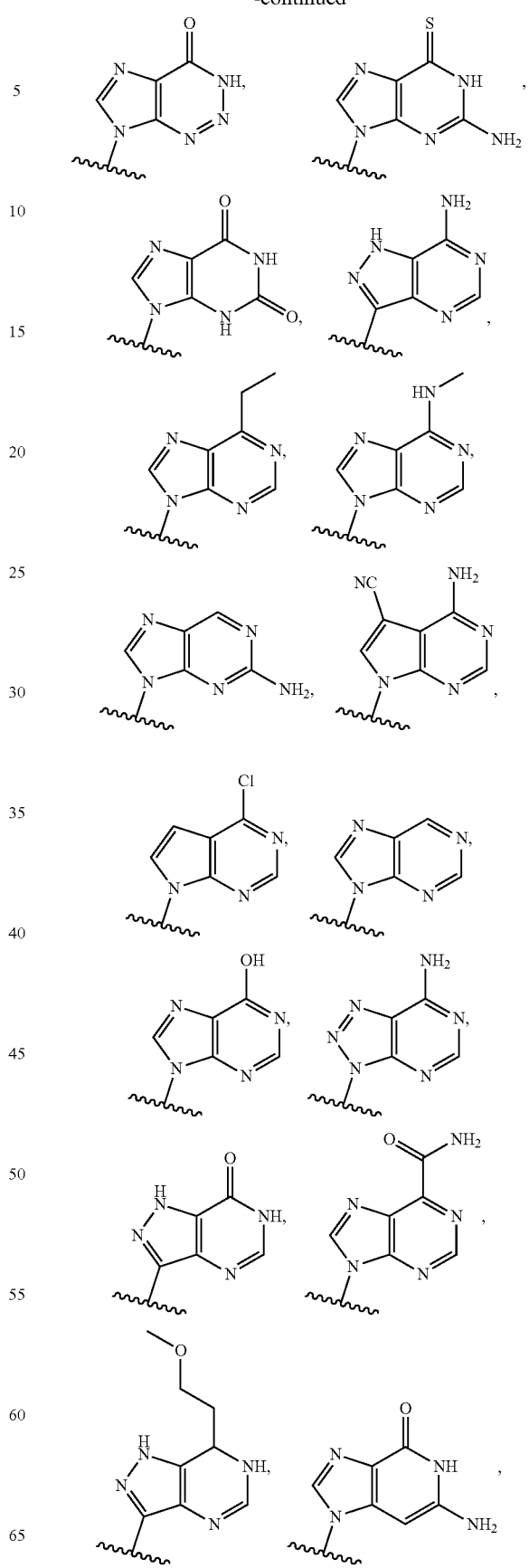

-continued

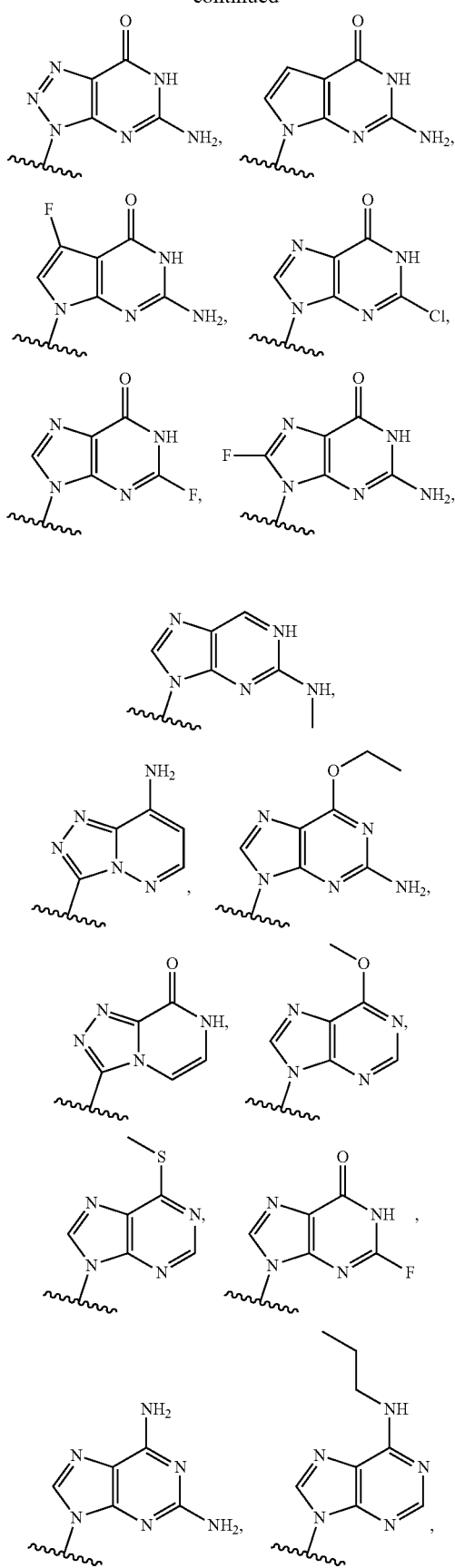
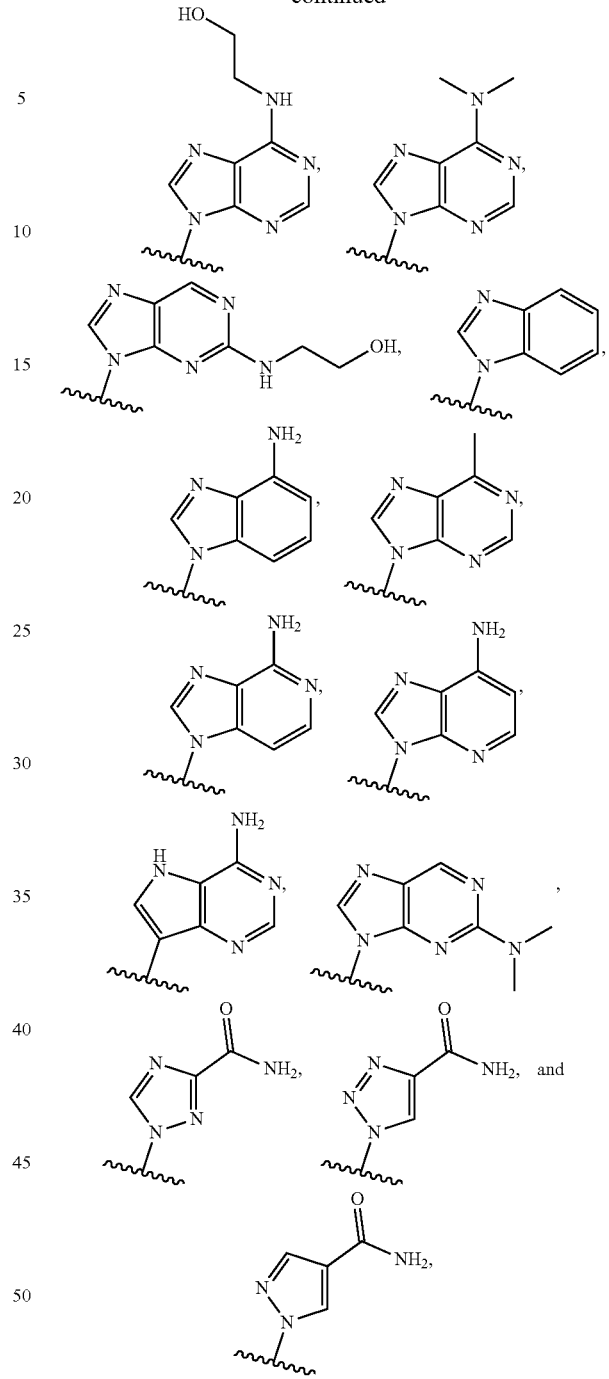

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^3$ are each independently selected from the group consisting of —O— and —S—;

$X^a$ and $X^{a1}$ are each independently selected from the group consisting of O, and S;

$X^b$ and $X^{b1}$ are each independently selected from the group consisting of O, and S;

$X^c$ and $X^{c1}$ are each independently selected from the group consisting of $OR^9$, $SR^9$, and $NR^9R^9$;

$X^d$ and $X^{d1}$ are each independently selected from the group consisting of O and S;

$R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_1$-$C_6$ alkenyl, $C_2$-$C_6$ alkynyl, $C_1$-$C_6$ haloalkyl, $C_2$-$C_6$ haloalkenyl, $C_2$-$C_6$, haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_2$-$C_6$ haloalkyl, $C_2$-$C_6$ haloalkynyl, —O—$C_1$-$C_6$ alkyl, —O—$C_2$-$C_6$, alkenyl, and —O—$C_2$-$C_6$ alkynyl are substituted by 0 to 3 substituents selected from the group consisting of F, Cl, Br, I, OH, CN, and $N_3$;

$R^{3a}$ is selected from the group consisting of H, F, Cl, Br, I, OH, CN, Nib, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{3a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are Substituted by 0 to 3 substituents selected from the group consisting of F, Cl, Br, I, OH, CN, and $N_3$;

$R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_1$-$C_6$, haloalkenyl, $C_2$-$C_6$ haloalkynyl, —O—$C_1$-$C_6$ alkyl, —O—$C_2$-$C_6$ alkenyl, and —O—O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^5$ is selected front the group consisting of H, F, Cl, Br, I, OH, CN, NR, $N_3$, $C_1$-$C_6$ alkyl, $C_2$-$C_6$ alkenyl, $C_1$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, $NR^9R^9$, and $N_3$;

$R^6$ and $R^{6a}$ are each independently selected from the group consisting of H, F, Cl, Br, I, OH, CN, $N_3$, $C_1$-$C_6$, alkyl, $C_2$-$C_6$, alkenyl, $C_2$-$C_6$ alkynyl, $C_1$-$C_6$ haloalkyl, $C_1$-$C_6$ haloalkynyl, $C_2$-$C_6$ haloalkynyl, —O—$C_2$-$C_6$, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_3$-$C_6$ alkynyl are substituted by 0 to 3 substituents selected from the group consisting of F, Cl, Br, I, OH, CN, and $N_3$;

$R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_2$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$, haloalkyl, $C_2$-$C_6$ haloalkenyl, $C_2$-$C_6$ haloalkynyl, —O—$C_2$-$C_6$ alkyl, —O—$C_2$-$C_6$ alkenyl and —O—$C_2$-$C_6$ alkynyl are substituted by 0 to 3 substituents selected from the group consisting of F, Cl, Br, I, OH, CN, and $N_3$;

$R^8$ and $R^{8a}$ are each independently selected from the group consisting of H, F, Cl, Br, I, OH, CN, $N_3$, $C_1$-$C_6$ alkyl, $C_2$-$C_6$ alkenyl $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

each $R^9$ is independently selected from the group consisting of H, $C_1$-$C_{20}$ alkyl,

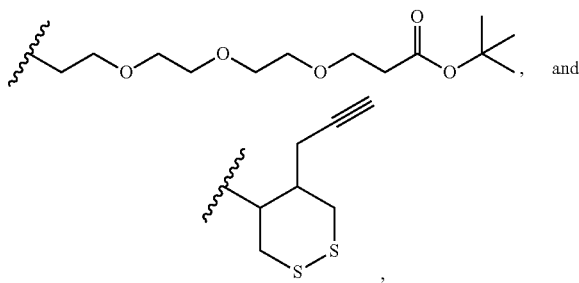

, and where each $R^9$ $C_1$-$C_{20}$ alkyl is optionally substituted by 0 to 3 substituents independently selected from the group consisting of OH, —O—$C_1$-$C_{20}$ alkyl-S—C(O)$C_1$-$C_6$ alkyl and C(O)O$C_1$-$C_6$ alkyl optionally $R^{3a}$ and $R^{6a}$ are connected to form —O—$C_1$-$C_6$, alkylene, —O—$C_2$-$C_6$ alkenylene, or —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$, alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^{3a}$ position;

optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where R⁵ and R⁶ are connected to form —O—C₁-C₆ alkylene, —O—C₂-C₆ alkenylene, or —O—C₂-C₆ alkynylene, said O is bound at the R⁵ position;

optionally R⁷ and R⁸ are connected to form C₁-C₆ alkylene, C₂-C₆ alkenylene, or C₂-C₆ alkynylene; and optionally $R^{7a}$ and $R^{8a}$ are connected to form C₁-C₆ alkylene, C₂-C₆ alkenylene, or C₂-C₆ alkynylene; and providing that when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base¹ and Base² are each selected from the group consisting of

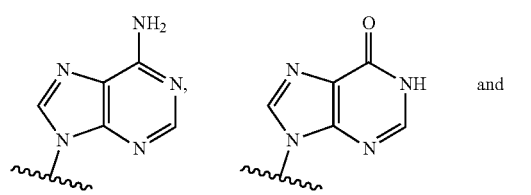

and

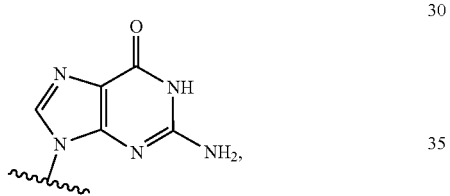

R⁵ and $R^{3a}$ are not both selected from the group consisting of H, F and OH.

5. The method according to claim 1, wherein the compound of formula (II) is a compound of formula (IIa):

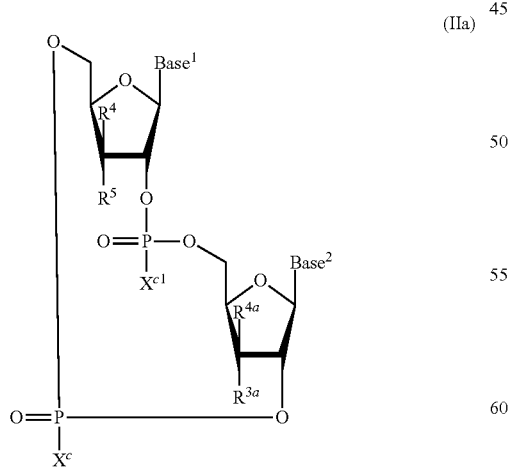

(IIa)

or a pharmaceutically acceptable salt thereof, wherein Base¹ and Base² are each independently selected from the group consisting of

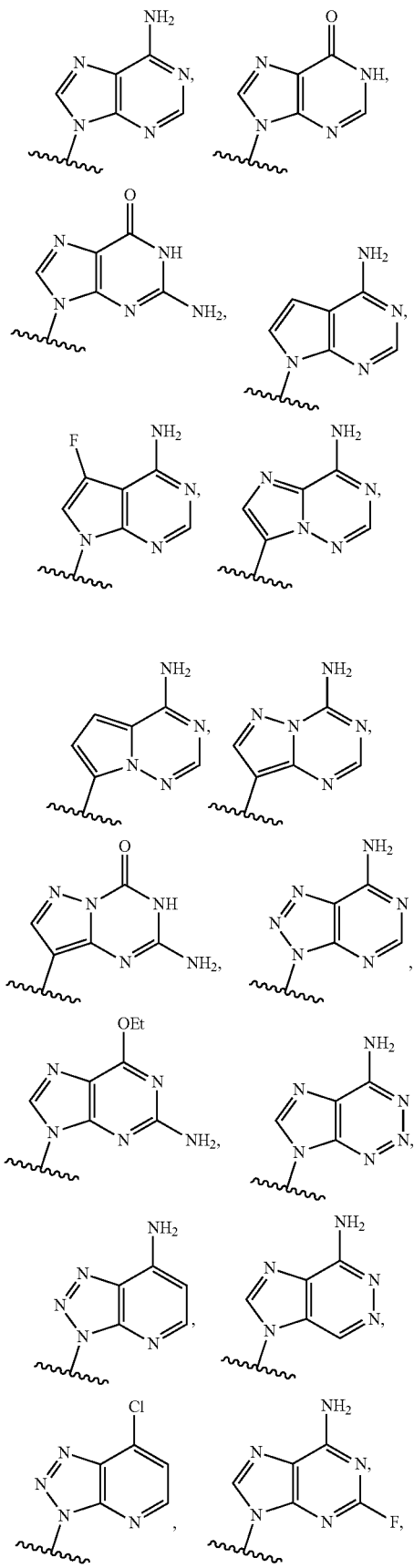

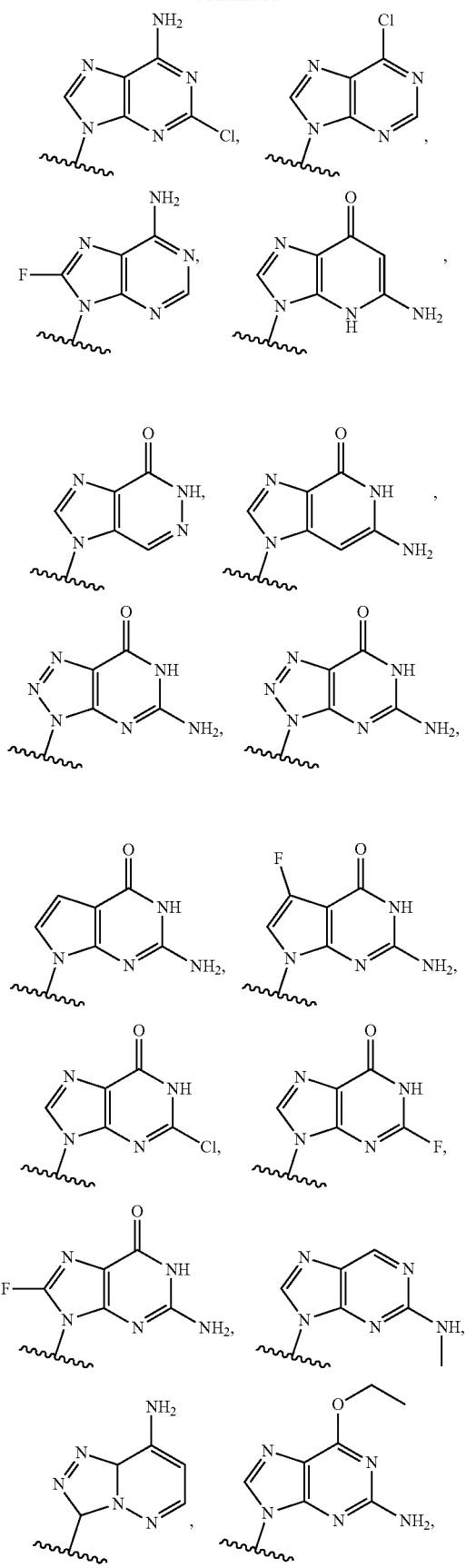
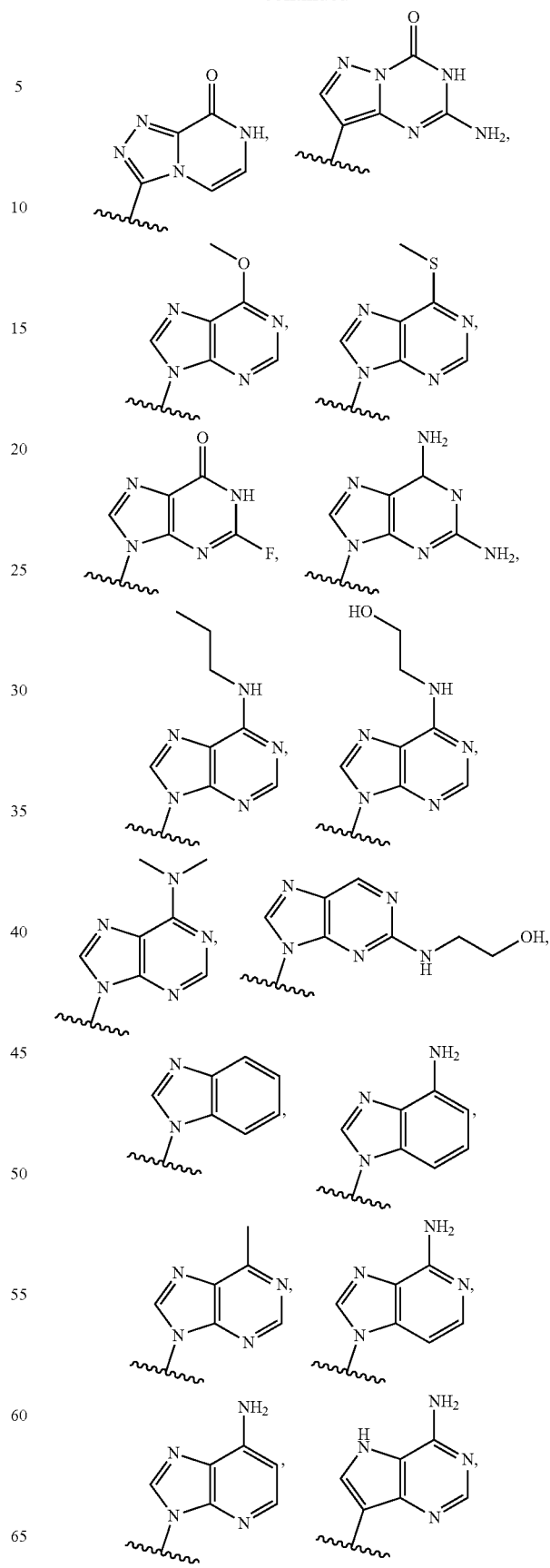

243
-continued

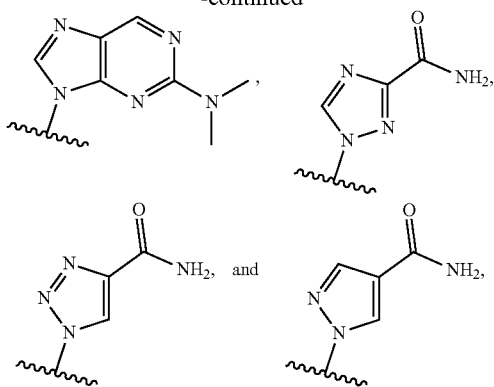

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$;

$X^c$ and $X^{c1}$ are each independently selected from the group consisting of $O^-$, $S^-$, $OR^9$, and $NR^9R^9$;

$R^{3a}$ is selected from the group consisting of H, F, Cl, Br, I, OH, CN, $N_3$, $C_1$-$C_6$ alkyl, and $C_1$-$C_6$ haloalkyl, where said $R^{3a}$ $C_1$-$C_6$ alkyl or $C_1$-$C_6$ haloalkyl are substituted by 0 to 3 substituents selected from the group consisting of F, Cl, Br, I, and OH;

$R^4$ and $R^{4a}$ are selected from the group consisting of H, F, Cl, Br, I, OH, CN, N?, $C_1$-$C_6$ alkyl, and $C_1$-$C_6$ haloalkyl, where said $R^4$ $C_1$-$C_6$ alkyl or $C_1$-$C_6$ haloalkyl are substituted by 0 to 3 substituents selected from the group consisting of F, Cl, Br, I, and OH;

$R^5$ is selected from the group consisting of H, F, Cl, Br, I, OH, CN, N?, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, and OH;

each $R^9$ is independently selected from the group consisting of H, $C_2$-$C_6$ alkyl,

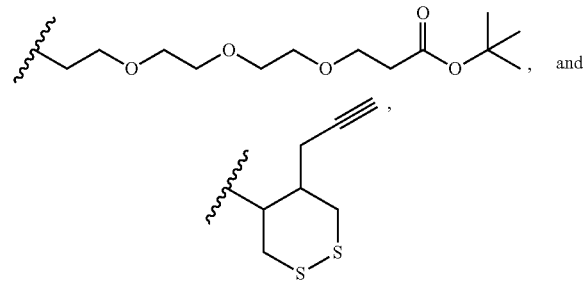

where each $R^9$ $C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl;

optionally $R^{3a}$ and $R^{4a}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene,

244

—O—$C_2$-$C_6$ alkenylene, or —O—$C_2$-$C_6$ alkynylene, said O is bound at the $R^5$ position; and optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position.

6. The method according to claim 3, wherein the compound of formula (II') is a compound of formula (II'a):

(II'a)

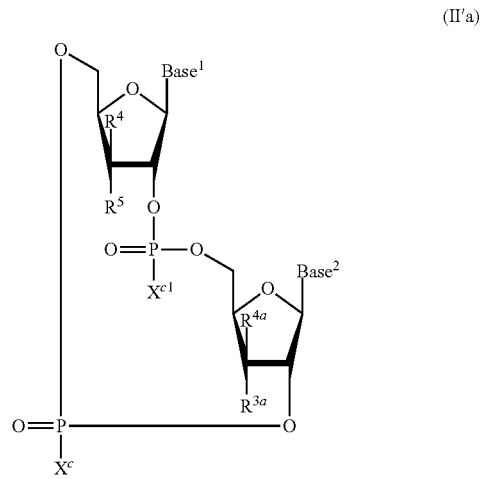

or a pharmaceutically acceptable salt thereof, wherein Base¹ and Base² are each independently selected from the group consisting of

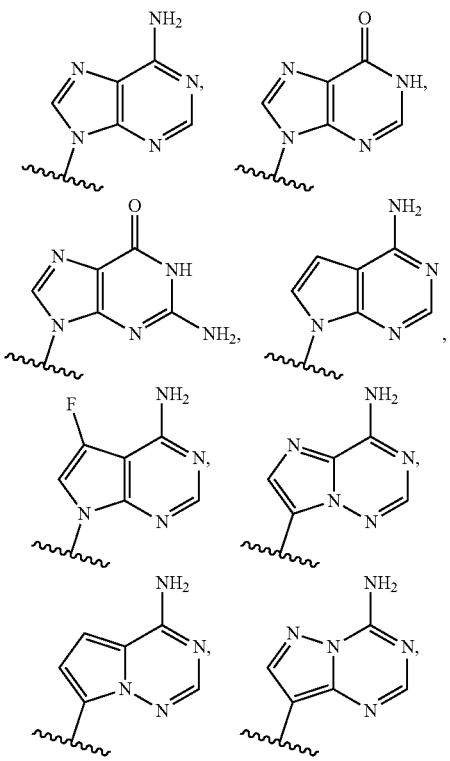

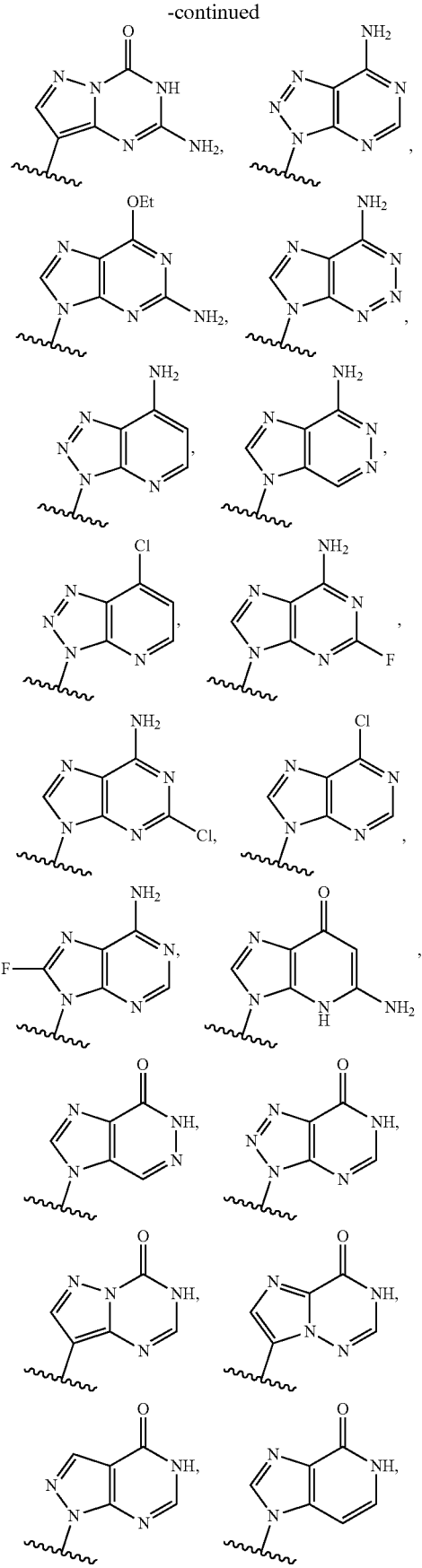
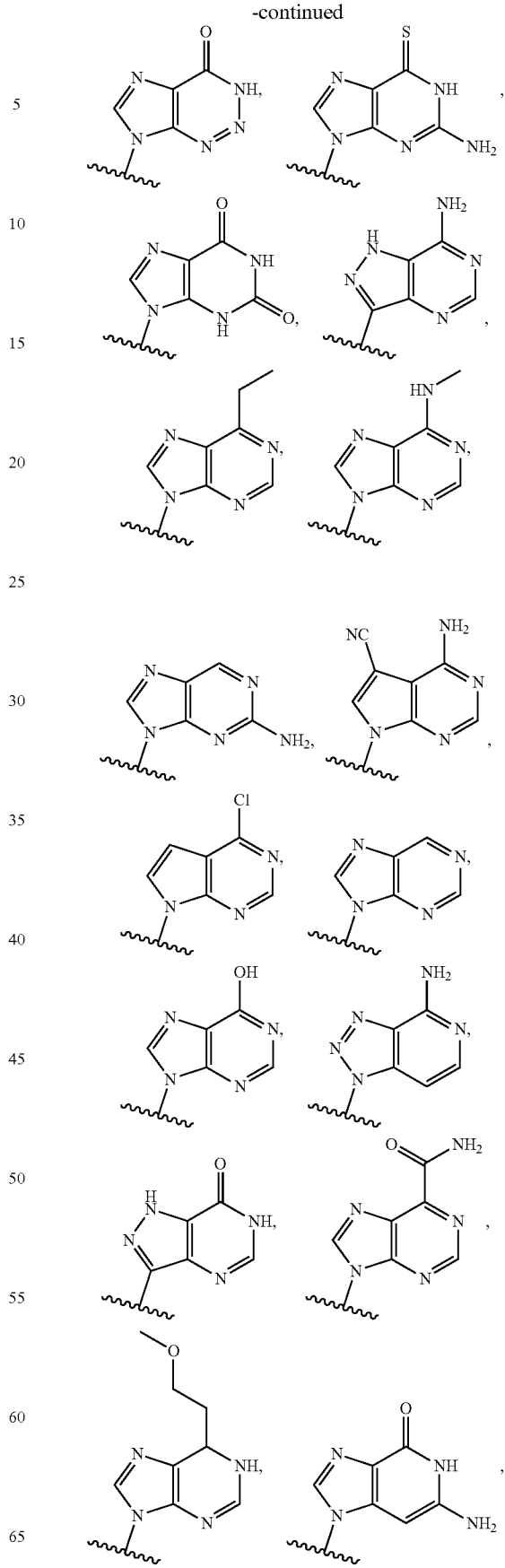

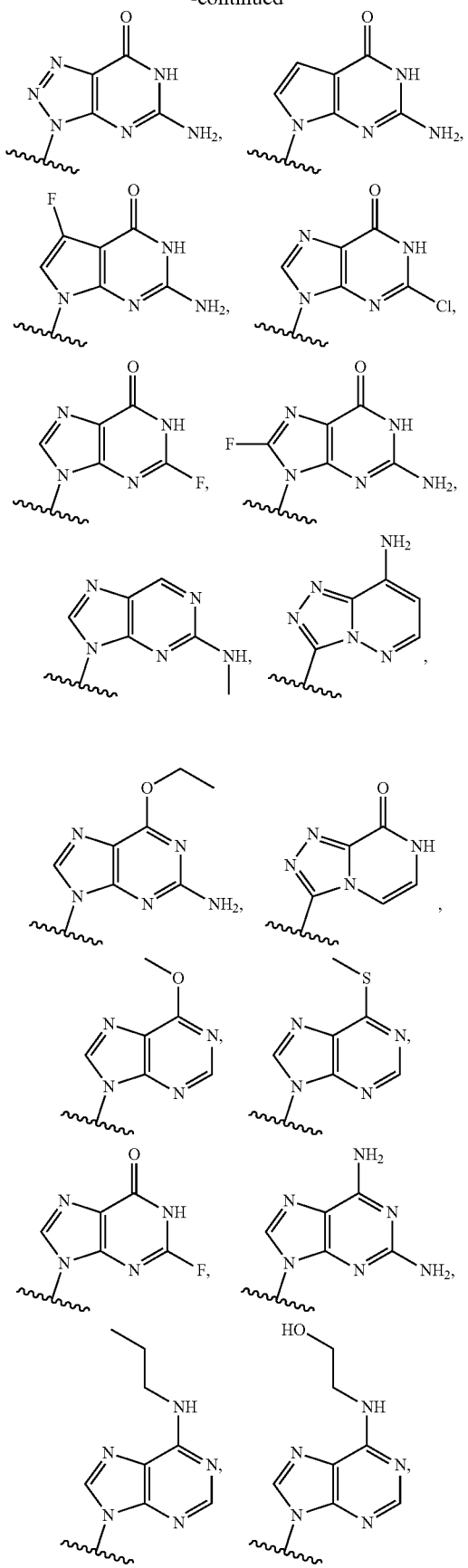
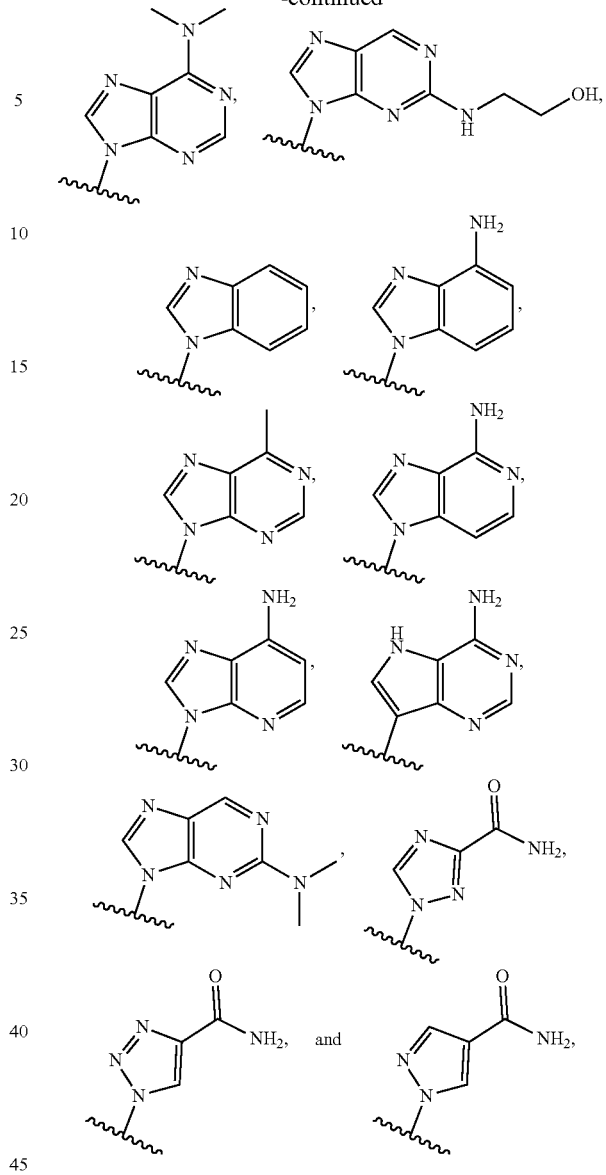

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

$X^c$ and $X^{c1}$ are each independently selected from the group consisting of $OR^9$, $SR^9$, and $NR^9R^9$;

$R^{3a}$ is selected from the group consisting of H, F, Cl, Br, I, OH, CN, $NH_2$, $N_3$, $C_1$-$C_6$ alkyl, and $C_1$-$C_6$ haloalkyl, where said $R^{3a}$ $C_1$-$C_6$ alkyl or $C_1$-$C_6$ haloalkyl are substituted by 0 to 3 substituents selected from the group consisting of F, Cl, Br, I, and OH;

$R^4$ and $R^{4a}$ are selected from the group consisting of H, F, Cl, Br, I, OH, CN, $N_3$, $C_1$-$C_6$ alkyl, and $C_1$-$C_6$ haloalkyl, where said $R^4$ $C_1$-$C_6$ alkyl or $C_1$-$C_6$ haloalkyl are substituted by 0 to 3 substituents selected from the group consisting of F, Cl, Br, I, and OH;

$R^5$ is selected from the group consisting of H, F, Cl, Br, I, OH, CN, $NH_2$, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, and OH;

each $R^9$ is independently selected from the group consisting of H, $C_2$-$C_3$ alkyl,

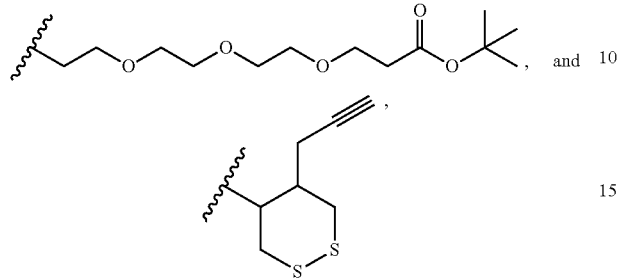
, and where each $R^9$ $C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl;

optionally $R^{3a}$ and $R^{4B}$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{3a}$ and $R^{4a}$ are connected to form —O—$C_1$-$C_6$ alkylene, —O—$C_2$-$C_6$ alkenylene, or —O—$C_2$-$C_6$ alkynylene, said O is bound at the $R^5$ position; and optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position.

7. The method according to claim 3, wherein

Base$^1$ and Base$^2$ are each independently selected from the group consisting of

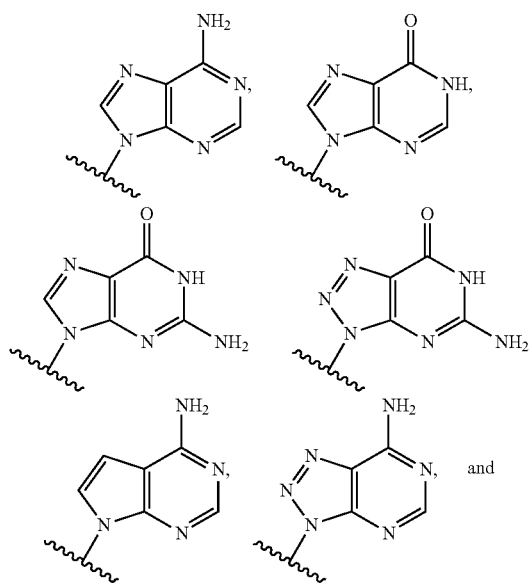

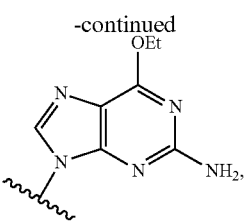

where Base$^1$ and Base$^2$ each may be independently substituted by 0-3 substituents $R^{10}$, where each $R^{10}$ is independently selected from the group consisting of F, Cl, I, Br, OH, SH, NH$_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$;

Y and Y$^a$ are each independently selected from the group consisting of —O— and —S—;

X$^a$ and X$^{a1}$ are each independently selected from the group consisting of O and S;

X$^b$ and X$^{b1}$ are each independently selected from the group consisting of O and S;

X$^c$ and X$^{c1}$ are each independently selected from the group consisting of SR$^9$, OR$^9$, and NR$^9$R$^9$;

X$^d$ and X$^{d1}$ are each independently selected from the group consisting of O and S;

$R^1$ and $R^{1a}$ are each H;

$R^2$ and $R^{2a}$ are each independently selected from the group consisting of H, F, Cl, Br, I, OH, N$_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of F, Cl, Br, I, OH, CN, and N$_3$;

$R^{3a}$ is selected from the group consisting of H, F, Cl, Br, I, OH, CN, N$_3$, $C_1$-$C_6$ alkyl, and $C_1$-$C_6$ haloalkyl, where said $R^{3a}$ $C_1$-$C_6$ alkyl or $C_1$-$C_6$ haloalkyl are substituted by 0 to 3 substituents selected from the group consisting of F, Cl, Br, I, OH, CN, and N$_3$;

$R^4$ and $R^{4a}$ are each independently selected from the group consisting of H, F, Cl, Br, I, OH, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and N$_3$;

$R^5$ is selected from the group consisting of H, F, Cl, Br, I, OH, NH$_2$, N$_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, and N$_3$;

$R^{3a}$ and $R^5$ are not both selected from the group consisting of: OH, $C_1$-$C_6$ alkyl substituted with OH, or $C_1$-$C_6$ haloalkyl substituted with OH; and $R^6$ and $R^{6a}$ are each independently selected from the group consisting of H, F, Cl, Br, I, OH, $C_1$-$C_6$ alkyl, $C_2$-$C_6$ alkenyl, $C_2$-$C_6$ alkynyl, and $C_1$-$C_6$ haloalkyl, where said $R^6$ and $R^{6a}$ $C_1$-$C_6$ alkyl or $C_1$-$C_6$ haloalkyl are substituted by 0 to 3 substituents selected from the group consisting of F, Cl, Br, I, OH, CN, and N$_3$;

$R^7$ and $R^{7a}$ are each H;

$R^8$ and $R^{8a}$ are each H;

each $R^9$ is independently selected from the group consisting of H, $C_2$-$C_3$ alkyl,

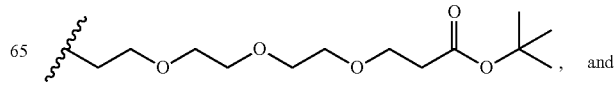
, and

251
-continued

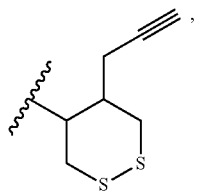

where each $R^9$ $C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl;

optionally $R^{3a}$ and $R^{6a}$ are connected to form —O—$C_1$-$C_6$ alkylene, —O—$C_2$-$C_6$ alkenylene, and —O—$C_2$-$C_6$ alkynylene, such that where $R^{3a}$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^{3a}$ position; and optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position.

8. A method of inducing STING-dependent type I interferon production in a subject, said method comprising:
(a) administering a therapeutically effective amount of a compound of formula (II″) to the subject, wherein the compound of formula (II″) is:

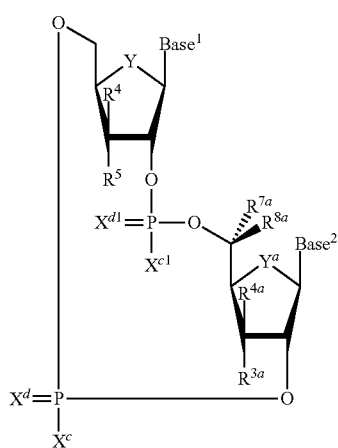

(II″)

or a pharmaceutically acceptable salt thereof, wherein $Base^1$ and $Base^2$ are each independently selected from the group consisting of

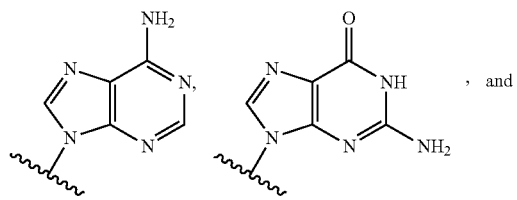

252
-continued

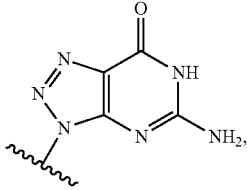

where $Base^1$ and $Base^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$;

Y and $Y^a$ are each independently selected from the group consisting of —O— and —S—;

$X^c$ and $X^{c1}$ are each independently selected from the group consisting of $SR^9$ and $OR^9$;

$X^d$ and $X^{d1}$ are each independently selected from the group consisting of O and S;

$R^{3a}$ is selected from the group consisting of H, F, OH, CN, $NH_2$, and $N_3$;

$R^4$ and $R^{4a}$ are each independently selected from the group consisting of H, F, and OH;

$R^5$ is selected from the group consisting of H, F, OH, $NH_2$, and $N_3$;

$R^{3a}$ and $R^5$ are not both selected from the group consisting of: OH, $C_1$-$C_6$ alkyl substituted with OH, or $C_1$-$C_6$ haloalkyl substituted with OH;

$R^{7a}$ is selected from the group consisting of H and $C_1$-$C_6$ alkyl;

$R^{8a}$ is selected from the group consisting of H and $C_1$-$C_6$ alkyl; and each $R^9$ is independently selected from the group consisting of H and $C_1$-$C_3$ alkyl.

9. A method of inducing STING-dependent type I interferon production in a subject, said method comprising:
(a) administering a therapeutically effective amount of a compound to the subject, wherein the compound is selected from the group consisting of:

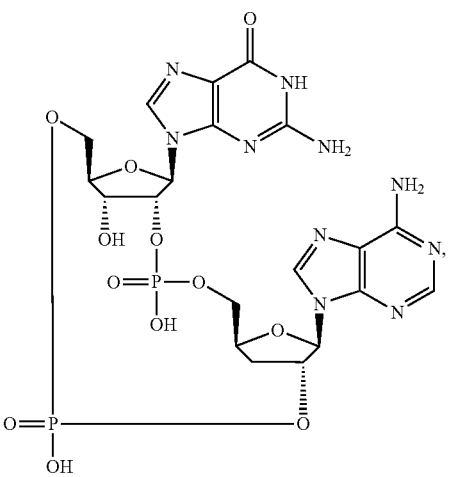

253
-continued
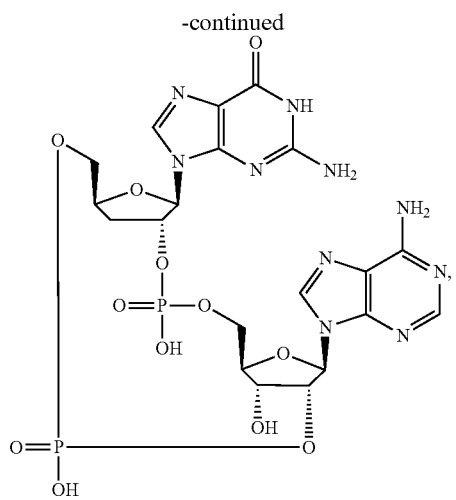
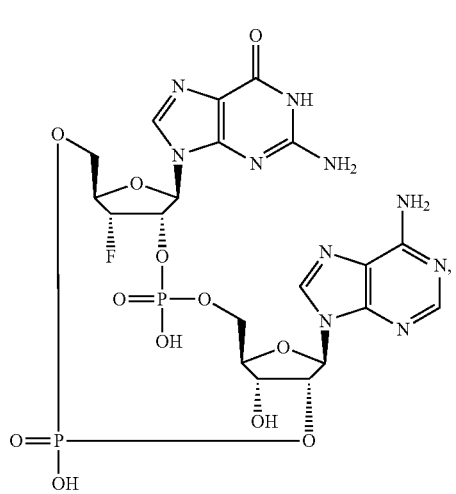
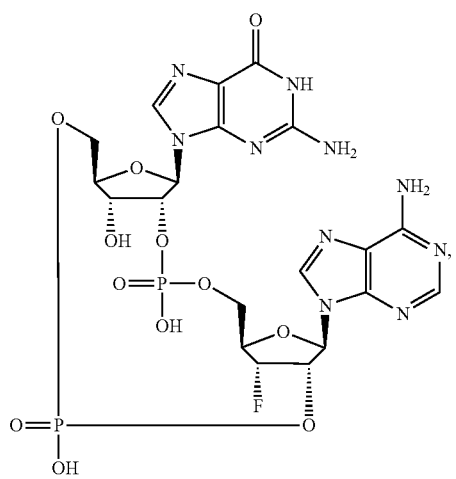
254
-continued
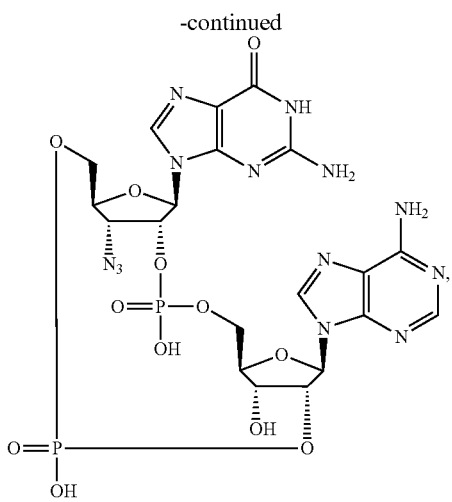
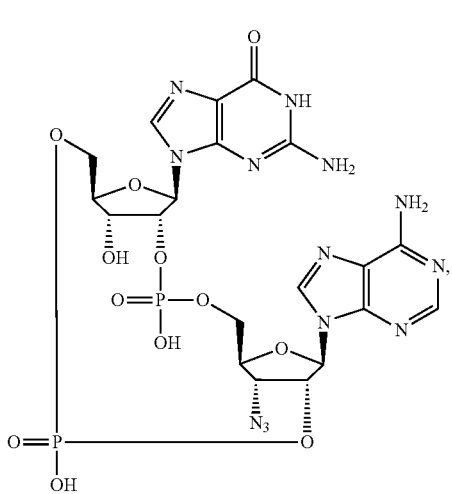
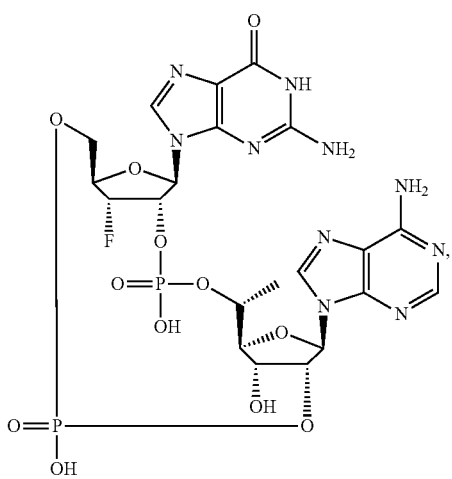

255
-continued
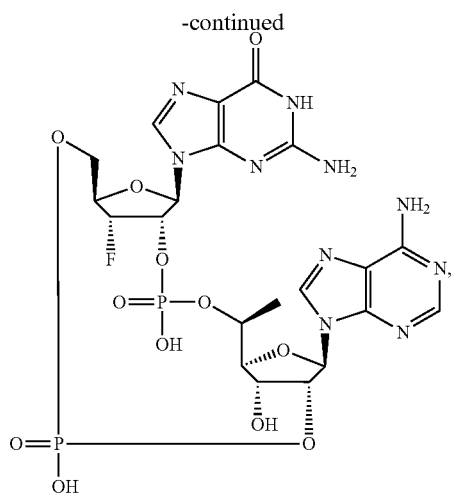
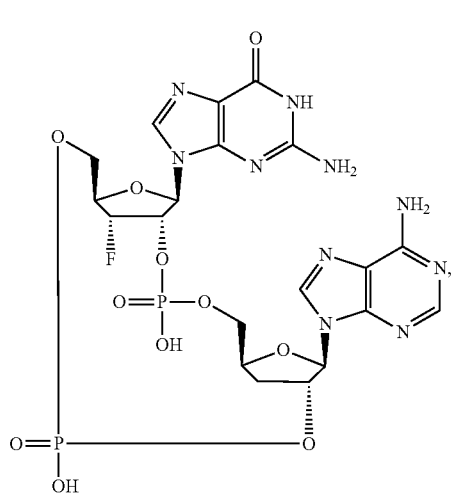
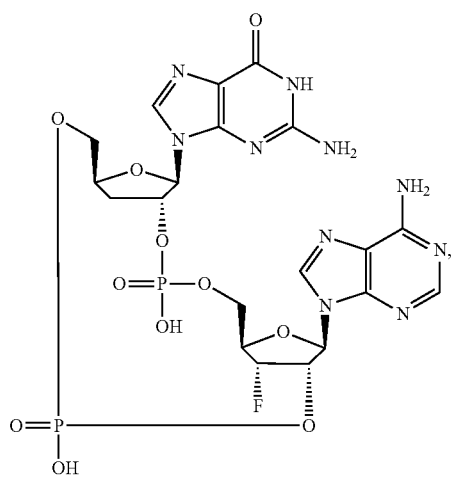
256
-continued
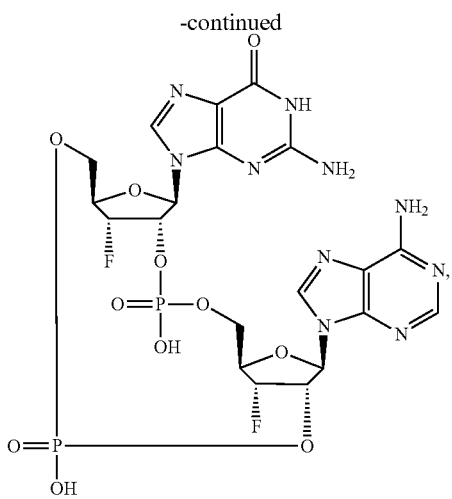
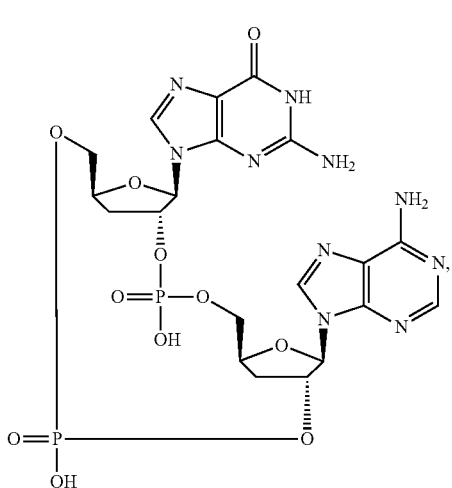
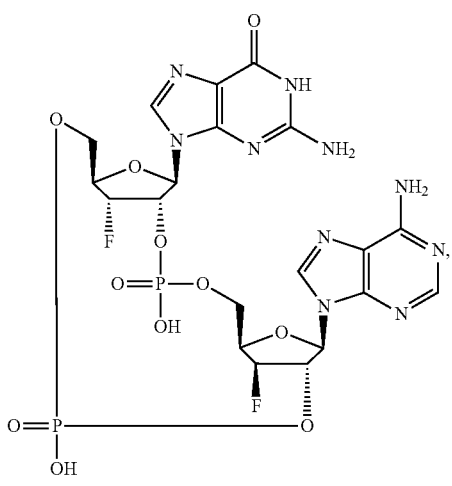

257
-continued
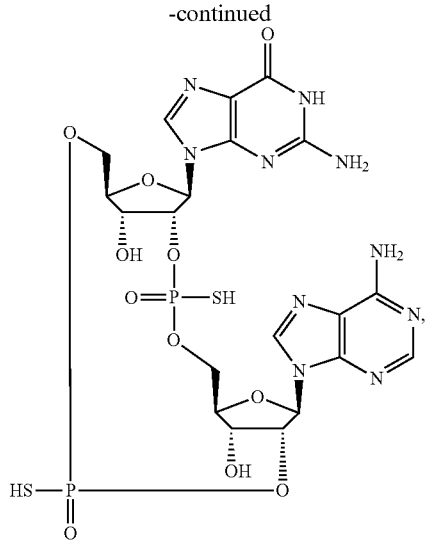
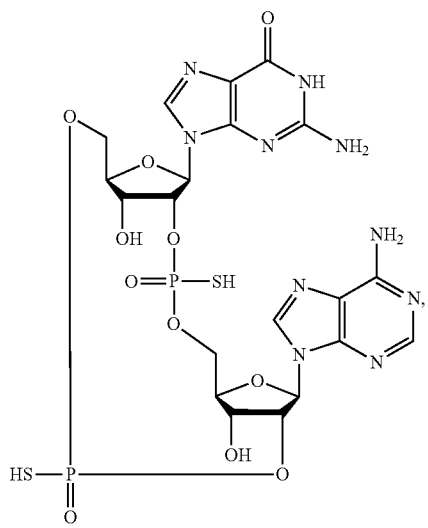
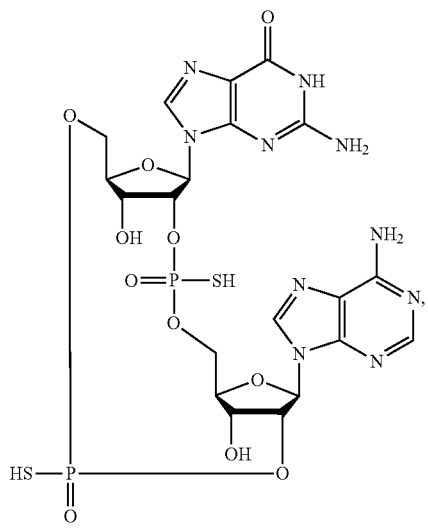
258
-continued
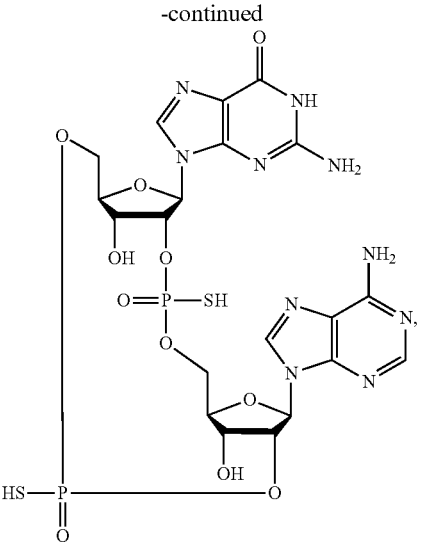
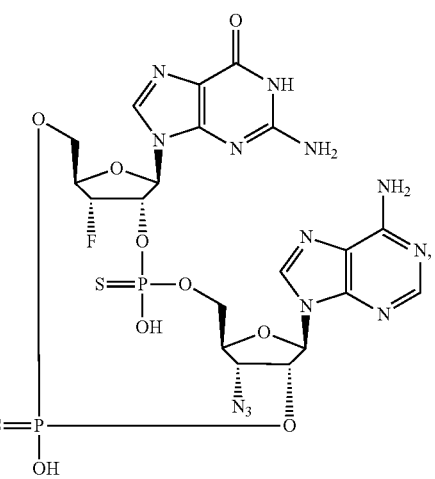
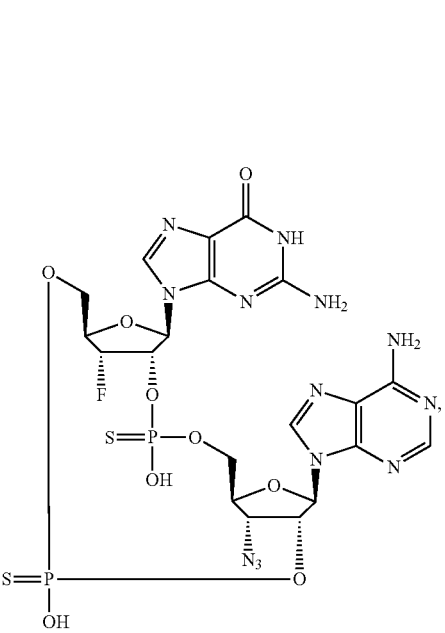

259                                   260
-continued                          -continued
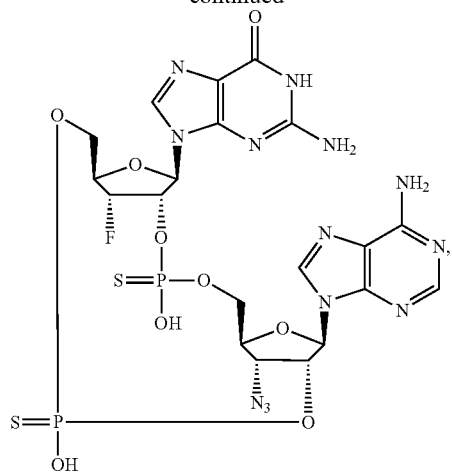 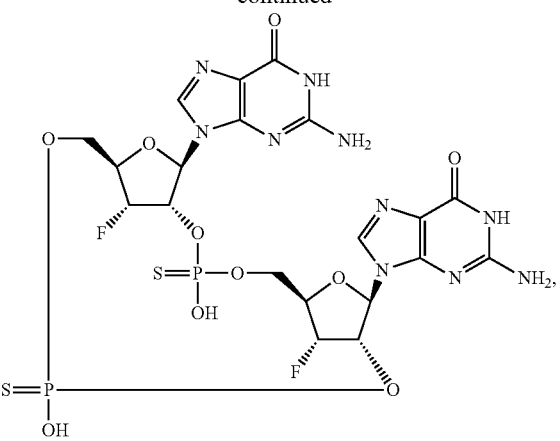
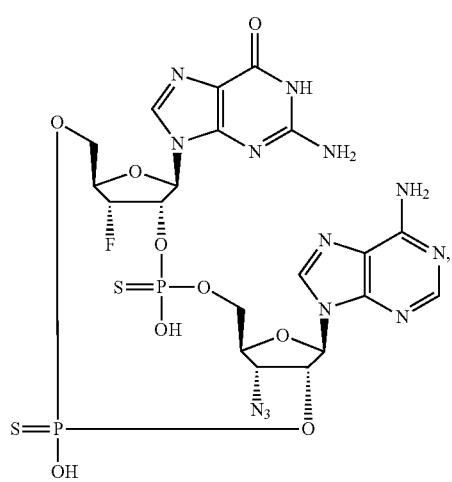 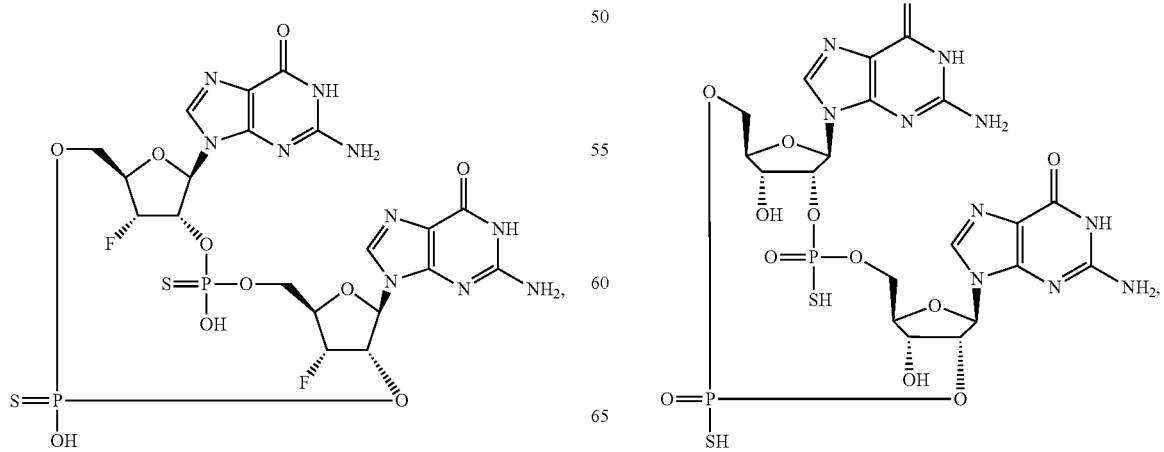

261
-continued
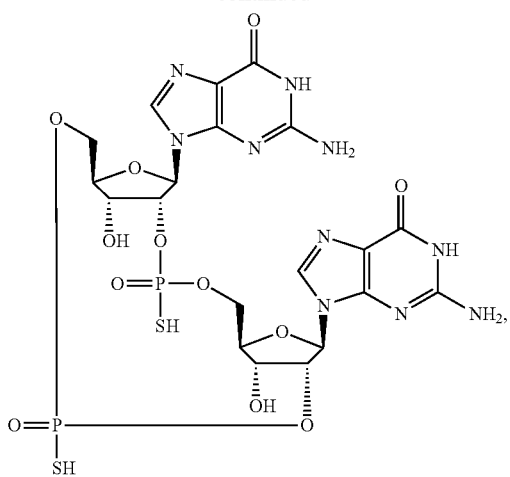
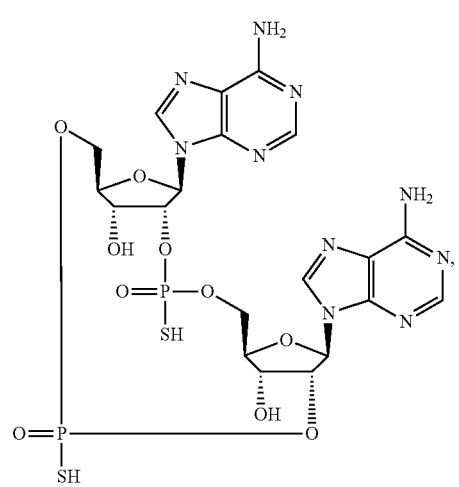
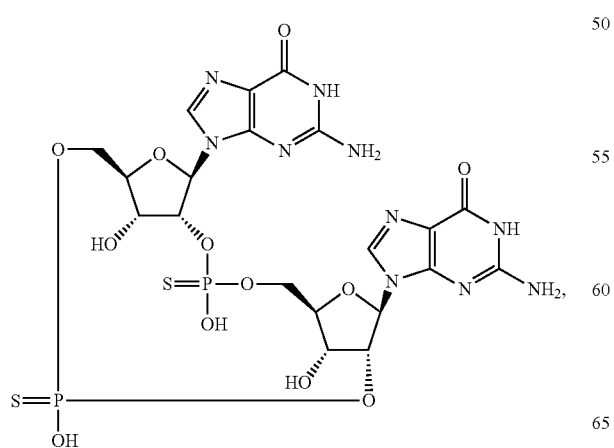
262
-continued
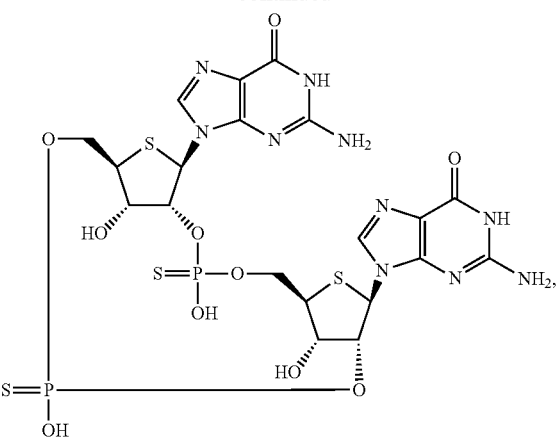
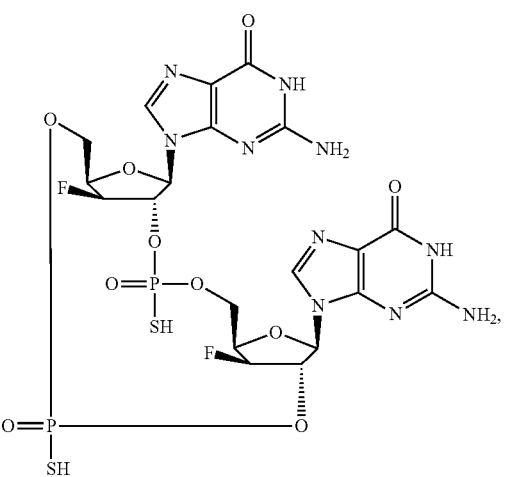
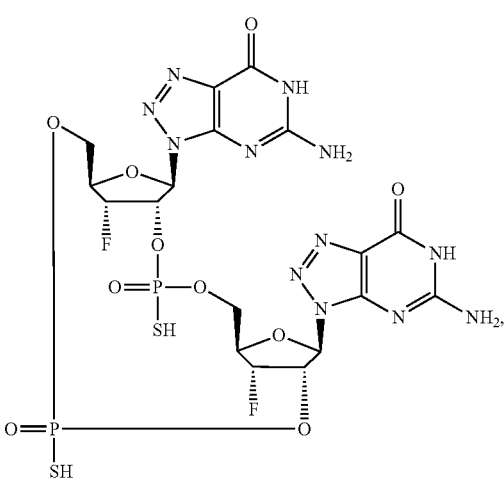

263
-continued
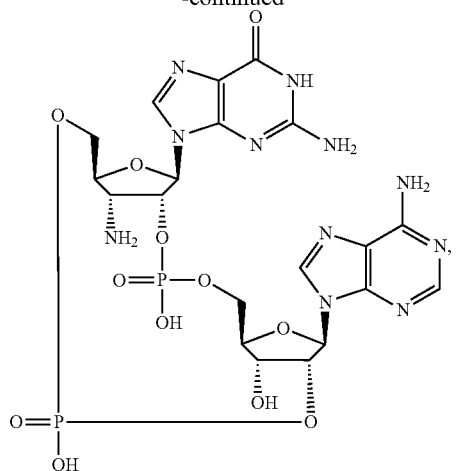
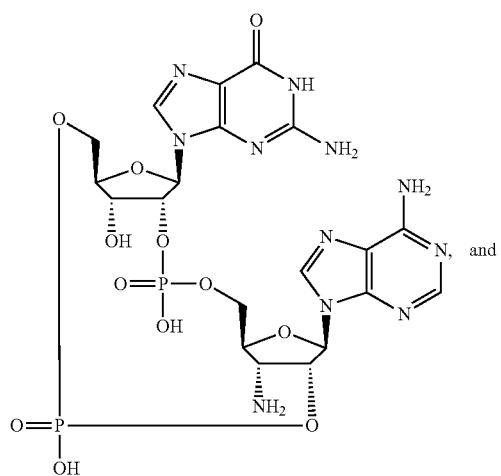
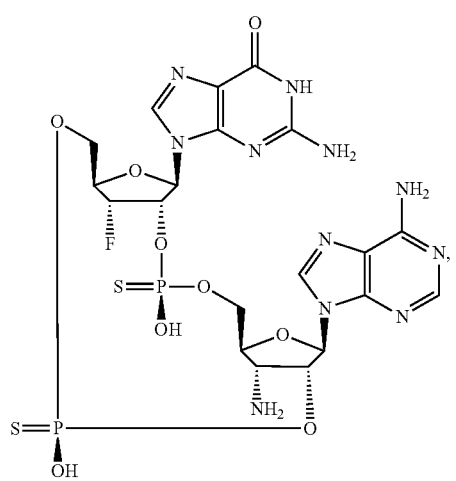
or a pharmaceutically acceptable salt thereof.
10. The method according to claim 9, wherein the compound is selected from the group consisting of:
264
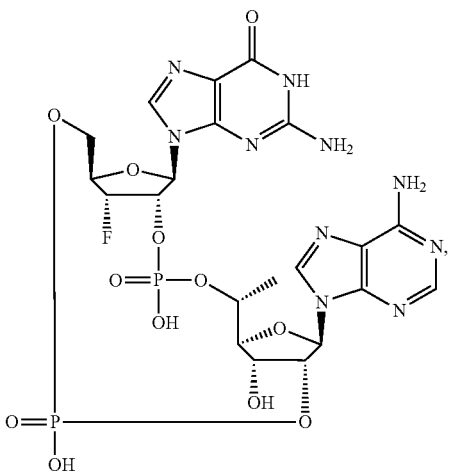
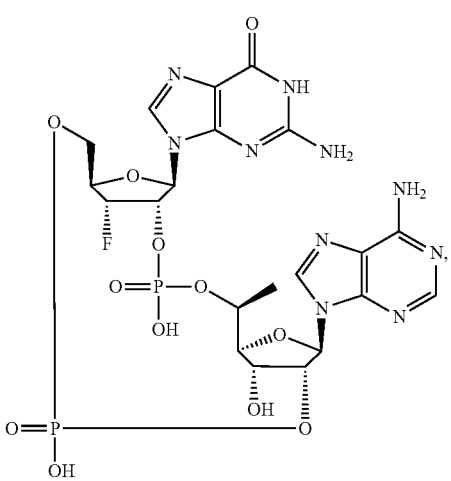
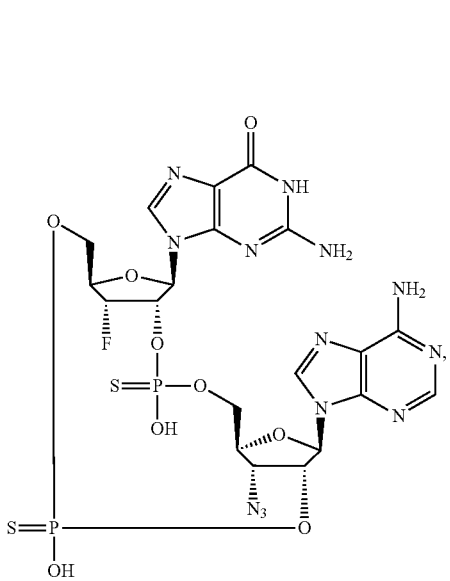

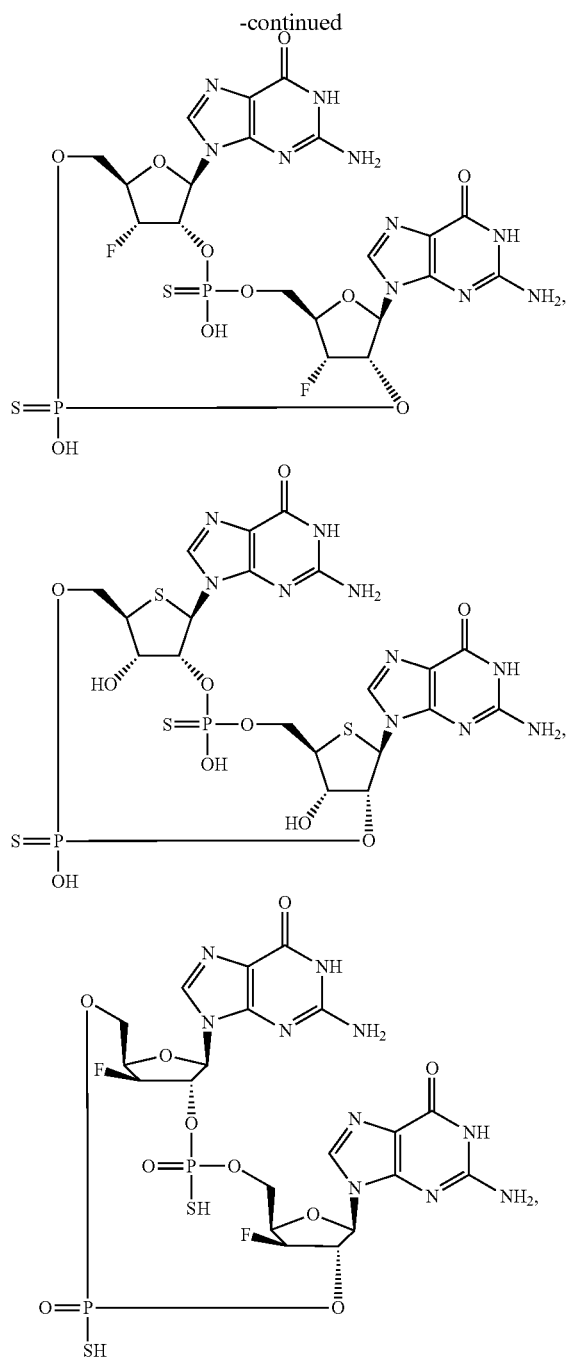
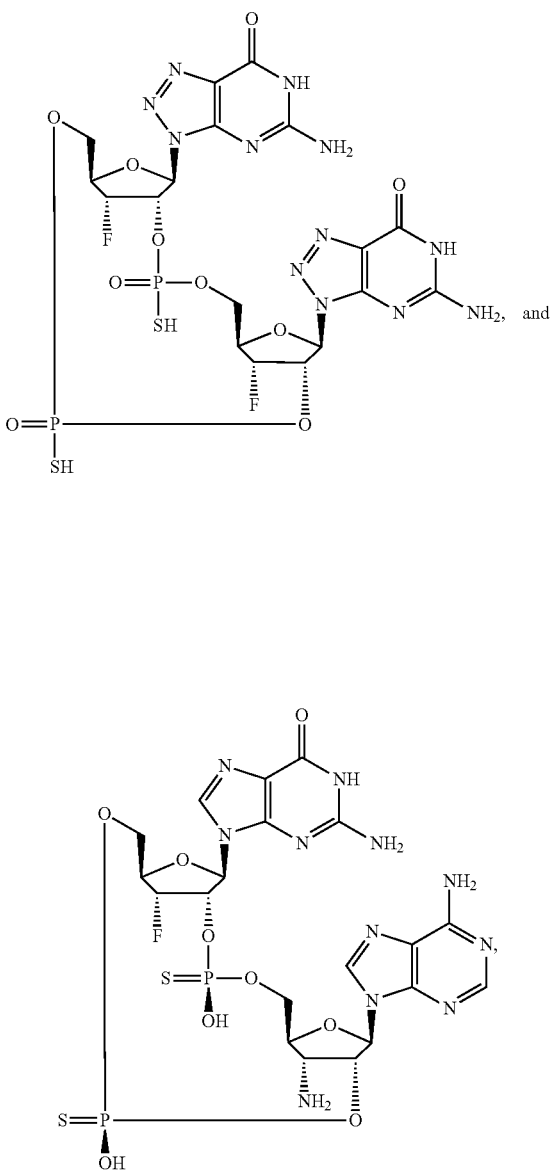
or a pharmaceutically acceptable salt thereof.
* * * * *